US012122776B2

(12) United States Patent
Jiang et al.

(10) Patent No.: US 12,122,776 B2
(45) Date of Patent: *Oct. 22, 2024

(54) TETRACYCLIC COMPOUNDS AND USES THEREOF

(71) Applicant: Gilead Sciences, Inc., Foster City, CA (US)

(72) Inventors: Lan Jiang, Foster City, CA (US); David W. Lin, Berkeley, CA (US); Michael L. Mitchell, Castro Valley, CA (US); Ezra Roberts, San Francisco, CA (US); Gregg M. Schwarzwalder, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,579

(22) Filed: May 12, 2023

(65) Prior Publication Data

US 2024/0010650 A1    Jan. 11, 2024

Related U.S. Application Data

(63) Continuation of application No. 17/182,559, filed on Feb. 23, 2021, now Pat. No. 11,697,652.

(60) Provisional application No. 63/128,670, filed on Dec. 21, 2020, provisional application No. 63/036,268, filed on Jun. 8, 2020, provisional application No. 62/980,857, filed on Feb. 24, 2020.

(51) Int. Cl.
   C07D 471/22    (2006.01)
   A61P 31/18    (2006.01)

(52) U.S. Cl.
   CPC ............ C07D 471/22 (2013.01); A61P 31/18 (2018.01)

(58) Field of Classification Search
   CPC .................................................. C07D 471/22
   See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,902,514 A | 2/1990 | Barclay et al. | |
| 4,992,445 A | 2/1991 | Lawter et al. | |
| 5,001,139 A | 3/1991 | Lawter et al. | |
| 5,023,252 A | 6/1991 | Hseih | |
| 5,616,345 A | 4/1997 | Geoghegan et al. | |
| 9,522,912 B2 | 12/2016 | Bacon et al. | |
| 10,087,178 B2 | 10/2018 | Miyazaki et al. | |
| 10,479,801 B2 * | 11/2019 | Graham ............... | C07D 471/22 |
| 11,084,832 B2 | 8/2021 | Chu et al. | |
| 11,492,352 B2 | 11/2022 | Ishii et al. | |
| 11,548,902 B1 | 1/2023 | Chu et al. | |
| 11,613,546 B2 | 3/2023 | Chu et al. | |
| 11,697,652 B2 * | 7/2023 | Jiang ................... | C07D 471/22 |
| | | | 514/214.02 |
| 11,884,683 B2 | 1/2024 | Yu et al. | |
| 11,897,892 B2 | 2/2024 | Chu et al. | |
| 12,024,528 B2 | 7/2024 | Chu et al. | |
| 2009/0253681 A1 | 10/2009 | Summa et al. | |
| 2009/0270412 A1 | 10/2009 | Hung et al. | |
| 2010/0143301 A1 | 6/2010 | Desai et al. | |
| 2013/0165489 A1 | 6/2013 | Cocklin et al. | |
| 2013/0171214 A1 | 7/2013 | Mundhra et al. | |
| 2014/0221356 A1 | 8/2014 | Jin et al. | |
| 2014/0221378 A1 | 8/2014 | Miyazaki et al. | |
| 2014/0221380 A1 | 8/2014 | Miyazaki et al. | |
| 2018/0155365 A1 | 6/2018 | Graham et al. | |
| 2019/0284208 A1 | 9/2019 | Johns et al. | |
| 2019/0315769 A1 | 10/2019 | Graham et al. | |
| 2019/0322666 A1 | 10/2019 | Yu et al. | |
| 2020/0317689 A1 | 10/2020 | Chu et al. | |
| 2021/0284642 A1 | 9/2021 | Jiang et al. | |
| 2022/0135565 A1 | 5/2022 | Chu et al. | |
| 2022/0267343 A1 | 8/2022 | Chu et al. | |
| 2023/0058677 A1 | 2/2023 | Tomida et al. | |
| 2023/0203061 A1 | 6/2023 | Chu et al. | |
| 2023/0257389 A1 | 8/2023 | Chu et al. | |
| 2023/0339971 A1 | 10/2023 | Chu et al. | |
| 2023/0339972 A1 | 10/2023 | Chu et al. | |

FOREIGN PATENT DOCUMENTS

| | | |
|---|---|---|
| CN | 104995198 | 10/2015 |
| CN | 116390924 | 7/2023 |
| EP | 3938047 A1 | 1/2022 |
| JP | 2006342115 A | 12/2006 |
| TW | 200716635 A | 5/2007 |
| TW | 202106689 A | 2/2021 |
| TW | 202120510 A | 6/2021 |
| WO | WO 2004096286 | 11/2004 |

(Continued)

OTHER PUBLICATIONS

Thenin-Houssier et al. Antimicrobial Agents and Chemotherapy 2016, 60, 2195-2208 (Year: 2016).*
2020) "Product Monograph Including Patient Medication Information" ViiV Healthcare ULC, 51 pages.
Benn, P. et al. (2021) "Long-Acting Cabotegravir + Rilpivirine in Older Adults: Pooled Phase 3 Week 48 Results" CROI 2021, Science Spotlight, 1-11.

(Continued)

Primary Examiner — Matthew P Coughlin
(74) Attorney, Agent, or Firm — Fish & Richardson P.C.

(57) ABSTRACT

The present disclosure relates generally to certain tetracyclic compounds, pharmaceutical compositions comprising said compounds, and methods of making said compounds and pharmaceutical compositions. The compounds of the disclosure are useful in treating or preventing human immunodeficiency virus (HIV) infection.

20 Claims, No Drawings

(56) References Cited

FOREIGN PATENT DOCUMENTS

| | | |
|---|---|---|
| WO | WO 2006015261 | 2/2006 |
| WO | WO-2006088173 A1 | 8/2006 |
| WO | WO 2006110157 | 10/2006 |
| WO | WO-2006116764 A1 | 11/2006 |
| WO | WO-2007/019098 A2 | 2/2007 |
| WO | WO-2007049675 A1 | 5/2007 |
| WO | WO-2007050510 A2 | 5/2007 |
| WO | WO-2007148780 A1 | 12/2007 |
| WO | WO-2008010964 A1 | 1/2008 |
| WO | WO-2008048538 A1 | 4/2008 |
| WO | WO 2009062285 | 5/2009 |
| WO | WO-2009088729 A1 | 7/2009 |
| WO | WO-2009/117540 A1 | 9/2009 |
| WO | WO-2009154870 A1 | 12/2009 |
| WO | WO-2010000030 A1 | 1/2010 |
| WO | WO-2010011812 A1 | 1/2010 |
| WO | WO-2010011814 A1 | 1/2010 |
| WO | WO-2010011815 A1 | 1/2010 |
| WO | WO-2010011816 A1 | 1/2010 |
| WO | WO-2010011818 A1 | 1/2010 |
| WO | WO-2010011819 A1 | 1/2010 |
| WO | WO-2010042391 A3 | 4/2010 |
| WO | WO-2010068253 A1 | 6/2010 |
| WO | WO-2010088167 A1 | 8/2010 |
| WO | WO 2010130034 | 11/2010 |
| WO | WO-2010147068 A1 | 12/2010 |
| WO | WO-2011011483 A1 | 1/2011 |
| WO | WO-2011025683 A1 | 3/2011 |
| WO | WO-2011045330 A1 | 4/2011 |
| WO | WO-2011094150 A1 | 8/2011 |
| WO | WO-2011105590 A1 | 9/2011 |
| WO | WO-2011121105 A1 | 10/2011 |
| WO | WO-2011129095 A1 | 10/2011 |
| WO | WO 2012003497 | 1/2012 |
| WO | WO 2012003498 | 1/2012 |
| WO | WO-2012018065 A1 | 2/2012 |
| WO | WO-2012058173 A1 | 5/2012 |
| WO | WO-2012078834 A1 | 6/2012 |
| WO | WO 2012145728 | 10/2012 |
| WO | WO 2013006738 | 1/2013 |
| WO | WO 2013006792 | 1/2013 |
| WO | WO-2013054862 A1 | 4/2013 |
| WO | WO 2013091096 | 6/2013 |
| WO | WO 2013159064 | 10/2013 |
| WO | WO-2014008636 A1 | 1/2014 |
| WO | WO-2014014933 A1 | 1/2014 |
| WO | WO-2014028384 A1 | 2/2014 |
| WO | WO-2014099586 A1 | 6/2014 |
| WO | WO-2014100323 A1 | 6/2014 |
| WO | WO-2014/172188 A2 | 10/2014 |
| WO | WO-2014183532 A1 | 11/2014 |
| WO | WO-2014200880 A1 | 12/2014 |
| WO | WO-2015006731 A1 | 1/2015 |
| WO | WO-2015006733 A1 | 1/2015 |
| WO | WO-2015039348 A1 | 3/2015 |
| WO | WO-2015048363 A1 | 4/2015 |
| WO | WO-2015/095258 A1 | 6/2015 |
| WO | WO-2015089847 A1 | 6/2015 |
| WO | WO-2015/196116 A1 | 12/2015 |
| WO | WO-2016027879 A1 | 2/2016 |
| WO | WO-2016033009 A1 | 3/2016 |
| WO | WO-2016/094197 A1 | 6/2016 |
| WO | WO-2016090545 A1 | 6/2016 |
| WO | WO-2016094198 A1 | 6/2016 |
| WO | WO-2016106237 A1 | 6/2016 |
| WO | WO-2016154527 A1 | 9/2016 |
| WO | WO-2016161382 A1 | 10/2016 |
| WO | WO-2016187788 A1 | 12/2016 |
| WO | WO-2017087256 A1 | 5/2017 |
| WO | WO-2017087257 A1 | 5/2017 |
| WO | WO-2017106071 A1 | 6/2017 |
| WO | WO-2017/116928 A1 | 7/2017 |
| WO | WO-2017113288 A1 | 7/2017 |
| WO | WO-2017223280 A2 | 12/2017 |
| WO | WO-2018102485 A1 | 6/2018 |
| WO | WO-2018102634 A1 | 6/2018 |
| WO | WO-2018109786 A1 | 6/2018 |
| WO | WO-2018140368 A1 | 8/2018 |
| WO | WO-2019/058393 A1 | 3/2019 |
| WO | WO-2019160783 A1 | 8/2019 |
| WO | WO 2019160883 | 8/2019 |
| WO | WO-2019209667 A1 * | 10/2019 ........... A61K 31/427 |
| WO | WO-2019223408 A1 | 11/2019 |
| WO | WO-2019/232216 A1 | 12/2019 |
| WO | WO-2019230857 A1 | 12/2019 |
| WO | WO-2019230858 A1 | 12/2019 |
| WO | WO-2019236396 A1 | 12/2019 |
| WO | WO-2019244066 A2 | 12/2019 |
| WO | WO-2020/003093 A1 | 1/2020 |
| WO | WO-2020086555 A1 | 4/2020 |
| WO | WO-2020112931 A1 | 6/2020 |
| WO | WO-2020197991 A1 | 10/2020 |
| WO | WO-2020221294 A1 | 11/2020 |
| WO | WO-2020246910 A1 | 12/2020 |
| WO | WO-2021093846 A1 | 5/2021 |
| WO | WO-2021/107066 A1 | 6/2021 |
| WO | WO 2022089562 | 5/2022 |
| WO | WO 2022159387 | 7/2022 |
| WO | WO-2022/177840 A1 | 8/2022 |

OTHER PUBLICATIONS

Bowers, G. et al. (2016) "Disposition and metabolism of cabotegravir: a comparison of biotransformation and excretion between different species and routes of administration in humans" Xenobiotica, 46(2):147-162.

Brooks, K. et al. (2019) "Integrase Inhibitors: After 10 Years of Experience, Is the Best Yet to Come?" Pharmacotherapy, 1-23.

Burns, J. et al. (2020) "No overall change in the rate of weight gain after switching to an integrase-inhibitor in virologically suppressed adults with HIV" AIDS, 34:109-114.

Castellino, S. et al. (2013) "Metabolism, Excretion, and Mass Balance of the HIV-1 Integrase Inhibitor Dolutegravir in Humans" 57(8):3536-3546.

Cook, N. et al. (2019) "Structural basis of second-generation HIV Integrase inhibitor action and viral resistance" Science, 1-9.

Correll, C. et al. (2021) "Pharmacokinetic Characteristics of Long-Acting Injectable Antipsychotics for Schizophrenia: An Overview" CNS Drugs, 35: 39-59.

Cottura, N. (2021) "In-Silico Prediction of Long-Acting Cabotegravir PK in Liver Impaired Patients" CROI 2021, Science Spotlight, 6 pages.

Flexner, C. (2020) "Novel Approaches to HIV Treatment and Prevention using Long Acting Drug Delivery" Johns Hopkins University, Division of Clinical Pharmacology, 45 pages.

Friedman, E. et al. (2016) "A Single Monotherapy Dose of MK-8591, a Novel NRTI, Suppresses HIV for 10 Days" CROI 2016, Poster, Abstract #437LB.

Gallant, J. et al. (2017) "Antiviral Activity, Safety, and Pharmacokinetics of Bictegravir as 10-Day Monotherapy in HIV-1-Infected Adults" J Acquir Immune Defic Syndr, 75(1):61-66.

Grobler, J. et al. (2019) "MK-8591 Potency and PK Provide High Inhibitory Quotients at Low Doses QD and QW" CROI 2019, Poster, Abstract #481.

Groseclose, M. et al. (2019) "Intramuscular and subcutaneous drug depot characterization of a long-acting abotegravir nanoformulation by MALDI IMS" International Journal of Mass Spectometry, 437:92-98.

Han, K. et al. (2021) "Cabotegravir Population Pharmacokinetic (PPK) Simulation to Inform Q2M Strategies Following Dosing Interruptions" CROI 2021, Science Spotlight, 9 pages.

Hill, L. et al. (2018) "Profile of bictegravir/emtricitabine/tenofovir alafenamide fixed dose combination and its potential in the treatment of HIV-1 infection: evidence to date" HIV/AIDS—Research and Palliative Care, 10:203-213.

Hughes, D. (2019) "Review of Synthetic Routes and Final Forms of Integrase Inhibitors Dolutegravir, Cabotegravir, and Bictegravir" Organic Process Research & Development, 23:716-729.

(56) References Cited

OTHER PUBLICATIONS

Intl. Search Report and Written Opinion dated May 4, 2021 for Intl. Appl. No. PCT/US2021/019179.
Jaeger, H. et al. (2021) "Week 96 Efficacy and Safety of Long-Acting Cabotegravir + Rilpivirine Every 2 Months: Atlas-2M" CROI 2021, Science Spotlight, 1-9.
Jiskoot, W. (2020) "Long-actinginjectables& implantables: immunogenicityconcerns" Third Long-Acting Injectables & Implantables Conference, 32 pages.
Jogiraju, V. (2021) "Pharmacokinetics of Lenacapavir, an HIV-1 Capsid Inhibitor, in Hepatic Impairment" CROI 2021, Science Spotlight, 6 pages.
Johns, B. et al. (2013) "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)" J. Med. Chem., 56:5901-5916.
Jucker, B. et al. (2021) "Multiparametric magnetic resonance imaging to characterize cabotegravir long-acting formulation depot kinetics in healthy adult volunteers" Br J Clin Pharmacol., 1-12.
Kalicharan, R. et al. (2017) "New Insights Into Drug Absorption From Oil Depots" University Medical Center Utrecht, Utrecht, the Netherlands, Thesis, 152 pages.
Kalicharan, R. et al. (2016) "Fundamental understanding of drug absorption from a parenteral oil depot" European Journal of Pharmaceutical Sciences, 83: 19-27.
Kandala, B. et al. (2021) "Model-informed dose selection for Islatravir/MK-8507 oral once-weekly phase 2B study" CROI 2021, Science Spotlight, 6 pages.
Kandel, C. et al. (2015) "Dolutegravir—a review of the pharmacology, efficacy, and safety in the treatment of HIV" Drug Design, Development and Therapy, 9:3547-3555.
Kinvig, H. (2021) "In-Silico Prediction of Monthly Bictegravir Microneedle Array Patches" CROI 2021, Science Spotlight, 6 pages.
Klooster, G. et al. (2010) "Pharmacokinetics and Disposition of Rilpivirine (TMC278) Nanosuspension as a Long-Acting Injectable Antiretroviral Formulation" Antimicrobial Agents and Chemotherapy, 54(5): 2042-2050.
Lalezari, J. et al. (2009) "Potent Antiviral Activity of S/GSK1349572, A Next Generation Integrase Inhibitor (INI), in INI-Naïve HIV-1-Infected Patients: ING111521 Protocol" IAS 2009, 5th Conference on HIV Pathogenesis, Abstract TUAB105, 15 pages.
Landovitz, R. et al. (2018) "Safety, tolerability, and pharmacokinetics of long-acting injectable cabotegravir in low-risk HIV-uninfected individuals: HPTN 077, a phase 2a randomized controlled trial" PLoS Med, 15(11):1-22.
Le Hingrat, Q. et al. (2018) "A New Mechanism of Resistance of Human Immunodeficiency Virus Type 2 to Integrase Inhibitors: A 5-Amino-Acid Insertion in the Integrase C-Terminal Domain" Clinical Infectious Diseases, 1-11.
Liu, S. et al. (2019) "Mechanistic Assessment of Extrahepatic Contributions to Glucuronidation of Integrase Strand Transfer Inhibitors" Drug Metabolism and Disposition, 47(5) 535-544.
Martin, C. et al. (2021) "Bictegravir and Cabotegravir: In Vitro Phenotypic Susceptibility of HIV-1 Nongroup M" CROI 2021, Science Spotlight, 1-6.
McMillan, J. et al. (2019) "Pharmacokinetic testing of a first generation cabotegravir prodrug in rhesus macaques" AIDS, 33(3):585-588.
Muller, R. et al. (2011) "State of the art of nanocrystals—Special features, production, nanotoxicology aspects and intracellular delivery" European Journal of Pharmaceuticals and Biopharmaceutics, 78:1-9.
Neary, M. (2021) "In Vitro / In Vivo Development of Long Acting Biodegradable Emtricitabine Implants" CROI 2021, Science Spotlight, 6 pages.
Office Action dated Feb. 11, 2022 for ROC (Taiwan) Application No. 110106560.
Orkin, C. et al. (2020) "Long-Acting Cabotegravir + Rilpivirine for HIV Treatment: Flair Week 96 Results" Conference on Retroviruses and Opportunistic Infections, Poster 0482, 1 page.
Passos, D. et al. (2020) "Structural basis for strand transfer inhibitor binding to HIV intasomes" Science, 1-9.
Passos, D. et al. (2020) Supplementary Materials for "Structural basis for strand transfer inhibitor binding to HIV intasomes" Science, Supplementary Text, 38 pages.
Provisional Application as filed on Apr. 6, 2022 for U.S. Appl. No. 63/328,061.
Raheem, I. et al. (2015) "Discovery of 2?Pyridinone Aminals: A Prodrug Strategy to Advance a Second Generation of HIV?1 Integrase Strand Transfer Inhibitors" J. Med. Chem., 58:8154-8165.
Rahnfeld, L. et al. (2020) "Injectable Lipid-Based Depot Formulations: Where Do We Stand?" Pharmaceutics 12(0567):1-28.
Rossenu, S. et al. (2021) "Population PK Modeling of Every 2 Months IM RPV LA for Managing Dosing Interruptions in HIV-1 Patients" CROI 2021, Science Spotlight, 1-7.
Rudd, D. et al. (2020) "Modeling-Supported Islatravir Dose Selection for Phase 3" CROI 2020, Poster, Abstract #462.
Scarsi, K. et al. (2020) "HIV-1 Integrase Inhibitors: A Comparative Review of Efficacy and Safety" Drugs, 80(16):1649-1676.
Shaik, J. et al. (2019) "A Phase 1 Study to Evaluate the Pharmacokinetics and Safety of Cabotegravir in Patients With Hepatic Impairment and Healthy Matched Controls" Clinical Pharmacology in Drug Development, 00(0):1-10.
Shi, Y. et al. (2021) "A review of existing strategies for designing longacting parenteral formulations: Focus on underlying mechanisms, and future perspectives" Acta Pharmaceutica Sinica B, 11(8): 2396-2415.
Spreen, W. et al. (2013) "Pharmacokinetics, Safety, and Monotherapy Antiviral Activity of GSK1265744, an HIV Integrase Strand Transfer Inhibitor" HIV Clinical Trials, 14(5):192-203.
Spreen, W. et al. (2014) "GSK1265744 Pharmacokinetics in Plasma and Tissue After Single-Dose Long-Acting Injectable Administration in Healthy Subjects" J Acquir Immune Defic Syndr, 67(5):481-486.
Trezza, C. et al. (2015) "Formulation and pharmacology of long-acting cabotegravir" Current Opinion—HIV and AIDS, 10(4):239-245.
Walji, A. et al. (2015) "Discovery of MK-8970: An Acetal Carbonate Prodrug of Raltegravir with Enhanced Colonic Absorption" ChemMedChem, 10:245-252.
Weller, S. et al. (2014) "Pharmacokinetics of dolutegravir in HIV-seronegative subjects with severe renal impairment" Eur J Clin Pharmacol 70:29-35.
Wilkinson, J. et al. (2022) "Lipid based intramuscular long-acting injectables: Current state of the art" European Journal of Pharmaceutical Sciences, 178(106253): 1-20.
Yoshinaga, T. et al. (2015) "Antiviral Characteristics of GSK1265744, an HIV Integrase Inhibitor Dosed Orally or by Long-Acting Injection" 59(1):397-406.
Yoshinaga, T. et al. (2018) "Novel secondary mutations C56S and G149A confer resistance to HIV-1 integrase strand transfer inhibitors" Antiviral Research, 152:1-9.
Zhang, W. et al. (2018) "Accumulation of Multiple Mutations In Vivo Confers Cross-Resistance to New and Existing Integrase Inhibitors" The Journal of Infectious Diseases, 218:1773-1776.
Opposition, by opponent Laboratorios Legrand S.A., dated Dec. 14, 2022 for Colombian Application No. NC2022-0011947.
First Examination Report dated Mar. 16, 2023 for Australian Patent Application No. 2021225809.
Akiyama, T. et al. (2013) "Discovery of Novel HIV Integrase Inhibitors Part 2. Selection and Evaluation of an Azabicyclic Carbamoyl Pyridone as a Pre-clinical Candidate", 245th ACS National Meeting and Exposition, Poster MEDI 403.
Andersson, V. et al. (2016) "Macrocyclic Prodrugs of a Selective Nonpeptidic Direct Thrombin Inhibitor Display High Permeability, Efficient Bioconversion but Low Bioavailability", J Med Chem, 59(14):6658-6670.
Anonymous (2013) "Thomson Reuters Drug News: Results from phase III trials of dolutegravir presented", Thomson Reuters. Retrieved

(56) References Cited

OTHER PUBLICATIONS from the Internet Jul. 5, 2013 <URL: http://drugnews.thomson-pharma.com/ddn/article.do?printerFriendlyFormat=true>.
Bari, H. (2010) "A Prolonged Release Parenteral Drug Delivery System—An Overview", Int J Pharm Sci Rev Res, 3(1):1-11.
Bocedi, A. et al. (2004) "Binding of Anti-HIV Drugs to Human Serum Albumin", IUBMB Life, 56(10):609-614.
Brinson, C. et al. (2013) "Dolutegravir Treatment Response and Safety by Key Subgroups in Treatment Naive HIV Infected Individuals", 20th CROI, Poster 554.
Cottrell, M. et al. (2013) "Clinical Pharmacokinetic, Pharmacodynamic and Drug-Interaction Profile of the Integrase Inhibitor Dolutegravir", Clin Pharmacokinet, 52(11):981-994.
Curley, P. et al. (2019) "Long-Acting Emtricitabine Prodrugs Provide Protection From HIV Infection In Vivo", 2019 CROI, Poster 2262.
Del Mar Gutierrez, M. et al. (2014) "Drug safety profile of integrase strand transfer inhibitors", Expert Opin Drug Saf, 13(4):431-445.
Dicker, I. et al. (2011) "Simple and Accurate In Vitro Method for Predicting Serum Protein Binding of HIV Integrase Strand Transfer Inhibitors", HIV-1 Integrase: Mechanism and Inhibitor Design, First Edition.
EFSA (European Food Safety Authority), (2005) "Opinion of the Scientific Panel on Dietetic Products, Nutrition and Allergies on a request from the Commission related to the Tolerable Upper Intake Level of Potassium", EFSA Journal 2005, 3(3):193, 19 pp.
Gelé, T. et al. (2020) "Characteristics of Dolutegravir and Bictegravir Plasma Protein Binding: a First Approach for the Study of Pharmacologic Sanctuaries", Antimicrob Agents Chemother, 64(11):e00895-20.
Grobler, J. et al. (2016) "Efficacy of once-weekly MK-8591 in SIV infected rhesus macaques", Merck & Co., Inc., 7th International Workshop on Clinical Pharmacology of HIV & Hepatitis Therapy.
Günthard, H. et al. (2016) "Antiretroviral Drugs for Treatment and Prevention of HIV Infection in Adults: 2016 Recommendations of the International Antiviral Society-USA Panel", JAMA, 316(2):191-210.
Gurevich, K. (2013) "Effect of blood protein concentrations on drug-dosing regimes: practical guidance", Theor Biol Med Model, 10:20.
Hare, S. et al. (2011) "Structural and Functional Analyses of the Second-Generation Integrase Strand Transfer Inhibitor Dolutegravir (S/GSK1349572)", Mol Pharmacol, 80(4):565-572.
Hurt, C. et al. (2013) "Characterization of Resistance to Integrase Strand Transfer Inhibitors among Clinical Specimens in the United States, 2009-2012", 20th CROI, Poster 591.
Johns, B. et al. (2010) "The Discovery of S/GSK1349572: A Once Daily Next Generation Integrase Inhibitor with a Superior Resistance Profile", 17th CROI.
Kochansky, C. et al. (2008) "Impact of pH on Plasma Protein Binding in Equilibrium Dialysis", Mol Pharm, 5(3):438-448.
Kulkarni, T. et al. (2019) "Prodrugs extend the half life and potency of Cabotegravir", CROI, Poster 489.
Kulkarni, T. et al. (2020) "A Year-Long Extended Release Nanoformulated Cabotegravir Prodrug", Nat Mater, 19(8):910-920.
Landovitz, R. et al. (2020) "Cabotegravir Is Not Associated With Weight Gain in Human Immunodeficiency Virus-uninfected Individuals in HPTN 077", Clin Infect Dis, 70(2):319-322.
Letendre, S. et al. (2013) "Distribution and Antiviral Activity in Cerebrospinal Fluid (CSF) of the Integrase Inhibitor, Dolutegravir (DTG): ING116070 Week 16 Results", 20th CROI, Poster 178LB.
Markowitz, M. (2017) "Weekly Oral MK-8591 Protects Male Rhesus Macaques against Repeated Low Dose Intrarectal Challenge with SHIV109CP3", 9th IAS Conference on HIV Science (IAS 2017), PowerPoint Presentation.
Matthews, R. et al. (2017) "Single doses as low as 0.5 mg of the novel NRTTI MK-8591 suppress HIV for at least seven days", IAS 2017: Conference on HIV Pathogenesis, Poster.
McElnay, J. & D'Arcy, P. (1983) "Protein Binding Displacement Interactions and their Clinical Importance", Drugs, 25(5):495-513.

Menéndez-Arias, L. & Alvarez, M. (2014) "Antiretroviral therapy and drug resistance in human immunodeficiency virus type 2 infection", Antiviral Res, 102:70-86.
Métifiot, M. et al. (2013) "HIV Integrase Inhibitors: 20-Year Landmark and Challenges", Adv Pharmacol, 67:75-105.
Min, S. et al. (2011) "Antiviral activity, safety, and pharmacokinetics/pharmacodynamics of dolutegravir as 10-day monotherapy in HIV-1-infected adults" AIDS 25(14):1737-1745.
Mullokandov, E. et al. (2014) "Protein Binding Drug-Drug Interaction between Warfarin and Tizoxanide in Human Plasma", Austin J Pharmacol Ther, 2(7):id1038.
Nair, V. et al. (2014) "Pharmacokinetics and Dose-range Finding Toxicity of a Novel anti-HIV Active Integrase Inhibitor", Antiviral Res, 108:25-29.
Nair, V. et al. (2014) "Pharmacokinetics and Dose-range Finding Toxicity of a Novel anti-HIV Active Integrase Inhibitor" Supplementary Materials.
Orkin, C. et al. (2019) "Long-Acting Cabotegravir + Rilpivirine for HIV Maintenance: Flair Week 48 Results", CROI 2019, PowerPoint Presentation.
Park, B. et al. (2001) "Metabolism of Fluorine-Containing Drugs" Annu. Rev. Pharmacol. Toxicol. 41:443-470.
Podany, A. et al. (2017) "Comparative Clinical Pharmacokinetics and Pharmacodynamics of HIV-1 Integrase Strand Transfer Inhibitors", Clin Pharmacokinet, 56(1):25-40.
Pozniak, A. et al. (2013) "Dolutegravir (DTG) Versus Raltegravir (RAL) in ART-Experienced, Integrase-Naive Subjects: 24-Week Interim Results From Sailing (ING111762)", 20th CROI.
Quashie, P. et al. (2013) "Evolution of HIV integrase resistance mutations", Curr Opin Infect Dis, 26(1):43-49.
Raffi, F. et al. (2013) "Once-daily dolutegravir versus raltegravir in antiretroviral-naive adults with HIV-1 infection: 48 week results from the randomised, double-blind, non-inferiority SPRING-2 study", Lancet, 381(9868):735-743.
Rajoli, R. et al. (2019) "In Silico Simulation Of Long-Acting Tenofovir Alafenamide Subcutaneous Implant", CROI 2019, Poster 487.
Rautio, J. et al. (2018), "The expanding role of prodrugs in contemporary drug design and development", Nat Rev Drug Discov, 17(8):559-587.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Rhodes, M. et al. (2012) "Assessing a Theoretical Risk of Dolutegravir-Induced Developmental Immunotoxicity in Juvenile Rats", Toxicol Sci, 130(1):70-81.
Roberts, J. et al. (2013) "The Clinical Relevance of Plasma Protein Binding Changes", Clin Pharmacokinet, 52(1):1-8.
Song, I. et al. (2013) "Dolutegravir Has No Effect on the Pharmacokinetics of Methadone or Oral Contraceptives With Norgestimate and Ethinyl Estradiol", 20th CROI.
Taoada, Y. et al. (2013) "Discovery of Novel HIV Integrase Inhibitors Part 1. Molecular Design and SAR of Azabicyclic Carbamoyl Pyridone Inhibitors", 245th ACS National Meeting and Exposition, Poster MEDI 402.
Tian, H. et al. (2018) "Effects of Plasma Albumin on the Pharmacokinetics of Esomeprazole in ICU Patients", Biomed Res Int, 2018:6374374.
Van Der Galiën, R. et al. (2019) "Pharmacokinetics of HIV-Integrase Inhibitors During Pregnancy: Mechanisms, Clinical Implications and Knowledge Gaps", Clin Pharmacokinet, 58(3):309-323.
Wang, Y. C. et al. (2002) "Switch in asymmetric induction sense in cycloadditions using camphor-based nitroso dienophiles", Tetrahedron: Asymmetry, 13(7):691-695.
Weaving, G. et al. (2016) "Age and sex variation in serum albumin concentration: an observational study", Ann Clin Biochem, 53(1):106-111.
Wolkowicz, U. et al. (2014) "Structural Basis of Mos1 Transposase Inhibition by the Anti-retroviral Drug Raltegravir", ACS Chem Biol, 9(3):743-751.
Wu, J. et al. (2012) "Implications of Plasma Protein Binding for Pharmacokinetics and Pharmacodynamics of the γ-Secretase Inhibitor RO4929097", Clin Cancer Res, 18(7):2066-2079.

(56) References Cited

OTHER PUBLICATIONS

Zhao, X. et al. (2014) "4-Amino-1-hydroxy-2-oxo-1,8-naphthyridine-Containing Compounds Having High Potency against Raltegravir-Resistant Integrase Mutants of HIV-1", J Med Chem, 57(12):5190-5202.
Williams, D. & Lemke, T. (2002), Foye's Principles of Medicinal Chemistry, 5th Ed., pp. 59-63.
Non-Final Office Action dated Jul. 13, 2022 for U.S. Appl. No. 17/182,559.
Notice of Allowance dated Nov. 2, 2022 for U.S. Appl. No. 17/182,559.
Notice of Allowance dated Feb. 15, 2023 for U.S. Appl. No. 17/182,559.
Corrected Notice of Allowability dated Jun. 7, 2023 for U.S. Appl. No. 17/182,559.
Intl. Preliminary Report on Patentability dated Sep. 9, 2022 for Intl. Appl. No. PCT/US2021/019179.
Office Action dated Aug. 8, 2023 for Japanese Appl. No. 2022-550787.
Ivashchenko et al., "Synthesis, biological evaluation and in silico modeling of novel integrase strand transfer inhibitors (INSTIs)," European Journal of Medicinal Chemistry, Mar. 1, 2020, 189:112064.
Patani et al., "Bioisoterism: A Rational Approach in Drug Design," Chem Rev., Dec. 1996, 8:3147-3176.
Office Action in Chinese Appln. No. 202180016403.3, dated Jan. 2, 2024, 13 pages (with English translation).
Office Action in Dominican Republic Appln. No. P2022-0171, dated Mar. 5, 2024, 16 pages (with English Translation).
clinicalinfo.hiv.gov [online], "Guidelines for the Use of Antiretroviral Agents in Adults and Adolescents with HIV," Dec. 18, 2019, retrieved on Feb. 19, 2020, retrieved from URL<https://files.aidsinfo.nih.gov/contentfiles/lvguidelines/AdultandAdo>, 379 pages.
Foster, "Deuterium isotope effects in studies of drug metabolism", Trends Pharmacol. Sci., 1984, 5(12):524-527.
Fulmali et al., "Phosphate moiety in FDA-approved pharmaceutical salts and prodrugs," Drug Dev. Res., Jun. 2, 2022, 83(5):1059-1074.
Hurt et al., "Resistance to HIV Integrase Strand Transfer Inhibitors Among Clinical Specimens in the United States, 2009-2012," Clinical Infectious Diseases, Feb. 2014, 58:423-431.
Levine et al., "Trimethyl lock: A trigger for molecular release in chemistry, biology, and pharmacology," Chem. Sci., Jan. 2012, 3(8):2412-2420.
Palella et al., "Declining morbidity and mortality among patients with advanced human immunodeficiency virus infection, HIV Outpatient Study Investigators," N. Engl. J Med., Mar. 1998, 338(13):853-860.
Randolph et al., "Prodrug Strategies to Improve the Solubility of the HCV NS5A Inhibitor Pibrentasvir (ABT-530)," J. Med. Chem., Sep. 3, 2020, 63:11034-11044.
Richman, "HIV chemotherapy," Nature, Apr. 2001, 410(6831):995-1001 (abstract only).
Tang et al., "HIV-1 antiretroviral resistance: scientific principles and clinical applications," Drugs, Jun. 2012, 72(9):e1-25.
Tantra et al., "Phosphate Prodrugs: An Approach to Improve the Bioavailability of Clinically Approved Drugs," Curr. Med. Chem., Mar. 21, 2023, 31(3):336-357.
Thierry et al., "Different Pathways Leading to Integrase Inhibitors Resistance," Front. Microbiol., Jan. 11, 2017, 7:2165, 13 pages.
Voight et al., "Desymmetrization of pibrentasvir for efficient prodrug synthesis," Chem. Sci., Jun. 29, 2021, 12(29):10076-10082.
Notice of Acceptance in Australian Appln. No. 2021225809, mailed Aug. 11, 2023, 3 pages.
Office Action in Canadian Appln. No. 3166480, mailed on Sep. 14, 2023, 4 pages.
Office Action in Eurasian Appln. No. 202292356, mailed on Nov. 11, 2023, 6 pages (with English translation).
Office Action in Japanese Appl. No. 2022-550787, mailed on Nov. 20, 2023, 6 pages (with English translation).
Office Action in Canadian Appln. No. 3166480, dated Jun. 12, 2024, 2 pages.
Office Action in Chilean Appln. No. 202202300, dated May 30, 2024, 30 pages (with English translation).
Office Action in Eurasian Appln. No. 202292356, mailed on Jun. 5, 2024, 5 pages (with English translation).

\* cited by examiner

TETRACYCLIC COMPOUNDS AND USES THEREOF

CROSS REFERENCE TO RELATED APPLICATIONS

This application is a Continuation of U.S. application Ser. No. 17/182,559, filed on Feb. 23, 2021, now issued U.S. Pat. No. 11,697,652, which claims the benefit of U.S. Provisional Application No. 62/980,857 filed on Feb. 24, 2020, U.S. Provisional Application No. 63/036,268 filed Jun. 8, 2020, and U.S. Provisional Application No. 63/128,670 filed Dec. 21, 2020. The entire contents of these applications are incorporated herein by reference in their entirety.

FIELD

This disclosure relates generally to certain tetracyclic compounds, pharmaceutical compositions comprising said compounds, and methods of making and using said compounds and pharmaceutical compositions.

BACKGROUND

Human immunodeficiency virus infection and related diseases are a major public health problem worldwide. Human immunodeficiency virus encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains may limit their usefulness (Palella, et al. *N. Engl. J Med.* (1998) 338:853-860; Richman, D. D. *Nature* (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes (Panel on Antiretroviral Guidelines for Adults and Adolescents. Guidelines for the Use of Antiretroviral Agents in Adults and Adolescents Living with HIV. Department of Health and Human Services. Available at https://files.aidsinfo.nih.gov/contentfiles/lvguidelines/AdultandAdolescentGL.pdf. Accessed Feb. 20, 2020). In addition, decisions regarding the treatment of HIV infected patients are complicated when the patient requires treatment for other medical conditions. Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang, et al. *Drugs* (2012) 72 (9) e1-e25). Because of the proclivity of the HIV virus to mutate, there is a need for anti-HIV drugs to be effective against a range of known HIV variants (Hurt, et al. *HIV/AIDS CID* (2014) 58, 423-431).

For certain patients, for example, those with difficult or limited access to health care, adherence to daily oral treatment or prophylactic regimens can be challenging. Drugs that offer favorable pharmaceutical properties (for example, improved potency, long-acting pharmacokinetics, low solubility, low clearance, and/or other properties) are amenable to less frequent administration and provide for better patient compliance. Such improvements can, in turn, optimize drug exposure and limit the emergence of drug resistance.

SUMMARY

In one aspect, provided herein is a compound of Formula I:

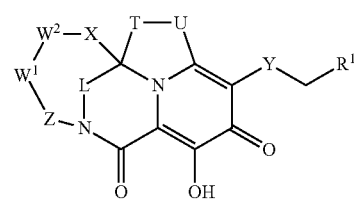

Formula I or a pharmaceutically acceptable salt thereof, wherein
$R^1$ is a H, $C_{6-10}$aryl or $C_{6-10}$heteroaryl, wherein the $C_{6-10}$aryl or $C_{6-10}$heteroaryl is optionally substituted with one to four $R^{41}$, wherein each $R^{41}$ is independently halo, $C_{1-4}$alkyl, $C_{1-4}$haloalkyl, $C_{3-6}$cycloalkyl, cyano, —O—$C_{1-4}$alkyl, —O—$C_{3-6}$cycloalkyl, or $C_{1-4}$alkyl-O—$C_{1-4}$alkyl;
Y is selected from the group consisting of —C(O)NH—,

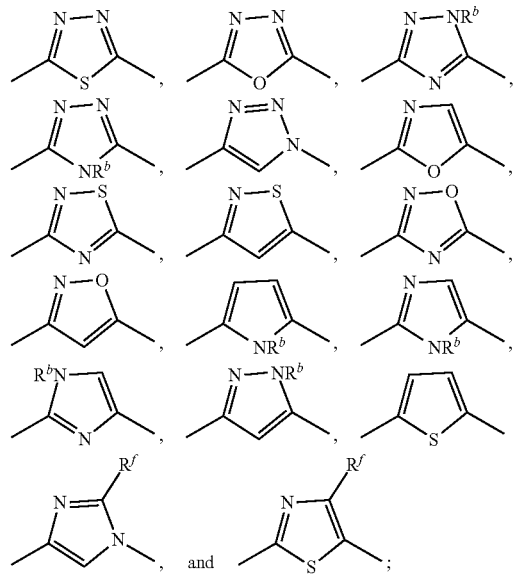

and ;

L is —$CR^{3a}R^{3b}$—, —C(O)—, —$SO_2$—, —$CR^{3a}R^{3b}$—$CR^{3c}R^{3d}$—, or —$N(R^a)$—;
$W^1$ is a bond or —$CR^{4a}R^{4b}$—;
$W^2$ is —$CR^{5a}R^{5b}$—, —$CR^{5a}R^{5b}CR^{5c}R^{5d}$—, —$CR^{6a}$=$CR^{6b}$—, —$N(R^7)$—, —O—, —$S(O)_n$—, —C(O)$NR^e$—, —$CR^{5a}R^{5b}$—$N(R^7)$—, —$CR^{5a}R^{5b}$—O—, —$CR^{5a}R^{5b}$—$S(O)_n$—, —$CR^{5a}R^{5b}$—C(O)$NR^e$—, —$CR^{5a}R^{5b}$—$NR^e$—C(O)—, —$S(O)_nN(R^e)$—$CR^{5a}R^{5b}$—, or —$N(R^e)$—$S(O)_n$—$CR^{5a}R^{5b}$—;
X is a bond or —$CR^{8a}R^{8b}$—;
Z is —$CR^{9a}R^{9b}$—, —$CR^{9a}R^{9b}CR^{9c}R^{9d}$—, or —$CR^{10a}$=$CR^{10b}$—;
T is —$CR^{2a}R^{2b}$— or —$CR^{2a}R^{2b}$—$CR^{2c}R^{2d}$— and U is —$NR^{11}$—, —$CR^{12a}R^{12b}$—, —$S(O)_n$—, —C(O)—, or —O—; or T and U together are

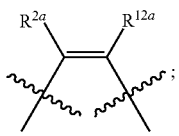

$R^{2a}$, $R^{2b}$, $R^{2c}$, $R^{2d}$, $R^{12a}$, and $R^{12b}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$— —$NR^e$—$S(O)_nR^a$—, —$S(O)_n$—NH($R^a$)—, or —$S(O)_n$—$R^a$—; or any one of (i) $R^{2a}$ and $R^{2b}$, (ii) $R^{2c}$ and $R^{2d}$ or (iii) $R^{12a}$ and $R^{12b}$ together with the carbon atom to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{42}$, wherein each $R^{42}$ is independently oxo, halo, cyano, $C_{1-6}$alkyl, $C_{3-6}$cycloalkyl or —$OR^e$;

$R^{3a}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{42}$, wherein each $R^{42}$ is independently oxo, halo, cyano, $C_{1-6}$alkyl, $C_{3-6}$cycloalkyl or —$OR^e$;

$R^{4a}$, $R^{4b}$, $R^{5a}$, $R^{5b}$, $R^{5c}$, $R^{5d}$, $R^{8a}$, $R^{8b}$, $R^{9a}$, $R^{9b}$, $R^{9c}$, and $R^{9d}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; or any one of (i) $R^{4a}$ and $R^{4b}$, (ii) $R^{5a}$ and $R^{5b}$, (iii) $R^{5c}$ and $R^{5d}$, (iv) $R^{5a}$ and $R^{5c}$, (v) $R^{5b}$ and $R^{5d}$, (vi) $R^{8a}$ and $R^{8b}$, (vii) $R^{9a}$ and $R^{9b}$, (viii) $R^{9c}$ and $R^{9d}$, (ix) $R^{9a}$ and $R^{9c}$, (x) $R^{9b}$ and $R^{9d}$, (xi) $R^{8b}$ and one of $R^{5a}$, $R^{5b}$, $R^{5c}$, $R^{5d}$, and $R^7$, or (xii) one of $R^{9a}$, $R^{9b}$, $R^{9c}$, and $R^{9d}$ and one of $R^{4a}$, $R^{4b}$, $R^{5a}$, $R^{5b}$, and $R^7$ together with the carbon atom to which they are attached form a (i) 3 to 7 membered carbocyclic ring or (ii) 4 to 7 membered heterocyclic ring containing 1 to 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$;

each $R^{6a}$, $R^{6b}$, $R^{10a}$, and $R^{10b}$ is independently H, halo, $C_{1-4}$haloalkyl, or $C_{1-4}$alkyl; or any one of (i) $R^{6a}$ and $R^{6b}$ or (ii) $R^{10a}$ and $R^{10b}$ together with the carbon atoms to which each is attached form (i) a 5 to 10 membered carbocyclic ring, (ii) 5 to 10 membered heterocyclic ring containing 1 or 2 heteroatom selected from N, O, and S, (iii) a 6 to 10 membered aromatic ring, or (iv) a 5 to 10 membered heteroaromatic ring containing 1 to 3 heteroatoms selected from N, O and S, wherein the 5 to 10 membered carbocyclic ring, 5 to 10 membered heterocyclic ring, the 6 to 10 membered aromatic ring, or the 5 to 10 membered heteroaromatic ring is optionally substituted with one to four $R^{44}$, wherein each $R^{44}$ is independently oxo, halo, cyano, $C_{1-4}$alkyl, $C_{3-6}$cycloalkyl or —$OR^e$;

$R^7$ is H, $C_{1-6}$alkyl, $C_{1-4}$haloalkyl, $C_{3-6}$cycloalkyl, $C_{3-6}$halocycloalkyl, C(O)$R^c$, or $SO_2R^c$;

$R^{11}$ is H, $C_{1-4}$alkyl, $C_{1-4}$haloalkyl, $C_{3-6}$cycloalkyl, $C_{3-6}$halocycloalkyl, —C(O)—$R^a$, —$S(O)_n$—$R^a$, —$CH_2$—$R^a$;

each $R^a$ is independently (i) H, (ii) $C_{1-6}$alkyl, (iii) $C_{3-6}$cycloalkyl, (iv) a 5 to 10 membered carbocyclic ring, (v) 5 to 10 membered heterocyclic ring containing 1 or 2 heteroatom selected from N, O, and S, (vi) a 6 to 10 membered aromatic ring, or (iv) a 5 to 10 membered heteroaromatic ring containing 1 to 3 heteroatoms selected from N, O and S;

wherein the $C_{1-6}$alkyl, $C_{3-6}$cycloalkyl, 5 to 10 membered carbocyclic ring, 5 to 10 membered heterocyclic ring, 6 to 10 membered aromatic ring or 5 to 10 membered heteroaromatic ring is optionally substituted with 0 to 4 substituents independently selected from the group consisting of (i) oxo (ii) halo, (iii) cyano, (iv) —O—$C_{1-4}$alkyl, (v) $C_{1-6}$alkyl, (vi) —$OR^e$ (vii) 3 to 10 membered carbocyclic ring, (viii) 5 to 10 membered heterocyclic ring containing 1 or 2 heteroatom selected from N, O, and S, (ix) 6 to 10 membered aromatic ring, or (x) a 5 to 10 membered heteroaromatic ring containing 1 to 3 heteroatoms selected from N, O and S;

wherein the 3 to 10 membered carbocyclic ring, 5 to 10 membered heterocyclic ring, 6 to 10 membered aromatic ring, or 5 to 10 membered heteroaromatic ring is optionally substituted with one to four $R^{45}$, wherein each $R^{45}$ is independently oxo, halo, cyano, $C_{1-6}$alkyl, $C_{3-6}$cycloalkyl or —$OR^e$;

$R^b$ is H, $C_{1-4}$alkyl, $C_{1-4}$haloalkyl or $C_{3-6}$cycloalkyl;

$R^f$ is H, halo, $C_{1-4}$alkyl, or $C_{1-4}$haloalkyl;

each $R^c$ is independently, H, $C_{1-4}$alkyl, $C_{1-4}$haloalkyl, $C_{3-6}$cycloalkyl, $C_{3-6}$halocycloalkyl; C(O)$R^d$, or —$SO_2R^d$;

each $R^d$ is independently $C_{1-4}$alkyl, $C_{1-4}$haloalkyl, $C_{3-6}$cycloalkyl, $C_{3-6}$halocycloalkyl, —$NR^e_2$, or —$OR^e$;

each $R^e$ is independently H, $C_{1-4}$alkyl or $C_{3-6}$cycloalkyl wherein each $C_{1-4}$alkyl or $C_{3-6}$cycloalkyl is optionally substituted by a halo or a cyano; and each n is 0, 1, or 2.

In another embodiment, the present disclosure provides a pharmaceutical composition comprising a therapeutically effective amount of a compound of the disclosure, or pharmaceutically acceptable salt thereof, and a pharmaceutically acceptable excipient.

In another embodiment, the disclosure provides a kit comprising a compound of the disclosure, or a pharmaceutically acceptable salt thereof, and instructions for use.

In another embodiment, the disclosure provides a method of treating an HIV infection in a human having or at risk of having the infection, wherein the method comprises administering to the human a therapeutically effective amount of a compound of the disclosure, or pharmaceutically acceptable salt thereof, or the pharmaceutical of the disclosure.

In another embodiment, the disclosure provides use of a compound of the disclosure, or pharmaceutically acceptable salt thereof, or a pharmaceutical composition of the disclosure, for treating an HIV infection in a human having or at risk of having the infection.

In another aspect, the disclosure provides a compound of the disclosure, or pharmaceutically acceptable salt thereof, or a pharmaceutical composition of the disclosure, for use in medical therapy.

In another embodiment, the disclosure provides use of a compound of the disclosure, or pharmaceutically acceptable salt thereof, or a pharmaceutical composition of the disclosure, for use in treating an HIV infection.

In another aspect, the disclosure provides use of a compound of the disclosure, or pharmaceutically acceptable salt thereof, or the pharmaceutical composition of the disclosure, in the manufacture of a medicament for treating an HIV infection in a human having or at risk of having the infection.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

I. Definitions

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.

"Hydroxy" or "hydroxyl" refers to the —OH radical.

"Oxo" refers to the =O substituent.

A prefix such as "C$_{u-v}$" or (C$_u$-C$_v$) indicates that the following group has from u to v carbon atoms. For example, "C$_{1-6}$alkyl" indicates that the alkyl group has from 1 to 6 carbon atoms.

"Alkyl" refers to a straight or branched chain hydrocarbon radical consisting of carbon and hydrogen atoms, which is saturated, having from one to twelve carbon atoms (C$_{1-12}$alkyl), in certain embodiments one to eight carbon atoms (C$_{1-8}$alkyl) or one to six carbon atoms (C$_{1-6}$alkyl), or one to four carbon atoms (C$_{1-4}$alkyl), and which is attached to the rest of the molecule by a single bond, e.g., methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl, hexyl, 3-methylhexyl, 2-methylhexyl, and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1 ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Aryl" or "aromatic ring" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include, but are not limited to, phenyl, naphthyl, fluorenyl, and anthryl. Aryl, however, does not encompass or overlap in any way with heteroaryl defined below.

"Cyano" or "carbonitrile" refers to the group —CN.

"Cycloalkyl" or "carbocyclic ring" refers to a saturated or partially saturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl. "Halocycloalkyl" refers to a cycloalkyl substituted with one or more halogens.

"Halo" or "halogen" refers to bromo, chloro, fluoro or iodo.

"Haloalkyl" refers to an alkyl group, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heteroaryl" or "heteroaromatic ring" refers to an aromatic group having a single ring, multiple rings, or multiple fused rings, with one or more ring heteroatoms independently selected from nitrogen, oxygen, and sulfur. As used herein, heteroaryl includes 5 to 20 ring atoms (5 to 20 membered heteroaromatic ring), 5 to 12 ring atoms (5 to 12 membered heteroaromatic ring), 5 to 10 ring atoms (5 to 10 membered heteroaromatic ring) or 5 to 6 ring atoms (5 to 6 membered heteroaromatic ring); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" refers to a non-aromatic radical or ring having from three to fifteen atoms wherein from one to six atoms are heteroatoms selected from the group consisting of nitrogen, oxygen and sulfur and attached to the rest of the molecule by a single bond. In certain embodiments, "heterocyclyl" has from three to ten atoms, wherein from one to four atoms are heteroatoms selected from the group consisting of nitrogen, oxygen and sulfur, or from three to seven atoms, wherein from one to two atoms are heteroatoms selected from the group consisting of nitrogen, oxygen and sulfur. The nitrogen, carbon or sulfur atoms in the heterocyclyl may be optionally oxidized; the nitrogen atom may be optionally quaternized. As used herein, "heterocyclyl" or "heterocyclic ring" refers to rings that are saturated unless otherwise indicated, e.g., in some embodiments "heterocyclyl" or "heterocyclic ring" refers to rings that are saturated or partially saturated where specified. Examples of such heterocyclyl include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

The embodiments disclosed herein are also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. In certain embodiments, these radiolabeled compounds are useful to help determine or measure the effectiveness of the compounds, by characterizing, for example, the site or mode of action, or binding affinity to pharmacologically important site of action. Certain isotopically-labeled compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

In certain embodiments, substitution with heavier isotopes such as deuterium, i.e., $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of Formula I, Ia, Ib, II, IIa, IIb, III, IIIa, IIIb, IV, IVa, IVb, V, Va, Vb, VI, VIa, VIb, VII, VIIa, VIb, VIII, VIIIa, or VIIIb can be prepared by techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., a compound of Formula I, Ia, Ib, II, IIa, IIb, III, IIIa, IIb, IV, IVa, IVb, V, Va, Vb, VI, VIa, VIb, VII, VIIa, VIIb, VIII, VIIIa, or VIIIb) or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Foster, "Deuterium Isotope Effects in Studies of Drug Metabolism", *Trends Pharmacol. Sci.*, 5(12):524-527 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or other pharmacologically inactive substance that is formulated in combination with a pharmacologically active ingredient of a pharmaceutical composition and is compatible with the other ingredients of the formulation and suitable for use in humans or domestic animals without undue toxicity, irritation, allergic response, and the like.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts of a nitrogen atom or an amino group include, for example, salts of organic carboxylic acids such as acetic, trifluoroacetic, adipic, ascorbic, aspartic, butyric, camphoric, cinnamic, citric, digluconic, glutamic, glycolic, glycerophosphoric, formic, hexanoic, benzoic, lactic, fumaric, tartaric, maleic, hydroxymaleic, malonic, malic, mandelic, isethionic, lactobionic, nicotinic, oxalic, pamoic, pectinic, phenylacetic, 3-phenylpropionic, pivalic, propionic, pyruvic, salicylic, stearic, sulfanilic, tartaric, undecanoic, and succinic acids; organic sulfonic acids, such as methanesulfonic, ethanesulfonic, camphorsulfonic, mesitylenesulfonic, benzenesulfonic, p-toluenesulfonic acids, naphthalenesulfonic, and 2-naphthalenesulfonic; and inorganic acids, such as hydrochloric, hydrobromic, sulfuric, phosphoric, nitric, and sulfamic acids. Pharmaceutically acceptable salts of a compound of a hydroxy group include the anion of said compound in combination with a suitable cation such as $Na^+$ and $NX_4^+$ (wherein X is independently selected from H or a $C_{1-4}$alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of Formula I or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Effective amount" or "therapeutically effective amount" refers to an amount of a compound according to the embodiments disclosed herein, which when administered to a patient in need thereof, is sufficient to effect treatment of disease-states, conditions, or disorders disclosed herein. Such an amount would be sufficient to elicit the biological or medical response of a tissue system, or patient that is sought by a researcher or clinician. The amount of a compound according to the embodiments disclosed herein which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination, or coincidentally, with the compounds of the embodiments disclosed herein, and the age, body weight, general health, sex and diet of the patient. Such a therapeutically effective amount can be determined by one of ordinary skill in the art having regard to their own knowledge, the state of the art, and this disclosure.

The terms "treating" and "treatment" as used herein are intended to mean the administration of a compound or composition according to the present embodiments disclosed herein to alleviate or eliminate one or more symptoms of HIV infection and/or to reduce viral load in a patient. In certain embodiments, the terms "treating" and "treatment" also encompass the administration of a compound or composition according to the present embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed herein to prevent perinatal transmission of HIV from mother to baby, by administration to the mother before giving birth and to the child within the first days of life. The terms "treating" and "treatment" also encompass the administration of a compound or composition according to the present embodiments disclosed herein before the exposure of the individual to the virus (also called pre-exposure prophylaxis or PrEP), to prevent HIV infection from taking hold if the individual is exposed to the virus and/or to keep the virus from establishing a permanent infection and/or to prevent the appearance of symptoms of the disease and/or to prevent the virus from reaching detectable levels in the blood. The terms "treating" and "treatment" also encompass the administration of a compound or composition according to the present embodiments disclosed herein both before and after the exposure of the individual to the virus.

As used herein, the terms "preventing" and "prevention" refer to the administration of a compound, composition, or pharmaceutically salt according to the present disclosure pre- or post-exposure of the human to the virus but before the appearance of symptoms of the disease, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby, by administration to the mother before giving birth and to the child within the first days of life. The terms also refer to prevention of transmission of HIV through blood transfusion.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. In any of the embodiments disclosed herein, compounds disclosed herein may be in the form of a stereoisomer thereof.

"Partially unsaturated" refers to a cyclic group which contains at least one double bond but is not aromatic.

II. Compounds

Disclosed herein are compounds of Formula I:

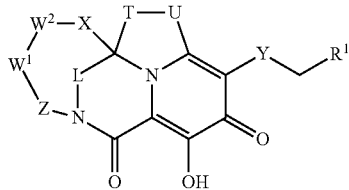

Formula I or a pharmaceutically acceptable salt thereof, wherein
$R^1$ is a H, $C_{6-10}$aryl or $C_{6-10}$heteroaryl, wherein the $C_{6-10}$aryl or $C_{6-10}$heteroaryl is optionally substituted with one to four $R^{41}$, wherein each $R^{41}$ is independently halo, $C_{1-4}$alkyl, $C_{1-4}$haloalkyl, $C_{3-6}$cycloalkyl, cyano, —O—$C_{1-4}$alkyl, or $C_{1-4}$alkyl-O—$C_{1-4}$alkyl;
Y is selected from the group consisting of —C(O)NH—,

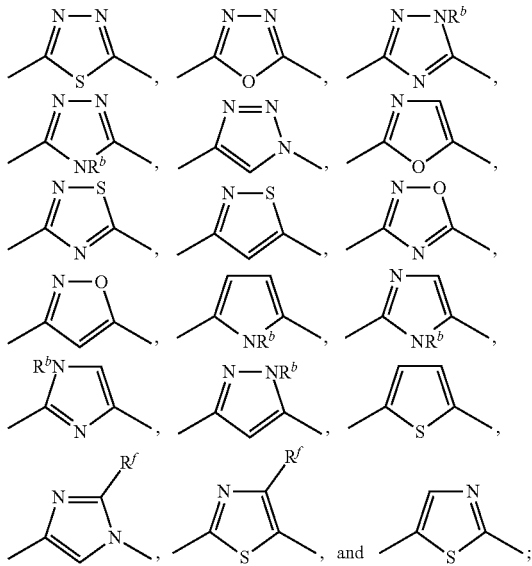

L is —$CR^{3a}R^{3b}$—, —C(O)—, —$SO_2$—, —$CR^{3a}R^{3b}$—$CR^{3c}R^{3d}$—, or —$N(R^a)$—;
$W^1$ is a bond or —$CR^{4a}R^{4b}$—;
$W^2$ is —$CR^{5a}R^{5b}$—, —$CR^{5a}R^{5b}CR^{5c}R^{5d}$—, —$CR^{6a}$=$CR^{6b}$—, —$N(R^7)$—, —O—, —$S(O)_n$—, —$C(O)NR^e$—, —$CR^{5a}R^{5b}$—$N(R^7)$—, —$CR^{5a}R^{5b}$—O—, —$CR^{5a}R^{5b}$—$S(O)_n$—, —$CR^{5a}R^{5b}$—C(O)$NR^e$—, or —$CR^{5a}R^{5b}$—$NR^e$—C(O)—; —$S(O)_nN(R^e)$—$CR^{5a}R^{5b}$—, —$N(R^e)$—$S(O)_n$—$CR^{5a}R^{5b}$—, —$N(R^e)$—C(O)—$CR^{5a}R^{5b}$— or —$CR^{5a}R^{5b}$—$NR^e$—C(O)—;
X is a bond or —$CR^{8a}R^{8b}$—;
Z is —$CR^{9a}R^{9b}$—, —$CR^{9a}R^{9b}CR^{9c}R^{9d}$—, or —$CR^{10a}$=$CR^{10b}$—;
T is —$CR^{2a}R^{2b}$— or —$CR^{2a}R^{2b}$—$CR^{2c}R^{2d}$— and U is —$NR^{11}$—, —$CR^{12a}R^{12b}$—, —$S(O)_n$—, —C(O)—, or —O—; or T and U together are

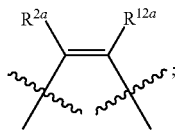

$R^{2a}$, $R^{2b}$, $R^{2c}$, $R^{2d}$, $R^{12a}$, and $R^{12b}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —C(O)—$NHR^a$, —$NHR^a$—, —C(O)—$NH(R^a)$—, —$NR^e$—C(O)$R^a$—, —$NR^e$—$S(O)_nR^a$—, —$S(O)_n$—$NH(R^a)$—, or —$S(O)_n$—$R^a$—; or
any one of (i) $R^{2a}$ and $R^{2b}$, (ii) $R^{2c}$ and $R^{2d}$ or (iii) $R^{12a}$ and $R^{12b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{42}$, wherein each $R^{42}$ is independently oxo, halo, cyano, $C_{1-6}$alkyl, $C_{3-6}$cycloalkyl or —$OR^e$;
$R^{3a}$ and $R^{3b}$ are independently H, $C_{1-6}$-alkyl, $C_{1-4}$haloalkyl, or —O—$C_{1-4}$alkyl; or
any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{42}$, wherein each $R^{42}$ is independently oxo, halo, cyano, $C_{1-6}$alkyl, $C_{3-6}$cycloalkyl or —$OR^e$;
$R^{4a}$, $R^{4b}$, $R^{5a}$, $R^{5b}$, $R^{5c}$, $R^{5d}$, $R^{8a}$, $R^{8b}$, $R^{9a}$, $R^{9b}$, $R^{9c}$, and $R^{9d}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; or
any one of (i) $R^{4a}$ and $R^{4b}$, (ii) $R^{5a}$ and $R^{5b}$, (iii) $R^{5c}$ and $R^{5d}$, (iv) $R^{5a}$ and $R^{5c}$, (v) $R^{5b}$ and $R^{5d}$, (vi) $R^{8a}$ and $R^{8b}$, (vii) $R^{9a}$ and $R^{9b}$, (viii) $R^{9c}$ and $R^{9d}$, (ix) $R^{9a}$ and $R^{9c}$, (x) $R^{9b}$ and $R^{9d}$, (xi) $R^{8b}$ and one of $R^{5a}$, $R^{5b}$, $R^{5c}$, $R^{5d}$, and $R^7$, or (xii) one of $R^{9a}$, $R^{9b}$, $R^{9c}$, and $R^{9d}$ and one of $R^{4a}$, $R^{4b}$, $R^{5a}$, $R^{5b}$, and $R^7$ together with the carbon atom to which they are attached form (i) a 3 to 7 membered carbocyclic ring or (ii) a 4 to 7 membered heterocyclic ring containing 0 to 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$;
each $R^{6a}$, $R^{6b}$, $R^{10a}$, and $R^{10b}$ is independently H, halo, $C_{1-4}$haloalkyl, or $C_{1-6}$alkyl; or
any one of (i) $R^{6a}$ and $R^{6b}$ or (ii) $R^{10a}$ and $R^{10b}$ together with the carbon atoms to which each is attached form (i) a 5 to 10 membered carbocyclic ring, (ii) 5 to 10 membered heterocyclic ring containing 1 or 2 heteroatom selected from N, O, and S, (iii) a 6 to 10 membered aromatic ring, or (iv) a 5 to 10 membered heteroaromatic ring containing 1 to 3 heteroatoms selected from N, O and S, wherein the 5 to 10 membered carbocyclic ring, 5 to 10 membered heterocyclic ring, the 6 to 10 membered aromatic ring, or the 5 to 10 membered heteroaromatic ring is optionally substituted with one to four $R^{44}$, wherein each $R^{44}$ is independently oxo, halo, cyano, $C_{1-6}$alkyl, $C_{3-6}$cycloalkyl or —$OR^e$;

$R^7$ is H, $C_{1-6}$alkyl, $C_{1-4}$haloalkyl, $C_{3-6}$cycloalkyl, $C_{3-6}$halocycloalkyl, $C(O)R^c$, or $SO_2R^c$;

$R^{11}$ is H, $C_{1-4}$alkyl, $C_{1-4}$haloalkyl, $C_{3-6}$cycloalkyl, $C_{3-6}$halocycloalkyl, —C(O)—$R^a$, —S(O)$_n$—$R^a$, —CH$_2$—$R^a$;

each $R^a$ is independently (i) H, (ii) $C_{1-6}$alkyl, (iii) $C_{3-6}$cycloalkyl, (iv) a 5 to 10 membered carbocyclic ring, (v) 5 to 10 membered heterocyclic ring containing 1 or 2 heteroatom selected from N, O, and S, (vi) a 6 to 10 membered aromatic ring, or (iv) a 5 to 10 membered heteroaromatic ring containing 1 to 3 heteroatoms selected from N, O and S; wherein the $C_{1-6}$alkyl, $C_{3-6}$cycloalkyl, 5 to 10 membered carbocyclic ring, 5 to 10 membered heterocyclic ring, 6 to 10 membered aromatic ring or the 5 to 10 membered heteroaromatic ring is optionally substituted with 0 to 4 substituents independently selected from the group consisting of (i) oxo (ii) halo, (iii) cyano, (iv) —O—$C_{1-4}$alkyl, (v) $C_{1-6}$alkyl, (vi) —$OR^e$ (vii) 3 to 10 membered carbocyclic ring, (viii) 5 to 10 membered heterocyclic ring containing 1 or 2 heteroatom selected from N, O, and S, (ix) 6 to 10 membered aromatic ring, or (x) a 5 to 10 membered heteroaromatic ring containing 1 to 3 heteroatoms selected from N, O and S; wherein the 3 to 10 membered carbocyclic ring, 5 to 10 membered heterocyclic ring, 6 to 10 membered aromatic ring, or 5 to 10 membered heteroaromatic ring is optionally substituted with one to four $R^{45}$, wherein each $R^{45}$ is independently oxo, halo, cyano, $C_{1-6}$alkyl, $C_{3-6}$cycloalkyl or —$OR^e$;

$R^b$ is H, $C_{1-4}$alkyl, $C_{1-4}$haloalkyl or $C_{3-6}$cycloalkyl;

$R^f$ is H, halo, $C_{1-4}$alkyl, or $C_{1-4}$haloalkyl;

each $R^c$ is independently, H, $C_{1-4}$alkyl, $C_{1-4}$haloalkyl, $C_{3-6}$cycloalkyl, $C_{3-6}$halocycloalkyl, $C(O)R^d$, or —$SO_2R^d$;

each $R^d$ is independently $C_{1-4}$alkyl, $C_{1-4}$haloalkyl, $C_{3-6}$cycloalkyl, $C_{3-6}$halocycloalkyl, —$NR^e_2$, or —$OR^e$;

each $R^e$ is independently H, $C_{1-4}$alkyl or $C_{3-6}$cycloalkyl wherein each $C_{1-4}$alkyl or $C_{3-6}$cycloalkyl is optionally substituted by a halo or a cyano; and each n is 0, 1, or 2.

In some embodiments, of the compounds of Formula I, $R^1$ is H, $C_{6-10}$aryl or $C_{6-10}$heteroaryl, wherein the $C_{6-10}$aryl or $C_{6-10}$heteroaryl are optionally substituted with one to four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl, or $C_{1-4}$alkyl-O—$C_{1-4}$alkyl;

Y is selected from the group consisting of —C(O)NH—,

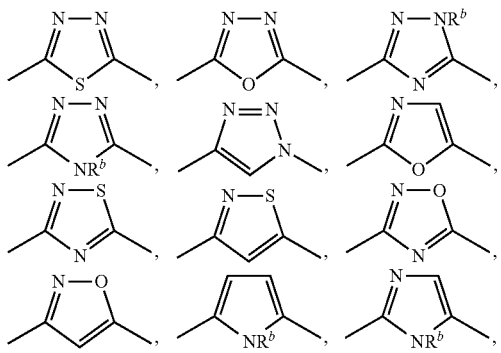

-continued

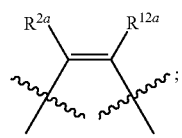

L is —$CR^{3a}R^{3b}$—, —C(O)—, —$SO_2$—, —$CR^{3a}R^{3b}$—$CR^{3c}R^{3d}$—, or —$N(R^a)$—;

$W^1$ is a bond or —$CR^{4a}R^{4b}$—;

$W^2$ is —$CR^{5a}R^{5b}$—, —$CR^{5a}R^{5b}CR^{5c}R^{5d}$—, —$CR^{6a}$=$CR^{6b}$—, —$N(R^7)$—, —O—, —$S(O)_n$—, —$C(O)NR^e$—, —$CR^{5a}R^{5b}$—$N(R^7)$—, —$CR^{5a}R^{5b}$—O—, —$CR^{5a}R^{5b}$—$S(O)_n$—, —$CR^{5a}R^{5b}$—$C(O)NR^e$—, —$CR^{5a}R^{5b}$—$NR^e$—C(O)—, —$S(O)_nN(R^e)$—$CR^{5a}R^{5b}$—, or —$N(R^e)$—$S(O)_n$—$CR^{5a}R^{5b}$—;

X is a bond or —$CR^{8a}R^{8b}$—;

Z is —$CR^{9a}R^{9b}$—, —$CR^{9a}R^{9b}CR^{9c}R^{9d}$—, or —$CR^{10a}$=$CR^{10b}$—;

T is —$CR^{2a}R^{2b}$— or —$CR^{2a}R^{2b}$—$CR^{2c}R^{2d}$; U is —$NR^{11}$—, —$CR^{12a}R^{12b}$—, —$S(O)_n$—, —C(O)—, or —O—; or T and U together are

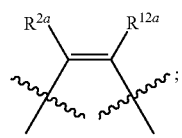

$R^{2a}$, $R^{2b}$, $R^{2c}$, $R^{2d}$, $R^{12a}$, and $R^{12b}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$, —$CH_2OR^a$, —$CH_2$—$S(O)_nR^a$—, —$OR^a$, —O—C(O)—$NHR^a$, —$NHR^a$, —C(O)—$NH(R^a)$—, —$NR^e$—$C(O)R^a$—, —$NR^e$—$S(O)_nR^a$—, —$S(O)_n$—$NH(R^a)$—, or —$S(O)_n$—$R^a$—; or any one of (i) $R^{2a}$ and $R^{2b}$, (ii) $R^{2c}$ and $R^{2d}$ or (iii) $R^{12a}$ and $R^{12b}$ together with the carbon atom to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{42}$, wherein each $R^{42}$ is independently oxo, halo, cyano, $C_{1-6}$alkyl, $C_{3-6}$cycloalkyl or —$OR^e$;

$R^{3a}$, $R^{3b}$, $R^{3c}$, and $R^{3d}$ are independently H, $C_{1-6}$-alkyl, $C_{1-4}$haloalkyl, or —O—$C_{1-4}$alkyl;

$R^{4a}$, $R^{4b}$, $R^{5a}$, $R^{5b}$, $R^{5c}$, $R^{5d}$, $R^{8a}$, $R^{8b}$, $R^{9a}$, $R^{9b}$, $R^{9c}$, and $R^{9d}$ are independently H, $C_{1-6}$-alkyl, $C_{1-4}$haloalkyl, $C_{3-6}$cycloalkyl, $C_{3-6}$halocycloalkyl, halo, hydroxyl, cyano, —O—$C_{1-4}$alkyl, or $C_{1-4}$alkylene-O—$C_{1-4}$alkyl;

each $R^{6a}$, $R^{6b}$, $R^{10a}$, and $R^{10b}$ is independently H, halo, $C_{1-4}$haloalkyl, or $C_{1-6}$alkyl;

$R^7$ is H, $C_{1-6}$-alkyl, $C_{1-4}$haloalkyl, $C_{3-6}$cycloalkyl, $C_{3-6}$halocycloalkyl, $C(O)R^c$, or $SO_2R^c$;

$R^{11}$ is H, $C_{1-6}$alkyl, $C_{1-4}$haloalkyl, $C_{3-6}$cycloalkyl, $C_{3-6}$halocycloalkyl, —C(O)—$R^a$, —S(O)$_n$—$R^a$, —$CH_2$—$R^a$;

each $R^a$ is independently (i) H, (ii) $C_{1-6}$alkyl, (iii) $C_{3-6}$cycloalkyl, (iv) a 5 to 10 membered carbocyclic ring, (v) 5 to 10 membered heterocyclic ring containing 1 or 2 heteroatom selected from N, O, and S, (vi) a 6 to 10 membered aromatic ring, or (iv) a 5 to 10 membered heteroaromatic ring containing 1 to 3 heteroatoms selected from N, O and S;
wherein the $C_{1-6}$alkyl, $C_{3-6}$cycloalkyl, 5 to 10 membered carbocyclic ring, 5 to 10 membered heterocyclic ring, 6 to 10 membered aromatic ring or 5 to 10 membered heteroaromatic ring is optionally substituted with 0 to 4 substituents independently selected from the group consisting of (i) oxo (ii) halo, (iii) cyano, (iv) —O—$C_{1-4}$alkyl, (v) $C_{1-6}$alkyl, (vi) —$OR^e$ (vii) 3 to 10 membered carbocyclic ring, (viii) 5 to 10 membered heterocyclic ring containing 1 or 2 heteroatom selected from N, O, and S, (ix) 6 to 10 membered aromatic ring, or (x) a 5 to 10 membered heteroaromatic ring containing 1 to 3 heteroatoms selected from N, O and S; wherein the 3 to 10 membered carbocyclic ring, 5 to 10 membered heterocyclic ring, 6 to 10 membered aromatic ring, or 5 to 10 membered heteroaromatic ring is optionally substituted with one to four $R^{45}$, wherein each $R^{45}$ is independently oxo, halo, cyano, $C_{1-6}$alkyl, $C_{3-6}$cycloalkyl or —$OR^e$;

$R^b$ is H, $C_{1-6}$alkyl, $C_{1-4}$haloalkyl or $C_{3-6}$cycloalkyl;
$R^f$ is H, halo, $C_{1-4}$alkyl, or $C_{1-4}$haloalkyl;
each $R^c$ is independently, H, $C_{1-6}$alkyl, $C_{1-4}$haloalkyl, $C_{3-6}$cycloalkyl, $C_{3-6}$halocycloalkyl; C(O)$R^d$, or —SO$_2R^d$;
each $R^d$ is independently $C_{1-4}$alkyl, $C_{1-4}$haloalkyl, $C_{3-6}$cycloalkyl, $C_{3-6}$halocycloalkyl, —$NR^e_2$, or —$OR^e$;
each $R^e$ is independently H, $C_{1-6}$alkyl or $C_{3-6}$cycloalkyl wherein each $C_{1-4}$alkyl or $C_{3-6}$cycloalkyl is optionally substituted by a halo or a cyano; and
each n is 0, 1, or 2.

In some embodiments, of the compounds of Formula I:
$R^1$ is H, $C_{6-10}$aryl or $C_{6-10}$heteroaryl, wherein the $C_{6-10}$aryl or $C_{6-10}$heteroaryl are optionally substituted with one to four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl, or $C_{1-4}$alkyl-O—$C_{1-4}$alkyl;
Y is selected from the group consisting of —C(O)NH—,

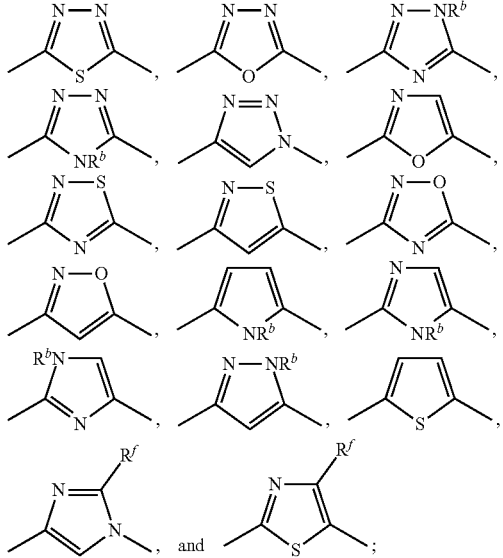

L is —$CR^{3a}R^{3b}$—, —C(O)—, —SO$_2$—, —$CR^{3a}R^{3b}$—$CR^{3c}R^{3d}$—, or —N($R^a$)—;

$W^1$ is a bond or —$CR^{4a}R^{4b}$—;
$W^2$ is —$CR^{5a}R^{5b}$—, —$CR^{5a}R^{5b}CR^{5c}R^{5d}$—, —$CR^{6a}$=$CR^{6b}$—, —N($R^7$)—, —O—, —S(O)$_n$—, —C(O)N$R^e$—, —$CR^{5a}R^{5b}$—N($R^7$)—, —$CR^{5a}R^{5b}$—O—, —$CR^{5a}R^{5b}$—S(O)$_n$—, —$CR^{5a}R^{5b}$—C(O)N$R^e$—, —$CR^{5a}R^{5b}$—N$R^e$—C(O)—, —S(O)$_n$N($R^e$)—$CR^{5a}R^{5b}$—, or —N($R^e$)—S(O)$_n$—$CR^{5a}R^{5b}$—;
X is a bond or —$CR^{8a}R^{8b}$—;
Z is —$CR^{9a}R^{9b}$—, —$CR^{9a}R^{9b}CR^{9c}R^{9d}$—, or —$CR^{10a}$=$CR^{10b}$—;
T is —$CR^{2a}R^{2b}$— or —$CR^{2a}R^{2b}$—$CR^{2c}R^{2d}$; U is —$NR^{11}$—, —$CR^{12a}R^{12b}$—, —S(O)$_n$—, —C(O)—, or —O—; or T and U together are

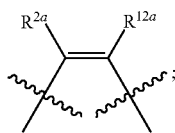

$R^{2a}$, $R^{2b}$, $R^{2c}$, $R^{2d}$, $R^{12a}$, and $R^{12b}$ are independently H, $C_{1-6}$alkyl, $C_{1-6}$haloalkyl, $C_{3-6}$cycloalkyl, $C_{3-6}$halocycloalkyl, halo, cyano, —CH$_2R^a$—, —CH$_2OR^a$, —CH$_2$—S(O)$_nR^a$—, —$OR^a$, —C(O)—NH$R^a$, —NH$R^a$—, —C(O)—NH($R^a$)—, —$NR^e$—C(O)$R^a$—, —$NR^e$—S(O)$_nR^a$—, —S(O)$_n$—NH($R^e$)—, or —S(O)$_n$—$R^a$;
$R^{3a}$, $R^{3b}$, $R^{3c}$, and $R^{3d}$ are independently H, $C_{1-6}$-alkyl, $C_{1-4}$haloalkyl, or —O—$C_{1-4}$alkyl; or
any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{42}$, wherein each $R^{42}$ is independently oxo, halo, cyano, $C_{1-6}$alkyl, $C_{3-6}$cycloalkyl or —$OR^e$;
$R^{4a}$, $R^{4b}$, $R^{5a}$, $R^{5b}$, $R^{5c}$, $R^{5d}$, $R^{8a}$, $R^{8b}$, $R^{9a}$, $R^{9b}$, $R^{9c}$, and $R^{9d}$ are independently H, $C_{1-6}$alkyl, $C_{1-4}$haloalkyl, $C_{3-6}$cycloalkyl, $C_{3-6}$halocycloalkyl, halo, hydroxyl, cyano, —O—$C_{1-4}$alkyl, or $C_{1-4}$alkylene-O—$C_{1-4}$alkyl;
each $R^{6a}$, $R^{6b}$, $R^{10a}$, and $R^{10b}$ is independently H, halo, $C_{1-4}$haloalkyl, or $C_{1-6}$alkyl;
$R^7$ is H, $C_{1-6}$-alkyl, $C_{1-4}$haloalkyl, $C_{3-6}$cycloalkyl, $C_{3-6}$halocycloalkyl, C(O)$R^c$, or SO$_2R^c$;
$R^{11}$ is H, $C_{1-6}$alkyl, $C_{1-4}$haloalkyl, $C_{3-6}$cycloalkyl, $C_{3-6}$halocycloalkyl, —C(O)—$R^a$, —S(O)$_n$—$R^a$, —CH$_2$—$R^a$;
each $R^a$ is independently (i) H, (ii) $C_{1-6}$alkyl, (iii) $C_{3-6}$cycloalkyl, (iv) a 5 to 10 membered carbocyclic ring, (v) 5 to 10 membered heterocyclic ring containing 1 or 2 heteroatom selected from N, O, and S, (vi) a 6 to 10 membered aromatic ring, or (iv) a 5 to 10 membered heteroaromatic ring containing 1 to 3 heteroatoms selected from N, O and S;
wherein the $C_{1-6}$alkyl, $C_{3-6}$cycloalkyl, 5 to 10 membered carbocyclic ring, 5 to 10 membered heterocyclic ring, 6 to 10 membered aromatic ring or 5 to 10 membered heteroaromatic ring is optionally substituted with 0 to 4 substituents independently selected from the group consisting of (i) oxo (ii) halo, (iii) cyano, (iv) —O—$C_{1-4}$alkyl, (v) $C_{1-6}$alkyl, (vi) —$OR^e$ (vii) 3 to 10 membered carbocyclic ring, (viii) 5 to 10 membered heterocyclic ring containing 1 or 2 heteroatom selected from N, O, and S, (ix) 6 to 10 membered aromatic ring, or (x) a 5 to 10 membered heteroaromatic ring containing 1 to 3 heteroatoms selected from N, O and S; wherein the 3 to 10 membered carbocyclic ring, 5 to 10 membered heterocyclic ring, 6 to 10 membered aromatic ring, or 5 to 10 membered heteroaromatic ring is optionally substituted with one to four $R^{45}$, wherein each $R^{45}$ is independently oxo, halo, cyano, $C_{1-6}$alkyl, $C_{3-6}$cycloalkyl or —$OR^e$;

$R^b$ is H, $C_{1-6}$alkyl, $C_{1-4}$haloalkyl or $C_{3-6}$cycloalkyl;
$R^f$ is H, halo, $C_{1-6}$alkyl, or $C_{1-4}$haloalkyl;
each $R^c$ is independently, H, $C_{1-6}$alkyl, $C_{1-4}$haloalkyl, $C_{3-6}$cycloalkyl, $C_{3-6}$halocycloalkyl; $C(O)R^d$, or —$SO_2R^d$;
each $R^d$ is independently $C_{1-4}$alkyl, $C_{1-4}$haloalkyl, $C_{3-6}$cycloalkyl, $C_{3-6}$halocycloalkyl, —$NR^e_2$, or —$OR^e$;
each $R^e$ is independently H, $C_{1-6}$alkyl or $C_{3-6}$cycloalkyl wherein each $C_{1-4}$alkyl or $C_{3-6}$cycloalkyl is optionally substituted by a halo or a cyano; and
each n is 0, 1, or 2.

In some embodiments, of the compounds of Formula I:
$R^1$ is H, $C_{6-10}$aryl or $C_{6-10}$heteroaryl, wherein the $C_{6-10}$aryl or $C_{6-10}$heteroaryl are optionally substituted with one to four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl, or $C_{1-4}$alkyl-O—$C_{1-4}$alkyl;
Y is selected from the group consisting of —C(O)NH—,

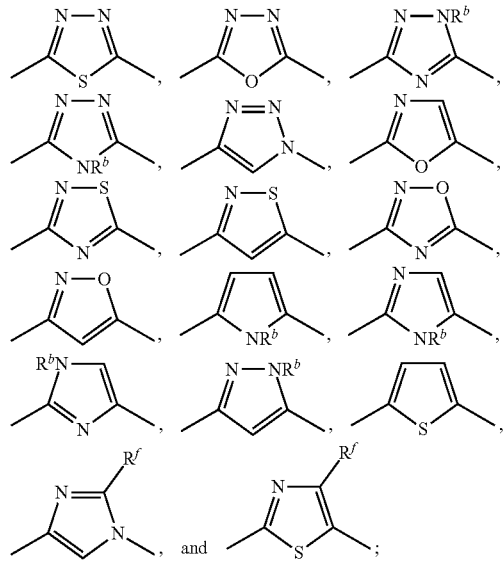

L is —$CR^{3a}R^{3b}$—, —C(O)—, —$SO_2$—, —$CR^{3a}R^{3b}$—$CR^{3c}R^{3d}$—, or —$N(R^a)$—;
$W^1$ is a bond or —$CR^{4a}R^{4b}$—;
$W^2$ is —$CR^{5a}R^{5b}$—, —$CR^{5a}R^{5b}CR^{5c}R^{5d}$—, —$CR^{6a}$=$CR^{6b}$—, —$N(R^7)$—, —O—, —$S(O)_n$—, —$C(O)NR^e$—, —$CR^{5a}R^{5b}$—$N(R^7)$—, —$CR^{5a}R^{5b}$—O—, —$CR^{5a}R^{5b}$—$S(O)_n$—, —$CR^{5a}R^{5b}$—$C(O)NR^e$—, —$CR^{5a}R^{5b}$—$NR^e$—$C(O)$—, —$S(O)_nN(R^e)$—$CR^{5a}R^{5b}$—, or —$N(R^e)$—$S(O)_n$—$CR^{5a}R^{5b}$—;
X is a bond or —$CR^{8a}R^{8b}$—;
Z is —$CR^{9a}R^{9b}$—, —$CR^{9a}R^{9b}CR^{9c}R^{9d}$—, or —$CR^{10a}$=$CR^{10b}$—;
T is —$CR^{2a}R^{2b}$— or —$CR^{2a}R^{2b}$—$CR^{2c}R^{2d}$—; U is —$NR^{11}$—, —$CR^{12a}R^{12b}$—, —$S(O)_n$—, —C(O)—, or —O—; or T and U together are

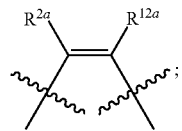

$R^{2a}$, $R^{2b}$, $R^{2c}$, $R^{2d}$, $R^{12a}$, and $R^{12b}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$, —$CH_2OR^a$, —$CH_2$—$S(O)_nR^a$—, —$OR^a$, —C(O)—$NHR^a$, —$NHR^a$—, —C(O)—$NH(R^a)$—, —$NR^e$—$C(O)R^a$—, —$NR^e$—$S(O)_nR^a$—, —$S(O)_n$—$NH(R^a)$—, or —$S(O)_n$—$R^a$—; or
$R^{3a}$, $R^{3b}$, $R^{3c}$, and $R^{3d}$ are independently H, $C_{1-6}$-alkyl, $C_{1-4}$haloalkyl, or —O—$C_{1-4}$alkyl; or
$R^{4a}$, $R^{4b}$, $R^{5a}$, $R^{5b}$, $R^{5c}$, $R^{5d}$, $R^{8a}$, $R^{8b}$, $R^{9a}$, $R^{9b}$, $R^{9c}$, and $R^{9d}$ are independently H, $C_{1-6}$-alkyl, $C_{1-4}$haloalkyl, $C_{3-6}$cycloalkyl, $C_{3-6}$halocycloalkyl, halo, hydroxyl, cyano, —O—$C_{1-4}$alkyl, or $C_{1-4}$alkylene-O—$C_{1-4}$alkyl; or any one of (i) $R^{4a}$ and $R^{4b}$, (ii) $R^{5a}$ and $R^{5b}$, (iii) $R^{5c}$ and $R^{5d}$, (iv) $R^{5a}$ and $R^{5c}$, (v) $R^{5b}$ and $R^{5d}$, (vi) $R^{8a}$ and $R^{8b}$, (vii) $R^{9a}$ and $R^{9b}$, (viii) $R^{9c}$ and $R^{9d}$, (ix) $R^{9a}$ and $R^{9c}$, (x) $R^{9b}$ and $R^{9d}$, (xi) $R^{8b}$ and one of $R^{5a}$, $R^{5b}$, $R^{5c}$, $R^{5d}$, and $R^7$, or (x) one of $R^{9a}$, $R^{9b}$, $R^{9c}$, and $R^{9d}$ and one of $R^{4a}$, $R^{4b}$, $R^{5a}$, $R^{5b}$, and $R^7$ together with the carbon atom to which they are attached form a (i) 3 to 7 membered carbocyclic ring or (ii) 4 to 7 membered heterocyclic ring containing 1 to 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$;
each $R^{6a}$, $R^{6b}$, $R^{10a}$, and $R^{10b}$ is independently H, halo, $C_{1-4}$haloalkyl, or $C_{1-6}$alkyl;
$R^7$ is H, $C_{1-6}$-alkyl, $C_{1-4}$haloalkyl, $C_{3-6}$cycloalkyl, $C_{3-6}$halocycloalkyl, $C(O)R^c$, or $SO_2R^c$;
$R^{11}$ is H, $C_{1-6}$alkyl, $C_{1-4}$haloalkyl, $C_{3-6}$cycloalkyl, $C_{3-6}$halocycloalkyl, —C(O)—$R^a$, —$S(O)_n$—$R^a$, —$CH_2$—$R^a$;
each $R^a$ is independently (i) H, (ii) $C_{1-6}$alkyl, (iii) $C_{3-6}$cycloalkyl, (iv) a 5 to 10 membered carbocyclic ring, (v) 5 to 10 membered heterocyclic ring containing 1 or 2 heteroatom selected from N, O, and S, (vi) a 6 to 10 membered aromatic ring, or (iv) a 5 to 10 membered heteroaromatic ring containing 1 to 3 heteroatoms selected from N, O and S;
wherein the $C_{1-6}$alkyl, $C_{3-6}$cycloalkyl, 5 to 10 membered carbocyclic ring, 5 to 10 membered heterocyclic ring, 6 to 10 membered aromatic ring or 5 to 10 membered heteroaromatic ring is optionally substituted with 0 to 4 substituents independently selected from the group consisting of (i) oxo (ii) halo, (iii) cyano, (iv) —O—$C_{1-4}$alkyl, (v) $C_{1-6}$alkyl, (vi) —$OR^e$ (vii) 3 to 10 membered carbocyclic ring, (viii) 5 to 10 membered heterocyclic ring containing 1 or 2 heteroatom selected from N, O, and S, (ix) 6 to 10 membered aromatic ring, or (x) a 5 to 10 membered heteroaromatic ring containing 1 to 3 heteroatoms selected from N, O and S; wherein the 3 to 10 membered carbocyclic ring, 5 to 10 membered heterocyclic ring, 6 to 10 membered aromatic ring, or 5 to 10 membered heteroaromatic ring is optionally substituted with one to four $R^{45}$, wherein each $R^{45}$ is independently oxo, halo, cyano, $C_{1-6}$alkyl, $C_{3-6}$cycloalkyl or —$OR^e$;

$R^b$ is H, $C_{1-6}$alkyl, $C_{1-4}$haloalkyl or $C_{3-6}$cycloalkyl;
$R^f$ is H, halo, $C_{1-4}$alkyl, or $C_{1-4}$haloalkyl;
each $R^c$ is independently, H, $C_{1-6}$alkyl, $C_{1-4}$haloalkyl, $C_{3-6}$cycloalkyl, $C_{3-6}$halocycloalkyl; C(O)$R^d$, or —SO$_2$$R^d$;
each $R^d$ is independently $C_{1-4}$alkyl, $C_{1-4}$haloalkyl, $C_{3-6}$cycloalkyl, $C_{3-6}$halocycloalkyl, —NR$^e_2$, or —OR$^e$;
each $R^e$ is independently H, $C_{1-6}$alkyl or $C_{3-6}$cycloalkyl wherein each $C_{1-4}$alkyl or $C_{3-6}$cycloalkyl is optionally substituted by a halo or a cyano; and
each n is 0, 1, or 2.

In some embodiments, of the compounds of Formula I:
$R^1$ is H, $C_{6-10}$aryl or $C_{6-10}$heteroaryl, wherein the $C_{6-10}$aryl or $C_{6-10}$heteroaryl are optionally substituted with one to four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl, or $C_{1-4}$alkyl-O—$C_{1-4}$alkyl;
Y is selected from the group consisting of —C(O)NH—,

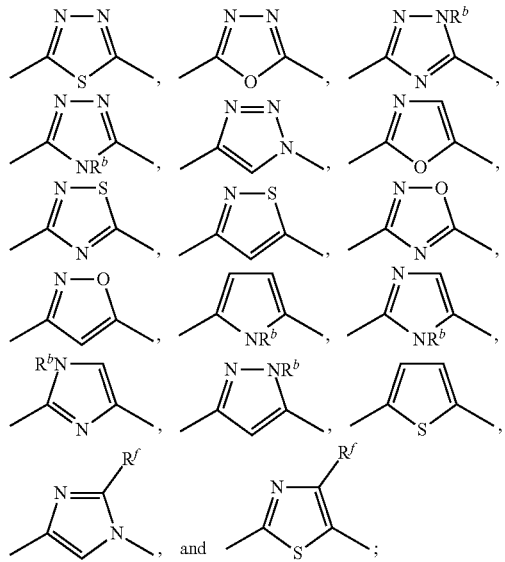

L is —CR$^{3a}$R$^{3b}$—, —C(O)—, —SO$_2$—, —CR$^{3a}$R$^{3b}$—CR$^{3c}$R$^{3d}$—, or —N(R$^a$)—;
W$^1$ is a bond or —CR$^{4a}$R$^{4b}$—;
W$^2$ is —CR$^{5a}$R$^{5b}$—, —CR$^{5a}$R$^{5b}$CR$^{5c}$R$^{5d}$—, —CR$^{6a}$=CR$^{6b}$—, —N(R$^7$)—, —O—, —S(O)$_n$—, —C(O)NR$^e$—, —CR$^{5a}$R$^{5b}$—N(R$^7$)—, —CR$^{5a}$R$^{5b}$—O—, —CR$^{5a}$R$^{5b}$—S(O)$_n$—, —CR$^{5a}$R$^{5b}$—C(O)NR$^e$—, —CR$^{5a}$R$^{5b}$—NR$^e$—C(O)—, —S(O)$_n$N(R$^e$)—CR$^{5a}$R$^{5b}$—, or —N(R$^e$)—S(O)$_n$—CR$^{5a}$R$^{5b}$—;
X is a bond or —CR$^{8a}$R$^{8b}$—;
Z is —CR$^{9a}$R$^{9b}$—, —CR$^{9a}$R$^{9b}$CR$^{9c}$R$^{9d}$—, or —CR$^{10a}$=CR$^{10b}$—;
T is —CR$^{2a}$R$^{2b}$— or —CR$^{2a}$R$^{2b}$—CR$^{2c}$R$^{2d}$—; U is —NR$^{11}$—, —CR$^{12a}$R$^{12b}$—, —S(O)$_n$—, —C(O)—, or —O—; or T and U together are

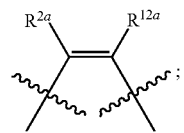

$R^{2a}$, $R^{2b}$, $R^{2c}$, $R^{2d}$, $R^{12a}$, and $R^{12b}$ are independently H, $C_{1-6}$alkyl, $C_{1-6}$haloalkyl, $C_{3-6}$cycloalkyl, $C_{3-6}$halocycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NHR$^a$, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$—;
$R^{3a}$, $R^{3b}$, $R^{3c}$, and $R^{3d}$ are independently H, $C_{1-6}$-alkyl, $C_{1-4}$haloalkyl, or —O—$C_{1-4}$alkyl; $R^{4a}$, $R^{4b}$, $R^{5a}$, $R^{5b}$, $R^{5c}$, $R^{5d}$, $R^{8a}$, $R^{8b}$, $R^{9a}$, $R^{9b}$, $R^{9c}$, and $R^{9d}$ are independently H, $C_{1-6}$-alkyl, $C_{1-4}$haloalkyl, $C_{3-6}$cycloalkyl, $C_{3-6}$halocycloalkyl, halo, hydroxyl, cyano, —O—$C_{1-4}$alkyl, or $C_{1-4}$alkylene-O—$C_{1-4}$alkyl;
each $R^{6a}$, $R^{6b}$, $R^{10a}$, and $R^{10b}$ is independently H, halo, $C_{1-4}$haloalkyl, or $C_{1-4}$alkyl; or
any one of (i) $R^{6a}$ and $R^{6b}$ or (ii) $R^{10a}$ and $R^{10b}$ together with the carbon atoms to which each is attached form (i) a 5 to 10 membered carbocyclic ring, (ii) 5 to 10 membered heterocyclic ring containing 1 or 2 heteroatom selected from N, O, and S, (iii) a 6 to 10 membered aromatic ring, or (iv) a 5 to 10 membered heteroaromatic ring containing 1 to 3 heteroatoms selected from N, O and S, wherein the 5 to 10 membered carbocyclic ring, 5 to 10 membered heterocyclic ring, the 6 to 10 membered aromatic ring, or the 5 to 10 membered heteroaromatic ring is optionally substituted with one to four $R^{44}$, wherein each $R^{44}$ is independently oxo, halo, cyano, $C_{1-6}$alkyl, $C_{3-6}$cycloalkyl or —OR$^e$;
$R^7$ is H, $C_{1-6}$alkyl, $C_{1-4}$haloalkyl, $C_{3-6}$cycloalkyl, $C_{3-6}$halocycloalkyl, C(O)R$^c$, or SO$_2$R$^c$;
$R^{11}$ is H, $C_{1-6}$alkyl, $C_{1-6}$haloalkyl, $C_{3-6}$cycloalkyl, $C_{3-6}$halocycloalkyl, —C(O)—R$^a$, —S(O)$_n$—R$^a$, —CH$_2$—R$^a$;
each $R^a$ is independently (i) H, (ii) $C_{1-6}$alkyl, (iii) $C_{3-6}$cycloalkyl, (iv) a 5 to 10 membered carbocyclic ring, (v) 5 to 10 membered heterocyclic ring containing 1 or 2 heteroatom selected from N, O, and S, (vi) a 6 to 10 membered aromatic ring, or (iv) a 5 to 10 membered heteroaromatic ring containing 1 to 3 heteroatoms selected from N, O and S;
wherein the $C_{1-6}$alkyl, $C_{3-6}$cycloalkyl, 5 to 10 membered carbocyclic ring, 5 to 10 membered heterocyclic ring, 6 to 10 membered aromatic ring or 5 to 10 membered heteroaromatic ring is optionally substituted with 0 to 4 substituents independently selected from the group consisting of (i) oxo (ii) halo, (iii) cyano, (iv) —O—$C_{1-4}$alkyl, (v) $C_{1-6}$alkyl, (vi) —OR$^e$ (vii) 3 to 10 membered carbocyclic ring, (viii) 5 to 10 membered heterocyclic ring containing 1 or 2 heteroatom selected from N, O, and S, (ix) 6 to 10 membered aromatic ring, or (x) a 5 to 10 membered heteroaromatic ring containing 1 to 3 heteroatoms selected from N, O and S; wherein the 3 to 10 membered carbocyclic ring, 5 to 10 membered heterocyclic ring, 6 to 10 membered aromatic ring, or 5 to 10 membered heteroaromatic ring is optionally substituted with one to four $R^{45}$, wherein each $R^{45}$ is independently oxo, halo, cyano, $C_{1-6}$alkyl, $C_{3-6}$cycloalkyl or —OR$^e$;
$R^b$ is H, $C_{1-6}$alkyl, $C_{1-4}$haloalkyl or $C_{3-6}$cycloalkyl;
$R^f$ is H, halo, $C_{1-4}$alkyl, or $C_{1-4}$haloalkyl;
each $R^c$ is independently, H, $C_{1-6}$alkyl, $C_{1-4}$haloalkyl, $C_{3-6}$cycloalkyl, $C_{3-6}$halocycloalkyl; C(O)R$^d$, or —SO$_2$R$^d$;
each $R^d$ is independently $C_{1-4}$alkyl, $C_{1-4}$haloalkyl, $C_{3-6}$cycloalkyl, $C_{3-6}$halocycloalkyl, —NR$^e_2$, or —OR$^e$;

each $R^e$ is independently H, $C_{1-6}$alkyl or $C_{3-6}$cycloalkyl wherein each $C_{1-6}$alkyl or $C_{3-6}$cycloalkyl is optionally substituted by a halo or a cyano; and each n is 0, 1, or 2.

In some embodiments, the compound of Formula I is a compound of Formula Ia:

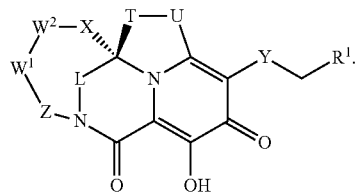

Formula Ia

In some embodiments, the compound of Formula I is a compound of Formula Ib:

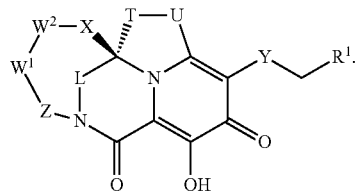

Formula Ib

In some embodiments for the compound of Formula I, Ia, or Ib, Y is selected from the group consisting of —C(O)NH—,

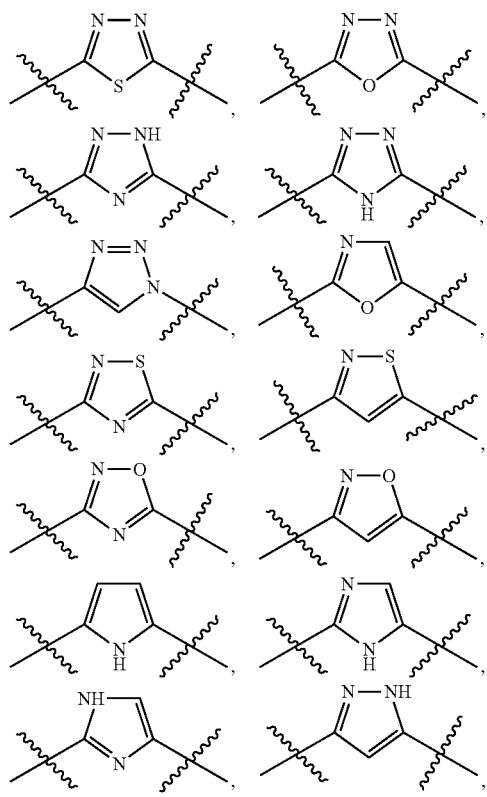

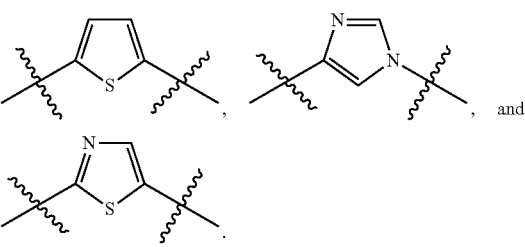

In some embodiments for the compounds of Formula I, Ia, or Ib, Y is

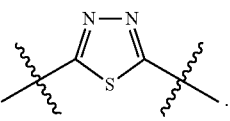 [SMILES: *c1nnc(*)s1]

In some embodiments, Y is

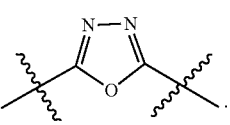 [SMILES: *c1nnc(*)o1]

In some embodiments, Y is

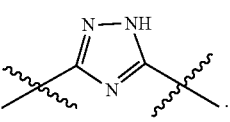 [SMILES: *c1n[nH]c(*)n1]

In some embodiments, Y is

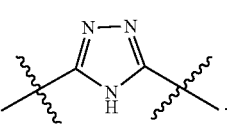 [SMILES: *c1nnc(*)[nH]1]

In some embodiments, Y is

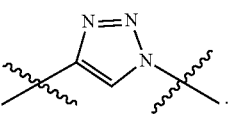 [SMILES: *c1cn(*)nn1]

In some embodiments, Y is

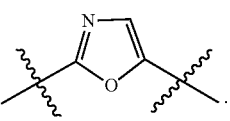 [SMILES: *c1cnc(*)o1]

In some embodiments, Y is

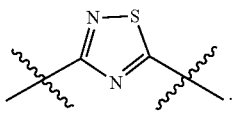 [SMILES: *c1nsc(*)n1]

In some embodiments, Y is

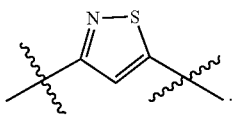 [SMILES: *c1cc(*)sn1]

In some embodiments, Y is

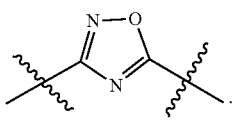 [SMILES: *c1noc(*)n1]

In some embodiments, Y is

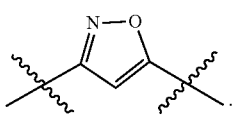 [SMILES: *c1cc(*)on1]

In some embodiments, Y is

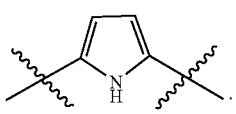 [SMILES: *c1ccc(*)[nH]1]

In some embodiments, Y is

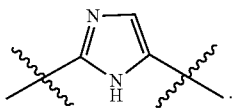 [SMILES: *c1cnc(*)[nH]1]

In some embodiments, Y is

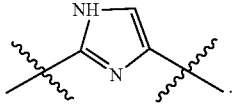 [SMILES: *c1c[nH]c(*)n1]

In some embodiments, Y is

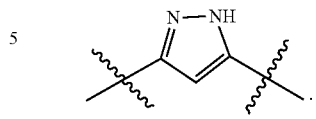

In some embodiments, Y is

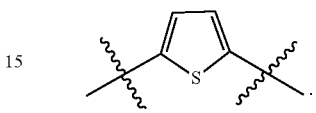

In some embodiments, Y is

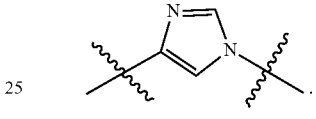

In some embodiments, Y is

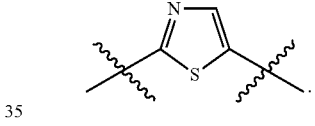

In some embodiments, for the compounds of Formula I, Ia, or Ib, Y is —CONH—.

In some embodiments, the compound of Formula I is a compound of Formula II:

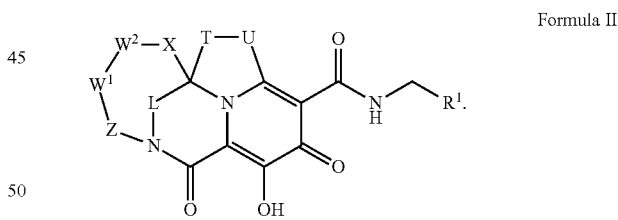

Formula II

In some embodiments, the compound of Formula I, Ia, or II is a compound of Formula IIa:

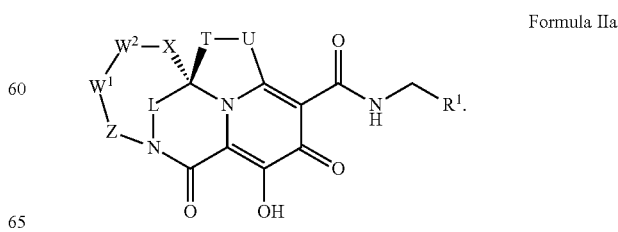

Formula IIa

In some embodiments, the compound of Formula I, Ib, or II is a compound of Formula IIb:

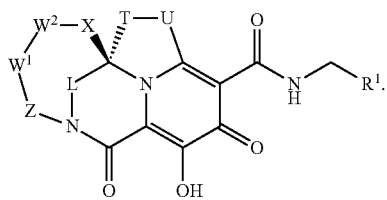

Formula IIb

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or any one of (i) $R^{2a}$ and $R^{2b}$ or (ii) $R^{2c}$ and $R^{2d}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$; or any one of (i) $R^{2a}$ and $R^{2b}$ or (ii) $R^{2c}$ and $R^{2d}$ together with the carbon atom to which they are attached form a 3 to 7 membered carbocyclic ring, wherein the 3 to 7 membered carbocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, or IIb, T is —$CR^{2a}R^{2b}$ or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or any one of (i) $R^{2a}$ and $R^{2b}$ or (ii) $R^{2c}$ and $R^{2d}$ together with the carbon atom to which they are attached form a 3 to 5 membered carbocyclic ring, wherein the 3 to 5 membered carbocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or any one of (i) $R^{2a}$ and $R^{2b}$ or (ii) $R^{2c}$ and $R^{2d}$ together with the carbon atom to which they are attached form a 3 membered carbocyclic ring, wherein the 3 membered carbocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or any one of (i) $R^{2a}$ and $R^{2b}$ or (ii) $R^{2c}$ and $R^{2d}$ together with the carbon atom to which they are attached form a 3 membered carbocyclic ring.

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or any one of (i) $R^{2a}$ and $R^{2b}$ or (ii) $R^{2c}$ and $R^{2d}$ together with the carbon atom to which they are attached form a 4 to 7 membered heterocyclic ring containing 1 or 2 heteroatoms selected from N, O, and S, wherein the 4 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; In some embodiments, T is —$CR^{2a}R^{2b}$— or —$CR^{2a}R^{2b}CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$OR^a$, —O—C(O)—$NHR^a$, —$NHR^a$—, —C(O)—NH($R^a$)—, or —$NR^e$—C(O)$R^a$—; In some embodiments, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, or —$OR^a$. In some embodiments, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, cyano, —$CH_2OR^a$, or —$OR^a$. In some embodiments, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl, $C_{3-6}$halocycloalkyl, halo, or cyano. In some embodiments, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, $C_{1-6}$haloalkyl, $C_{3-6}$cycloalkyl or $C_{3-6}$halocycloalkyl. In some embodiments, T is —$CR^{2a}R^{2b}$— or —$CR^{2a}R^{2b}$—$CR^{2c}R^{2d}$; wherein each $R^{2a}$, $R^{2b}$, $R^{2c}$, and $R^{2d}$ is independently H, $C_{1-6}$alkyl, or $C_{3-6}$cycloalkyl.

In some embodiments, of the compound of Formula I, Ia, Ib, II, IIa, or IIb, T is —$CR^{2a}R^{2b}$— or —$CR^{2a}R^{2b}$—$CR^{2c}R^{2d}$; wherein $R^{2a}$, $R^{2b}$, $R^{2c}$, and $R^{2d}$ are independently H, $C_{1-6}$alkyl, $C_{1-6}$haloalkyl, $C_{3-6}$cycloalkyl, $C_{3-6}$halocycloalkyl, halo, cyano, —CH$_2$R$^a$—, —CH$_2$OR$^a$, —OR$^a$ or —NHR$^a$. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, or —OR$^a$. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H, C$_{1-6}$alkyl, C$_{1-6}$haloalkyl, C$_{3-6}$cycloalkyl, C$_{3-6}$halocycloalkyl, or halo. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H or halo. In some embodiments, T is —CR$^{2a}$R$^{2b}$— or —CR$^{2a}$R$^{2b}$—CR$^{2c}$R$^{2d}$, wherein, R$^{2a}$, R$^{2b}$, R$^{2c}$, and R$^{2d}$ are independently H, —C(O)—NH(R$^a$)—, —NR$^e$—C(O)R$^a$—, —NR$^e$—S(O)$_n$R$^a$—, —S(O)$_n$—NH(R$^a$)—, —S(O)$_n$R$^a$—, or —O—C(O)—NHR$^a$. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H, —OR$^a$, —NHR$^a$, —C(O)—NH(R$^a$), —NR$^e$—C(O)R$^a$, or —NR$^e$—S(O)$_n$R$^a$. In some embodiments, T is —CR$^{2a}$R$^{2b}$— or —CR$^{2a}$R$^{2b}$—CR$^{2c}$R$^{2d}$d, wherein R$^{2a}$, R$^{2b}$, R$^{2c}$, and R$^{2d}$ are independently H, —OR$^a$, or —O—C(O)—NHR$^a$. In some embodiments, T is —CR$^{2a}$R$^{2b}$— or —CR$^{2a}$R$^{2b}$CR$^{2c}$R$^{2d}$, wherein R$^{2a}$, R$^{2b}$, R$^{2c}$, and R$^{2d}$ are independently H, —S(O)$_n$—NH(R$^a$), or —S(O)$_n$—R$^a$—. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H, halo, cyano, —NHR$^a$— or —OR$^a$. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H or —NHR$^a$. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently is H, halo, cyano, or —OR$^a$. In some embodiments, T is —CR$^{2a}$R$^{2b}$— or —CR$^{2a}$R$^{2b}$—CR$^{2c}$R$^{2d}$, wherein R$^{2a}$, R$^{2b}$, R$^{2c}$, and R$^{2d}$ are independently H or cyano.

In some embodiments, of the compound of Formula I, Ia, Ib, II, IIa, or IIb, T is —CR$^{2a}$R$^{2b}$— wherein, R$^{2a}$ and R$^{2b}$ together with the carbon to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, or IIb, T is —CR$^{2a}$R$^{2b}$— wherein R$^{2a}$ and R$^{2b}$ together with the carbon to which they are attached form a 3 to 7 membered carbocyclic ring, wherein the 3 to 7 membered carbocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, or IIb, T is —CR$^{2a}$R$^{2b}$— wherein R$^{2a}$ and R$^{2b}$ together with the carbon to which they are attached form a 3 to 5 membered carbocyclic ring, wherein the 3 to 5 membered carbocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, or IIb, T is —CR$^{2a}$R$^{2b}$— wherein, R$^{2a}$ and R$^{2b}$ together with the carbon to which they are attached form a 3 to 5 membered carbocyclic ring, wherein the 3 to 5 membered carbocyclic ring.

In some embodiments, of the compound of Formula I, Ia, Ib, II, IIa, or IIb, T is —CR$^{2a}$R$^{2b}$— wherein R$^{2a}$ and R$^{2b}$ together with the carbon to which they are attached form a 4 to 7 membered heterocyclic ring containing 1 or 2 heteroatoms selected from N, O, and S, wherein the 4 to 7 membered heterocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, or IIb, T is —CR$^{2a}$R$^{2b}$— wherein, R$^{2a}$ and R$^{2b}$ together with the carbon to which they are attached form a 4 to 5 membered heterocyclic ring containing 1 or 2 heteroatoms selected from N, O, and S, wherein the 4 to 5 membered heterocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, or IIb, T is —CR$^{2a}$R$^{2b}$— wherein, R$^{2a}$ and R$^{2b}$ together with the carbon to which they are attached form a 4 to 5 membered heterocyclic ring containing 1 or 2 heteroatoms selected from N, O, and S.

In some embodiments, of the compound of Formula I, Ia, Ib, II, IIa, or IIb, T is —CR$^{2a}$R$^{2b}$—, wherein R$^{2a}$ and R$^{2b}$ are independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —OR$^a$ or —NHR$^a$. In some embodiments, T is —CR$^{2a}$R$^{2b}$—, wherein R$^{2a}$ and R$^{2b}$ are independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, or —OR$^a$. In some embodiments, T is —CR$^{2a}$R$^{2b}$—, wherein R$^{2a}$ and R$^{2b}$ are independently H, C$_{1-6}$alkyl, C$_{1-6}$haloalkyl, C$_{3-6}$cycloalkyl, C$_{3-6}$halocycloalkyl, or halo. In some embodiments, T is —CR$^{2a}$R$^{2b}$—, wherein R$^{2a}$ and R$^{2b}$ are independently H, C$_{1-6}$alkyl, C$_{3-6}$cycloalkyl, or halo. In some embodiments, T is —CR$^{2a}$R$^{2b}$—, wherein R$^{2a}$ and R$^{2b}$ are independently H or halo. In some embodiments, T is —CR$^{2a}$R$^{2b}$—, wherein, R$^{2a}$ and R$^{2b}$ are independently H, —C(O)—NH(R$^a$)—, —NR$^e$—C(O)R$^a$—, —NR$^e$—S(O)$_n$R$^a$—, —S(O)$_n$—NH(R$^a$)—, —S(O)$_n$—R$^a$—, or —O—C(O)—NHR$^a$. In some embodiments, T is —CR$^{2a}$R$^{2b}$, wherein R$^{2a}$ and R$^{2b}$ are independently H, —OR$^a$, —NHR$^a$, —C(O)—NH(R$^a$), —NR$^e$—C(O)R$^a$, or —NR$^e$—S(O)$_n$R$^a$. In some embodiments, T is —CR$^{2a}$R$^{2b}$—, wherein R$^{2a}$ and R$^{2b}$ are independently H, —OR$^a$, or —O—C(O)—NHR$^a$. In some embodiments, T is —CR$^{2a}$R$^{2b}$—, wherein R$^{2a}$ and R$^{2b}$ are independently H, —S(O)$_n$—NH(R$^a$), or —S(O)$_n$—R$^a$—. In some embodiments, T is —CR$^{2a}$R$^{2b}$—, wherein R$^{2a}$ and R$^{2b}$ are independently H, halo, cyano, —NHR$^a$— or —OR$^a$. In some embodiments, T is —CR$^{2a}$R$^{2b}$—, wherein R$^{2a}$ and R$^{2b}$ are independently H or —NHR$^a$. In some embodiments, T is —CR$^{2a}$R$^{2b}$—, wherein R$^{2a}$ and R$^{2b}$ are independently is H, halo, cyano, or —OR$^a$. In some embodiments, T is —CR$^{2a}$R$^{2b}$—, wherein R$^{2a}$ and R$^{2b}$ are independently H or cyano. In some embodiments, T is —CR$^{2a}$R$^{2b}$—, wherein R$^{2a}$ and R$^{2b}$ are each H.

In some embodiments, of the compound of Formula I, Ia, Ib, II, IIa, or IIb, T is —CR$^{2a}$R$^{2b}$—; wherein each R$^{2a}$ and R$^{2b}$ is independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NR$^a$—, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$—; or R$^{2a}$ and R$^{2b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three R$^{A2}$, wherein each R$^{A2}$ is independently oxo, halo, cyano, C$_{1-6}$alkyl, C$_{3-6}$cycloalkyl or —OR$^e$.

In some embodiments, of the compound of Formula I, Ia, Ib, II, IIa, or IIb, T is —CR$^{2a}$R$^{2b}$—; wherein each R$^{2a}$ and R$^{2b}$ is independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NR$^a$—, —C(O)—NH(R$^a$)—, —NR$^e$—C(O)R$^a$—, —NR$^e$—S(O)$_n$—R$^a$—, —S(O)$_n$—NH(R$^a$)—, or —S(O)$_n$—R$^a$—; or R$^{2a}$ and R$^{2b}$ together with the carbon atom to which they are attached form a 3 to 7 membered carbocyclic ring wherein the 3 to 7 membered carbocyclic ring is optionally substituted with one to three R$^{A2}$, wherein each R$^{A2}$ is independently oxo, halo, cyano, C$_{1-6}$alkyl, C$_{3-6}$cycloalkyl or —OR$^e$.

In some embodiments, of the compound of Formula I, Ia, Ib, II, IIa, or IIb, T is —CR$^{2a}$R$^{2b}$—; wherein each R$^{2a}$ and R$^{2b}$ is independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NR$^a$—, —C(O)—NH(R$^a$)—, —NR$^e$—C(O)R$^a$—, —NR$^e$—S(O)$_n$—R$^a$—, —S(O)$_n$—NH(R$^a$)—, or —S(O)$_n$—R$^a$—; or R$^{2a}$ and R$^{2b}$ together with the carbon atom to which they are attached form a 3 to 5 membered carbocyclic ring, wherein the 3 to 5 membered carbocyclic ring is optionally substituted with one to three R$^{A1}$, wherein each R$^{A2}$ is independently oxo, halo, cyano, C$_{1-6}$alkyl, C$_{3-6}$cycloalkyl or —OR$^e$.

In some embodiments, of the compound of Formula I, Ia, Ib, II, IIa, or IIb, T is —CR$^{2a}$R$^{2b}$—; wherein each R$^{2a}$ and R$^{2b}$ is independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NR$^a$—, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$—; or R$^{2a}$ and R$^{2b}$ together with the carbon atom to which they are attached form a 3 membered carbocyclic ring, wherein the 3 membered carbocyclic ring is optionally substituted with one to three R$^{A2}$, wherein each R$^{A2}$ is independently oxo, halo, cyano, C$_{1-6}$alkyl, C$_{3-6}$cycloalkyl or —OR$^e$.

In some embodiments, of the compound of Formula I, Ia, Ib, II, IIa, or IIb, T is —CR$^{2a}$R$^b$; wherein each R$^{2a}$ and R$^{2b}$ is independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NR$^a$—, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$—; or R$^{2a}$ and R$^{2b}$ together with the carbon atom to which they are attached form a 3 membered carbocyclic ring.

In some embodiments, of the compound of Formula I, Ia, Ib, II, IIa, or IIb, T —CR$^{2a}$R$^{2b}$, wherein R$^{2a}$ and R$^{2b}$ are independently H, halo, or —OR$^a$. In some embodiments, T is —CR$^{2a}$R$^b$—, wherein R$^{2a}$ and R$^{2b}$ are independently H, halo, or —OR$^a$, and each R$^a$ is independently H or C$_{1-6}$alkyl. In some embodiments, T is —CR$^{2a}$R$^b$, wherein R$^{2a}$ and R$^{2b}$ are independently H, halo, or —OR$^a$, and each R$^a$ is independently H or C$_{1-3}$ alkyl. In some embodiments, T is —CR$^{2a}$R$^b$—, wherein R$^{2a}$ and R$^{2b}$ are independently H, halo, or —OR$^a$, and each R$^a$ is independently H or methyl.

In some embodiments, of the compound of Formula I, Ia, Ib, II, IIa, or IIb, T —CR$^{2a}$R$^{2b}$—CR$^{2c}$R$^{2d}$; wherein R$^{2a}$, R$^{2b}$, R$^{2c}$, and R$^{2d}$ are independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, —OR$^a$ or —NHR$^a$. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H, C$_{1-6}$alkyl, C$_{1-6}$haloalkyl, C$_{3-6}$cycloalkyl, C$_{3-6}$halocycloalkyl, halo, cyano, —CH$_2$R$^a$—, —CH$_2$OR$^a$, or —OR$^a$. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H, C$_{1-6}$-alkyl, C$_{1-6}$haloalkyl, C$_{3-6}$cycloalkyl, C$_{3-6}$halocycloalkyl, or halo. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H, C$_{1-6}$alkyl, C$_{3-6}$cycloalkyl or halo. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H or halo. In some embodiments, T is —CR$^{2a}$R$^{2b}$—CR$^{2c}$R$^{2d}$, wherein, R$^{2a}$, R$^{2b}$, R$^{2c}$, and R$^{2d}$ are independently H, —C(O)—NH(R$^a$)—, —NR$^e$—C(O)R$^a$—, —NR$^e$—S(O)$_n$R$^a$—, —S(O)$_n$—NH(R$^a$), —S(O)$_n$—R$^a$—, or —O—C(O)—NHR$^a$. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H, —OR$^a$, —NHR$^a$, —C(O)—NH(R$^a$), —NR$^e$—C(O)R$^a$, or —NR$^e$—S(O)$_n$R$^a$. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H, —OR$^a$, or —O—C(O)—NHR$^a$. In some embodiments, T is —CR$^{2a}$R$^{2b}$CR$^{2c}$R$^{2d}$, wherein R$^{2a}$, R$^{2b}$, R$^{2c}$, and R$^{2d}$ are independently H, —S(O)$_n$—NH(R$^a$), or —S(O)$_n$—R$^a$—; In some embodiments, T is —CR$^{2a}$R$^{2b}$CR$^{2c}$R$^{2d}$, wherein R$^{2a}$, R$^{2b}$, R$^{2c}$, and R$^{2d}$ are independently H, halo, cyano, —NHR$^a$— or —OR$^a$. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H or —NHR$^a$. In some embodiments, T is —CR$^{2a}$R$^{2b}$CR$^{2c}$R$^{2d}$, wherein R$^{2a}$, R$^{2b}$, R$^{2c}$, and R$^{2d}$ are independently is H, halo, cyano, or —OR$^a$. In some embodiments, T is —CR$^{2a}$R$^{2b}$—CR$^{2c}$R$^{2d}$, wherein R$^{2a}$, R$^{2b}$, R$^{2c}$, and R$^{2d}$ are independently H or cyano. In some embodiments, T is —CR$^{2a}$R$^{2b}$—CR$^{2c}$R$^{2d}$, wherein R$^{2a}$, R$^{2b}$, R$^{2c}$, and R$^{2d}$ are each H.

In some embodiments, of the compound of Formula I, Ia, Ib, II, IIa, or IIb, T —CR$^{2a}$R$^{2b}$—CR$^{2c}$R$^{2d}$—; wherein R$^{2}$, R$^{2b}$, R$^{2c}$, and R$^{2d}$ are independently H, halo, or —OR$^a$. In some embodiments, T is —CR$^{2a}$R$^{2b}$CR$^{2c}$R$^{2d}$—, wherein R$^{2a}$, R$^{2b}$, R$^{2c}$, and R$^{2d}$ are independently H, halo, or —OR$^a$, and each R$^a$ is independently H or C$_{1-6}$alkyl. In some embodiments, T is —CR$^{2a}$R$^{2b}$CR$^{2c}$R$^{2d}$—, wherein R$^{2a}$, R$^{2b}$, R$^{2c}$, and R$^{2}$ are independently H, halo, or —OR$^a$, and each R$^a$ is independently H or C$_{1-3}$ alkyl. In some embodiments, T is —CR$^{2a}$R$^{2b}$—CR$^{2c}$R$^{2d}$—, wherein R$^{2a}$, R$^{2b}$, R$^{2c}$, and R$^{2d}$ are independently H, halo, or —OR$^a$, and each R$^a$ is independently H or methyl.

In some embodiments, the compound of Formula I or II is a compound of Formula III:

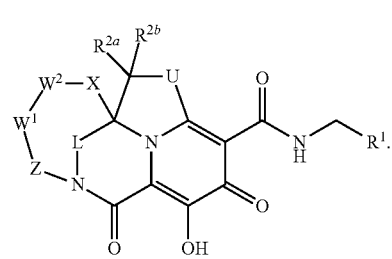

Formula III

In some embodiments, the compound of Formula I, Ia, II, or IIa is a compound of Formula IIIa:

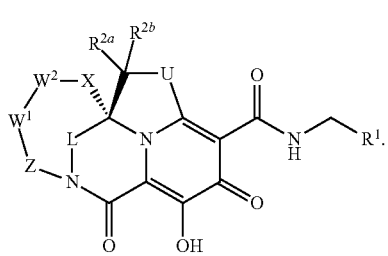

Formula IIIa

In some embodiments, the compound of Formula I, Ib, II, or IIb is a compound of Formula IIIb:

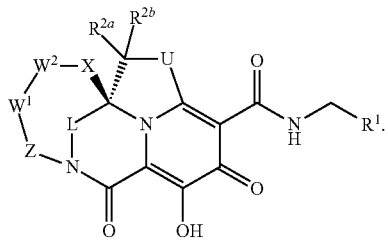

Formula IIIb

In some embodiments of the compound of Formula I, Ia, Ib, II, IIa, IIb, III, IIIa, or IIIb, U is —NR$^{11}$—, —CR$^{12a}$R$^{12b}$—, —S—, —S(O)$_n$—, —S(O)$_2$—, —C(O)—, or —O—. In some embodiments, the compound of Formula I, Ia, Ib, II, IIa, IIb, III, IIIa, or IIIb, II is —NR$^{11}$, —CR$^{12a}$R$^{12b}$, —C(O)— or —O—. In some embodiments, U is —NR$^{11}$, —CR$^{12a}$R$^{12b}$, or —O—. In some embodiments, U is —NR$^{11}$ or —CR$^{12a}$R$^{12b}$. In some embodiments, U is —NR$^{11}$.

In some embodiments of the compound of Formula I, Ia, Ib, II, IIa, IIb, III, IIIa, or IIIb, U is —O—, —C(O)—, —S—, —S(O)$_n$—, or —S(O)$_2$—. In some embodiments, U is —O— or —C(O)—. In some embodiments, U is —S—, —S(O)$_n$—, or —S(O)$_2$—. In some embodiments, U is —S—. In some embodiments, U is —S(O)$_n$—. In some embodiments, U is —S(O)$_2$—. In some embodiments, U is —C(O)—. In some embodiments, U is —O—.

In some embodiments of the compound of Formula I, Ia, Ib, II, IIa, IIb, III, IIIa, or IIIb, R$^{11}$ is H, C$_{1-4}$alkyl, C$_{1-4}$haloalkyl, C$_{3-6}$cycloalkyl, C$_{3-6}$halocycloalkyl, —C(O)—R$^a$, —S—R$^a$, —S(O)—R$^a$, —S(O)$_2$—R$^a$, —CH$_2$—R$^a$. In some embodiments, R$^{11}$ is H, C$_1$-C$_4$ alkyl, C$_1$-C$_4$ haloalkyl, C$_3$-C$_6$cycloalkyl, or C$_3$-C$_6$halocycloalkyl. In some embodiments, R$^{11}$ is H, C$_3$-C$_6$cycloalkyl, or C$_3$-C$_6$halocycloalkyl. In some embodiments, R$^{11}$ is H, C$_1$-C$_4$ alkyl or C$_1$-C$_4$ haloalkyl. In some embodiments, R$^{11}$ is H or C$_1$-C$_4$ alkyl. In some embodiments, R$^{11}$ is C$_3$-C$_6$halocycloalkyl. In some embodiments, R$^{11}$ is C$_3$-C$_6$cycloalkyl. In some embodiments, R$^{11}$ is C$_1$-C$_4$ haloalkyl. In some embodiments, R$^{11}$ is C$_1$-C$_4$ alkyl. In some embodiments, R$^{11}$ is H. In some embodiments, R$^{11}$ is —C(O)—R$^a$, —S—R$^a$, —S(O)—R$^a$, —S(O)$_2$—R$^a$, —CH$_2$—R$^a$.

In some embodiments, the compound of Formula I, II, or III has a Formula IV:

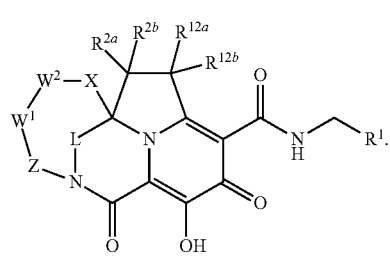

Formula IV

In some embodiments, the compound of Formula I, Ia, II, IIa, III, IIIa, or IV has a Formula IVa:

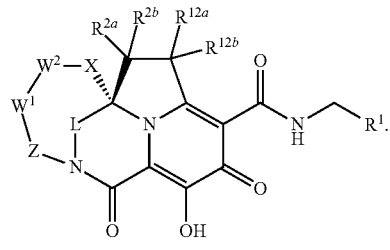

Formula IVa

In some embodiments, the compound of Formula I, Ib, II, IIb, III, IIIb, or IV has a Formula IVb:

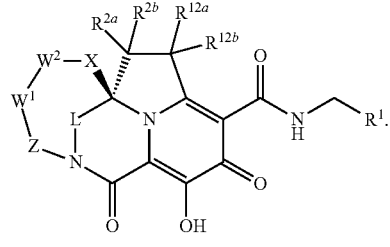

Formula IVb

In some embodiments, of the compound of Formula I, Ia, Ib, II, IIa, IIb, III, IIIa, IIIb, IV, IVa, and IVb, R$^{2a}$ and R$^{2b}$ together with the carbon to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, IIb, III, IIIa, IIIb, IV, IVa, and IVb, R$^{2a}$ and R$^{2b}$ together with the carbon to which they are attached form a 3 to 7 membered carbocyclic ring, wherein the 3 to 7 membered carbocyclic ring is optionally substituted with one to three R$^{A2}$, wherein each R$^{A2}$ is independently oxo, halo, cyano, C$_1$-C$_6$alkyl, C$_3$-C$_6$cycloloalkyl or —OR$^e$.

In some embodiments, of the compound of Formula I, Ia, Ib, II, IIa, IIb, III, IIIa, IIIb, IV, IVa, and IVb, R$^{2a}$ and R$^{2b}$ together with the carbon to which they are attached form a 3 to 5 membered carbocyclic ring, wherein the 3 to 5 membered carbocyclic ring is optionally substituted with one to three $R^{A2}$, wherein each $R^{A2}$ is independently oxo, halo, cyano, $C_1$-$C_6$alkyl, $C_3$-$C_6$cycloloalkyl or —$OR^e$.

In some embodiments, of the compound of Formula I, Ia, Ib, II, IIa, IIb, III, IIIa, IIIb, IV, IVa, and IVb, $R^{2a}$ and $R^{2b}$ together with the carbon to which they are attached form a 3 to 5 membered carbocyclic ring, wherein the 3 to 5 membered carbocyclic ring.

In some embodiments, of the compound of Formula I, Ia, Ib, II, IIa, IIb, III, IIIa, IIIb, IV, IVa, and IVb, $R^{2a}$ and $R^{2b}$ together with the carbon to which they are attached form a 4 to 7 membered heterocyclic ring containing 1 or 2 heteroatoms selected from N, O, and S, wherein the 4 to 7 membered heterocyclic ring is optionally substituted with one to three $R^{A2}$, wherein each $R^{A2}$ is independently oxo, halo, cyano, $C_1$-$C_6$alkyl, $C_3$-$C_6$cycloloalkyl or —$OR^e$.

In some embodiments, of the compound of Formula I, Ia, Ib, II, IIa, IIb, III, IIIa, IIIb, IV, IVa, and IVb, $R^{2a}$ and $R^{2b}$ together with the carbon to which they are attached form a 3 to 5 membered heterocyclic ring containing 1 or 2 heteroatoms selected from N, O, and S, wherein the 3 to 5 membered heterocyclic ring is optionally substituted with one to three $R^{A2}$, wherein each $R^{A2}$ is independently oxo, halo, cyano, $C_1$-$C_6$alkyl, $C_3$-$C_6$cycloloalkyl or —$OR^e$.

In some embodiments, of the compound of Formula I, Ia, Ib, II, IIa, IIb, III, IIIa, IIIb, IV, IVa, and IVb, $R^{2a}$ and $R^{2b}$ together with the carbon to which they are attached form a 3 to 5 membered heterocyclic ring containing 1 or 2 heteroatoms selected from N, O, and S.

In some embodiments, of the compound of Formula I, Ia, Ib, II, IIa, IIb, III, IIIa, IIIb, IV, IVa, and IVb, $R^{2a}$ and $R^{2b}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$OR^a$ or —$NHR^a$. In some embodiments, T is —$CR^{2a}R^{2b}$—, wherein $R^{2a}$ and $R^{2b}$ are independently H, $C_{1-6}$-alkyl, $C_{34}$cycloalkyl, halo, cyano, —$CH_2R^a$—, —$CH_2OR^a$, or —$OR^a$. In some embodiments, T is —$CR^{2a}R^{2b}$—, wherein $R^{2a}$ and $R^{2b}$ are independently H, $C_{1-6}$alkyl, $C_{3-6}$cycloalkyl, or halo. In some embodiments, T is —$CR^{2a}R^{2b}$—, wherein $R^{2a}$ and $R^{2b}$ are independently H or halo. In some embodiments, T is —$CR^{2a}R^{2b}$—, wherein, $R^{2a}$ and $R^{2b}$ are independently H, —C(O)—NH($R^a$)—, —$NR^e$—C(O)$R^a$—, —S(O)$_n$$R^a$—, —S(O)$_n$—NH($R^a$)—, —S(O)$_n$—$R^a$—, or —O—C(O)—$NHR^a$. In some embodiments, T is —$CR^{2a}R^{2b}$, wherein $R^{2a}$ and $R^{2b}$ are independently H, —$OR^a$, —$NHR^a$, —C(O)—NH($R^a$), —$NR^e$—C(O)$R^a$, or —$NR^e$—S(O)$_n$$R^a$. In some embodiments, T is —$CR^{2a}R^{2b}$—, wherein $R^{2a}$ and $R^{2b}$ are independently H, —$OR^a$, or —O—C(O)—$NHR^a$. In some embodiments, T is —$CR^{2a}R^{2b}$, wherein $R^{2'}$ and $R^b$ are independently H, —S(O)$_n$—NH($R^a$), or —S(O)$_n$—$R^a$—. In some embodiments, T is —$CR^{2a}R^{2b}$, wherein $R^{2a}$ and $R^{2b}$ are independently H, halo, cyano, —$NHR^a$— or —$OR^a$. In some embodiments, T is —$CR^{2a}R^{2b}$, wherein $R^{2a}$ and $R^{2b}$ are independently H or —$NHR^a$. In some embodiments, T is —$CR^{2a}R^{2b}$, wherein $R^{2a}$ and $R^{2b}$ are independently is H, halo, cyano, or —$OR^a$. In some embodiments, T is —$CR^{2a}R^{2b}$, wherein $R^{2a}$ and $R^{2b}$ are independently H or cyano. In some embodiments, T is —$CR^{2a}R^{2b}$, wherein $R^{2a}$ and $R^{2b}$ are each H.

In some embodiments, of the compound of Formula I, Ia, Ib, II, IIa, IIb, III, IIIa, IIIb, IV, IVa, and IVb, each $R^{2a}$ and $R^{2b}$ is independently H, $C_{1-6}$alkyl, $C_{3-6}$cycloalkyl, halo, cyano, —$CH_2R^a$—, —$CH_2OR^a$, —$CH_2$—S(O)$_n$$R^a$—, —$OR^a$, —O—C(O)—$NHR^a$, —$NHR^a$—, —C(O)—NH($R^a$)—, —$NR^e$—C(O)$R^a$—, —$NR^e$—S(O)$_n$$R^a$—, —S(O)$_n$—NH($R^a$)—, or —S(O)$_n$$R^a$—; or $R^{2a}$ and $R^{2b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^a$.

In some embodiments, of the compound of Formula I, Ia, Ib, II, IIa, IIb, III, IIIa, IIIb, IV, IVa, and IVb, each $R^{2a}$ and $R^{2b}$ is independently H, $C_{1-6}$alkyl, $C_{3-6}$cycloalkyl, halo, cyano, —$CH_2R^a$—, —$CH_2OR^a$, —$CH_2$—S(O)$_n$$R^a$—, —$OR^a$, —O—C(O)—$NHR^a$, —$NR^a$—, —C(O)—NH($R^a$)—, —$NR^a$—C(O)$R^a$—, —$NR^e$—S(O)$_n$$R^a$—, —S(O)$_n$—NH($R^a$)—, or —S(O)$_n$—$R^a$—; or $R^{2a}$ and $R^{2b}$ together with the carbon atom to which they are attached form a 3 to 7 membered carbocyclic ring wherein the 3 to 7 membered carbocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, IIb, III, IIIa, IIIb, IV, IVa, and IVb, each $R^{2a}$ and $R^{2b}$ is independently H, $C_{1-6}$alkyl, $C_{3-6}$cycloalkyl, halo, cyano, —$CH_2R^a$—, —$CH_2OR^a$, —$CH_2$—S(O)$_n$$R^a$—, —$OR^a$, —O—C(O)—$NHR^a$, —$NR^a$—, —C(O)—NH($R^a$)—, —$NR^e$—C(O)$R^a$—, —$NR^e$—S(O)$_n$$R^a$—, —S(O)$_n$—NH($R^a$)—, or —S(O)$_n$—$R^a$—; or $R^{2a}$ and $R^{2b}$ together with the carbon atom to which they are attached form a 3 to 5 membered carbocyclic ring, wherein the 3 to 5 membered carbocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, IIb, III, IIIa, IIIb, IV, IVa, and IVb, each $R^{2a}$ and $R^{2b}$ is independently H, $C_{1-6}$alkyl, $C_{3-6}$cycloalkyl, halo, cyano, —$CH_2R^a$—, —$CH_2OR^a$, —$CH_2$—S(O)$_n$$R^a$—, —$OR^a$, —O—C(O)—$NHR^a$, —$NR^a$—, —C(O)—NH($R^a$)—, —$NR^e$—C(O)$R^a$—, —$NR^e$—S(O)$_n$$R^a$—, —S(O)$_n$—NH($R^a$)—, or —S(O)$_n$—$R^a$—; or $R^{2a}$ and $R^{2b}$ together with the carbon atom to which they are attached form a 3 membered carbocyclic ring, wherein the 3 membered carbocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$.

In some embodiments, of the compound of Formula I, Ia, Ib, II, IIa, IIb, III, IIIa, IIIb, IV, IVa, and IVb, each $R^{2a}$ and $R^{2b}$ is independently H, $C_{1-6}$alkyl, $C_{3-6}$cycloalkyl, halo, cyano, —$CH_2R^a$—, —$CH_2OR^a$, —$CH_2$—S(O)$_n$$R^a$—, —$OR^a$, —O—C(O)—$NHR^a$—, —$NR^a$—, —C(O)—NH($R^a$)—, —$NR^a$—C(O)$R^a$—, —$NR^e$—S(O)$_n$$R^a$—, —S(O)$_n$—NH($R^a$)—, or —S(O)$_n$—$R^a$—; or $R^{2a}$ and $R^{2b}$ together with the carbon atom to which they are attached form a 3 membered carbocyclic ring.

In some embodiments for the compound of Formula I, Ia, Ib, II, IIa, IIb, III, IIIa, IIIb, IV, IVa, and IVb, $R^{12a}$ and $R^{12b}$ are independently H, —$OR^a$, or —O—C(O)—$NHR^a$. In some embodiments, $R^{12a}$ and $R^{12b}$ are independently H, —$NHR^a$, —C(O)—NH($R^a$), —$NR^e$—C(O)$R^a$, —$NR^e$—S(O)$_n$$R^a$. In some embodiments, $R^{12a}$ and $R^{12b}$ are independently H, —S(O)$_n$—NH($R^a$), or —S(O)$_n$—$R^a$—. In some embodiments, $R^{12a}$ and $R^{12b}$ are independently H, halo, cyano, —$NHR^a$— or —$OR^a$. In some embodiments, $R^{12a}$ and $R^{12b}$ are independently H or —$NHR^a$. In some embodiments, $R^{12a}$ and $R^{12b}$ are independently H, halo, cyano, or —$OR^a$. In some embodiments, $R^{12a}$ and $R^{12b}$ are independently H or cyano. In some embodiments, $R^{12a}$ and $R^{12b}$ are independently H or —$OR^a$. In some embodiments, $R^{12a}$ and $R^{12b}$ are independently H or —$OR^a$, and $R^a$ is $C_{3-6}$cycloalkyl. In some embodiments, $R^{12a}$ and $R^{12b}$ are independently H or —$OR^a$, and $R^a$ is $C_{1-4}$ haloalkyl. In some embodiments, $R^{12a}$ and $R^{12b}$ are independently H or —$OR^a$, and $R^a$ is $C_{1-6}$alkyl optionally substituted with —O—$C_{1-6}$alkyl.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{42}$, wherein each $R^{42}$ is independently oxo, halo, cyano, $C_{1-6}$alkyl, $C_{1-6}$cycloloalkyl or —$OR^e$.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 3 to 7 membered carbocyclic ring, wherein the 3 to 7 membered carbocyclic ring is optionally substituted with one to three $R^{42}$, wherein each $R^{42}$ is independently oxo, halo, cyano, $C_{1-6}$alkyl, $C_{1-6}$cycloloalkyl or —$OR^e$.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 4 to 7 membered heterocyclic ring containing 1 or 2 heteroatoms selected from N, O, and S, wherein the 4 to 7 membered heterocyclic ring is optionally substituted with one to three $R^{42}$, wherein each $R^{42}$ is independently oxo, halo, cyano, $C_{1-6}$alkyl, $C_{1-6}$cycloloalkyl or —$OR^e$.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{42}$, wherein each $R^{42}$ is independently oxo, halo, cyano, $C_{1-6}$alkyl, or $C_{1-6}$cycloloalkyl.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a (i) 3 to 7 membered carbocyclic ring or (ii) 3 to 5 membered heterocyclic ring containing 1 or 2 heteroatoms selected from N, O, and S, wherein the 3 to 5 membered carbocyclic ring or the 3 to 5 membered heterocyclic ring is optionally substituted with one to three $R^{42}$, wherein each $R^{42}$ is independently oxo, halo, cyano, $C_{1-6}$alkyl, or $C_{1-6}$cycloloalkyl.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a (i) 3 to 7 membered carbocyclic ring or (ii) 3 to 5 membered heterocyclic ring containing 1 or 2 heteroatoms selected from N, O, and S.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 3 to 5 membered carbocyclic ring, wherein the 3 to 5 membered carbocyclic ring is optionally substituted with one to three $R^{42}$, wherein each $R^{42}$ is independently oxo, halo, cyano, $C_{1-6}$alkyl, or $C_{1-6}$cycloloalkyl.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 3 to 5 membered heterocyclic ring containing 1 or 2 heteroatoms selected from N, O, and S, wherein the 3 to 5 membered heterocyclic ring is optionally substituted with one to three $R^{42}$, wherein each $R^{42}$ is independently oxo, halo, cyano, $C_{1-6}$alkyl, or $C_{1-6}$cycloloalkyl.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 3 to 5 membered carbocyclic ring.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 3 to 5 membered heterocyclic ring containing 1 or 2 heteroatoms selected from N, O, and S.

In some embodiments, of the compounds of Formula I, Ia, Ib, II, IIa, IIb, III, IIIa, IIIb, IV, IVa, or IVb, $R^{12a}$ and $R^{12b}$ together with the carbon atom to which they are attached form a 3 membered carbocyclic ring.

In some embodiments, of the compound of Formula I, Ia, Ib, II, IIa, IIb, III, IIIa, IIIb, IV, IVa, or IVb, each $R^{2a}$, $R^{2b}$, $R^{12a}$, and $R^{12b}$ is independently H, halo, or —$OR^a$. In some embodiments, each $R^{2a}$, $R^{2b}$, $R^{12a}$, and $R^{12b}$ is independently H, halo, or —$OR^a$ and each $R^a$ is independently H or $C_{1-6}$alkyl. In some embodiments, each $R^{2a}$, $R^{2b}$, $R^{12a}$, and $R^{12b}$ is independently H, halo, or —$OR^a$ and each $R^a$ is independently H or $C_{1-3}$ alkyl. In some embodiments, each $R^{2a}$, $R^{2b}$, $R^{12a}$, and $R^{12b}$ is independently H, halo, or —$OR^a$ and each $R^a$ is independently H or methyl.

In some embodiments, the compound of Formula I or II has a Formula V:

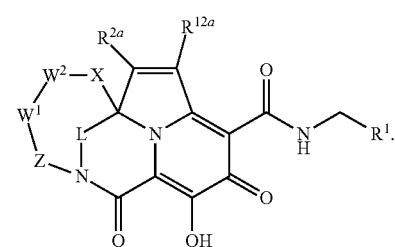

Formula V

In some embodiments, the compound of Formula I, Ia, II, or IIa has a Formula Va:

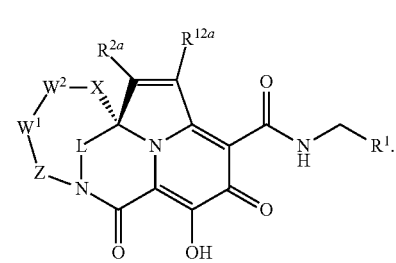

Formula Va

In some embodiments, the compound of Formula I, Ib, II, or IIb has a Formula Vb:

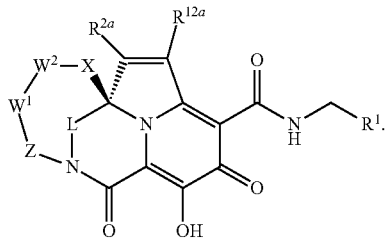

Formula Vb

In some embodiments, of the compound of Formula V, Va, and Vb, $R^{2a}$ and $R^{12a}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, —$OR^a$ or —$NHR^a$. In some embodiments, $R^{2a}$ and $R^{12a}$ are independently H, $C_{1-6}$alkyl, $C_{3-6}$cycloalkyl, halo, cyano, —$CH_2R^a$—, —$CH_2OR^a$, or —$OR^a$. In some embodiments, $R^{2a}$ and $R^{12a}$ are independently H, $C_{1-6}$alkyl, $C_{3-6}$cycloalkyl, or halo. In some embodiments, $R^{2a}$ and $R^{12a}$ are independently H or halo. In some embodiments, $R^{2a}$ and $R^{12a}$ are independently H, —C(O)—NH($R^a$)—, —$NR^e$—C(O)$R^a$—, —$NR^e$—S(O)$_n R^a$—, —S(O)$_n$—NH($R^a$)—, —S(O)$_n$—$R^a$—, or —O—C(O)—NH$R^a$. In some embodiments, $R^{2a}$ and $R^{12a}$ are independently H, —$OR^a$, —$NHR^a$, —C(O)—NH($R^a$), —$NR^e$—C(O)$R^a$, or —$NR^e$—S(O)$_n R^a$. In some embodiments, $R^{2a}$ and $R^{12a}$ are independently H, —$OR^a$, or —O—C(O)—NH$R^a$. In some embodiments, $R^{2a}$ and $R^{12a}$ are independently H, —S(O)$_n$—NH($R^a$), or —S(O)$_n$—$R^a$—; In some embodiments, $R^{2a}$ and $R^{12a}$ are independently H, halo, cyano, —NH$R^a$— or —$OR^a$. In some embodiments, $R^{2a}$ and $R^{12a}$ are independently H or —NH$R^a$. In some embodiments, $R^{2a}$ and $R^{12a}$ are independently is H, halo, cyano, or —$OR^a$. In some embodiments, $R^{2a}$ and $R^{12a}$ are independently H or cyano. In some embodiments, $R^{2a}$ and $R^{12a}$ are each H.

In some embodiments, of the compound of Formula V, Va, and Vb, $R^{2a}$ and $R^{12a}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, $CH_2$—S(O)$_n R^a$—, —$OR^a$, —O—C(O)—NH$R^a$—, —NH$R^a$—, —C(O)—NH($R^a$)—, —$NR^e$—C(O)$R^a$—, —$NR^e$—S(O)$_n R^a$—, —S(O)$_n$—NH ($R^a$)—, or —S(O)$_n$—$R^a$.

In some embodiments, of the compound of Formula V, Va, and Vb, $R^{2a}$ and $R^{12a}$ are independently H, $C_{1-6}$alkyl, $C_{1-6}$haloalkyl, $C_{3-6}$cycloalkyl, $C_{3-6}$halocycloalkyl, halo, cyano, —$CH_2R^a$—, —$CH_2OR^a$, $CH_2$—S(O)$_n R^a$—, —$OR^a$, —O—C(O)—NH$R^a$—, —NH$R^a$—, C(O)—NH($R^a$)—, —$NR^e$—C(O)$R^a$—, —$NR^e$—S(O)$_n R^a$—, —S(O)$_n$—NH ($R^a$)—, or —S(O)$_n$—$R^a$—.

In some embodiments, of the compound of Formula V, Va, and Vb, $R^{2a}$ and $R^{12a}$ are independently H, $C_{1-6}$alkyl, $C_{3-4}$cycloalkyl, halo, cyano, —$CH_2R^a$—, —$CH_2OR^a$, —$CH_2$—S(O)$_n R^a$, —$OR^a$, —O—C(O)—NH$R^a$, —NH$R^a$—, —C(O)—NH($R^a$)—, —$NR^e$—C(O)$R^a$—, —$NR^e$—S(O)$_n R^a$—, —S(O)$_n$—NH($R^a$)—, or —S(O)$_n$—$R^a$—;

In some embodiments, of the compound of Formula V, Va, and Vb, $R^{2a}$ and $R^{12a}$ are independently H, $C_{1-6}$alkyl, $C_{3-6}$cycloalkyl, halo, cyano, —$CH_2R^a$—, —$CH_2OR^a$, —$CH_2$—S(O)$_n R^a$, —$OR^a$, —O—C(O)—NH$R^a$, —NH$R^a$—, —C(O)—NH($R^a$)—, —$NR^e$—C(O)$R^a$—, —$NR^e$—S(O)$_n R^a$—, —S(O)$_n$—NH($R^a$)—, or —S(O)$_n$—$R^a$—;

In some embodiments, of the compound of Formula V, Va, and Vb, $R^{2a}$ and $R^{12a}$ are independently H, $C_{1-6}$alkyl, $C_{3-6}$cycloalkyl, halo, cyano, —$CH_2R^a$—, —$CH_2OR^a$, —$CH_2$—S(O)$_n R^a$, —$OR^a$, —O—C(O)—NH$R^a$, —NH$R^a$—, —C(O)—NH($R^a$)—, —$NR^e$—C(O)$R^a$—, —$NR^e$—S(O)$_n R^a$—, —S(O)$_n$—NH($R^a$)—, or —S(O)$_n$—$R^a$—;

In some embodiments, of the compound of Formula I, Ia, Ib, II, IIa, IIb, III, IIIa, IIIb, IV, IVa, IVb, V, Va, or Vb, $W^1$ is a bond or —$CR^{4a}R^{4b}$—$R^{4a}$; wherein $R^{4b}$ and $R^{4b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; or $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$. In some embodiments, of the compound of Formula I, Ia, Ib, II, IIa, IIb, III, IIIa, IIIb, IV, IVa, IVb, V, Va, or Vb, $W^1$ is a bond or —$CR^{4a}R^{4b}$—$R^{4a}$, wherein $R^{4a}$ and $R^{4b}$ are independently H, $C_{1-6}$alkyl, $C_{1-4}$haloalkyl, halo, hydroxyl, cyano, —O—$C_{1-4}$alkyl, or $C_{1-6}$alkylene-O—$C_{1-4}$alkyl. In some embodiments, $W^1$ is a bond or —$CR^{4a}R^{4b}$—$R^{4a}$, wherein $R^{4a}$ and $R^{4b}$ are independently H, $C_{1-6}$ alkyl, halo, $C_{1-4}$haloalkyl, or cyano. In some embodiments, $W^1$ is a bond or —$CR^{4a}R^{4b}$—$R^{4a}$, wherein $R^{4a}$ and $R^{4b}$ are independently H, $C_1$-$C_6$ alkyl, halo, or cyano. In some embodiments, $W^1$ is a bond or —$CR^{4a}R^{4b}$—$R^{4a}$, wherein $R^{4a}$ and $R^{4b}$ are independently H, halo, or $C_1$-$C_4$ alkyl. In some embodiments, $W^1$ is a bond or —$CR^{4a}R^{4b}$—$R^{4a}$, wherein $R^{4a}$ and $R^{4b}$ are independently H, fluoro, chloro, or $C_1$-$C_4$ alkyl. In some embodiments, $W^1$ is a bond or —$CR^{4a}R^{4b}$—$R^{4a}$, wherein $R^{4a}$ and $R^{4b}$ are independently H or cyano. In some embodiments, $W^1$ is a bond or —$CR^{4a}R^{4b}$—$R^{4a}$, wherein $R^{4a}$ and $R^{4b}$ are independently H or $C_{1-4}$haloalkyl.

In some embodiments, $W^1$ is a bond or —$CR^{4a}R^{4b}$—, wherein $R^{4a}$ and $R^{4b}$ together with the carbon atom to which they are attached form (i) a 3 to 7 membered carbocyclic ring or (ii) a 4 to 7 membered heterocyclic ring containing 0 to 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$. In some embodiments, $W^1$ is a bond or —$CR^{4b}$—, wherein $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, $W^1$ is a bond or —$CR^{4a}$% $R^b$—$R^{4a}$, wherein $R^{4a}$ and $R^{4b}$ together with the carbon atom to which they are attached form a 3 to 7 membered carbocyclic ring, wherein the 3 to 7 membered carbocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, $W^1$ is a bond or —$CR^{4a}$% $R^b$—, wherein $R^{4a}$ and $R^{4b}$ together with the carbon atom to which they are attached form a 4 to 7 membered heterocyclic ring containing 1 or 2 heteroatoms selected from N, O, and S, wherein the 4 to 7 membered heterocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, $W^1$ is a bond or —$CR^{4a}R^{4b}$—, wherein $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S. In some embodiments, $W^1$ is a bond or —$CR^{4\%}$ $R^b$—, wherein $R^{4a}$ and $R^{4b}$ together with the carbon atom to which they are attached form a 3 to 7 membered carbocyclic ring.

In some embodiments, $W^1$ is a bond or —$CR^{4\%}$ $R^b$—, wherein $R^{4a}$ and $R^{4b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl.

In some embodiments of the compound of Formula I, Ia, Ib, II, IIa, IIb, III, IIIa, IIIb, IV, IVa, IVb, V, Va, or Vb, $W^1$ is —$CR^{4a}R^{4b}$—, wherein $R^{4b}$ and $R^{4b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$-alkyl; or $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$. In some embodiments of the compound of Formula I, Ia, Ib, II, IIa, IIb, III, IIIa, IIIb, IV, IVa, IVb, V, Va, or Vb, $W^1$ is —$CR^{4a}R^{4b}$—, wherein $R^{4a}$ and $R^{4b}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-6}$alkyl. In some embodiments $W^1$ is-$CR^{4a}R^{4b}$—, wherein $R^{4a}$ and $R^{4b}$ are independently H, $C_1$-$C_6$ alkyl, halo, $C_{1-4}$haloalkyl, or cyano. In some embodiments, $W^1$ is —$CR^{4a}R^{4b}$—, wherein $R^{4a}$ and $R^{4b}$ are independently H, $C_1$-$C_6$ alkyl, halo, or cyano. In some embodiments, $W^1$ is a bond or —$CR^{4a}R^{4b}$—, wherein $R^{4a}$ and $R^{4b}$ are independently H, halo, or $C_1$-$C_4$alkyl. In some embodiments, $W^1$ is a bond or —$CR^{4a}R^{4b}$—, wherein $R^{4a}$ and $R^{4b}$ are independently H, fluoro, chloro, or $C_1$-$C_4$ alkyl. In some embodiments, $W^1$ is a bond or —$CR^{4a}R^{4b}$—, wherein $R^{4a}$ and $R^{4b}$ are independently H or cyano. In some embodiments, $W^1$ is a bond or —$CR^{4a}R^{4b}$—, wherein $R^{4a}$ and $R^{4b}$ are independently H or $C_{1-6}$haloalkyl.

In some embodiments, $W^1$ is —$CR^{4a}R^{4b}$—, wherein $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, $C_{3-6}$cycloalkyl or —$OR^e$. In some embodiments, $W^1$ is-$CR^{4a}R^{4b}$—, wherein $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, $W^1$ is —$CR^{4a}R^{4b}$—, wherein $R^{4a}$ and $R^{4b}$ together with the carbon atom to which they are attached form a 3 to 7 membered carbocyclic ring, wherein the 3 to 7 membered carbocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, $W^1$ is —$CR^{4a}R^{4b}$—, wherein $R^{4a}$ and $R^{4b}$ together with the carbon atom to which they are attached form a 4 to 7 membered heterocyclic ring containing 1 or 2 heteroatoms selected from N, O, and S, wherein the 4 to 7 membered heterocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, $W^1$ is —$CR^{4a}R^{4b}$—, wherein $R^{4a}$ and $R^{4b}$ together with the carbon atom to which they are attached form (i) a 3 to 7 membered carbocyclic ring or (ii) a 4 to 7 membered heterocyclic ring containing 1 or 2 heteroatoms selected from N, O, and S. In some embodiments, $W^1$ is a bond or —$CR^{4a}R^{4b}$—, wherein $R^{4a}$ and $R^{4b}$ together with the carbon atom to which they are attached form a 3 to 7 membered carbocyclic ring. In some embodiments, $W^1$ is —$CR^{4a}R^{4b}$—, wherein $R^{4a}$ and $R^{4b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl.

In some embodiments, of the compound of Formula I, Ia, Ib, II, IIa, IIb, III, IIIa, IIIb, IV, IVa, IVb, V, Va, or Vb, $W^1$ is a bond.

In some embodiments, of the compound of Formula I, Ia, Ib, II, IIa, IIb, III, IIIa, IIIb, IV, IVa, IVb, V, Va, or Vb, $W^2$ is —$CR^{5a}R^{5b}$—.

In some embodiments, of the compound of Formula I, Ia, Ib, II, IIa, IIb, III, IIIa, IIIb, IV, IVa, IVb, V, Va, or Vb, $W^2$ is —$CR^{6a}$=$CR^{6b}$—, wherein $R^{6a}$ and $R^{6b}$ is independently H, halo, $C_{1-4}$haloalkyl, or $C_{1-6}$alkyl. In some embodiments, $W^2$ is —$CR^{6a}$=$CR^{6b}$—, wherein each $R^{6a}$ and $R^{6b}$ together with the carbon atoms to which each is attached form (i) a 5 to 10 membered carbocyclic ring, (ii) 5 to 10 membered heterocyclic ring containing 1 or 2 heteroatom selected from N, O, and S, (iii) a 6 to 10 membered aromatic ring, or (iv) a 5 to 10 membered heteroaromatic ring containing 1 to 3 heteroatoms selected from N, O and S, wherein the 5 to 10 membered carbocyclic ring, 5 to 10 membered heterocyclic ring, 6 to 10 membered aromatic ring, or 5 to 10 membered heteroaromatic ring is optionally substituted with one to four $R^{44}$, wherein each $R^{44}$ is independently halo or $C_{1-6}$alkyl.

In some embodiments, $W^2$ is —$CR^{6a}$=$CR^{6b}$—, wherein each $R^{6a}$ and $R^{6b}$ together with the carbon atoms to which each is attached form (i) a 6 to 10 membered aromatic ring, or (ii) a 5 to 10 membered heteroaromatic ring containing 1 to 3 heteroatoms selected from N, O and S, wherein the 6 to 10 membered aromatic ring or the 5 to 10 membered heteroaromatic ring is optionally substituted with one to four $R^{44}$, wherein each $R^{44}$ is independently halo or $C_{1-6}$alkyl.

In some embodiments, $W^2$ is —$CR^{6a}$=$CR^{6b}$—, wherein each $R^{6a}$ and $R^{6b}$ together with the carbon atoms to which each is attached form (i) a 5 to 10 membered carbocyclic ring or (ii) a 5 to 10 membered heterocyclic ring containing 1 or 2 heteroatom selected from N, O, and S, wherein the 5 to 10 membered carbocyclic ring or the 5 to 10 membered heterocyclic ring, is optionally substituted with one to four $R^{44}$, wherein each $R^{44}$ is independently halo or $C_{1-4}$alkyl.

In some embodiments, of the compound of Formula I, Ia, Ib, II, IIa, IIb, III, IIIa, IIIb, IV, IVa, IVb, V, Va, or Vb, X is a bond. In some embodiments, of the compound of Formula I, Ia, Ib, II, IIa, IIb, III, IIIa, IIIb, IV, IVa, or IVb, X is —$CR^{8a}R^{8b}$—.

In some embodiments, of the compound of Formula I, Ia, Ib, II, IIa, IIb, III, IIIa, IIIb, IV, IVa, IVb, V, Va, or Vb, Z is —CR$^{9a}$R$^{9b}$—.

In some embodiments, of the compound of Formula I, Ia, Ib, II, IIa, IIb, III, IIIa, IIIb, IV, IVa, IVb, V, Va, or Vb, Z is —CR$^{10a}$=R$^{10b}$—, wherein each R$^{10a}$ and R$^{10b}$ is independently H, halo, C$_{1-4}$haloalkyl, or C$_{1-6}$alkyl. In some embodiments, Z is —CR$^{10a}$=CR$^{10b}$—, wherein each R$^{10a}$ and R$^{10b}$ together with the carbon atoms to which each is attached form (i) a 5 to 10 membered carbocyclic ring, (ii) 5 to 10 membered heterocyclic ring containing 1 or 2 heteroatom selected from N, O, and S, (iii) a 6 to 10 membered aromatic ring, or (iv) a 5 to 10 membered heteroaromatic ring containing 1 to 3 heteroatoms selected from N, O and S, wherein the 5 to 10 membered carbocyclic ring, 5 to 10 membered heterocyclic ring, 6 to 10 membered aromatic ring, or 5 to 10 membered heteroaromatic ring is optionally substituted with one to four R$^{44}$, wherein each R$^{44}$ is independently halo, oxo, cyano, or C$_{1-6}$alkyl. In some embodiments, Z is —CR$^{10a}$=CR$^{10b}$—, wherein each R$^{10a}$ and R$^{10b}$ together with the carbon atoms to which each is attached form (i) a 6 to 10 membered aromatic ring, or (ii) a 5 to 10 membered heteroaromatic ring containing 1 to 3 heteroatoms selected from N, O and S, wherein the 6 to 10 membered aromatic ring or the 5 to 10 membered heteroaromatic ring is optionally substituted with one to four R$^{44}$, wherein each R$^{44}$ is independently halo or C$_{1-6}$alkyl. In some embodiments, Z is —CR$^{10a}$=CR$^{10b}$—, wherein each R$^{10a}$ and R$^{10b}$ together with the carbon atoms to which each is attached form (i) a 5 to 10 membered carbocyclic ring or (ii) a 5 to 10 membered heterocyclic ring containing 1 or 2 heteroatom selected from N, O, and S, wherein the 5 to 10 membered carbocyclic ring or the 5 to 10 membered heterocyclic ring, is optionally substituted with one to four R$^{44}$, wherein each R$^{44}$ is independently halo or C$_{1-4}$alkyl.

In some embodiments, the compound of Formula I, IL, III, or IV has a Formula VI:

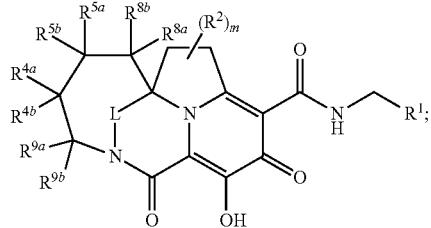

Formula VI wherein m is 0, 1, 2, 3, or 4; and
each R$^2$ is independently C$_{1-6}$alkyl, C$_{3-6}$cycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NHR$^a$—, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$—; or
two R$^2$ on same carbon atom, together with the carbon atom to which they both are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three R$^{42}$, wherein each R$^{42}$ is independently oxo, halo, cyano, C$_{1-6}$alkyl, C$_{3-6}$cycloalkyl or —OR$^e$.

In some embodiments, the compound of Formula I, Ia, II, IIa, III, IIIa, IV, or IVa has a Formula VIa:

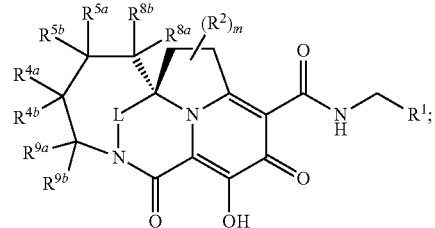

Formula VIa wherein m is 0, 1, 2, 3, or 4; and
each R$^2$ is independently C$_{1-6}$alkyl, or C$_{3-6}$cycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NHR$^a$—, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$—;
or two R$^2$ on same carbon atom, together with the carbon atom to which they both are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three R$^{42}$, wherein each R$^{42}$ is independently oxo, halo, cyano, C$_{1-6}$alkyl, C$_{3-6}$cycloalkyl or —OR$^e$.

In some embodiments, the compound of Formula I, Ib, II, IIb, III, IIIb, IV, or IVb has a Formula VIb:

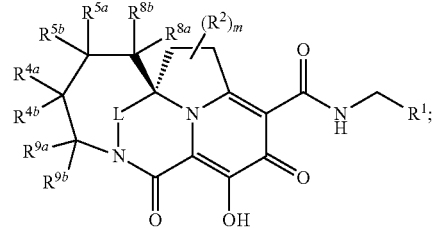

Formula VIb wherein m is 0, 1, 2, 3, or 4; and
each R$^2$ is independently C$_{1-6}$alkyl, C$_{3-6}$cycloalkyl, halo, cyano, —CH$_2$R$^a$—, —CH$_2$OR$^a$, —CH$_2$—S(O)$_n$R$^a$—, —OR$^a$, —O—C(O)—NHR$^a$, —NHR$^a$—, —C(O)—NH(R$^a$)—, —NR$^e$—C(O)R$^a$—, —NR$^e$—S(O)$_n$R$^a$—, —S(O)$_n$—NH(R$^a$)—, or —S(O)$_n$—R$^a$; or
two R$^2$ on same carbon atom, together with the carbon atom to which they both are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three R$^{42}$, wherein each R$^{42}$ is independently oxo, halo, cyano, C$_{1-6}$alkyl, C$_{3-6}$cycloalkyl or —OR$^e$.

In some embodiments, the compound of Formula I, Ia, Ib, II, IIa, IIb, III, IIIa, IIIb, IV, IVa, IVb, V, Va, Vb, VI, VIa, or VIb, L is —CR$^{3a}$R$^{3b}$—, —C(O)—, —SO$_2$—, —CR$^{3a}$R$^{3b}$—CR$^{3c}$R$^{3d}$—, or —N(R$^a$)—. In some embodiments, L is —CR$^{3a}$R$^{3b}$—, —C(O)—, —CR$^{3a}$R$^{3b}$—CR$^{3c}$R$^{3d}$—, or —$SO_2$—. In some embodiments, L is —$CR^{3a}R^{3b}$—, —C(O)— or —$CR^{3a}R^{3b}$—$CR^{3c}R^{3d}$—. In some embodiments, L is —$CR^{3a}R^{3b}$— or —$CR^{3a}R^{3b}$—$CR^{3c}R^{3d}$—. In some embodiments, L is —C(O)—. In some embodiments, L is —$SO_2$—. In some embodiments, L is —$CR^{3a}R^{3b}$—$CR^{3c}R^{3d}$—. In some embodiments, L is —N($R^a$)—. In some embodiments, L is —$CR^{3a}R^{3b}$—.

In some embodiments, the compound of Formula I, Ia, Ib, II, IIa, IIb, III, IIIa, IIIb, IV, IVa, IVb, V, Va, Vb, VI, VIa, or VIb, $R^{3a}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$. In some embodiments, $R^{3a}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a (i) 3 to 7 membered carbocyclic ring or (ii) 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, $R^{3a}$, $R^{3b}$, $R^{3c}$, and $R^{3d}$ are independently H, $C_{1-6}$alkyl, $C_{1-6}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a 3 membered carbocyclic ring, wherein the 3 membered carbocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, $R^{3a}$, $R^{3b}$, $R^{3c}$, and $R^{3d}$ are independently H, $C_{1-6}$alkyl, $C_{1-6}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a 3 membered carbocyclic ring. In some embodiments, $R^{3a}$, $R^{3b}$, $R^{3c}$, and $R^{3d}$ are independently H, $C_{1-6}$alkyl, $C_{1-4}$haloalkyl, or —O—$C_{1-4}$alkyl. In some embodiments, $R^{3a}$, $R^{3b}$, $R^{3c}$, and $R^{3d}$ are independently H, $C_{1-3}$alkyl, $C_{1-3}$haloalkyl, or —O—$C_{1-3}$alkyl. In some embodiments, $R^{3a}$, $R^{3b}$, $R^{3c}$, and $R^{3d}$ are independently H or $C_{1-3}$alkyl. In some embodiments, $R^{3a}$, $R^{3b}$, $R^{3c}$, and $R^{4d}$ are each H.

In some embodiments, the compound of Formula I, Ia, Ib, II, IIa, IIb, III, Ia, IIIb, IV, IVa, IVb, V, Va, Vb, VI, VIa, or VIb, L is —$CR^{3a}R^{3b}$— or —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$. In some embodiments, L is —$CR^{3a}R^{3b}$— or —$CR^{3a}R^{3b}$—$CR^{3c}R^{3d}$—, wherein $R^{38}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a (i) 3 to 7 membered carbocyclic ring or (ii) 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, L is —$CR^{3a}R^{3b}$— or —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-6}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a 3 membered carbocyclic ring, wherein the 3 membered carbocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, L is —$CR^{3a}R^{3b}$— or —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-6}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a 3 membered carbocyclic ring. In some embodiments, L is —$CR^{3a}R^{3b}$— or —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-4}$haloalkyl, or —O—$C_{1-4}$alkyl. In some embodiments, $R^{3a}$, $R^{3b}$, $R^{3c}$, and $R^{3d}$ are independently H, $C_{1-3}$alkyl, $C_{1-3}$haloalkyl, or —O—$C_{1-3}$alkyl. In some embodiments, L is —$CR^{3a}R^{3b}$— or —$CR^{3a}R^{3b}$—$CR^{3c}R^{3d}$—, wherein $R^{3a}$, $R^{3b}$, $R^{3c}$, and $R^{3d}$ are independently H or $C_{1-3}$alkyl. In some embodiments, $R^{3a}$, $R^{3b}$, $R^{3c}$, and $R^{3d}$ are each H.

In some embodiments, the compound of Formula I, Ia, Ib, II, IIa, IIb, III, IIIa, IIIb, IV, IVa, IVb, V, Va, Vb, VI, VIa, or VIb, L is —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$. In some embodiments, L is —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a (i) 3 to 7 membered carbocyclic ring or (ii) 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, L is —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-6}$haloalkyl, or —O—$C_{1-6}$alkyl; or any one of (i) $R^{3a}$ and $R^{3b}$ or (ii) $R^{3c}$ and $R^{3d}$ together with the carbon atom to which they are attached form a 3 membered carbocyclic ring, wherein the 3 membered carbocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, L is —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-6}$haloalkyl, or —O—$C_{1-6}$alkyl; or any one of (i) $R^{3a}$ and $R^{3b}$ or (ii) $R^{3c}$ and $R^{3d}$ together with the carbon atom to which they are attached form a 3 membered carbocyclic ring. In some embodiments, L is —$CR^{3a}R^{3b}$—$CR^{3c}R^{3d}$—, wherein $R^{3a}$, $R^{3b}$, $R^{3c}$, and $R^{3d}$ are independently H, $C_{1-6}$alkyl, $C_{1-4}$haloalkyl, or —O—$C_{1-6}$alkyl. In some embodiments, $R^{3a}$, $R^{3b}$, $R^{3c}$, and $R^{3d}$ are independently H, $C_{1-3}$alkyl, $C_{1-3}$haloalkyl, or —O—$C_{1-3}$alkyl. In some embodiments, L is —$CR^{3a}R^{3b}$—$CR^{3c}R^{3d}$—, wherein $R^{3a}$, $R^{3b}$, $R^{3c}$, and $R^{3d}$ are independently H or $C_{1-3}$alkyl. In some embodiments, L is —$CR^{3a}R^{3b}$—$CR^{3c}R^{3d}$—, wherein $R^{3a}$, $R^{3b}$, $R^{3c}$, and $R^{3d}$ are each H.

In some embodiments, the compound of Formula I, Ia, Ib, II, IIa, IIb, III, Ia, IIIb, IV, IVa, IVb, V, Va, Vb, VI, VIa, or VIb, L is —$CR^{3a}R^{3b}$—, wherein $R^{3a}$ and $R^{3b}$ are independently H, $C_{1-6}$alkyl, $C_{1-4}$haloalkyl, or —O—$C_{1-6}$alkyl; or any one of (i) $R^{3a}$ and $R^{3b}$ or (ii) $R^{3c}$ and $R^{3d}$ together with the carbon atom to which they are attached form (i) a 3 to 7 membered carbocyclic ring or (ii) a 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one to three $R^{A2}$, wherein each $R^{A2}$ is independently oxo, halo, cyano, $C_{1-6}$alkyl, $C_{3-6}$cycloalkyl or —$OR^e$. In some embodiments, L is —$CR^{3a}R^{3b}$—, wherein $R^{3a}$ and $R^{3b}$ are independently H, $C_{1-6}$alkyl, $C_{1-4}$haloalkyl, or —O—$C_{1-6}$alkyl; or any one of (i) $R^{3a}$ and $R^{3b}$ or (ii) $R^3$ and $R^{3d}$ together with the carbon atom to which they are attached form a (i) 3 to 7 membered carbocyclic ring or (ii) 3 to 7 membered heterocyclic ring containing 1 or 2 heteroatoms selected from N, O, and S, wherein the 3 to 7 membered carbocyclic ring or the 3 to 7 membered heterocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, L is —$CR^{3a}R^{3b}$—, wherein $R^{3a}$ and $R^{3b}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a 3 membered carbocyclic ring, wherein the 3 membered carbocyclic ring is optionally substituted with one or two $R^{A2}$, wherein each $R^{A2}$ is independently oxo, halo, cyano, $C_{1-6}$alkyl, or $C_{3-6}$cycloalkyl. In some embodiments, L is —$CR^{3a}R^{3b}$—, wherein $R^{3a}$ and $R^{3b}$ are independently H, $C_{1-6}$alkyl, $C_{1-4}$haloalkyl, or —O—$C_{1-4}$alkyl; or any one of (i) $R^{3a}$ and $R^{3b}$ or (ii) $R^{3c}$ and $R^{3d}$ together with the carbon atom to which they are attached form a 3 membered carbocyclic ring. In some embodiments, L is —$CR^{3a}R^{3b}$—, wherein $R^{3a}$ and $R^{3b}$ are independently H, $C_{1-6}$alkyl, $C_{1-4}$haloalkyl, or —O—$C_{1-4}$alkyl. In some embodiments, L is —$CR^{3a}R^{3b}$—, wherein $R^{3a}$ and $R^{3b}$ are independently H, $C_{1-3}$alkyl, $C_{1-3}$haloalkyl, or —O—$C_{1-3}$alkyl. In some embodiments, L is —$CR^{3a}R^{3b}$—, wherein $R^{3a}$ and $R^{3b}$ are independently H or $C_{1-3}$alkyl. In some embodiments, L is —$CR^{3a}R^{3b}$—, wherein $R^{3a}$ and $R^{3b}$ are each H.

In some embodiments, the compound of Formula I, IL, III, IV, or VI, has a Formula VII:

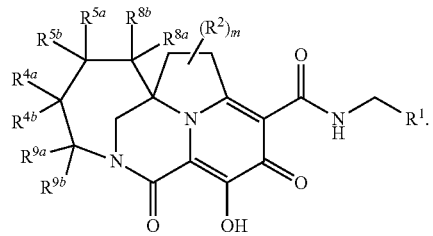

Formula VII

In some embodiments, the compound of Formula I, Ia, II, IIa, III, IIIa, IV, IVa, VI, or VIa, has a Formula VIIa:

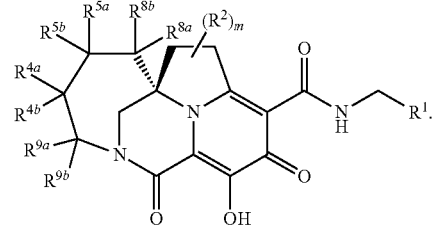

Formula VIIa

In some embodiments, the compound of Formula I, Ib, II, IIb, III, IIIb, IV, IVb, VI, or VIb, has a Formula VIIb:

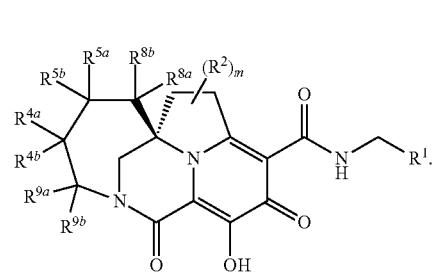

Formula VIIb

In some embodiments, of the compound of Formula I, Ia, Ib, II, IIa, IIb, III, IIIa, IIIb, IV, IVa, IVb, V, Va, Vb, VI, VIa, VIb, VII, VIIa, and VIIb, $R^1$ is a H, $C_{6-10}$aryl or $C_{6-10}$heteroaryl, wherein the $C_{6-10}$aryl or $C_{6-10}$heteroaryl are optionally substituted with one to four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl, or $C_{1-4}$alkyl-O—$C_{1-4}$alkyl.

In some embodiments, $R^1$ is H, phenyl, pyridyl, pyridazine, pyrazine, or pyrimidine, wherein the phenyl, pyridyl, pyridazine, pyrazine, or pyrimidine is optionally substituted with one to four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is phenyl, pyridyl, pyridazine, pyrazine, or pyrimidine, wherein the phenyl, pyridyl, pyridazine, pyrazine, or pyrimidine is optionally substituted with one, two, three, or four $R^{41}$, wherein each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo, $C_{1-4}$alkyl, $C_{1-4}$haloalkyl, or —O—$C_{1-6}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo, $C_{1-4}$alkyl, or —O—$C_{1-4}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo or $C_{1-4}$alkyl. In some embodiments, $R^1$ is phenyl, pyridyl, pyridazine, pyrazine, or pyrimidine, optionally substituted with one, two, three, or four $R^{41}$, wherein each $R^{41}$ is independently halo or —O—$C_{1-4}$alkyl.

In some embodiments, $R^1$ is phenyl, pyridyl, pyridazine, pyrazine, or pyrimidine substituted with one, two, three, or four halogens. In some embodiments, $R^1$ is phenyl, pyridyl, pyridazine, pyrazine, or pyrimidine substituted with two or three halogens. In some embodiments, $R^1$ is phenyl, pyridyl, pyridazine, pyrazine, or pyrimidine substituted with two or three halogens selected from chloro and fluoro.

In some embodiments, $R^1$ is H, phenyl or pyridyl, wherein the phenyl or pyridyl is optionally substituted with one to four $R^{A1}$, wherein each $R^{A1}$ is independently halo, $C_{1-4}$alkyl, $C_{1-6}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is phenyl or pyridyl, wherein the phenyl or pyridyl is optionally substituted with one, two, three, or four $R^{A1}$, wherein each $R^{A1}$ is independently halo, $C_{1-6}$alkyl, $C_{1-6}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is phenyl or pyridyl, optionally substituted with one, two, three, or four $R^{A1}$, wherein each $R^{A1}$ is independently halo, $C_{1-4}$alkyl, $C_{1-6}$haloalkyl, or —O—$C_{1-6}$alkyl. In some embodiments, $R^1$ is phenyl or pyridyl, optionally substituted with one, two, three, or four $R^{A1}$, wherein each $R^{A1}$ is independently halo, $C_{1-4}$alkyl, or —O—$C_{1-4}$alkyl. In some embodiments, $R^1$ is phenyl or pyridyl, optionally substituted with one, two, three, or four $R^{A1}$, wherein each $R^{A1}$ is independently halo or $C_{1-4}$alkyl. In some embodiments, $R^1$ is phenyl or pyridyl, optionally substituted with one, two, three, or four $R^{A1}$, wherein each $R^{A1}$ is independently halo or —O—$C_{1-4}$alkyl. In some embodiments, $R^1$ is phenyl or pyridyl substituted with one, two, three, or four halogens. In some embodiments, $R^1$ is phenyl or pyridyl substituted with two or three halogens. In some embodiments, $R^1$ is phenyl or pyridyl substituted with two or three halogens selected from chloro and fluoro.

In some embodiments, of the compound of Formula I, Ia, Ib, II, IIa, IIb, III, IIIa, IIIb, IV, IVa, IVb, V, Va, Vb, VI, VIa, VIb, VII, VIIa, or VIIb, $R^1$ is H or a $C_{6-10}$aryl, wherein the $C_{6-10}$aryl is optionally substituted with one to four $R^{A1}$, wherein each $R^{A1}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is H or phenyl, wherein the phenyl is optionally substituted with one to four $R^{A1}$, wherein each $R^{A1}$ is independently halo, $C_{1-6}$alkyl, $C_{1-6}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is phenyl, optionally substituted with one, two, three, or four $R^{A1}$, wherein each $R^{A1}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is phenyl, optionally substituted with one, two, three, or four $R^{A1}$, wherein each $R^{A1}$ is independently halo, $C_{1-4}$alkyl, $C_{1-4}$haloalkyl, or —O—$C_{1-6}$alkyl. In some embodiments, $R^1$ is phenyl, optionally substituted with one, two, three, or four $R^{A1}$, wherein each $R^{A1}$ is independently halo, $C_{1-6}$alkyl, or —O—$C_{1-4}$alkyl. In some embodiments, $R^1$ is phenyl, optionally substituted with one, two, three, or four $R^{A1}$, wherein each $R^{A1}$ is independently halo or $C_{1-4}$alkyl. In some embodiments, $R^1$ is phenyl, optionally substituted with one, two, three, or four $R^{A1}$, wherein each $R^{A1}$ is independently halo or —O—$C_{1-4}$alkyl. In some embodiments, $R^1$ is phenyl substituted with one, two, three, or four halogens. In some embodiments, $R^1$ is phenyl substituted with two or three halogens. In some embodiments, $R^1$ is phenyl substituted with two or three halogens selected from chloro and fluoro.

In some embodiments, $R^1$ is selected from the group consisting of

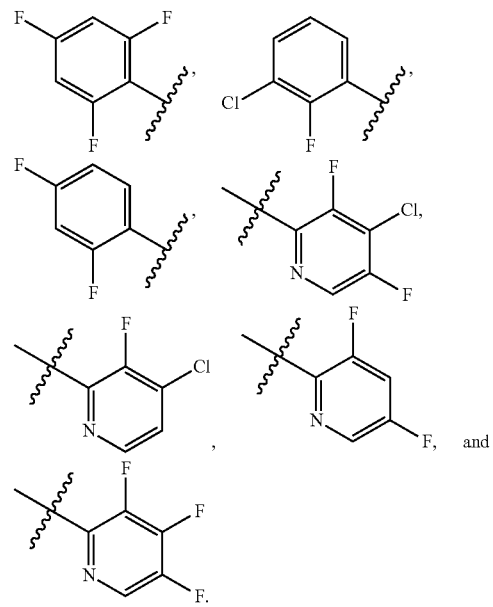

In some embodiments, $R^1$ is selected from the group consisting of:

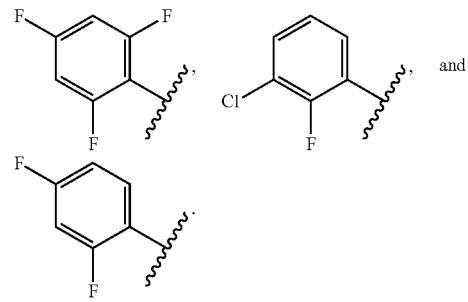

In some embodiments, $R^1$ is selected from the group consisting of

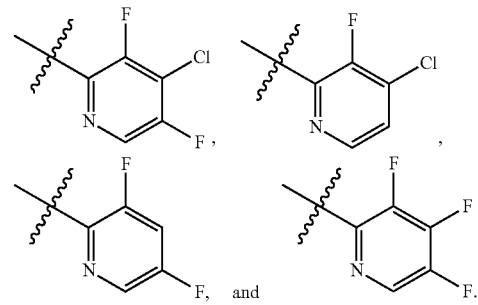

In some embodiments, $R^1$ is pyridyl, optionally substituted with one, two, three, or four $R^{A1}$, wherein each $R^{A1}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, $R^1$ is pyridyl, optionally substituted with one, two, three, or four $R^{A1}$, wherein each $R^{A1}$ is independently halo, $C_{1-4}$alkyl, $C_{1-4}$haloalkyl, or —O—$C_{1-4}$alkyl. In some embodiments, $R^1$ is pyridyl, optionally substituted with one, two, three, or four $R^{A1}$, wherein each $R^{A1}$ is independently halo, $C_{1-4}$alkyl, or —O—$C_{1-4}$alkyl. In some embodiments, $R^1$ is pyridyl, optionally substituted with one, two, three, or four $R^{A1}$, wherein each $R^{A1}$ is independently halo or $C_{1-6}$alkyl. In some embodiments, $R^1$ is pyridyl, optionally substituted with one, two, three, or four $R^{A1}$, wherein each $R^{A1}$ is independently halo or —O—$C_{1-4}$alkyl. In some embodiments, $R^1$ is pyridyl substituted with one, two, three, or four halogens. In some embodiments, $R^1$ is pyridyl substituted with two or three halogens. In some embodiments, $R^1$ is pyridyl substituted with two or three halogens selected from chloro and fluoro.

In some embodiments, the compound of Formula I, IL, III, IV, VI, or VII, has a Formula VIII:

Formula VIII

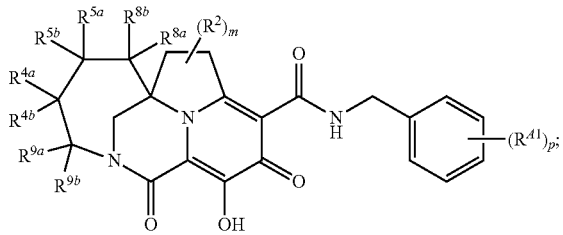

wherein p is 2 or 3.

In some embodiments, the compound of Formula I, Ia, II, IIa, III, IIIa, IV, IVa, VI, VIa, VII, or VIIa, has a Formula VIIIa:

Formula VIIIa

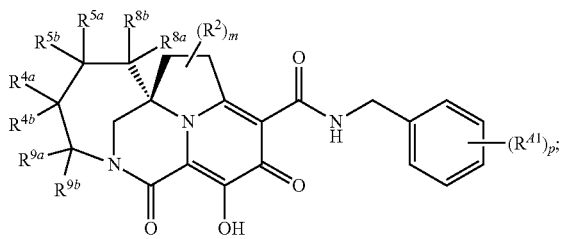

wherein p is 2 or 3.

In some embodiments, the compound of Formula I, Ib, II, IIb, III, IIIb, IV, IVb, VI, VIb, VII, or VIIb, has a Formula VIIIb:

Formula VIIIb

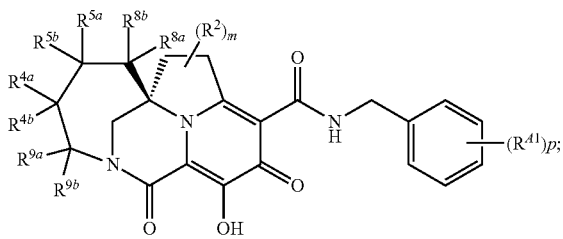

wherein p is 2 or 3.

In some embodiments, for the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, each $R^{A1}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, each $R^{A1}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-6}$alkyl-O—$C_{1-4}$alkyl. In some embodiments, each $R^{A1}$ is independently halo, $C_{1-6}$alkyl, $C_{1-6}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, each $R^{A1}$ is independently halo, $C_{1-4}$alkyl, $C_{1-4}$haloalkyl, or —O—$C_{1-4}$alkyl. In some embodiments, each $R^{A1}$ is independently halo, $C_{1-4}$alkyl, or —O—$C_{1-6}$alkyl. In some embodiments, each $R^{A1}$ is independently halo, $C_{1-4}$alkyl, cyano, or —O—$C_{1-6}$alkyl. In some embodiments, each $R^{A1}$ is independently halo, cyano, or $C_{1-4}$alkyl. In some embodiments, each $R^{A1}$ is independently halo or $C_{1-4}$alkyl. In some embodiments, each $R^{A1}$ is independently halo, cyano, or —O—$C_{1-4}$alkyl. In some embodiments, each $R^{A1}$ is independently halo or —O—$C_{1-4}$alkyl. In some embodiments, each $R^{A1}$ is independently a halogen. In some embodiments, each $R^{A1}$ is independently chloro or fluoro.

In some embodiments, for the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, $R^{4a}$, $R^{4b}$, $R^{5a}$, $R^{5b}$, $R^{8a}$, $R^{8b}$, $R^{9a}$ and $R^{9b}$ are each independently H, $C_{1-6}$alkyl, $C_{1-6}$haloalkyl, halo, hydroxyl, cyano, —O—$C_{1-4}$alkyl, or $C_{1-4}$alkylene-O—$C_{1-4}$alkyl. In some embodiments, $R^{4a}$, $R^{4b}$, $R^{5a}$, $R^{5b}$, $R^{8a}$, $R^{8b}$, $R^{9a}$ and $R^{9b}$ are each independently H, $C_1$-$C_6$ alkyl, halo, or cyano. In some embodiments, $R^{4a}$, $R^{4a}$, $R^{5a}$, $R^{5b}$, $R^{8a}$, $R^{8b}$, $R^{9a}$ and $R^{9b}$ are each independently H, halo, or $C_1$-$C_4$ alkyl. In some embodiments, $R^{4a}$, $R^{4b}$, $R^{5a}$, $R^{5b}$, $R^{8a}$, $R^{8b}$, $R^{9a}$ and $R^{9b}$ are each independently H, fluoro, chloro, or $C_1$-$C_4$ alkyl. In some embodiments, $R^{4a}$, $R^{4b}$, $R^{5a}$, $R^{5b}$, $R^{8a}$, $R^{8b}$, $R^{9a}$ and $R^{9b}$ are each independently H or cyano. In some embodiments, $R^{4a}$, $R^{4b}$, $R^{5a}$, $R^{5b}$, $R^{6a}$, $R^{6b}$, $R^{9a}$ and $R^{9b}$ are each independently H or $C_{1-4}$haloalkyl.

In some embodiments, for the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a (i) 3 to 7 membered carbocyclic ring or (ii) 4 to 7 membered heterocyclic ring containing 1 to 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-4}$alkyl, $C_{3-6}$cycloalkyl or —$OR^e$. In some embodiments, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a (i) 3 to 7 membered carbocyclic ring or (ii) 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a 3 to 7 membered carbocyclic ring, wherein the 3 to 7 membered carbocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a 4 to 7 membered heterocyclic ring containing 1 or 2 heteroatoms selected from N, O, and S, wherein the 3 to 7 membered carbocyclic ring or the 4 to 7 membered heterocyclic ring is optionally substituted with one to three $R^{43}$, wherein each $R^{43}$ is independently oxo, halo, cyano, $C_{1-6}$alkyl, or $C_{3-6}$cycloalkyl. In some embodiments, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a (i) 3 to 7 membered carbocyclic ring or a (ii) 3 to 7 membered heterocyclic ring containing 1 or 2 heteroatoms selected from N, O, and S. In some embodiments, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl. In some embodiments, any one of (i) $R^{4a}$ and $R^{4b}$, (ii) $R^{5a}$ and $R^{5b}$, (iii) $R^{8a}$ and $R^{8b}$, or (iv) $R^{9a}$ and $R^{9b}$ together with the carbon atom to which they are attached form a 3 to 7 membered carbocyclic ring. In some embodiments, $R^{4a}$ and $R^{4b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl. In some embodiments $R^{5a}$ and $R^{5b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl. In some embodiments, $R^{8a}$ and $R^{8b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl. In some embodiments, $R^{9a}$ and $R^{9b}$ together with the carbon atom to which they are attached form a 3 membered carbocyclic ring optionally substituted with one to three $R^{43}$, wherein each $R^{43}$ is independently oxo, halo, cyano, $C_{1-6}$alkyl, or $C_{3-6}$cycloalkyl. In some embodiments, $R^{4a}$ and $R^{4b}$ together with the carbon atom to which they are attached form a 3 membered carbocyclic ring. In some embodiments $R^{5a}$ and $R^{5b}$ together with the carbon atom to which they are attached form a 3 membered carbocyclic ring. In some embodiments, $R^{8a}$ and $R^{8b}$ together with the carbon atom to which they are attached form a 3 membered carbocyclic ring. In some embodiments, $R^{9a}$ and $R^{9b}$ together with the carbon atom to which they are attached form a 3 membered carbocyclic ring.

In some embodiments, for the compounds of Formula VI, VIa, VIb, VII, VIIa, VIIb, VIII VIIIa or VIIIb, m is 0, 1, or 2. In some embodiments, m is 0. In some embodiments, m is 1. In some embodiments, m is 2.

In some embodiments, for the compounds of Formula VI, VIa, VIb, VII, VIIa, VIIb, VIII VIIIa or VIIIb, each $R^2$ is independently $C_{1-6}$alkyl, $C_{3-6}$cycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or two $R^2$ on same carbon atom together with the carbon atom to which they both are attached form a 3 to 7 membered carbocyclic ring wherein the 3 to 7 membered carbocyclic ring is optionally substituted with one to three $R^{42}$, wherein each $R^{42}$ is independently oxo, halo, cyano, $C_{1-6}$alkyl, $C_{3-6}$cycloalkyl or —$OR^e$.

In some embodiments, for the compounds of Formula VI, VIa, VIb, VII, VIIa, VIIb, VII, VIIIa or VIIIb, each $R^2$ is independently $C_{1-6}$alkyl, $C_{3-6}$cycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or $R^{2a}$ and $R^{2b}$ or two $R^2$ on same carbon atom together with the carbon atom to which they both are attached form a 3-5 membered carbocyclic ring wherein the 3-5 membered carbocyclic ring is optionally substituted with one to three $R^{42}$, wherein each $R^{42}$ is independently oxo, halo, cyano, $C_{1-6}$alkyl, $C_{3-6}$cycloalkyl or —$OR^e$.

In some embodiments, for the compounds of Formula VI, VIa, VIb, VII, VIIa, VIIb, VIII, VIIIa or VIIIb, each $R^2$ is independently $C_{1-4}$alkyl, $C_{3-6}$cycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—; —$NR^e$—$S(O)_nR^a$—, —$S(O)_n$—NH($R^a$)—, or —$S(O)_n$—$R^a$—; or two $R^2$ on same carbon atom together with the carbon atom to which they both are attached form a 3 membered carbocyclic ring, wherein the 3 membered carbocyclic ring is optionally substituted with one to three $R^{42}$, wherein each $R^{42}$ is independently oxo, halo, cyano, $C_{1-6}$alkyl, $C_{3-6}$cycloalkyl or —$OR^e$.

In some embodiments, for the compounds of Formula VI, VIa, VIb, VII, VIIa, VIIb, VIII, VIIIa or VIIb, each $R^2$ is independently $C_{1-6}$alkyl, $C_{3-6}$cycloalkyl, halo, cyano, —$CH_2R^a$—, —$CH_2OR^a$, —$CH_2$—$S(O)_nR^a$—, —$OR^a$, —O—C(O)—$NHR^a$, —$NHR^a$—, —C(O)—NH($R^a$)—, —$NR^e$—C(O)$R^a$—, —$NR^e$—$S(O)_nR^a$—, —$S(O)_n$—NH($R^a$)—, or —$S(O)_n$—$R^a$—; or two $R^2$ on same carbon atom together with the carbon atom to which they both are attached form a 3 membered carbocyclic ring.

In some embodiments, the compounds of Formula VI, VIa, VIb, VII, VIIa, VIIb, VIII, VIIIa or VIIIb, each $R^2$ is independently $C_{1-6}$alkyl, $C_{3-6}$cycloalkyl, halo, cyano, —$CH_2R^a$—, —$CH_2OR^a$, —$OR^a$ or —$NHR^a$. In some embodiments, each $R^2$ is independently $C_{1-6}$alkyl, $C_{3-6}$cycloalkyl, halo, cyano, —$CH_2R^a$—, —$CH_2OR^a$, or —$OR^a$. In some embodiments, each $R^2$ is independently $C_{1-6}$alkyl, $C_{3-6}$cycloalkyl, or halo. In some embodiments, each $R^2$ is independently halo. In some embodiments, each $R^2$ is independently —C(O)—NH($R^a$)—, —$NR^e$—C(O)$R^a$—, —$NR^e$—$S(O)_nR^a$—, —$S(O)_n$—NH($R^a$)—, —$S(O)_n$—$R^a$—, or —O—C(O)—$NHR^a$. In some embodiments, each $R^2$ is independently —$OR^a$, —$NHR^a$, C(O)—NH($R^a$), $NR^e$—C(O)$R^a$, or —$NR^e$—$S(O)_nR^a$. In some embodiments, each $R^2$ is independently —$OR^a$, or —O—C(O)—$NHR^a$. In some embodiments, each $R^2$ is independently —S(O)NH($R^a$), or —$S(O)_n$—$R^a$—; In some embodiments, each $R^2$ is independently halo, cyano, —$NHR^a$— or —$OR^a$. In some embodiments, each $R^2$ is —$NHR^a$. In some embodiments, each $R^2$ is independently is halo, cyano, or —$OR^a$. In some embodiments, each $R^2$ is cyano. In some embodiments, each $R^2$ is independently —$OR^a$. In some embodiments, each $R^2$ is independently —OR and each $R^a$ is independently $C_3$-$C_6$ cycloalkyl optionally substituted optionally substituted with 1 to 2 substituents independently selected from the group consisting of halo, cyano, and —O—$C_1$-$C_4$alkyl. In some embodiments, each $R^2$ is independently —$OR^a$; wherein each $R^a$ is independently $C_1$-$C_6$ alkyl optionally substituted with 1 to 2 substituents independently selected from the group consisting of halo, cyano, —O—$C_1$-$C_4$ alkyl. In some embodiments, each $R^2$ is independently —$OR^a$; wherein each $R^a$ is independently $C_1$-$C_6$ alkyl optionally substituted with a —O—$C_{1-4}$alkyl or halo. In some embodiments, each $R^2$ is independently —$OR^a$; wherein each $R^a$ is independently $C_1$-$C_6$ alkyl optionally substituted with a —O—$C_{1-4}$alkyl.

In some embodiments, the compounds of Formula VI, VIa, VIb, VII, VIIa, VIIb, VIII, VIIIa or VIIIb, m is 2 and each $R^2$ is independently $C_{1-6}$alkyl, $C_{3-6}$cycloalkyl, halo, cyano, —$CH_2R^a$—, —$CH_2OR^a$, —$OR^a$ or —$NHR^a$. In some embodiments, m is 2 and each $R^2$ is independently $C_{1-6}$alkyl, $C_{3-6}$cycloalkyl, halo, cyano, —$CH_2R^a$—, —$CH_2OR^a$, or —$OR^a$. In some embodiments, m is 2 and each $R^2$ is independently $C_{1-6}$alkyl, $C_{3-6}$cycloalkyl, or halo. In some embodiments, m is 2 and each $R^2$ is independently halo. In some embodiments, m is 2 and each $R^2$ is independently —C(O)—NH($R^a$)—, —$NR^e$—C(O)$R^a$—, —$NR^e$—S(O)$_n$$R^a$—, —S(O)$_n$—NH($R^a$)—, —S(O)$_n$—$R^a$—, or —O—C(O)—$NHR^a$. In some embodiments, m is 2 and each $R^2$ is independently-$OR^a$, —$NHR^a$—, —C(O)—NH($R^a$), —$NR^e$—C(O)$R^a$, or —$NR^e$—S(O)$_n$$R^a$. In some embodiments, m is 2 and each $R^2$ is independently-$OR^a$, or —O—C(O)—$NHR^a$. In some embodiments, m is 2 and each $R^2$ is independently —S(O)$_n$—NH($R^a$), or —S(O)$_n$—$R^a$—. In some embodiments, m is 2 and each $R^2$ is independently halo, cyano, —$NHR^a$— or —$OR^a$. In some embodiments, m is 2 and each $R^2$ is independently —$NHR^a$. In some embodiments, m is 2 and each $R^2$ is independently is halo, cyano, or —$OR^a$. In some embodiments, m is 2 and each $R^2$ is cyano. In some embodiments, m is 2 and each $R^2$ is independently a halo. In some embodiments, m is 2 and each $R^2$ is independently —$OR^a$. In some embodiments, m is 2 and each $R^2$ is independently —$OR^a$ and each $R^a$ is independently $C_3$-$C_6$ cycloalkyl optionally substituted optionally substituted with 1 to 2 substituents independently selected from the group consisting of halo, cyano, and —O—$C_1$-$C_4$alkyl. In some embodiments, m is 2 and each $R^2$ is independently —$OR^a$; wherein each $R^a$ is independently $C_1$-$C_6$ alkyl optionally substituted with 1 to 2 substituents independently selected from the group consisting of halo, cyano, —O—$C_1$-$C_4$ alkyl. In some embodiments, m is 2 and each $R^2$ is independently —$OR^a$; wherein each $R^a$ is independently $C_1$-$C_6$ alkyl optionally substituted with a —O—$C_{1-4}$alkyl or halo. In some embodiments, each m is 2 and $R^2$ is independently —$OR^a$; wherein each $R^a$ is independently $C_1$-$C_6$ alkyl optionally substituted with a —O—$C_{1-4}$alkyl.

In some embodiments, the compounds of Formula VI, VIa, VIb, VII, VIIa, VIIb, VIII, VIIIa or VIIIb, m is 1 and $R^2$ is $C_{1-6}$alkyl, $C_{3-6}$cycloalkyl, halo, cyano, —$CH_2R^a$—, —$CH_2OR^a$, —$OR^a$ or —$NHR^a$. In some embodiments, m is 1 and $R^2$ is $C_{1-4}$alkyl, $C_{3-6}$cycloalkyl, halo, cyano, —$CH_2R^a$—, —$CH_2OR^a$, or —$OR^a$. In some embodiments, m is 1 and $R^2$ is $C_{1-6}$alkyl, $C_{3-6}$cycloalkyl, or halo. In some embodiments, m is 1 and $R^2$ is halo. In some embodiments, m is 1 and $R^2$ is —C(O)—NH($R^a$)—, —$NR^e$—C(O)$R^a$—, —$NR^e$—S(O)$_n$$R^a$—, —S(O)$_n$—NH($R^a$)—, —S(O)$_n$—$R^a$—, or —O—C(O)—$NHR^a$. In some embodiments, m is 1 and $R^2$ is —$OR^a$, —$NHR^a$, —C(O)—NH($R^a$), —$NR^e$—C(O)$R^a$, or —$NR^e$—S(O)$_n$$R^a$. In some embodiments, m is 1 and $R^2$ is —$OR^a$, or —O—C(O)—$NHR^a$. In some embodiments, m is 1 and $R^2$ is —S(O)$_n$—NH($R^a$), or —S(O)$_n$—$R^a$—. In some embodiments, m is 1 and $R^2$ is halo, cyano, —$NHR^a$— or —$OR^a$. In some embodiments, m is 1 and $R^2$ is —$NHR^a$. In some embodiments, m is 1 and $R^2$ is halo, cyano, or —$OR^a$. In some embodiments, m is 1 and $R^2$ is cyano. In some embodiments, m is 1 and $R^2$ is halo. In some embodiments, m is 1 and $R^2$ is —$OR^a$. In some embodiments, m is 1 and $R^2$ is —$OR^{6a}$ and $R^{6b}$ is $C_3$-$C_6$ cycloalkyl optionally substituted optionally substituted with 1 to 2 substituents independently selected from the group consisting of halo, cyano, and —O—$C_1$-$C_4$alkyl. In some embodiments, m is 1 and $R^2$ is —$OR^a$; wherein $R^a$ is $C_1$-$C_6$ alkyl optionally substituted with 1 to 2 substituents independently selected from the group consisting of halo, cyano, —O—$C_1$-$C_4$ alkyl. In some embodiments, m is 1 and $R^2$ is —$OR^a$; wherein $R^a$ is $C_1$-$C_6$ alkyl optionally substituted with a —O—$C_{1-4}$alkyl or halo. In some embodiments, each m is 1 and $R^2$ is —$OR^a$; wherein each $R^a$ is $C_1$-$C_6$ alkyl optionally substituted with a —O—$C_{1-6}$alkyl.

In some embodiments, the compounds of Formula VI, VIa, VIb, VII, VIIa, VIIb, VIII, VIIIa or VIIIb, m is 1 or 2, each $R^2$ is independently halo or —$OR^a$, and each $R^a$ is independently H or $C_1$-$C_6$ alkyl. In some embodiments, m is 1 or 2, each $R^2$ is independently halo or —$OR^a$, and each $R^a$ is independently H or $C_1$-$C_3$ alkyl. In some embodiments, m is 1 or 2, each $R^2$ is independently halo or —$OR^a$, and each $R^a$ is independently H or methyl. In some embodiments, m is 1 or 2, each $R^2$ is independently halo or —$OR^a$, and each $R^a$ is H. In some embodiments, m is 1 or 2, each $R^2$ is independently halo or —$OR^a$, and each $R^a$ is methyl.

In some embodiments, the compounds of Formula VI, VIa, VIb, VII, VIIa, VIIb, VIII, VIIIa or VIIIb, m is 1, $R^2$ is halo or —$OR^a$, and $R^a$ is H or $C_1$-$C_6$ alkyl. In some embodiments, m is 1, $R^2$ is halo or —$OR^a$, and $R^a$ is H or $C_1$-$C_3$ alkyl. In some embodiments, m is 1, $R^2$ is halo or —$OR^a$, and $R^a$ is H or methyl. In some embodiments, m is 1, $R^2$ is halo or —$OR^a$, and $R^a$ is H. In some embodiments, m is 1, $R^2$ is halo or —$OR^a$, and $R^a$ is methyl.

In some embodiments, the compounds of Formula VI, VIa, VIb, VII, VIIa, VIIb, VIII, VIIIa or VIIIb, m is 2, each $R^2$ is independently halo or —$OR^a$, and each $R^a$ is independently H or $C_1$-$C_6$ alkyl. In some embodiments, m is 2, each $R^2$ is independently halo or —$OR^a$, and each R is independently H or $C_1$-$C_3$ alkyl. In some embodiments, m is 2, each $R^2$ is independently halo or —$OR^a$, and each $R^a$ is independently H or methyl. In some embodiments, m is 2, each $R^2$ is independently halo or —$OR^a$, and each $R^a$ is H. In some embodiments, m is 2, each $R^2$ is independently halo or —$OR^a$, and each $R^a$ is methyl.

In some embodiments, of the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, and VIIIb, each $R^a$ is independently H, $C_{1-4}$alkyl, or $C_{3-6}$cycloalkyl; wherein the $C_{1-6}$alkyl or $C_{3-6}$cycloloalkyl is optionally substituted with 0 to 4 substituents independently selected from the group consisting of halo, cyano, —O—$C_{1-4}$alkyl, 5 to 10 membered carbocyclic ring, 5 to 10 membered heterocyclic ring containing 1 or 2 heteroatom selected from N, O, and S, 6 to 10 membered aromatic ring, and 5 to 10 membered heteroaromatic ring containing 1 or 3 heteroatoms selected from N, O and S, wherein the 5 to 10 membered carbocyclic ring, 5 to 10 membered heterocyclic ring, the 6 to 10 membered aromatic ring, or the 5 to 10 membered heteroaromatic ring is optionally substituted with one to four $R^{A5}$, wherein each $R^{A5}$ is independently oxo, halo, cyano, $C_{1-6}$alkyl, $C_{1-6}$cycloloalkyl or —$OR^e$.

In some embodiments, of the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, and VIIIb, each $R^a$ is independently H, $C_1$-$C_6$ alkyl, or $C_3$-$C_6$ cycloalkyl optionally substituted with 1 to 2 substituents independently selected from the group consisting of halo, cyano, —O—$C_1$-$C_4$ alkyl, 5 to 10 membered carbocyclic ring, and 5 to 10 membered heterocyclic ring containing 1 or 2 heteroatoms selected from N, O and S.

In some embodiments, of the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, and VIIIb, each $R^a$ is independently H, $C_1$-$C_4$ alkyl, or $C_3$-$C_6$ cycloalkyl optionally substituted with 1 to 2 substituents independently selected from the group consisting of halo, cyano, and —O—$C_1$-$C_4$ alkyl.

In some embodiments, of the compounds of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, and VIIIb, each $R^a$ is independently $C_3$-$C_6$ cycloalkyl optionally substituted optionally substituted with 1 to 2 substituents independently selected from the group consisting of halo, cyano, and —O—$C_1$-$C_4$alkyl.

In some embodiments, of the compounds of Formula I, Ia, Ib, II, IIa, IIb, III, IIIa, IIIb, IV, IVa, IVb, V, Va, Vb, VI, VIa, VIb, VII, VIIa, VIb, VIII, VIIIa, and VIIIb, each $R^a$ is independently $C_1$-$C_6$ alkyl optionally substituted with 1 to 2 substituents independently selected from the group consisting of halo, cyano, —O—$C_1$-$C_4$ alkyl.

In some embodiments, of the compounds of Formula I, Ia, Ib, II, IIa, IIb, III, IIa, IIIa, IIIb, IV, IVa, IVb, V, Va, Vb, VI, VIa, VIb, VII, VIIa, VIIb, VIII, VIIIa, and VIIIb, each $R^a$ is independently $C_{1-6}$alkyl optionally substituted with a —O—$C_{1-4}$alkyl or halo.

In some embodiments, of the compounds of Formula I, Ia, Ib, II, IIa, IIb, ILI, IIIa, IIIb, IV, IVa, IVb, V, Va, Vb, VI, VIa, VIb, VII, VIIa, VIIb, VIII, VIIIa, and VIIIb, each $R^a$ is independently a 5 to 10 membered carbocyclic ring, 5 to 10 membered heterocyclic ring containing 1 or 2 heteroatom selected from N, O, and S, a 6 to 10 membered aromatic ring, or a 5 to 10 membered heteroaromatic ring containing 1 or 3 heteroatoms selected from N, O and S, wherein the 5 to 10 membered carbocyclic ring, 5 to 10 membered heterocyclic ring, the 6 to 10 membered aromatic ring, or the 5 to 10 membered heteroaromatic ring is optionally substituted with one to four $R^{44}$, wherein each $R^{44}$ is independently oxo, halo, cyano, $C_{1-6}$alkyl, $C_{1-6}$cycloloalkyl or —$OR^e$.

In some embodiments of the compound of Formula I, Ia, Ib, II, IIa, IIb, ILI, IIIa, IIIb, IV, IVa, IVb, V, Va, Vb, VI, VIa, VIb, VII, VIIa, VIIb, VIII, VIIIa, and VIIIb, each $R^e$ is independently H, $C_{1-6}$alkyl or $C_{3-6}$cycloalkyl wherein each $C_{1-6}$alkyl or $C_{3-6}$cycloalkyl is optionally substituted by a halo or a cyano. In some embodiments, each $R^e$ is independently H, $C_{1-6}$alkyl or $C_{3-6}$cycloalkyl. In some embodiments, each $R^e$ is independently H or $C_{1-4}$alkyl wherein the $C_{1-4}$alkyl is optionally substituted by a halo or a cyano. In some embodiments, each $R^e$ is independently H or $C_{3-6}$cycloalkyl wherein each $C_{3-6}$cycloalkyl is optionally substituted by a halo or a cyano. In some embodiments, each $R^e$ is independently H or $C_{1-6}$alkyl. In some embodiments, each $R^e$ is independently H or $C_{34}$cycloalkyl. In some embodiments, each $R^e$ is H. In some embodiments, each $R^e$ is independently $C_{1-4}$alkyl. In some embodiments, each $R^e$ is independently $C_{3-6}$cycloalkyl.

In some embodiments, for the compounds of Formula VIII, VIIIa, and VIIb, p is 2 or 3 and each $R^{41}$ is independently halo, $C_{1-6}$alkyl, $C_{1-4}$haloalkyl, $C_{3-6}$cycloalkyl, cyano, —O—$C_1$. 4alkyl, —O—$C_{3-6}$cycloalkyl or $C_{1-4}$alkyl-O—$C_{1-4}$alkyl. In some embodiments, p is 2 or 3 and each $R^{41}$ is independently halo, $C_{1-4}$alkyl, $C_{1-4}$haloalkyl, or —O—$C_{1-4}$alkyl. In some embodiments, p is 2 or 3 and each $R^{41}$ is independently halo, $C_{1-4}$alkyl, or —O—$C_{1-4}$alkyl. In some embodiments, p is 2 or 3 and each $R^{41}$ is independently halo or $C_{1-4}$alkyl. In some embodiments, p is 2 or 3 each $R^{41}$ is independently halo or —O—$C_{1-4}$alkyl. In some embodiments, p is 2 or 3 and each $R^{41}$ is independently a halogen. In some embodiments, p is 2 or 3 and each $R^{41}$ is independently selected from chloro and fluoro.

In some embodiments, for the compounds of Formula VIII, VIIIa, and VIIb, p is 2 and each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-6}$alkyl-O—$C_{1-4}$alkyl. In some embodiments, p is 2 and each $R^{41}$ is independently halo, $C_{1-4}$alkyl, $C_{1-6}$haloalkyl, or —O—$C_{1-6}$alkyl. In some embodiments, p is 2 and each $R^{41}$ is independently halo, $C_{1-4}$alkyl, or —O—$C_{1-4}$alkyl. In some embodiments, p is 2 and each $R^{41}$ is independently halo or $C_{1-4}$alkyl. In some embodiments, p is 2 and each $R^{41}$ is independently halo or —O—$C_{1-4}$alkyl. In some embodiments, p is 2 and each $R^{41}$ is independently a halogen. In some embodiments, p is 2 and each $R^{41}$ is independently selected from chloro and fluoro.

In some embodiments, for the compounds of Formula VIII, VIIIa, and VIIb, p is 3 and each $R^{41}$ is independently halo, $C_{1-6}$alkyl, $C_{1-4}$haloalkyl, $C_{3-6}$cycloalkyl, cyano, —O—$C_{1-4}$alkyl, —O—$C_{3-6}$cycloalkyl or $C_{1-4}$alkyl-O—$C_{1-4}$alkyl. In some embodiments, p is 3 and each $R^{41}$ is independently halo, $C_{1-4}$alkyl, $C_{1-6}$haloalkyl, or —O—$C_{1-4}$alkyl. In some embodiments, p is 3 and each $R^{41}$ is independently halo, $C_{1-4}$alkyl, or —O—$C_{1-4}$alkyl. In some embodiments, p is 3 and each $R^{41}$ is independently halo or $C_{1-4}$alkyl. In some embodiments, p is 3 and each $R^{41}$ is independently halo or —O—$C_{1-4}$alkyl. In some embodiments, p is 3 and each $R^{41}$ is independently a halogen. In some embodiments, p is 3 and each $R^{41}$ is independently selected from chloro and fluoro.

In some embodiments of the compounds of Formula IV, IVa, or IVb:

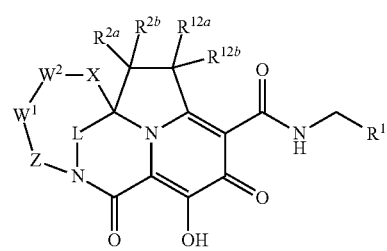

Formula IV

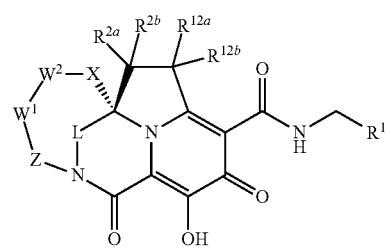

Formula IVa

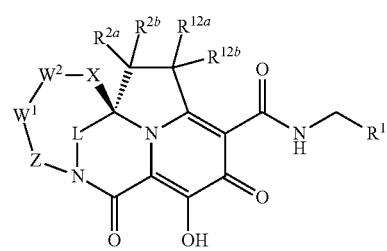

Formula IVb

X is —CR$^{8a}$R$^{8b}$—;

W$^1$ is a bond or —CR$^{4a}$R$^{4b}$—;

W$^2$ is —CR$^{5a}$R$^{5b}$— or —CR$^{6a}$=CR$^{6a}$—;

Z is —CR$^{9a}$R$^{9b}$—;

L is —CH$_2$—;

R$^{2a}$, R$^{2b}$, R$^{12a}$, and R$^{12b}$ are independently H, C$_{1-6}$alkyl, halo, —OR$^a$—, or —CH$_2$OR$^a$;

R$^a$ is H or C$_{1-6}$alkyl;

R$^{4a}$, R$^{4b}$, R$^{5a}$, R$^{5b}$, R$^{8a}$, R$^{8b}$, R$^{9a}$, R$^{9b}$ are independently H, hydroxyl, C$_{1-6}$alkyl, or —O—C$_{1-4}$alkyl;

both R$^{6a}$ and R$^{6b}$ are H and

R$^1$ is C$_{6-10}$aryl optionally substituted with one to four R$^{A1}$, wherein each R$^{A1}$ is independently fluoro or chloro.

In some embodiments, the compound of Formula I, Ia, Ib, II, IIa, IIb, III, IIIa, IIIb, IV, IVa, IVb, V, Va, Vb, VI, VIa, VIb, VIII VIIa, VIb, VIII VIIIa, or VIIIb, is a compound selected from the group consisting of:

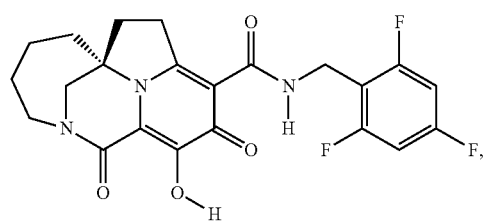

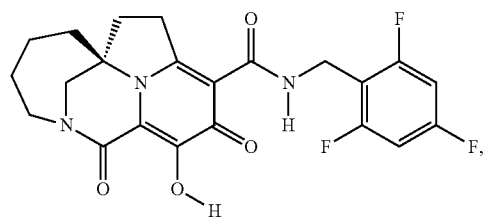

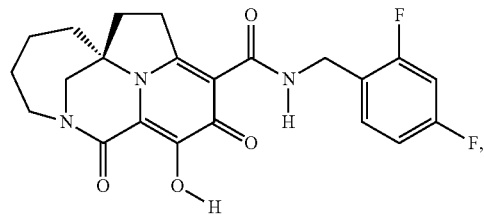

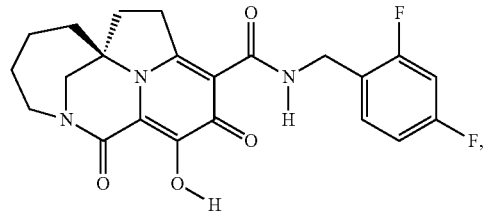

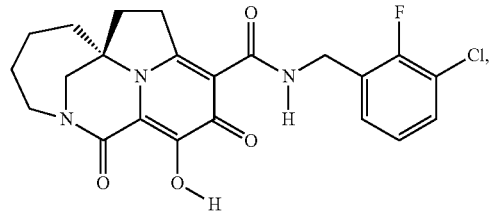

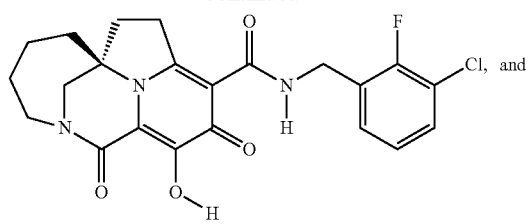

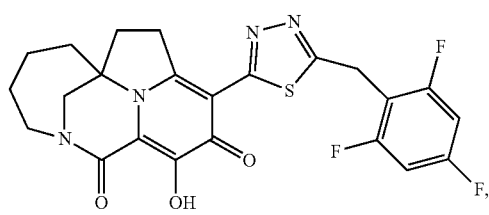

or a pharmaceutically acceptable salt thereof.

In some embodiments, the compound of Formula I, Ia, Ib, II, IIa, IIb, III, IIIa, IIIb, IV, IVa, IVb, V, Va, Vb, VI, VIa, VIb, VII VIIa, VIIb, VIII VIIIa, or VIIIb, is a compound selected from the group consisting of:

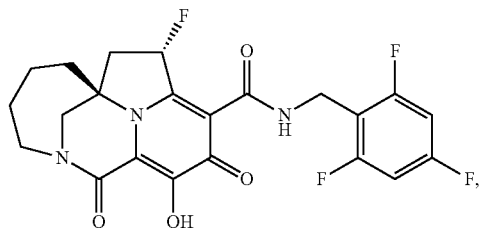

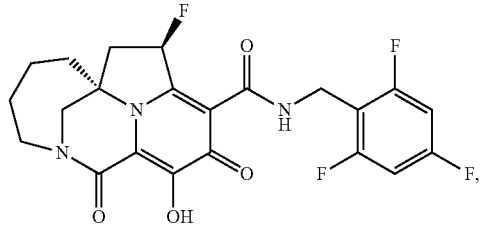

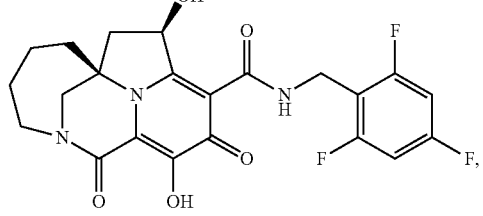

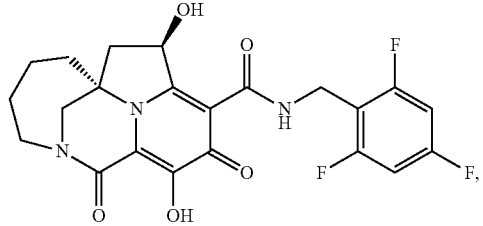

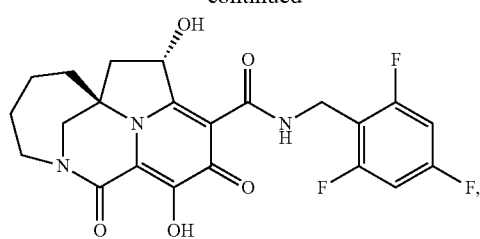
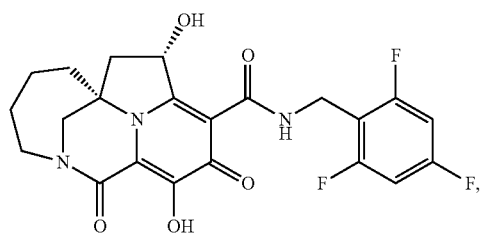
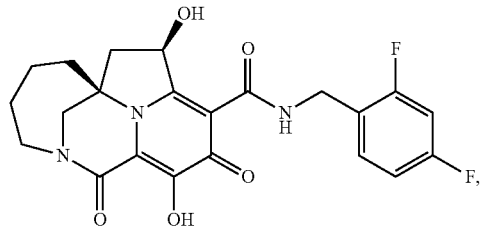
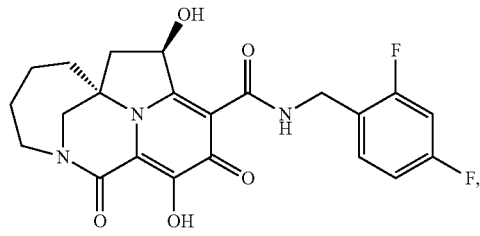
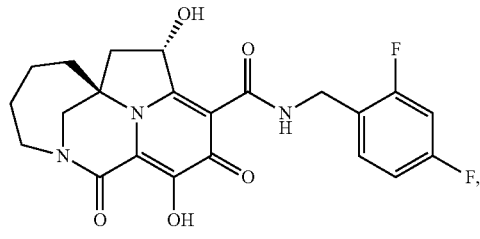
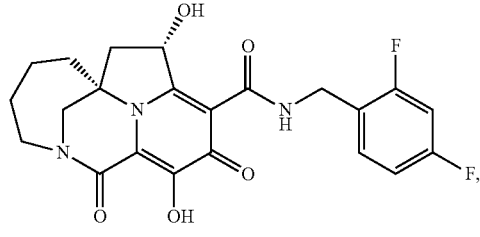
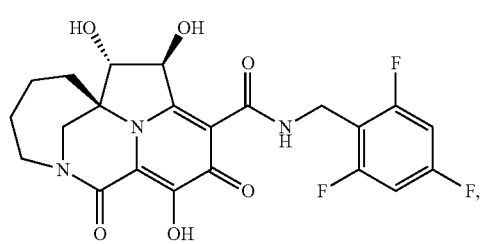
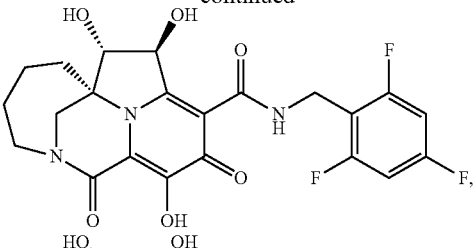
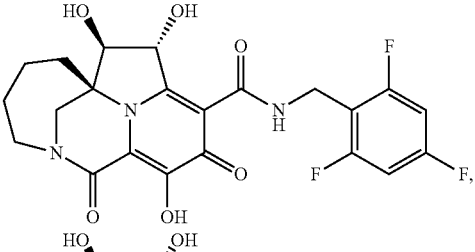
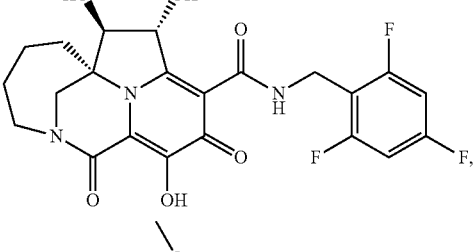
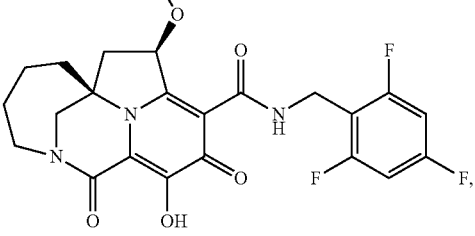
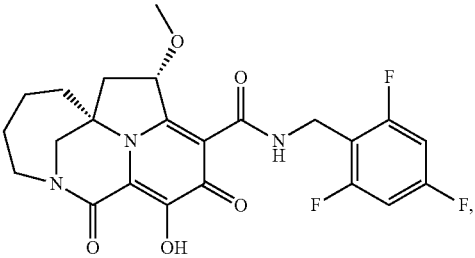
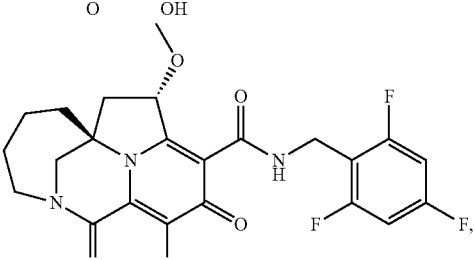

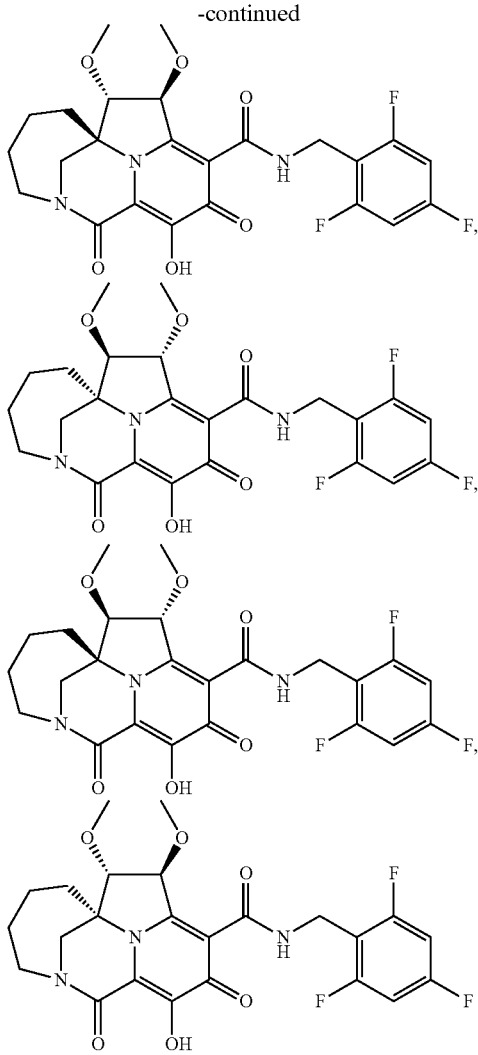
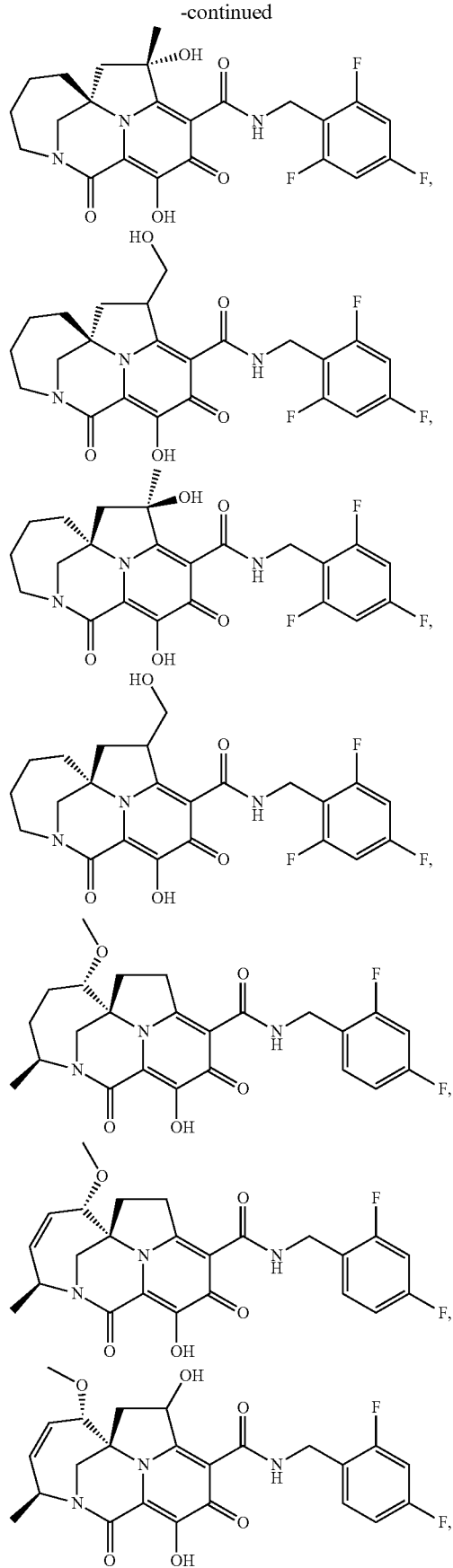
or a pharmaceutically acceptable salt thereof.
In some embodiments, the compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, is a compound selected from the group consisting of:
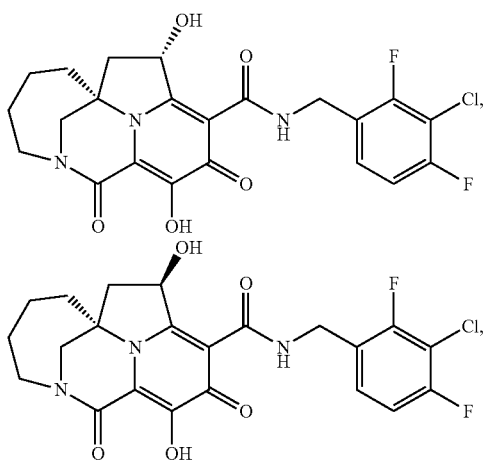

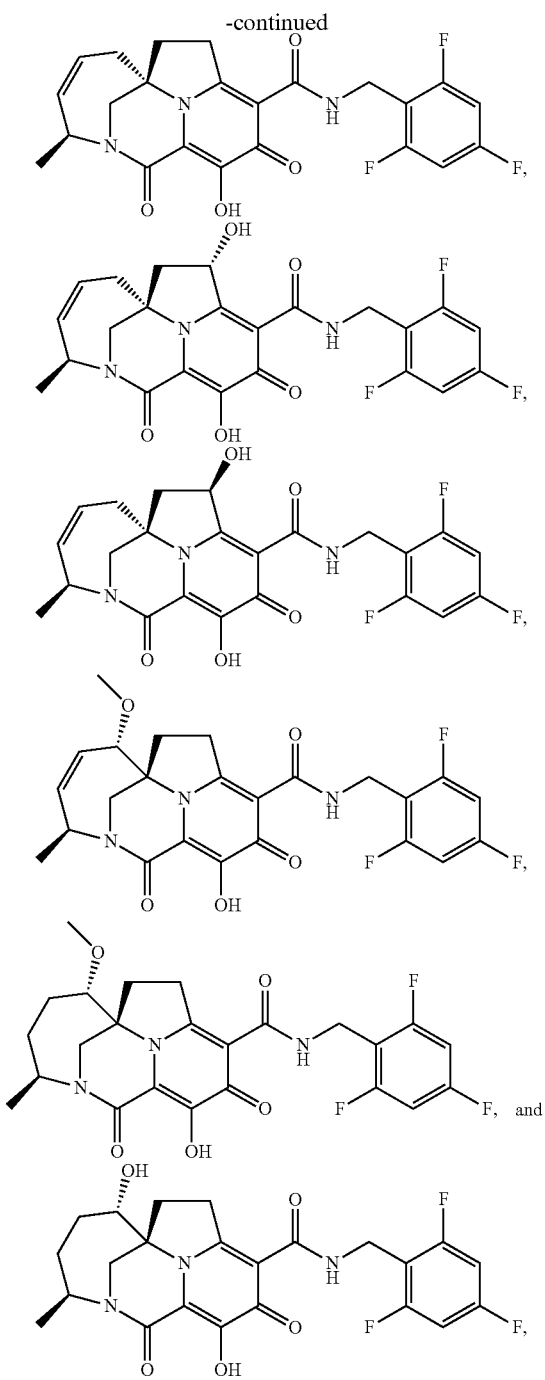

or a pharmaceutically acceptable salt thereof.

III. Compositions and Kits

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (e.g., a compound of Formula I, Ia, Ib, II, IIa, Ib, III, IIIa, IIIb, IV, IVa, IVb, V, Va, Vb, VI, VIa, VIb, VII, VIIa, VIb, VIII, VIIIa, or VIIIb), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art.

Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein are kits that comprise a compound provided herein, (e.g., a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb), or a pharmaceutically acceptable salt, stereoisomer, prodrug, or solvate thereof, and suitable packaging. In some embodiments, the kit further comprises instructions for use. In some embodiments, the kit comprises a compound provided herein (e.g., a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

In one embodiment, methods of treating an HIV (e.g., HIV-1 and/or HIV-2) infection in a human having or at risk of having the infection comprising administering to the human a therapeutically effective amount of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, or a pharmaceutical composition of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, are provided.

In some embodiments, the methods further comprise administering to the human a therapeutically effective amount of one, two, three, or four additional therapeutic agents. In certain embodiments, the additional therapeutic agent or agents are anti-HIV agents. In particular embodiments, the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs (broadly neutralizing HIV antibodies), TLR7 agonists, pharmacokinetic enhancers, other drugs for treating HIV, or combinations thereof. In one embodiment, the additional therapeutic agent or agents are abacavir, tenofovir alafenamide, tenofovir disoproxil, N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, or a pharmaceutically acceptable salt thereof.

In another embodiment, a use of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, or a pharmaceutical composition of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, for treating an HIV (e.g., HIV-1 and/or HIV-2) infection in a human having or at risk of having the infection is provided.

In another embodiment, a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIb, or a pharmaceutically acceptable salt thereof, or a pharmaceutical composition of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, for use in medical therapy is provided.

In another embodiment, a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, or a pharmaceutical composition of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or pharmaceutically acceptable salt thereof, for use in treating an HIV infection is provided.

In another embodiment, a compound of Formula I, Ia, Ib, II, IIa, IIb, III, IIIa, IIIb, IV, IVa, IVb, V, Va, Vb, VI, VIa, VIb, VIII VIIa, VIb, VIII, VIIIa, or VIIIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIIa, VIIb, VIII, VIIIa, or VIIb, or a pharmaceutically acceptable salt thereof for use in a method of treating an HIV infection in a human having or at risk of having the infection, is provided.

In another embodiment, a compound of Formula I, Ia, Ib, II, IIa, IIb, III, IIIa, IIIb, IV, IVa, IVb, V, Va, Vb, VI, VIa, VIb, VII, VIIa, VIb, VIII, VIIIa, or VIIIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIa, VIIb, VIII, VIIIa, or VIIb, or a pharmaceutically acceptable salt thereof for use in a method of treating an HIV infection in a human having or at risk of having the infection, is provided wherein said method further comprises administering to the human one, two, three, or four additional therapeutic agents.

In another embodiment, a compound of Formula I, Ia, Ib, II, IIa, IIb, III, IIIa, IIIb, IV, IVa, IVb, V, Va, Vb, VI, VIa, VIb, VII, VIIa, VIb, VII, VIIIa, or VIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIa, VIIb, VIII, VIIIa, or VIIb, or a pharmaceutically acceptable salt thereof for use in a method of treating an HIV infection in a human having or at risk of having the infection, is provided wherein said method further comprises administering to the human one, two, three, or four additional therapeutic agents selected from the group consisting of HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof. In one embodiment, the one, two, three, or four additional therapeutic agents are selected from HIV protease inhibitors, HIV non-nucleoside inhibitors of reverse transcriptase, HIV nucleoside or nucleotide inhibitors of reverse transcriptase, latency reversing agents, HIV capsid inhibitors, HIV bNAbs, TLR7 agonists, and combinations thereof.

In another embodiment, a compound of Formula I, Ia, Ib, II, IIa, IIb, III, IIIa, IIIb, IV, IVa, IVb, V, Va, Vb, VI, VIa, VIb, VIII VIIa, VIb, VIII, VIIIa, or VIIIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof for use in a method of treating an HIV infection in a human having or at risk of having the infection, is provided wherein said method further comprises administering to the human a therapeutically effective amount of tenofovir disoproxil and emtricitabine.

In another embodiment, a compound of Formula I, Ia, Ib, II, IIa, IIb, III, IIIa, IIIb, IV, IVa, IVb, V, Va, Vb, VI, VIa, VIb, VII, VIIa, VIb, VIII, VIIIa, or VIIIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIa, VIIb, VIII, VIIIa, or VIIIb, or a pharmaceutically acceptable salt thereof for use in a method of treating an HIV infection in a human having or at risk of having the infection, is provided wherein said method further comprises administering to the human a therapeutically effective amount of tenofovir alafenamide and emtricitabine.

In another embodiment, a compound of Formula I, Ia, Ib, II, IIa, IIb, III, IIIa, IIIb, IV, IVa, IVb, V, Va, Vb, VI, VIa, VIb, VII, VIIa, VIb, VII, VIIIa, or VIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIa, VIIb, VIII, VIIIa, or VIIIb, or a pharmaceutically acceptable salt thereof for use in a method of treating an HIV infection in a human having or at risk of having the infection, is provided wherein said method further comprises administering to the human a therapeutically effective amount of tenofovir disoproxil.

In another embodiment, a compound of Formula I, Ia, Ib, II, IIa, Ib, III, IIIa, IIIb, IV, IVa, IVb, V, Va, Vb, VI, VIa, VIb, VII, VIIa, VIIb, VII, VIIIa, or VIb, or a pharmaceutically acceptable salt thereof, or a pharmaceutical composition of a compound of Formula I, Ia, Ib, II, Ha, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof for use in a method of treating an HIV infection in a human having or at risk of having the infection, is provided wherein said method further comprises administering to the human a therapeutically effective amount of tenofovir alafenamide.

In another embodiment, a method of using a compound of Formula I, Ia, Ib, II, IIa, IIb, III, Ia, IIIb, IV, IVa, IVb, V, Va, Vb, VI, VIa, VIb, VII VIIa, VIIb, VIII, VIIIa, or VIIIb in therapy is provided. In particular, a method of treating the proliferation of the HIV virus, treating AIDS, or delaying the onset of AIDS or ARC symptoms in a mammal (e.g., a human) is provided, comprising administering to the mammal a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIb, or a pharmaceutically acceptable salt thereof, and a pharmaceutically acceptable excipient.

In another embodiment, a composition comprising a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In one embodiment, a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIb, or a pharmaceutically acceptable salt thereof, or a pharmaceutical composition of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, is provided for use in preventing HIV infection.

For example, in one embodiment, a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, or a pharmaceutical composition of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, is provided for use in pre-exposure prophylaxis (PrEP), i.e., before the exposure of the individual to the HIV virus to prevent HIV infection from taking hold if the individual is exposed to the virus and/or to keep the virus from establishing a permanent infection and/or to prevent the appearance of symptoms of the disease and/or to prevent the virus from reaching detectable levels in the blood.

In another embodiment, the use of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, for the manufacture of a medicament for treating an HIV infection in a human being having or at risk of having the infection is disclosed.

In another embodiment, the use of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof, as a research tool is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a pharmaceutically acceptable salt thereof.

In still another embodiment, a method of inhibiting the replication of HIV is disclosed. The method comprises exposing the virus to an effective amount of the compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a salt thereof, under conditions where replication of HIV is inhibited.

In another embodiment, the use of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, to inhibit the activity of the HIV integrase enzyme is disclosed.

In another embodiment, the use of a compound of Formula I, Ia, Ib, II, IIa, IIb, III, IIIa, IIIb, IV, IVa, IVb, V, Va, Vb, VI, VIa, VIb, VII, VIIa, VIIb, VIII, VIIIa, or VIIIb, or a salt thereof, to inhibit the replication of HIV is disclosed.

V. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, Ia, Ib, II, IIa, Ib, III, IIIa, IIIb, IV, IVa, IVb, V, Va, Vb, VI, VIa, VIb, VII, VIIa, VIb, VIII, VIIIa, or VIIIb, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 μg to about 30 mg per day, or from about 30 μg to about 300 μg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, IL, Ha, IIb, III, Ia, IIIb, IV, IVa, IVb, V, Va, Vb, VI, VIa, VIb, VII, VIIa, VIIb, VIII, VIIIa, or VIIIb are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound p herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VI. Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.
Administration of HIV Combination Therapy In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents.

Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula I is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.
HIV Combination Therapy In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1

Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, CD4 modulators, CD4 antagonists, HIV ribonuclease H inhibitors, retrocyclin modulators, CDK-9 inhibitors, CCR5 chemokine antagonists, CCR5 gene modulators, dendritic ICAM-3 grabbing nonintegrin 1 inhibitors, HIV GAG protein inhibitors, HIV POL protein inhibitors, hyaluronidase inhibitors, Nef antagonists, Nef inhibitors, Protease-activated receptor-1 antagonists, TNF alpha ligand inhibitors, PDE4 inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENRVOYA® (tenofovir alafenamide, emtricitabine, cobicistat, and elvitegravir); SYMTUZA® (darunavir, tenofovir alafenamide hemifumarate, emtricitabine, and cobicistat); SYMFITM (efavirenz, lamivudine, and tenofovir disoproxil fumarate); CIMDUTM (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

Other HIV Drugs

Examples of other drugs for treating HIV include acemannan, alisporivir, astodrimer, BanLec, CC-11050, deferiprone, Gamimune, griffithsin, metenkefalin, naltrexone, Prolastin, REP 9, RPI-MN, Vorapaxar, VSSP, H1viral, SB-728-T, 1,5-dicaffeoylquinic acid, rHIV7-shl-TAR-CCR5RZ, MazF gene therapy, MK-8527, BlockAide, PSC-RANTES, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, and elsulfavirine (VM-1500).

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, DS-003 (BMS-599793), gp120 inhibitors, and CXCR4 inhibitors.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176, BMS-986197, GSK-3640254 and GSK-2838232.

Latency Reversing Agents

Examples of latency reversing agents include histone deacetylase (HDAC) inhibitors, proteasome inhibitors such as velcade, and ixazomib citrate, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), IL-15 modulating antibodies, JQ1, disulfiram, amphotericin B, and ubiquitin inhibitors such as largazole analogs, APH-0812, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207, AVI-621, AVI-101, AVI-201, AVI-301, and AVI-CAN1-15 series.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103.

Examples of TLR agonists: vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bnABs (broadly neutralizing HIV-1 antibodies), BMS-936559, TMB-360, and those targeting HIV gp120 or gp41, antibody-recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

Examples of those targeting HIV in such a manner include bavituximab, UB-421, C2F5, 2G12, C4E10, C2F5+C2G12+C4E10, 8ANC195, 3BNC117, 3BNC117-LS, 3BNC60, D1D2, 10-1074, 10-1074-LS, GS-9722, DH411-2, BG18, PGT145, PGT121, PGT122, PGT-151, PGT-133, PGT-135, PGT-128, MDXO10 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PG9, PG16, 8ANC195, 2Dm2m, 4Dm2m, 6Dm2m, VRC-01, VRC-01-LS, PGDM1400, A32, 7B2, 10E8, 10E8VLS, 3810109, 10E8v4, 10E8.4/iMab, VRC-01/PGDM-1400/10E8v4, IMC-HIV, iMabm36, 10E8v4/PGT121-VRCO1, eCD4-Ig, IOMA, CAP256-VRC26.25, DRVIA7, SAR-441236, VRC-07-523, VRC07-523LS, VRC-HIVMAB080-00-AB, VRC-HIVMAB060-00-AB, P2G12, and VRC07. Examples of HIV bispecific antibodies include MGD014, TMB-bispecific.

Example of in vivo delivered bnABs such as AAV8-VRC07; mRNA encoding anti-HIV antibody VRC01.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines using viral vectors such as arenavirus, lymphocytic choriomeningitis virus (LCMV), pichinde virus, modified vaccinia Ankara virus (MVA), adenovirus, adeno-associated virus (AAV), vesicular stomatitis virus (VSV) and Chimpanzee adenovirus (ChAd), DNA vaccines, CD4-derived peptide vaccines, vaccine combinations, BG505 SOSIP.664 gp140, rgp120 (AIDSVAX), ALVAC HIV, (vCP1521)/AIDSVAX B/E (gp120) (RV144), monomeric gp120 HIV-1 subtype C vaccine, Remune, ITV-1, Contre Vir, Ad4-Env145NFL, Ad5-ENRVA-48, HB-500, DCVax-001 (CDX-2401), Vacc-4x, Vacc-C5, Vacc-CRX, VVX-004, VAC-3S, multiclade DNA recombinant adenovirus-5 (rAd5), rAd5 gag-pol env A/B/C vaccine, Pennvax-G, Pennvax-GP/MVA-CMDR, HIV-TriMix-mRNA vaccine, HIV-LAMP-vax, Ad35, Ad35-GRIN, NAcGM3NSSP ISA-51, poly-ICLC adjuvanted vaccines, TatImmune, GTU-multiHIV (FIT-06), gpl40[delta] V2.TVI+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based immunotherapies (Vaxwave, TheraT), MVA-BN HIV-1 vaccine regimen, MVA.tHIVconsv4, MVA.tHIVconsv3, UBI HIV gp120, mRNA based prophylactic vaccines, TBL-1203HI, VRC-HIVRGP096-00-VP, VAX-3S, and HIV MAG DNA vaccine.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENRVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In some embodiments, a compound disclosed herein, or a pharmaceutically acceptable salt thereof, is used in combination with a HIV capsid inhibitor and/or a nucleoside reverse transcriptase translocation inhibitor. In some embodiments a compound disclosed herein is used in combination with lenacapavir and/or islatravir. In some embodiments a compound disclosed herein is used in combination with lenacapavir. In some embodiments a compound disclosed herein is used in combination with islatravir.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula I) may be combined with one or more additional therapeutic agents in any dosage amount of the compound of Formula I (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula I) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula I) may be combined with the agents provided herein in any dosage amount of the compound (e.g., from 1 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Birth Control (Contraceptive) Combination Therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.
Example of CCR5 gene editing drugs such as SB-728T.
Example of CCR5 gene inhibitors such as Cal-1.
C34-CCR5/C34-CXCR4 expressing CD4-positive T cells.
AGT-103-transduced autologous T cell therapy.
AAV-eCD4-Ig gene therapy.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT-101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof. Cells can be autologous or allogeneic.

Examples of HIV CAR-T include VC-CAR-T, anti-CD4 CART cell therapy, autologous hematopoietic stem cells genetically engineered to express a CD4 CAR and the C46 peptide.

TCR-T Cell Therapy

TCR-T cells are engineered to target HIV derived peptides present on the surface of virus-infected cells.

VII. Examples

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent.

Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Example 1: Preparation of ((6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1)

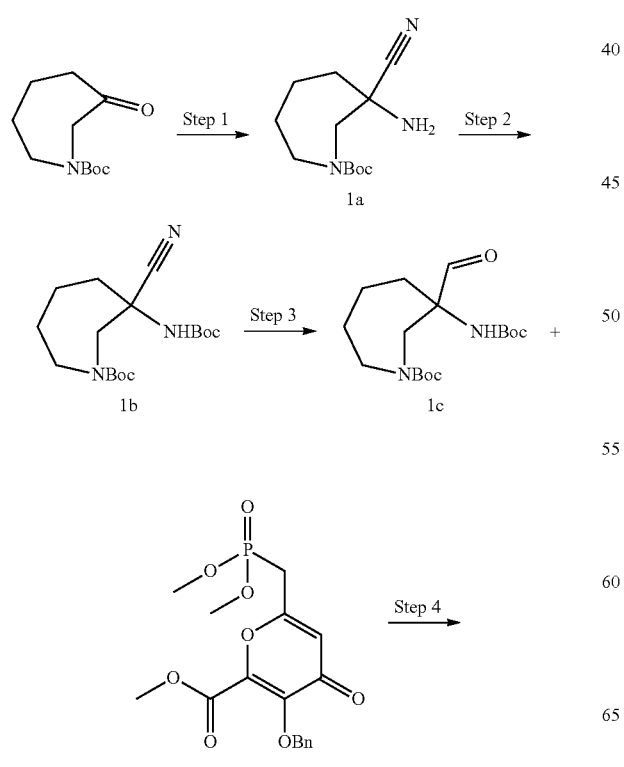

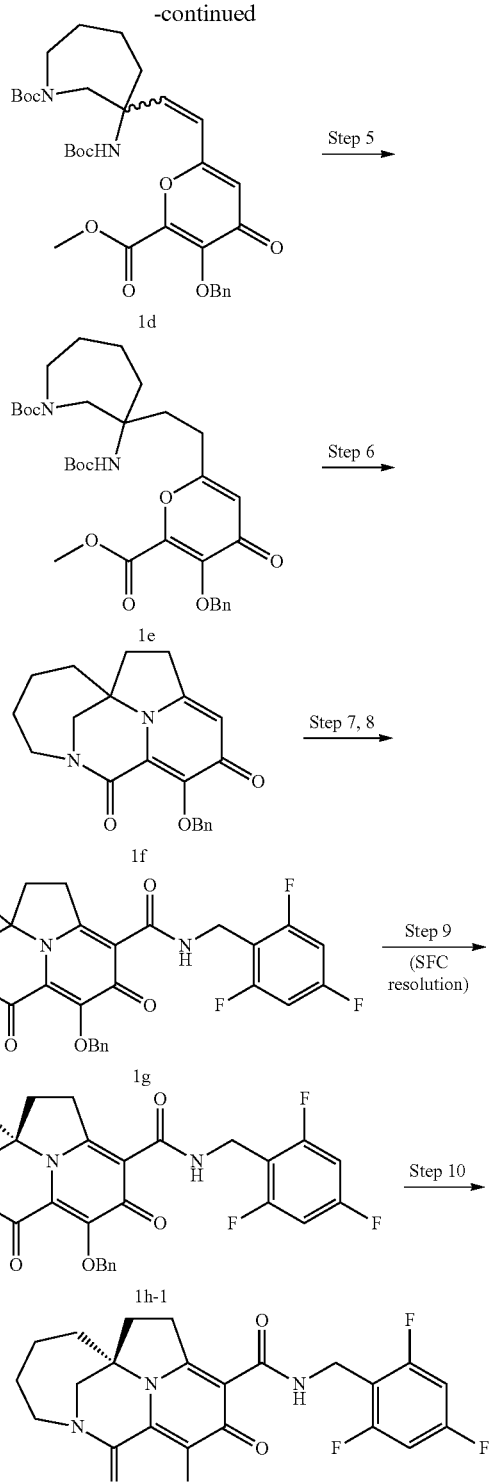

Step 1. Synthesis of tert-butyl 3-amino-3-cyanoazepane-1-carboxylate (1a)

tert-Butyl 3-oxoazepane-1-carboxylate (3.5 g, 16.4 mmol), potassium cyanide (1.60 g, 24.6 mmol), ammonium chloride (1.32 g, 24.6 mmol) in ammonium hydroxide (19.5 mL), ethanol (20 mL) and water (6.5 mL) were heated at 60° C. overnight. Reaction mixture was concentrated to ~30 mL, and extracted with dichloromethane (3×). Combined organic layers were washed with brine, dried (MgSO$_4$), filtered and purified by CombiFlash (80 g, ethyl acetate/hex) to give title compound. MS (m/z) 239.82 [M+H]$^+$.

Step 2: Synthesis of tert-butyl 3-((tert-butoxycarbonyl)amino)-3-cyanoazepane-1-carboxylate (1b)

To a solution of tert-butyl 3-amino-3-cyano-azepane-1-carboxylate (1a, 3.3 g, 13.8 mmol) in ethyl acetate (20 mL) was added saturated sodium carbonate (5 mL) and di-tert-butyl dicarbonate (4.51 g, 20.7 mmol). Reaction mixture was stirred for 2 days at room temperature. Reaction mixture was extracted with dichloromethane (3×), dried (MgSO$_4$), filtered and concentrated. Purification of the residue via CombiFlash (80 g, ethyl acetate/hexanes) gave title compound and recovered starting material. MS (m/z) 339.9 [M+H]$^+$.

Step 3: Synthesis of tert-butyl 3-((tert-butoxycarbonyl)amino)-3-formylazepane-1-carboxylate (1c)

To a solution of tert-butyl 3-((tert-butoxycarbonyl) amino)-3-cyanoazepane-1-carboxylate (1b, 0.952 g, 2.81 mmol) in dichloromethane (14.0 mL) at 0° C. was added bis(cyclopentadienyl) zirconium(IV) chloride hydride (1.45 g, 5.61 mmol). Reaction mixture was stirred for 20 h at 0° C. Additional bis(cyclopentadienyl)zirconium(IV) chloride hydride (1.45 g, 5.61 mmol) was added and reaction mixture was warmed to room temperature over 3 hours. Reaction mixture was adsorbed onto silica gel, loaded into dry load cartridge and purified by CombiFlash (120 g, 0-30% EtOAc/Hex) to give title compound. MS (m/z) 342.73 [M+H]$^+$.

Step 4: Synthesis of tert-butyl 3-(2-(5-(benzyloxy)-6-(methoxycarbonyl)-4-oxo-4H-pyran-2-yl)vinyl)-3-((tert-butoxycarbonyl)amino)azepane-1-carboxylate (1d)

To a solution of methyl 3-(benzyloxy)-6-((dimethoxyphosphoryl)methyl)-4-oxo-4H-pyran-2-carboxylate (prepared according to WO2018102485) (0.826 g, 2.16 mmol) in THF (15 mL) at −78° C. was added dropwise 1.0 M lithium diisopropylamide in THF/hexanes (2.30 mL, 2.30 mmol). Reaction mixture was stirred for 60 minutes, then a solution of tert-butyl 3-((tert-butoxycarbonyl)amino)-3-formylazepane-1-carboxylate (1c, 0.370 g, 1.08 mmol) in THF (5.0 mL) was added. Reaction mixture was stirred for 0.5 hours at −78° C., then warmed to −40° C. After 1 hour, the reaction mixture was stirred at 0° C. for 4 hours. Reaction mixture was quenched with 1 N HCl, brine was added and extracted with ethyl acetate (2×). Combined organic layers were dried (MgSO$_4$), filtered, concentrated, and purified by CombiFlash (120 g, 0-60% EtOAc/Hex) to give title compound. MS (m/z) 598.88 [M+H]$^+$.

Step 5: Synthesis of tert-butyl 3-(2-(5-(benzyloxy)-6-(methoxycarbonyl)-4-oxo-4H-pyran-2-yl)ethyl)-3-((tert-butoxycarbonyl)amino)azepane-1-carboxylate (1e)

tert-Butyl 3-(2-(5-(benzyloxy)-6-(methoxycarbonyl)-4-oxo-4H-pyran-2-yl)vinyl)-3-((tert-butoxycarbonyl)amino) azepane-1-carboxylate (1d, 490 mg, 0.80 mmol) and 20% palladium hydroxide on carbon, wet (114 mg) in THF (20 mL) was stirred under hydrogen atmosphere (1 atm) for 1 hour. Reaction mixture was filtered through a pad of Celite, washed with ethyl acetate and concentrated to obtain tert-butyl 3-((tert-butoxycarbonyl)amino)-3-(2-(5-hydroxy-6-(methoxycarbonyl)-4-oxo-4H-pyran-2-yl)ethyl)azepane-1-carboxylate, which was used in next step without further purification.

tert-Butyl 3-((tert-butoxycarbonyl)amino)-3-(2-(5-hydroxy-6-(methoxycarbonyl)-4-oxo-4H-pyran-2-yl)ethyl) azepane-1-carboxylate from above (0.427 g) was dissolved in DMF (8 mL) and benzyl bromide (193 µL, 1.63 mmol) and potassium carbonate (0.451 g, 3.26 mmol) were added. Reaction mixture was stirred for 2 hours. Reaction mixture was diluted with ethyl acetate, washed with 5% LiCl solution (3×) and brine, dried (MgSO$_4$), and filtered. Concentration and purification (40 g, 0-60% EtOAc/Hex) gave title compound. MS (m/z) 600.83 [M+H]$^+$.

Step 6: Synthesis of 11-(benzyloxy)-3,4,5,6,7,8-hexahydro-2,6a-methano[1,4]diazonino[9,1,2-cd]indolizine-1,10-dione (1f)

A solution of tert-butyl 3-(2-(5-(benzyloxy)-6-(methoxycarbonyl)-4-oxo-4H-pyran-2-yl)ethyl)-3-((tert-butoxycarbonyl)amino)azepane-1-carboxylate (1e, 0.252 g, 0.410 mmol) and trifluoroacetic acid (2.0 mL) in dichloromethane (10.0 mL) was stirred at 0° C. for 2 hours, then warmed to room temperature over 4 hours. Reaction mixture was concentrated and dried under high vacuum overnight.

Methyl 6-(2-(3-aminoazepan-3-yl)ethyl)-3-(benzyloxy)-4-oxo-4H-pyran-2-carboxylate from above was dissolved in ethanol (10 mL) and heated at 90° C. for 5 hours. Reaction mixture was concentrated and purified via CombiFlash (24 g, 0-20% MeOH/CH$_2$Cl$_2$) to give title compound. MS (m/z) 351.28 [M+H]$^+$.

Step 7: Synthesis of 11-(benzyloxy)-9-iodo-3,4,5,6,7,8-hexahydro-2,6a-methano[1,4]diazonino[9,1,2-cd]indolizine-1,10-dione To a solution of 11-(benzyloxy)-3,4,5,6,7,8-hexahydro-2,6a-methano[1,4]diazonino [9,1,2-cd]indolizine-1,10-dione (1f, 260 mg, 0.626 mmol) in anhydrous methanol (6.3 mL) was added 3-chloroperoxybenzoic acid (0.432 g, 2.51 mmol), followed by N-iodosuccinimide (0.564 g, 2.51 mmol). Reaction mixture was heated at 70° C. for 15 minutes. Reaction mixture was diluted with dichloromethane and washed with 10% sodium sulfite. Aqueous layer was back-extracted and combined organic layers were dried (MgSO$_4$), filtered and concentrated. Purification via CombiFlash (40 g, 0-10% MeOH/CH$_2$Cl$_2$) gave title compound. MS (m/z) 477.14 [M+H]$^+$.

Step 8: Synthesis of 11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1g)

To a solution of 11-(benzyloxy)-9-iodo-3,4,5,6,7,8-hexahydro-2,6a-methano[1,4]diazonino[9,1,2-cd]indolizine-1,10-dione (210 mg, 0.441 mmol) in DMSO (6.5 mL) was added 2,4,6-trifluorobenzyl amine (355 mg, 2.20 mmol), N,N-Diisopropylethylamine (384 µL, 2.20 mmol) and tetrakis(triphenylphosphine)palladium (25.5 mg, 0.022 mmol). Reaction mixture was degassed under vacuum and back-filled with CO (3×). Reaction mixture was slowly sparged with CO using 22 gauge needle connected to a gas bag filled CO and heated at 80° C. for 4 hours. Reaction mixture was cooled to room temperature, diluted with ethyl acetate, washed with 0.05 N HCl, saturated sodium bicarbonate solution, and brine, dried (MgSO$_4$), and concentrated. The residue was purified by CombiFlash (40 g, 0 to −100% EtOAc/Hex) to give desired product. MS (m/z) 538.15 [M+H]$^+$.

Step 9: Resolution of (6aR)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1h-1) and (6aS)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1h-2)

Racemic 11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (119 mg) was resolved using chiral SFC (IB, 30% MeOH).

(6aR)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide: Peak 1, MS (m/z) 538.16 [M+H]$^+$.

(6aS)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide: Peak 2, MS (m/z) 538.18 [M+H]$^+$.

Step 10: Synthesis of (6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1)

To a solution of (6aR)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1h-1, 37 mg, 0.069 mmol) in dichloromethane (1.5 mL) was added trifluoroacetic acid (1.0 mL). Reaction mixture was stirred at room temperature for 4 hours. Reaction mixture was aged in a freezer for 30 hours. Reaction mixture was concentrated and purified by Gilson HPLC (Gemini 5-100% ACN/H$_2$O+0.1% TFA) to give title compound after lyophilization. MS (m/z) 448.24 [M+H]$^+$. $^1$H NMR (400 MHz, Methanol-d4) δ 7.07-6.79 (m, 2H), 4.73-4.54 (m, 2H), 4.35 (dt, J=13.4, 8.0 Hz, 1H), 3.98-3.73 (m, 3H), 3.49 (ddd, J=18.8, 11.2, 7.7 Hz, 1H), 3.19 (ddd, J=13.2, 7.0, 3.4 Hz, 1H), 2.31-2.07 (m, 3H), 2.07-1.85 (m, 3H), 1.79 (dd, J=15.6, 6.9 Hz, 1H), 1.39-1.23 (m, 1H).

Example 2: Preparation of (6aS)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (2)

2

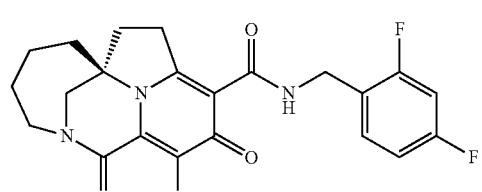

(6aS)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (2) was prepared in a manner similar to (6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1) except using (6aS)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1h-2) instead of (6aR)-11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1h-1) in Step 10. MS (m/z) 448.19 [M+H]$^+$. $^1$H NMR (400 MHz, Chloroform-d) δ 10.79 (t, J=5.0 Hz, 1H), 8.77 (s, 1H), 6.75-6.59 (m, 2H), 4.65 (qd, J=14.4, 5.4 Hz, 2H), 4.44 (dt, J=13.7, 8.1 Hz, 1H), 4.10 (dd, J=18.9, 8.3 Hz, 1H), 3.81-3.61 (m, 2H), 3.53 (ddd, J=19.0, 11.5, 7.7 Hz, 1H), 3.14 (ddd, J=13.7, 7.2, 3.3 Hz, 1H), 2.15 (dddd, J=31.2, 18.6, 11.4, 5.4 Hz, 4H), 1.83 (dddd, J=23.1, 16.1, 12.3, 5.0 Hz, 3H), 1.42-1.26 (m, 1H).

Example 3: Preparation of (6aR)—N-(2,4-difluorobenzyl)-11-hydroxy-1,10-dioxo-1,3,4,5,6,7,8,10-octahydro-2,6a-methano[1,4]diazonino[9,1,2-cd]indolizine-9-carboxamide (3)

3

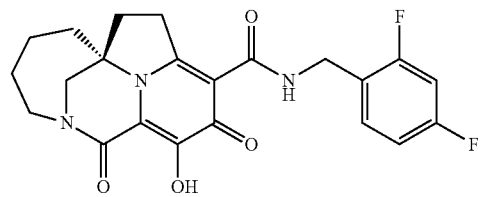

(6aR)—N-(2,4-difluorobenzyl)-11-hydroxy-1,10-dioxo-1,3,4,5,6,7,8,10-octahydro-2,6a-methano[1,4]diazonino[9,1,2-cd]indolizine-9-carboxamide (3) was prepared in a manner similar to (6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1) except using 2,4-drifluorobenzyl amine instead of 2,4,6-trifluorobenzyl amine in Step 8. MS (m/z) 430.30 [M+H]$^+$. $^1$H NMR (400 MHz, Methanol-d4) δ 7.44 (q, J=8.4 Hz, 1H), 7.02-6.88 (m, 2H), 4.68-4.54 (m, 2H), 4.37 (dt, J=13.6, 7.9 Hz, 1H), 3.99-3.74 (m, 3H), 3.57-3.44 (m, 1H), 3.24-3.13 (m, 1H), 2.29-2.06 (m, 3H), 2.04-1.86 (m, 3H), 1.86-1.72 (m, 1H), 1.32 (q, J=12.7, 12.2 Hz, 1H).

Example 4: Preparation of (6aS)—N-(2,4-difluorobenzyl)-11-hydroxy-1,10-dioxo-1,3,4,5,6,7,8,10-octahydro-2,6a-methano[1,4]diazonino[9,1,2-cd]indolizine-9-carboxamide (4)

4

(6aS)—N-(2,4-difluorobenzyl)-11-hydroxy-1,10-dioxo-1,3,4,5,6,7,8,10-octahydro-2,6a-methano[1,4]diazonino[9,1,2-cd]indolizine-9-carboxamide (4) was prepared in a manner similar to (6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1) except by using 2,4-driflurobenzyl amine instead of 2,4,6-trifluorobenzyl amine in Step 8 and (6aS)-11-(benzyloxy)-N-(2,4-difluorobenzyl)-1,10-dioxo-1,3,4,5,6,7,8,10-octahydro-2,6a-methano[1,4]diazonino [9,1,2-cd]indolizine-9-carboxamide (1h-2) instead of (6aR)-11-(benzyloxy)-N-(2,4-difluorobenzyl)-1,10-dioxo-1,3,4,5,6,7,8,10-octahydro-2,6a-methano[1,4]diazonino[9,1,2-cd]indolizine-9-carboxamide (1h-1) in Step 10. MS (m/z) 430.31 [M+H]$^+$. $^1$H NMR (400 MHz, Methanol-d4) δ 7.44 (q, J=8.3 Hz, 1H), 7.05-6.87 (m, 2H), 4.68-4.55 (m, 2H), 4.37 (dt, J=13.5, 8.0 Hz, 1H), 3.98-3.75 (m, 3H), 3.51 (ddd, J=18.7, 11.5, 7.7 Hz, 1H), 3.24-3.14 (m, 1H), 2.30-2.09 (m, 3H), 2.09-1.86 (m, 3H), 1.81 (dd, J=15.8, 6.5 Hz, 1H), 1.39-1.25 (m, 1H).

Example 5: Preparation (6aR)—N-(3-chloro-2-fluorobenzyl)-11-hydroxy-1,10-dioxo-1,3,4,5,6,7,8,10-octahydro-2,6a-methano[1,4]diazonino[9,1,2-cd]indolizine-9-carboxamide (5)

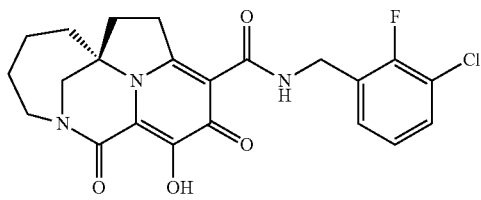

5

(6aR)—N-(3-chloro-2-fluorobenzyl)-11-hydroxy-1,10-dioxo-1,3,4,5,6,7,8,10-octahydro-2,6a-methano[1,4]diazonino[9,1,2-cd]indolizine-9-carboxamide (5) was prepared in a manner similar to (6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1) except by using 3-chloro-2-fluorobenzyl amine instead of 2,4,6-trifluorobenzyl amine in Step 8. MS (m/z) 446.30 [M+H]$^+$. $^1$H NMR (400 MHz, Methanol-d4) δ 7.43-7.38 (m, 1H), 7.35 (t, J=7.2 Hz, 1H), 7.14 (t, J=7.8 Hz, 1H), 4.69 (dd, J=15.4, 5.3 Hz, 2H), 4.37 (dt, J=13.7, 8.1 Hz, 1H), 3.98-3.74 (m, 3H), 3.58-3.44 (m, 1H), 3.20 (ddd, J=12.3, 7.0, 3.7 Hz, 1H), 2.31-2.09 (m, 3H), 2.08-1.86 (m, 3H), 1.86-1.73 (m, 1H), 1.32 (q, J=12.8, 12.4 Hz, 1H).

Example 6: Preparation of (6aS)—N-(3-chloro-2-fluorobenzyl)-11-hydroxy-1,10-dioxo-1,3,4,5,6,7,8,10-octahydro-2,6a-methano[1,4]diazonino[9,1,2-cd]indolizine-9-carboxamide (6)

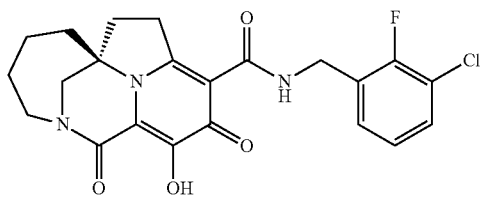

6

(6aS)—N-(3-chloro-2-fluorobenzyl)-11-hydroxy-1,10-dioxo-1,3,4,5,6,7,8,10-octahydro-2,6a-methano[1,4]diazonino[9,1,2-cd]indolizine-9-carboxamide (6) was prepared in a manner similar to (6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1) except by using 3-chloro-2-fluorobenzyl amine instead of 2,4,6-trifluorobenzyl amine in Step 8 and (6aS)-11-(benzyloxy)-N-(3-chloro-2-fluorobenzyl)-1,10-dioxo-1,3,4,5,6,7,8,10-octahydro-2,6a-methano[1,4]diazonino[9,1,2-cd]indolizine-9-carboxamide (1h-2) instead of (6aR)-11-(benzyloxy)-N-(2,4-difluorobenzyl)-1,10-dioxo-1,3,4,5,6,7,8,10-octahydro-2,6a-methano[1,4]diazonino[9,1,2-cd]indolizine-9-carboxamide (1h-1) in Step 10. MS (m/z) 446.30 [M+H]$^+$. $^1$H NMR (400 MHz, Methanol-d4) δ 7.43-7.38 (m, 1H), 7.35 (t, J=7.2 Hz, 1H), 7.14 (t, J=7.8 Hz, 1H), 4.69 (dd, J=15.4, 5.3 Hz, 2H), 4.37 (dt, J=13.7, 8.1 Hz, 1H), 3.98-3.74 (m, 3H), 3.58-3.44 (m, 1H), 3.20 (ddd, J=12.3, 7.0, 3.7 Hz, 1H), 2.31-2.09 (m, 3H), 2.08-1.86 (m, 3H), 1.86-1.73 (m, 1H), 1.32 (q, J=12.8, 12.4 Hz, 1H).

Example 7: Preparation of ((6aR)-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (7)

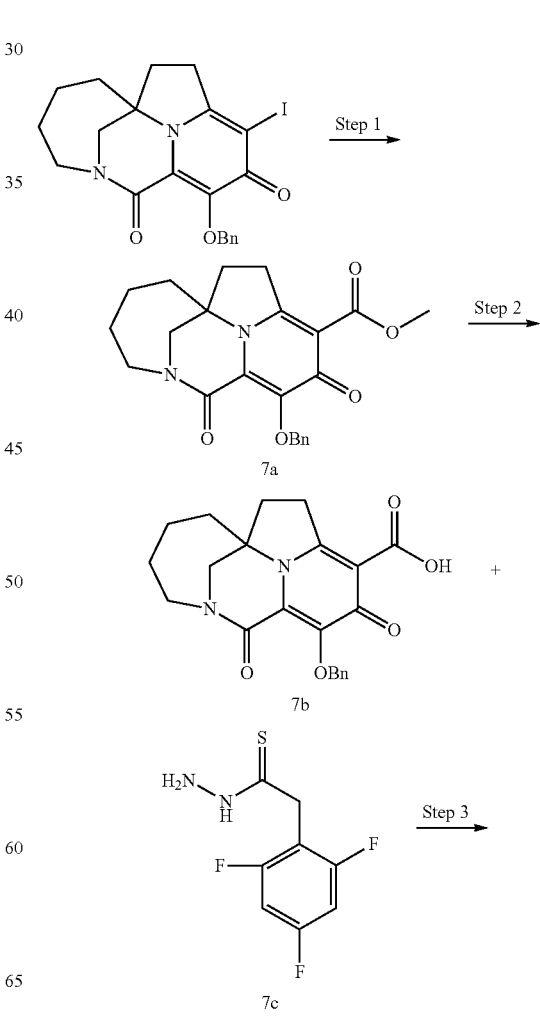

-continued

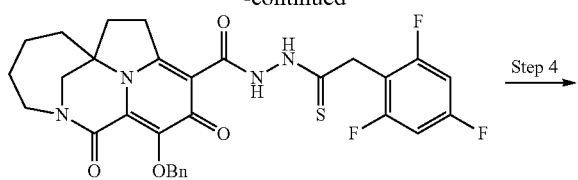

7d

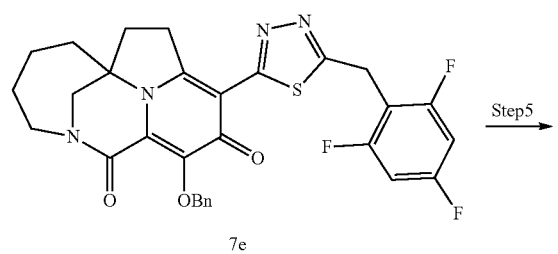

7e

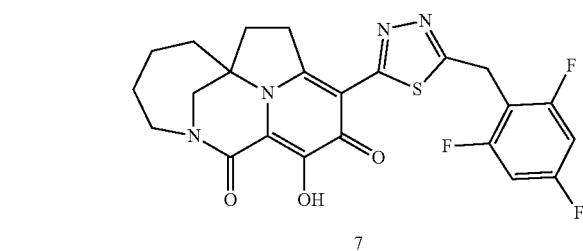

7

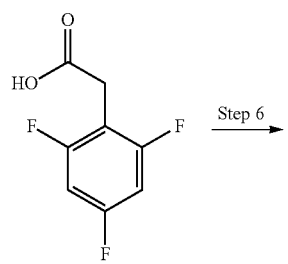

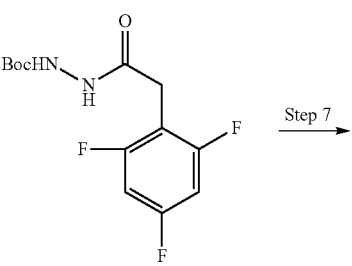

7f

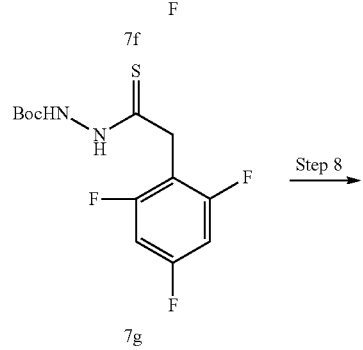

7g

-continued

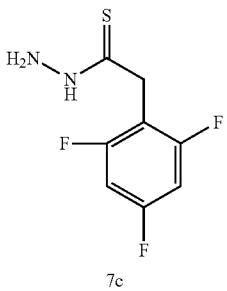

7c

Step 1: Synthesis of methyl 11-(benzyloxy)-1,10-dioxo-1,3,4,5,6,7,8,10-octahydro-2,6a-methano[1,4]diazonino[9,1,2-cd]indolizine-9-carboxylate (7a)

To a solution of 7-benzyloxy-5-iodo-10,15-diazatetracyclo[6.6.1.11,10.04,15] hexadeca-4,7-diene-6,9-dione (0.169 g, 0.355 mmol) in anhydrous tetrahydrofuran (2.0 mL) and anhydrous methanol (2.0 mL) was added N,N-diisopropylethylamine (185 μL, 1.06 mmol) and tetrakis(triphenylphosphine)palladium (0.021, 0.018 mmol). Reaction mixture was degassed under vacuum and backfilled with CO (3×). Reaction mixture was sparged with CO using 18 gauge needle connected to a gas bag filled CO and heated at 65° C. for 18 hours. Additional methanol (4.0 mL) and 1,1'-Bis(diphenylphosphino)ferrocene-palladium(II)dichloride dichloromethane complex (0.029 g, 0.0355 mmol) were added and reaction mixture was heated under CO atmosphere (1 atm) for 24 hours. Reaction mixture was cooled to room temperature, diluted with ethyl acetate and washed with 0.05 N HCl, saturated sodium bicarbonate solution, brine and dried (MgSO$_4$) and concentrated. Crude product was purified by CombiFlash (40 g, 0 to –100% EtOAc/Hept) to give desired product. MS (m/z) 409.1 [M+H]$^+$.

Step 2: Synthesis of 11-(benzyloxy)-1,10-dioxo-1,3,4,5,6,7,8,10-octahydro-2,6a-methano[1,4]diazonino[9,1,2-cd]indolizine-9-carboxylic acid (7b)

A solution of methyl 11-(benzyloxy)-1,10-dioxo-1,3,4,5,6,7,8,10-octahydro-2,6a-methano[1,4]diazonino[9,1,2-cd]indolizine-9-carboxylate (7a) (46 mg, 0.113 mmol) and lithium hydroxide (5M, 68 μL, 0.338 mmol) in THF (1.0 mL) and methanol (0.5 mL) was heated at 45° C. for 2 hours. Reaction mixture was acidified with 1 M HCl and extracted with ethyl acetate (3×). Combined organic layer was dried (MgSO$_4$), filtered and concentrated to give desired product that was used in the next step without further purification. MS (m/z) 395.05 [M+H]$^+$.

Step 3: Synthesis of 11-(benzyloxy)-1,10-dioxo-N'-(2-(2,4,6-trifluorophenyl)ethanethioyl)-1,3,4,5,6,7,8,10-octahydro-2,6a-methano[1,4]diazonino[9,1,2-cd]indolizine-9-carbohydrazide (7d)

To a solution of 11-(benzyloxy)-1,10-dioxo-1,3,4,5,6,7,8,10-octahydro-2,6a-methano[1,4]diazonino[9,1,2-cd]indolizine-9-carboxylic acid (7b) (44 mg, 0.112 mmol) in anhydrous THF (2.0 mmol) was added N-methyl morpholine (49 μL, 0.446 mmol) and isobutyl chloroformate (19 μL, 0.145 mmol) at 0° C. Reaction mixture was stirred for 2 hours. 2-(2,4,6-trifluorophenyl)ethanethiohydrazide, TFA salt (7c) (55.9 mg, 0.167 mmol) was added, followed by N-methyl morpholine (49 μL, 0.446 mmol). Reaction mixture was stirred for 1 hour. Reaction mixture was diluted with ethyl acetate, washed with saturated bicarbonate, dried (MgSO₄), filtered and concentrated. Reaction product was used in next step without further purification. MS (m/z) 596.93 [M+H]⁺.

Step 4: Synthesis of 11-(benzyloxy-9-(5-(2,4,6-trifluorobenzyl)-1,3,4-thiadiazol-2-yl)-3,4,5,6,7,8-hexahydro-2,6a-methano[1,4]diazonino[9,1,2-cd]indolizine-1,10-dione (7e)

11-(benzyloxy)-1,10-dioxo-N'-(2-(2,4,6-trifluorophenyl)ethanethioyl)-1,3,4,5,6,7,8,10-octahydro-2,6a-methano[1,4]diazonino[9,1,2-cd]indolizine-9-carbohydrazide (7d) (approximately 0.0033 mmol) was dissolved in acetic acid (1.5 mL) and heated at 100° C. for 7 hours. Reaction mixture was concentrated and purified by Gilson HPLC (Gemini, 5-100% ACN/H2O+0.1% TFA) and lyophilized to give desired product. MS (m/z) 489.36 [M+H]⁺.

Step 5: Synthesis of 11-hydroxy-9-(5-(2,4,6-trifluorobenzyl)-1,3,4-thiadiazol-2-yl)-3,4,5,6,7,8-hexahydro-2,6a-methano[1,4]diazonino[9,1,2-cd]indolizine-1,10-dione (7)

A solution of 7-benzyloxy-5-[5-[(2,4,6-trifluorophenyl)methyl]-1,3,4-thiadiazol-2-yl]-10,15-diazatetracyclo[6.6.1.11,10.04,15]hexadeca-4,7-diene-6,9-dione (7e) (1.5 mg, 0.0026 mmol) and trifluoroacetic acid (0.5 mL) in toluene (1.0 mL) was stirred at room temperature for 1.5 hours. Reaction mixture was concentrated and purified by Gilson HPLC (Gemini, 5-100% ACN/H₂O+0.1% TFA) to give desired product after lyophilization. MS (m/z) 579.04 [M+H]⁺. ¹H NMR (400 MHz, Methanol-d4) δ 7.05-6.88 (m, 2H), 4.52 (s, 2H), 4.38 (dt, J=13.3, 8.1 Hz, 1H), 4.05 (dd, J=18.5, 7.6 Hz, 1H), 3.96 (d, J=14.2 Hz, 1H), 3.86 (d, J=14.1 Hz, 1H), 3.67 (ddd, J=18.7, 10.9, 8.0 Hz, 1H), 3.23 (dq, J=9.9, 3.5 Hz, 1H), 2.47-2.18 (m, 3H), 1.99 (ddd, J=32.1, 14.1, 6.8 Hz, 3H), 1.83 (dd, J=13.7, 5.7 Hz, 1H), 1.33 (q, J=11.2, 10.7 Hz, 1H).

Example 8: Preparation of (6aS,8S)-8-fluoro-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (8-1) and (6aR,8R)-8-fluoro-11-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (8-2)

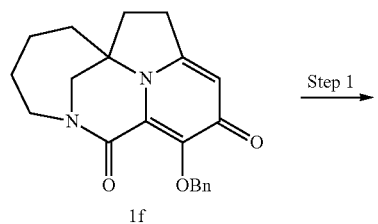

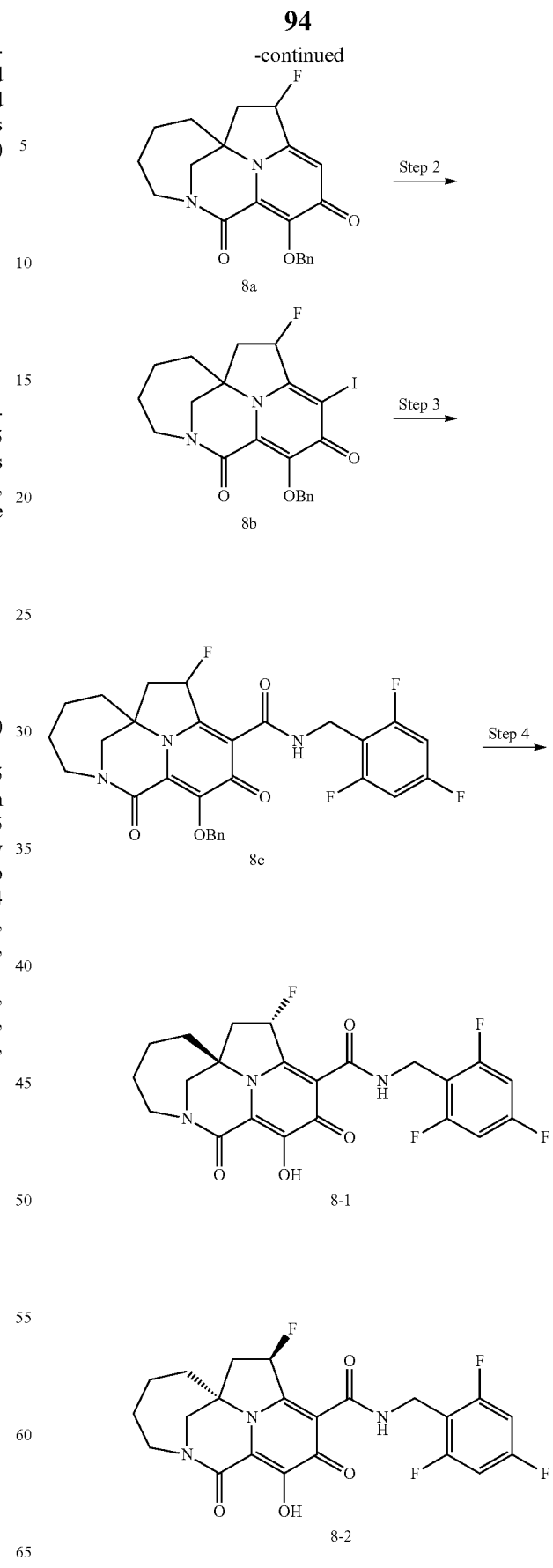

Step 1. Synthesis of 11-(benzyloxy)-8-fluoro-3,4,5,
6,7,8-hexahydro-2,6a-methano[1,4]diazonino[9,1,2-
cd]indolizine-1,10-dione (8a)

To a solution of 11-(benzyloxy)-3,4,5,6,7,8-hexahydro-2,6a-methano[1,4]diazonino[9,1,2-cd]indolizine-1,10-dione (0.050 g, 0.143 mmol), prepared according to the preparation of intermediate if in Example 1, in THF (3 mL) under Ar (g) was added N-fluorobenzenesulfonimide (0.135 g, 0.428 mmol). The reaction mixture was cooled to −78° C. and a 1.0 M solution of LiHMDS in THF (0.428 mL, 0.428 mmol) was added dropwise. After stirring for 0.5 h, the reaction was warmed to room temperature and left to stir overnight. Methanol was added to quench and the solution was concentrated. The residue was purified by column chromatography (0-20% MeOH/$CH_2Cl_2$) to provide 11-(benzyloxy)-8-fluoro-3,4,5,6,7,8-hexahydro-2,6a-methano[1,4]diazonino[9,1,2-cd]indolizine-1,10-dione. MS (m/z) 369.26 $[M+H]^+$.

Step 2. Synthesis of 11-(benzyloxy-8-fluoro-9-iodo-
3,4,5,6,7,8-hexahydro-2,6a-methano[1,4]diazonino
[9,1,2-cd]indolizine-1,10-dione (8b)

To a solution of 11-(benzyloxy)-8-fluoro-3,4,5,6,7,8-hexahydro-2,6a-methano[1,4]diazonino[9,1,2-cd]indolizine-1,10-dione (0.022 g, 0.059 mmol) in anhydrous methanol (0.5 mL) was added 77% m-CPBA (meta-chloroperbenzoic acid) (0.053 g, 0.237 mmol) and N-iodosuccinimide (0.053 g, 0.237 mmol). The reaction mixture was heated at 80° C. for 24 h and cooled to room temperature. The solution was diluted with $CH_2Cl_2$ and washed with 10% aqueous $Na_2SO_3$ solution. The aqueous phase was extracted with $CH_2Cl_2$ and the combined organic phase was dried over $Na_2SO_4$, filtered, and concentrated. The residue was purified by column chromatography (0-10% MeOH/$CH_2Cl_2$) to provide 11-(benzyloxy)-8-fluoro-9-iodo-3,4,5,6,7,8-hexahydro-2,6a-methano[1,4]diazonino[9,1,2-cd]indolizine-1,10-dione. MS (m/z) 495.10 $[M+H]^+$.

Step 3. Synthesis of 11-(benzyloxy)-8-fluoro-1,10-
dioxo-N-(2,4,6-trifluorobenzyl)-1,3,4,5,6,7,8,10-
octahydro-2,6a-methano[1,4]diazonino[9,1,2-cd]
indolizine-9-carboxamide (8e)

To a solution of 11-(benzyloxy)-8-fluoro-9-iodo-3,4,5,6,7,8-hexahydro-2,6a-methano[1,4]diazonino[9,1,2-cd]indolizine-1,10-dione (0.026 g, 0.053 mmol) in DMSO (1 mL) was added 2,4,6-trifluorobenzylamine (0.042 g, 0.263 mmol), i-$Pr_2$NEt (0.046 mL, 0.263 mmol), and Pd($PPh_3$)$_4$ (0.003 g, 0.003 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (1×), saturated aqueous $NaHCO_3$ (1×), and brine (1×). The organic phase was dried over $Na_2SO_4$, filtered, and concentrated. The residue was purified by column chromatography (0-100% EtOAc/heptane) to provide 11-(benzyloxy)-8-fluoro-1,10-dioxo-N-(2,4,6-trifluorobenzyl)-1,3,4,5,6,7,8,10-octahydro-2,6a-methano[1,4]diazonino[9,1,2-cd]indolizine-9-carboxamide. MS (m/z) 556.17 $[M+H]^+$.

Step 4. Synthesis of (6aS,8S)-8-fluoro-11-hydroxy-
1,10-dioxo-N-(2,4,6-trifluorobenzyl)-1,3,4,5,6,7,8,
10-octahydro-2,6a-methano[1,4]diazonino[9,1,2-cd]
indolizine-9-carboxamide (8-1) and (6aR,8R)-8-
fluoro-11-hydroxy-1,10-dioxo-N-(2,4,6-
trifluorobenzyl)-1,3,4,5,6,7,8,10-octahydro-2,6a-
methano[1,4]diazonino[9,1,2-cd]indolizine-9-
carboxamide (8-2)

rac-(6aR,8S)-11-(benzyloxy)-8-fluoro-1,10-dioxo-N-(2,4,6-trifluorobenzyl)-1,3,4,5,6,7,8,10-octahydro-2,6a-methano[1,4]diazonino[9,1,2-cd]indolizine-9-carboxamide was separated into its individual enantiomers by preparative SFC on an AD-H column using 40% MeOH co-solvent to provide two separated enantiomers. Each of the separated enantiomers was dissolved in 1:1 toluene/TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are not confirmed.

Peak 1: MS (m/z) 466.24 $[M+H]^+$. $^1$H NMR (400 MHz, DMSO-$d_6$) δ 10.83 (t, J=5.7 Hz, 1H), 7.30-7.16 (m, 2H), 6.84-6.69 (m, 1H), 4.61 (dd, J=14.5, 5.8 Hz, 1H), 4.52 (dd, J=14.6, 5.5 Hz, 1H), 4.19 (dt, J=12.8, 7.4 Hz, 1H), 3.86 (d, J=14.3 Hz, 1H), 3.68 (d, J=14.2 Hz, 1H), 3.05 (dt, J=12.3, 5.7 Hz, 1H), 2.44 (d, J=2.9 Hz, 1H), 2.38 (s, 1H), 2.16-2.00 (m, 2H), 1.83 (dd, J=15.6, 8.1 Hz, 2H), 1.74-1.65 (m, 1H), 1.24 (s, 1H). $^{19}$F NMR (376 MHz, DMSO-$d_6$) δ −109.31 (ddd, J=15.5, 9.3, 6.4 Hz), −112.48 (t, J=7.2 Hz), −167.67 (ddd, J=50.1, 35.0, 24.1 Hz).

Peak 2: MS (m/z) 466.27 $[M+H]^+$. $^1$H NMR (400 MHz, DMSO-$d_6$) δ 10.82 (t, J=5.7 Hz, 1H), 7.31-7.13 (m, 2H), 6.85-6.63 (m, 1H), 4.60 (dd, J=14.6, 5.9 Hz, 1H), 4.51 (dd, J=14.5, 5.5 Hz, 1H), 4.19 (dt, J=14.0, 7.4 Hz, 1H), 3.86 (d, J=14.3 Hz, 1H), 3.67 (d, J=14.2 Hz, 1H), 3.04 (dt, J=12.5, 5.8 Hz, 1H), 2.44 (d, J=3.0 Hz, 1H), 2.40-2.29 (m, 1H), 2.16-1.98 (m, 2H), 1.90-1.77 (m, 2H), 1.69 (d, J=16.1 Hz, 1H), 1.33-1.18 (m, 1H). $^{19}$F NMR (376 MHz, DMSO-$d_6$) δ −109.31 (tt, J=9.4, 6.4 Hz), −112.48 (t, J=7.2 Hz), −167.67 (ddd, J=50.0, 35.1, 24.2 Hz).

Example 9: Preparation of (6aS,8R)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-1), (6aR,8R)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-2), (6aS,8S)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-3), and (6aR,8S)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-4)

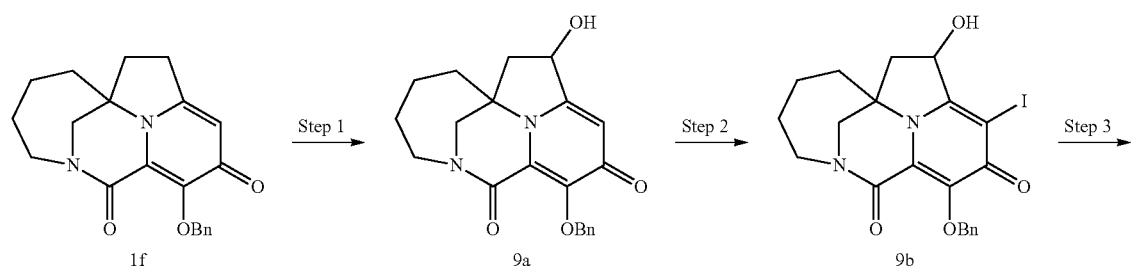

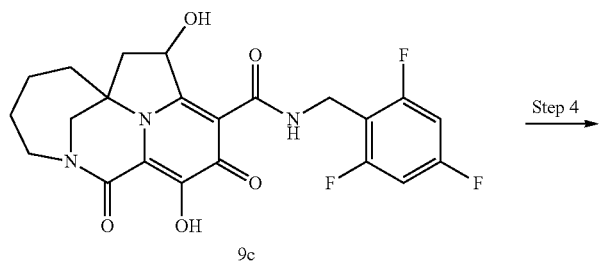

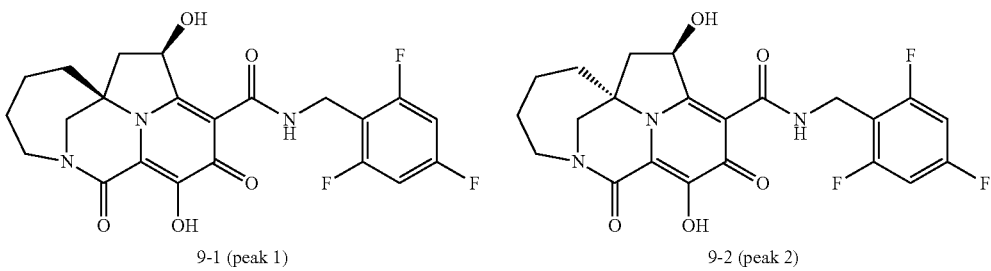

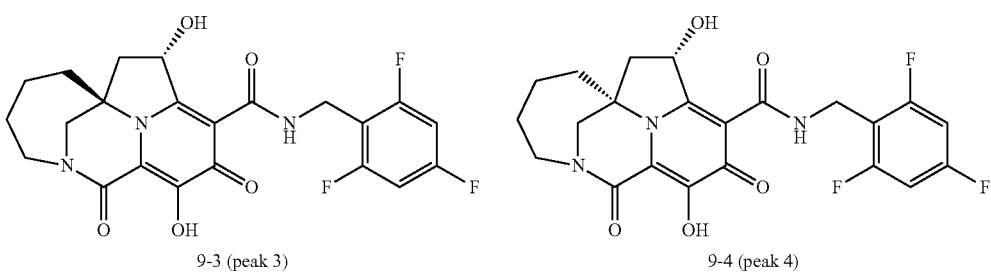

Step 1. Synthesis of 11-(benzyloxy)-8-hydroxy-3,4,5,6,7,8-hexahydro-2,6a-methano[1,4]diazonino[9,1,2-cd]indolizine-1,10-dione (9a)

A solution of 11-(benzyloxy)-3,4,5,6,7,8-hexahydro-2,6a-methano[1,4]diazonino[9,1,2-cd]indolizine-1,10-dione (0.100 g, 0.285 mmol), prepared according to the preparation of intermediate if in Example 1, in THF (5 mL) under Ar (g) was cooled to −78° C. A 1.0 M solution of LiHMDS in THF (0.856 mL, 0.856 mmol) was added dropwise. After 10 min, a solution of 2-(benzenesulfonyl)-3-phenyl-oxaziridine (0.164 g, 0.628 mmol) in THF (1 mL) was added. The reaction mixture was warmed to room temperature and left to stir for 3 h. Methanol was added to quench and the solution was concentrated. The residue was purified by column chromatography (0-20% MeOH/CH$_2$Cl$_2$) to provide 11-(benzyloxy)-8-hydroxy-3,4,5,6,7,8-hexahydro-2,6a-methano[1,4]diazonino[9,1,2-cd]indolizine-1,10-dione as a mixture of diastereomers. MS (m/z) 367.27 [M+H]$^+$.

Step 2. Synthesis of 11-(benzyloxy)-8-hydroxy-9-iodo-3,4,5,6,7,8-hexahydro-2,6a-methano[1,4]diazonino[9,1,2-cd]indolizine-1,10-dione (9b)

To a solution 11-(benzyloxy)-8-hydroxy-3,4,5,6,7,8-hexahydro-2,6a-methano[1,4]diazonino[9,1,2-cd]indolizine-1,10-dione (0.057 g, 0.155 mmol) in anhydrous methanol (1 mL) was added 77% m-CPBA (0.139 g, 0.620 mmol) and N-iodosuccinimide (0.140 g, 0.620 mmol). The reaction mixture was heated at 80° C. for 1 h and cooled to room temperature. The solution was diluted with CH$_2$Cl$_2$ and washed with 10% aqueous Na$_2$SO$_3$ solution. The aqueous phase was extracted with CH$_2$Cl$_2$ and the combined organic phase was dried over Na$_2$SO$_4$, filtered, and concentrated. The residue was purified by column chromatography (0-10% MeOH/CH$_2$Cl$_2$) to provide 11-(benzyloxy)-8-hydroxy-9-iodo-3,4,5,6,7,8-hexahydro-2,6a-methano[1,4]diazonino[9,1,2-cd]indolizine-1,10-dione. MS (m/z) 493.11 [M+H]$^+$.

Step 3. Synthesis of 11-(benzyloxy)-8-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9c)

To a solution of 11-(benzyloxy)-8-hydroxy-9-iodo-3,4,5,6,7,8-hexahydro-2,6a-methano[1,4]diazonino[9,1,2-cd]indolizine-1,10-dione (0.052 g, 0.105 mmol) in DMSO (2 mL) was added 2,4,6-trifluorobenzylamine (0.084 g, 0.524 mmol), i-Pr$_2$NEt (0.091 mL, 0.524 mmol), and Pd(PPh$_3$)$_4$ (0.006 g, 0.005 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (1×), saturated aqueous NaHCO$_3$ (1×), and brine (1×). The organic phase was dried over Na$_2$SO$_4$, filtered, and concentrated. The residue was purified by column chromatography (0-100% EtOAc/heptane) to provide 11-(benzyloxy)-8-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide. MS (m/z) 554.21 [M+H]$^+$.

Step 4. Synthesis of (6aS,8R)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-1), (6aR,8R)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-2), (6aS,8S)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-3), (6aR,8S)-8,11-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (9-4)

11-(benzyloxy)-8-hydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide was separated into its individual stereoisomers by preparative SFC on an AD-H column using 50% i-PrOH (containing 0.1% NH$_3$) co-solvent to provide four separate peaks sequentially numbered as peak 1 through 4 according to order of eluting. Among them, peaks 1 and 4 are enantiomers; peak 2 and 3 are enantiomers. Absolute configurations are not confirmed.

The separated stereoisomers were each dissolved in 1:1 toluene/TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are not confirmed.

Peak 1: MS (m/z) 464.25 [M+H]$^+$. $^1$H NMR (400 MHz, DMSO-d$_6$) δ 11.52 (t, J=5.7 Hz, 1H), 7.23 (t, J=8.6 Hz, 2H), 6.85 (s, 1H), 5.60 (dd, J=9.4, 7.0 Hz, 1H), 4.66 (dd, J=14.6, 5.9 Hz, 1H), 4.55 (dd, J=14.5, 5.5 Hz, 1H), 4.16 (dt, J=13.8, 7.3 Hz, 1H), 3.83 (s, 2H), 3.09-3.00 (m, 1H), 2.61 (dd, J=12.2, 7.1 Hz, 1H), 2.02-1.90 (m, 2H), 1.88-1.76 (m, 3H), 1.70-1.55 (m, 1H), 1.21-1.07 (m, 1H). $^{19}$F NMR (376 MHz, DMSO-d$_6$) δ −108.99 (td, J=9.3, 4.4 Hz), −112.44 (t, J=7.2 Hz).

Peak 2: MS (m/z) 464.26 [M+H]$^+$. $^1$H NMR (400 MHz, DMSO-d$_6$) δ 10.88 (t, J=5.7 Hz, 1H), 7.32-7.16 (m, 2H), 5.68 (d, J=6.7 Hz, 1H), 4.62 (dd, J=14.5, 5.8 Hz, 1H), 4.54 (dd, J=14.6, 5.6 Hz, 1H), 4.18 (dt, J=14.3, 7.4 Hz, 1H), 3.81 (d, J=14.2 Hz, 1H), 3.65 (d, J=14.1 Hz, 1H), 3.03 (dt, J=12.1, 5.7 Hz, 1H), 2.25 (dd, J=13.5, 6.9 Hz, 1H), 2.21-2.07 (m, 2H), 2.04 (d, J=13.4 Hz, 1H), 1.89-1.76 (m, 2H), 1.73-1.59 (m, 1H), 1.30-1.14 (m, 1H). $^{19}$F NMR (376 MHz, DMSO-d$_6$) δ −109.24 (ddd, J=15.5, 9.2, 6.2 Hz), −112.44 (t, J=7.2 Hz).

Peak 3: MS (m/z) 464.26 [M+H]$^+$. $^1$H NMR (400 MHz, DMSO-d$_6$) δ 10.88 (t, J=5.7 Hz, 1H), 7.32-7.13 (m, 2H), 5.68 (d, J=6.7 Hz, 1H), 4.62 (dd, J=14.5, 5.8 Hz, 1H), 4.54 (dd, J=14.5, 5.6 Hz, 1H), 4.18 (dt, J=14.1, 7.4 Hz, 1H), 3.81 (d, J=14.2 Hz, 1H), 3.65 (d, J=14.1 Hz, 1H), 3.03 (dt, J=12.3, 5.5 Hz, 1H), 2.25 (dd, J=13.4, 6.8 Hz, 1H), 2.21-2.07 (m, 2H), 2.04 (d, J=13.4 Hz, 1H), 1.90-1.76 (m, 2H), 1.73-1.59 (m, 1H), 1.31-1.13 (m, 1H). $^{19}$F NMR (376 MHz, DMSO-d$_6$) δ −109.24 (ddd, J=15.6, 9.5, 6.3 Hz), −112.44 (t, J=7.1 Hz).

Peak 4: MS (m/z) 464.22 [M+H]$^+$. $^1$H NMR (400 MHz, DMSO-d$_6$) δ 11.52 (t, J=5.6 Hz, 1H), 7.23 (t, J=8.7 Hz, 2H), 6.86 (s, 1H), 5.61 (dd, J=9.4, 7.1 Hz, 1H), 4.66 (dd, J=14.5, 6.0 Hz, 1H), 4.56 (dd, J=14.7, 5.5 Hz, 1H), 4.17 (dt, J=14.5, 7.6 Hz, 1H), 3.84 (s, 2H), 3.06 (dt, J=12.5, 5.7 Hz, 1H), 2.62 (dd, J=12.2, 7.0 Hz, 1H), 2.03-1.90 (m, 2H), 1.87-1.78 (m, 3H), 1.69-1.55 (m, 1H), 1.23-1.08 (m, 1H). $^{19}$F NMR (376 MHz, DMSO-d$_6$) δ −108.87--109.12 (m), −112.44 (t, J=7.3 Hz).

Example 10: Preparation of (6aS,8R)—N-(2,4-difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-1), (6aR,8R)—N-(2,4-difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-2), (6aS,8S)—N-(2,4-difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-3), and (6aR,8S)—N-(2,4-difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-4)

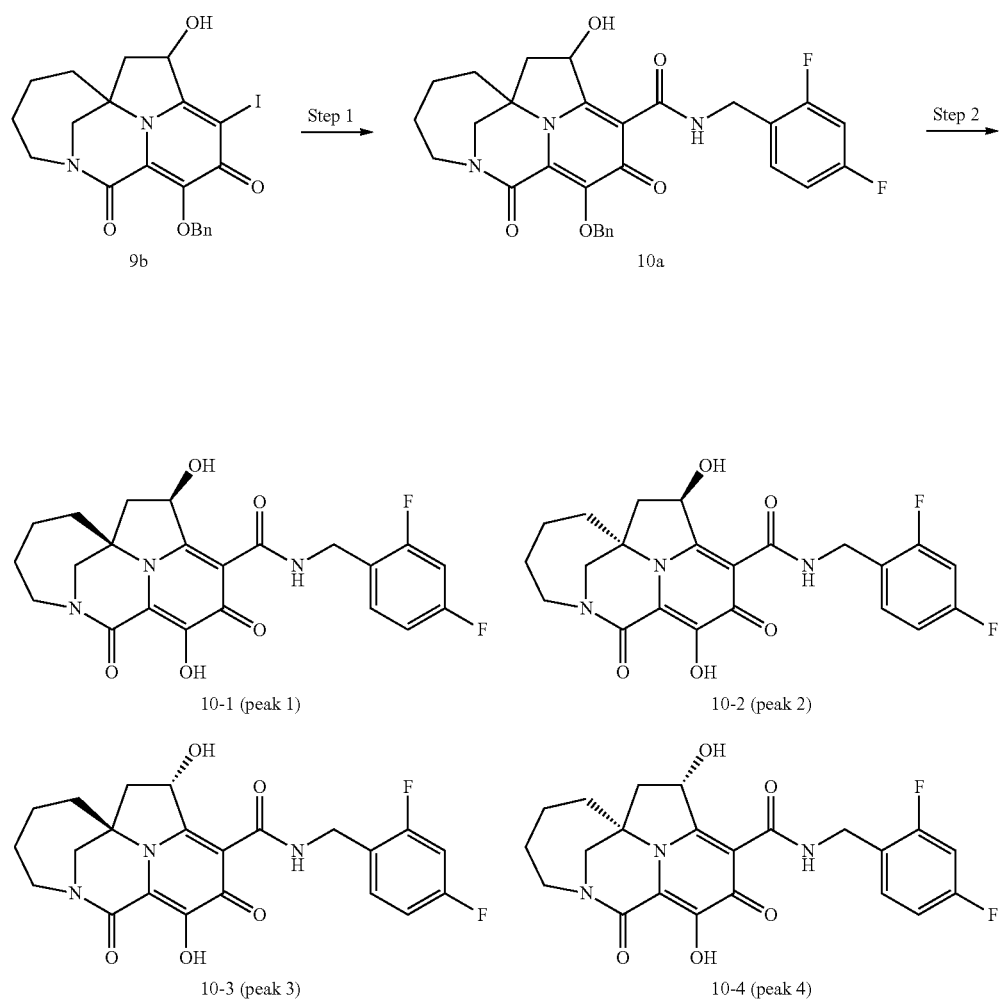

Step 1. Synthesis of 11-(benzyloxy)-N-(2,4-difluorobenzyl)-8-hydroxy-1,10-dioxo-1,3,4,5,6,7,8,10-octahydro-2,6a-methano[1,4]diazonino[9,1,2-cd]indolizine-9-carboxamide (10a)

To a solution of 11-(benzyloxy)-8-hydroxy-9-iodo-3,4,5,6,7,8-hexahydro-2,6a-methano[1,4]diazonino[9,1,2-cd]indolizine-1,10-dione (0.091 g, 0.185 mmol), prepared according to the preparation of intermediate 9b in Example 9, in DMSO (3.7 mL) was added 2,4-difluorobenzylamine (0.149 g, 1.04 mmol), i-Pr$_2$NEt (0.161 mL, 0.924 mmol), and Pd(PPh$_3$)$_4$ (0.011 g, 0.009 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (x), saturated aqueous NaHCO$_3$ (x), and brine (1x). The organic phase was dried over Na$_2$SO$_4$, filtered, and concentrated. The residue was purified by column chromatography (0-100% EtOAc/heptane) to provide 11-(benzyloxy)-N-(2,4-difluorobenzyl)-8-hydroxy-1,10-dioxo-1,3,4,5,6,7,8,10-octahydro-2,6a-methano[1,4]diazonino[9,1,2-cd]indolizine-9-carboxamide. MS (m/z) 536.16 [M+H]$^+$.

Step 2. Synthesis of (6aS,8R)—N-(2.4 difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-1), (6aR,8R)—N-(2.4 difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-2), (6aS,8S)—N-(2,4-difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-3), and (6aR,8S)—N-(2,4-difluorobenzyl)-8,11-dihydroxy-1,10-dioxo-1,3,4,5,6,7,8,10-octahydro-2,6a-methano[1,4]diazonino[9,1,2-cd]indolizine-9-carboxamide (10-4)

11-(benzyloxy)-N-(2,4-difluorobenzyl)-8-hydroxy-1,10-dioxo-1,3,4,5,6,7,8,10-octahydro-2,6a-methano[1,4]diazonino[9,1,2-cd]indolizine-9-carboxamide was separated into its individual stereoisomers by preparative SFC on an AD-H column using 50% i-PrOH (containing 0.1% NH$_3$) co-solvent to provide four separate peaks sequentially numbered as peak 1 through 4 according to order of eluting. Among them, peaks 1 and 4 are enantiomers; peak 2 and 3 are enantiomers. Absolute configurations are assigned not confirmed.

The separated stereoisomers were each dissolved in 1:1 toluene/TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are assigned not confirmed.

Peak 1: MS (m/z) 446.23 [M+H]$^+$. $^1$H NMR (400 MHz, DMSO-d$_6$) δ 11.44 (t, J=5.8 Hz, 1H), 7.45 (td, J=8.6, 6.6 Hz, 1H), 7.33-7.19 (m, 1H), 7.09 (td, J=8.6, 2.6 Hz, 1H), 5.61 (dd, J=9.4, 7.1 Hz, 1H), 4.60 (qd, J=15.0, 5.7 Hz, 2H), 4.18 (dt, J=14.1, 7.4 Hz, 1H), 3.85 (s, 2H), 3.07 (dt, J=12.5, 5.7 Hz, 1H), 2.63 (dd, J=12.2, 7.0 Hz, 1H), 2.04-1.92 (m, 2H), 1.89-1.77 (m, 3H), 1.71-1.55 (m, 1H), 1.22-1.08 (m, 1H). $^{19}$F NMR (376 MHz, DMSO-d$_6$) δ -112.03 (p, J=8.1 Hz), -114.77 (q, J=8.9 Hz).

Peak 2: MS (m/z) 446.27 [M+H]$^+$. $^1$H NMR (400 MHz, DMSO-d$_6$) δ 10.80 (t, J=5.8 Hz, 1H), 7.44 (td, J=8.7, 6.6 Hz, 1H), 7.26 (ddd, J=10.6, 9.3, 2.6 Hz, 1H), 7.08 (td, J=8.5, 2.6 Hz, 1H), 5.68 (d, J=6.7 Hz, 1H), 4.63-4.52 (m, 2H), 4.19 (dt, J=13.2, 7.5 Hz, 1H), 3.83 (d, J=14.2 Hz, 1H), 3.68 (dd, J=14.1, 1.4 Hz, 1H), 3.05 (ddd, J=13.3, 6.6, 4.7 Hz, 1H), 2.28 (dd, J=13.5, 6.9 Hz, 1H), 2.20 (dd, J=15.5, 6.4 Hz, 1H), 2.15-2.08 (m, 1H), 2.06 (d, J=13.5 Hz, 1H), 1.91-1.77 (m, 2H), 1.73-1.62 (m, 1H), 1.30-1.16 (m, 1H). $^{19}$F NMR (376 MHz, DMSO-d$_6$) δ -112.32 (p, J=7.7 Hz), -114.96 (q, J=8.8 Hz).

Peak 3: MS (m/z) 446.26 [M+H]$^+$. $^1$H NMR (400 MHz, DMSO-d$_6$) δ 10.80 (t, J=5.9 Hz, 1H), 7.50-7.37 (m, 1H), 7.26 (td, J=10.0, 2.6 Hz, 1H), 7.08 (td, J=8.5, 2.5 Hz, 1H), 5.68 (d, J=6.8 Hz, 1H), 4.64-4.51 (m, 2H), 4.19 (dt, J=14.1, 7.5 Hz, 1H), 3.83 (d, J=14.2 Hz, 1H), 3.68 (d, J=14.1 Hz, 1H), 3.05 (dt, J=12.3, 5.5 Hz, 1H), 2.28 (dd, J=13.5, 6.8 Hz, 1H), 2.20 (dd, J=15.4, 6.4 Hz, 1H), 2.16-2.09 (m, 1H), 2.06 (d, J=13.4 Hz, 1H), 1.92-1.78 (m, 2H), 1.74-1.62 (m, 1H), 1.30-1.15 (m, 1H). $^{19}$F NMR (376 MHz, DMSO-d$_6$) δ -112.32 (p, J=7.6 Hz), -114.96 (q, J=8.5 Hz).

Peak 4: MS (m/z) 446.24 [M+H]$^+$. $^1$H NMR (400 MHz, DMSO-d$_6$) δ 11.43 (t, J=5.8 Hz, 1H), 7.44 (td, J=8.7, 6.6 Hz, 1H), 7.26 (td, J=9.9, 2.6 Hz, 1H), 7.08 (td, J=8.5, 2.7 Hz, 1H), 5.61 (dd, J=9.4, 7.1 Hz, 1H), 4.59 (qd, J=14.9, 5.8 Hz, 2H), 4.17 (dt, J=14.2, 7.4 Hz, 1H), 3.84 (s, 2H), 3.05 (dd, J=12.8, 5.9 Hz, 1H), 2.62 (dd, J=12.2, 7.1 Hz, 1H), 2.03-1.92 (m, 2H), 1.89-1.76 (m, 3H), 1.69-1.57 (m, 1H), 1.22-1.08 (m, 1H). $^{19}$F NMR (376 MHz, DMSO-d$_6$) δ -112.03 (p, J=8.2 Hz), -114.77 (q, J=8.9 Hz).

Example 11: Preparation of (6aR,7S,8S)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-1), (6aS,7S,8S)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-2), (6aR,7R,8R)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-3), and (6aS,7R,8R)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-4)

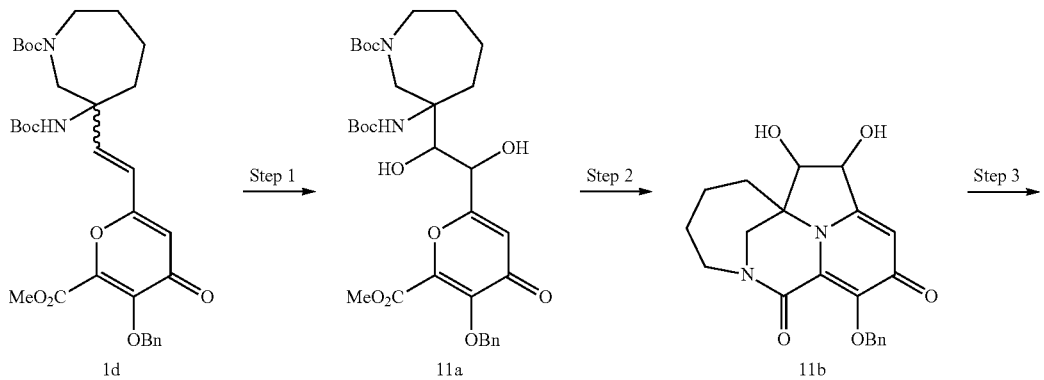

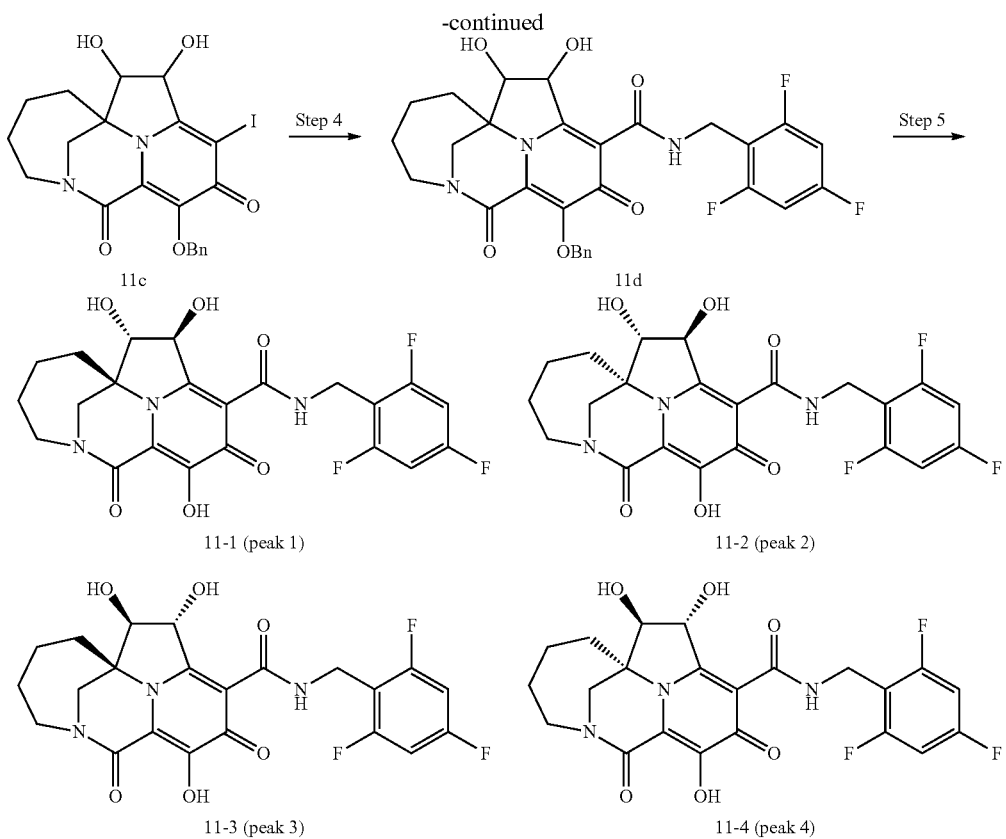

11-3 (peak 3)

11-4 (peak 4)

Step 1. Synthesis of tert-butyl 3-(2-(5-(benzyloxy)-6-(methoxycarbonyl)-4-oxo-4H-pyran-2-yl)-1,2 dihydroxyethyl)-3-((tert-butoxycarbonyl)amino) azepane-1-carboxylate (11a)

To a solution of tert-butyl (E)-3-(2-(5-(benzyloxy)-6-(methoxycarbonyl)-4-oxo-4H-pyran-2-yl)vinyl)-3-((tert-butoxycarbonyl)amino)azepane-1-carboxylate (0.595 g, 0.994 mmol), prepared according to the preparation of intermediate 1d in Example 1, in 1:1 acetone/water (14.3 mL) was added NMO (0.233 g, 1.99 mmol) and 2.5% $OsO_4$ solution in tBuOH (0.125 mL, 0.010 mmol). The reaction mixture was stirred at rt for 24 h, quenched with saturated aqueous sodium thiosulfate and $NaHCO_3$, and stirred 1 h. The mixture was concentrated and $CH_2Cl_2$ was added. The phases were separated and the aqueous phase was extracted with $CH_2Cl_2$ (2×). The combined organic phase was dried over $Na_2SO_4$, filtered, concentrated, and purified by column chromatography (0-80% EtOAc/hexanes) to provide tert-butyl 3-(2-(5-(benzyloxy)-6-(methoxycarbonyl)-4-oxo-4H-pyran-2-yl)-1,2-dihydroxyethyl)-3-((tert-butoxycarbonyl) amino)azepane-1-carboxylate. MS (m/z) 632.87 [M+H]$^+$.

Step 2. Synthesis of 11-(benzyloxy)-7,8-dihydroxy-3,4,5,6,7,8-hexahydro-2,6a-methano[1,4]diazonino[9,1,2-cd]indolizine-1,10-dione (11b)

To a solution of tert-butyl 3-(2-(5-(benzyloxy)-6-(methoxycarbonyl)-4-oxo-4H-pyran-2-yl)-1,2-dihydroxyethyl)-3-((tert-butoxycarbonyl)amino)azepane-1-carboxylate (0.519 g, 0.821 mmol) in $CH_2Cl_2$ (20 mL) at 0° C. was added trifluoroacetic acid (4.00 mL, 50.5 mmol). The reaction mixture was stirred for 2 h, warmed to rt, concentrated, and dried under high vacuum for 1 h. The residue was dissolved in ethanol (20 mL) and heated at 90° C. for 3 h. The reaction mixture was cooled to rt, concentrated, and purified by column chromatography to provide 11-(benzyloxy)-7,8-dihydroxy-3,4,5,6,7,8-hexahydro-2,6a-methano[1,4]diazonino[9,1,2-cd]indolizine-1,10-dione. MS (m/z) 383.26 [M+H]$^+$.

Step 3. Synthesis of 11-(benzyloxy)-7,8-dihydroxy-9-iodo-3,4,5,6,7,8-hexahydro-2,6a-methano[1,4]diazonino[9,1,2-cd]indolizine-1,10-dione (11c)

To a solution 11-(benzyloxy)-7,8-dihydroxy-3,4,5,6,7,8-hexahydro-2,6a-methano[1,4]diazonino[9,1,2-cd]indolizine-1,10-dione (0.100 g, 0.261 mmol) in anhydrous methanol (2 mL) was added 77% m-CPBA (0.234 g, 1.05 mmol) and N-iodosuccinimide (0.235 g, 1.05 mmol). The reaction mixture was heated at 80° C. for 0.5 h and cooled to room temperature. The solution was diluted with $CH_2Cl_2$ and washed with 10% aqueous $Na_2SO_3$ solution. The aqueous phase was extracted with $CH_2Cl_2$ and the combined organic phase was washed with brine, dried over $Na_2SO_4$, filtered, and concentrated. The residue was purified by column chromatography (0-10% MeOH/$CH_2Cl_2$) to provide 11-(benzyloxy)-7,8-dihydroxy-9-iodo-3,4,5,6,7,8-hexahydro-2,6a-methano[1,4]diazonino[9,1,2-cd]indolizine-1,10-dione. MS (m/z) 509.09 [M+H]$^+$.

Step 4. Synthesis of 11-(benzyloxy)-7,8-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11d)

To a solution of 11-(benzyloxy)-7,8-dihydroxy-9-iodo-3,4,5,6,7,8-hexahydro-2,6a-methano[1,4]diazonino[9,1,2-cd]

indolizine-1,10-dione (0.027 g, 0.053 mmol) in DMSO (2 mL) was added 2,4,6-trifluorobenzylamine (0.043 g, 0.266 mmol), i-Pr$_2$NEt (0.046 mL, 0.266 mmol), and Pd(PPh$_3$)$_4$ (0.003 g, 0.003 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (1×), saturated aqueous NaHCO$_3$ (1×), and brine (1×). The organic phase was dried over Na$_2$SO$_4$, filtered, concentrated, and purified by column chromatography (0-20% MeOH/CH$_2$Cl$_2$) to provide 11-(benzyloxy)-7,8-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide. MS (m/z) 570.21 [M+H]$^+$.

Step 5. Synthesis of (6aR,7S,8S)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-1), (6aS,7S,8S)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-2), (6aR,7R,8R)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-3), and (6aS,7R,8R)-7,8,11-trihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (11-4)

11-(benzyloxy)-7,8-dihydroxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide was separated into its individual stereoisomers by preparative SFC on an IB column using 40% MeOH co-solvent to provide four separate peaks sequentially numbered as peak 1 through 4 according to order of eluting. Among them, peaks 1 and 4 are enantiomers; peak 2 and 3 are enantiomers. Absolute configurations are assigned not confirmed.

The separated stereoisomers were each dissolved in 1:1 toluene/TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are assigned not confirmed.

Peak 1: MS (m/z) 480.20 [M+H]$^+$. $^1$H NMR (400 MHz, DMSO-d$_6$) δ 10.86 (t, J=5.7 Hz, 1H), 7.22 (t, J=8.6 Hz, 2H), 5.74 (s, 1H), 5.53 (s, 1H), 4.57 (qd, J=14.6, 5.7 Hz, 2H), 4.20 (dt, J=13.7, 6.9 Hz, 1H), 4.06 (s, 1H), 3.79 (d, J=14.6 Hz, 1H), 3.65 (d, J=14.6 Hz, 1H), 3.03 (dt, J=12.6, 6.0 Hz, 1H), 2.49-2.43 (m, 1H), 2.17-2.06 (m, 1H), 2.00 (dd, J=15.5, 7.1 Hz, 1H), 1.86-1.75 (m, 2H), 1.78-1.59 (m, 1H), 1.25 (d, J=15.5 Hz, 1H). $^{19}$F NMR (376 MHz, DMSO-d$_6$) δ −109.28 (ddd, J=15.6, 9.3, 6.2 Hz), −112.43 (t, J=7.2 Hz).

Peak 2: MS (m/z) 480.21 [M+H]$^+$. $^1$H NMR (400 MHz, DMSO-d$_6$) δ 11.50 (t, J=5.7 Hz, 1H), 7.23 (t, J=8.6 Hz, 2H), 6.98 (s, 1H), 5.10 (d, J=8.0 Hz, 1H), 4.65 (dd, J=14.6, 5.8 Hz, 1H), 4.55 (dd, J=14.6, 5.4 Hz, 1H), 4.15 (dt, J=13.5, 6.9 Hz, 1H), 4.06 (d, J=7.9 Hz, 1H), 3.83-3.70 (m, 2H), 3.05 (dt, J=12.8, 6.0 Hz, 1H), 2.32-2.25 (m, 1H), 1.86-1.74 (m, 2H), 1.75-1.69 (m, 1H), 1.69-1.59 (m, 1H), 1.50 (dd, J=15.1, 7.2 Hz, 1H), 1.34-1.26 (m, 1H). $^{19}$F NMR (376 MHz, DMSO-d$_6$) δ −108.87--109.08 (m), −112.43 (t, J=7.4 Hz).

Peak 3: MS (m/z) 480.22 [M+H]$^+$. $^1$H NMR (400 MHz, DMSO-d$_6$) δ 11.51 (t, J=5.7 Hz, 1H), 7.28-7.18 (m, 2H), 6.99 (s, 1H), 5.10 (d, J=8.0 Hz, 1H), 4.66 (dd, J=14.7, 5.8 Hz, 1H), 4.56 (dd, J=14.6, 5.5 Hz, 1H), 4.21-4.11 (m, 1H), 4.07 (d, J=8.2 Hz, 1H), 3.81-3.72 (m, 2H), 3.10-3.02 (m, 1H), 2.33-2.25 (m, 1H), 1.88-1.70 (m, 3H), 1.70-1.59 (m, 1H), 1.51 (dd, J=14.6, 7.5 Hz, 1H), 1.32-1.24 (m, 1H). $^{19}$F NMR (376 MHz, DMSO-d$_6$) δ −108.87--109.07 (m), −112.43 (t, J=7.2 Hz).

Peak 4: MS (m/z) 480.20 [M+H]$^+$. $^1$H NMR (400 MHz, DMSO-d$_6$) δ 10.86 (t, J=5.7 Hz, 1H), 7.28-7.13 (m, 2H), 5.74 (s, 1H), 5.53 (s, 1H), 4.57 (qd, J=14.5, 5.7 Hz, 2H), 4.20 (dt, J=13.4, 6.8 Hz, 1H), 4.06 (s, 1H), 3.79 (d, J=14.5 Hz, 1H), 3.65 (d, J=14.6 Hz, 1H), 3.03 (dt, J=13.0, 6.1 Hz, 1H), 2.17-2.06 (m, 1H), 2.00 (dd, J=15.4, 7.3 Hz, 1H), 1.85-1.74 (m, 2H), 1.74-1.61 (m, 1H), 1.35-1.24 (m, 1H). $^{19}$F NMR (376 MHz, DMSO-d$_6$) δ −109.28 (ddd, J=9.4, 6.5, 3.0 Hz), −112.43 (t, J=7.1 Hz).

Example 12: Preparation of (6aS,8R)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-1), (6aR,8S)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-2), (6aS,8S)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-3), and (6aR,8R)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-4)

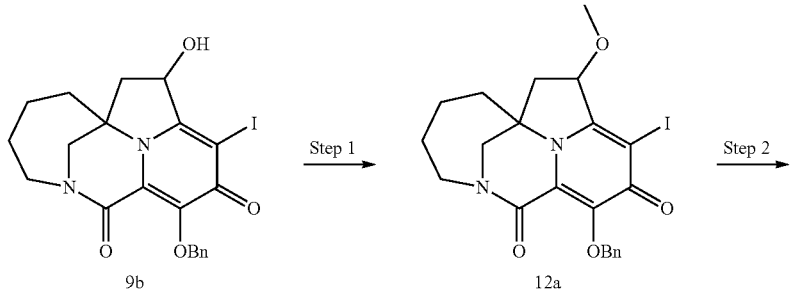

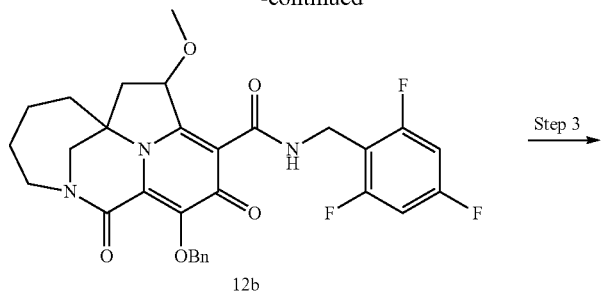

12b

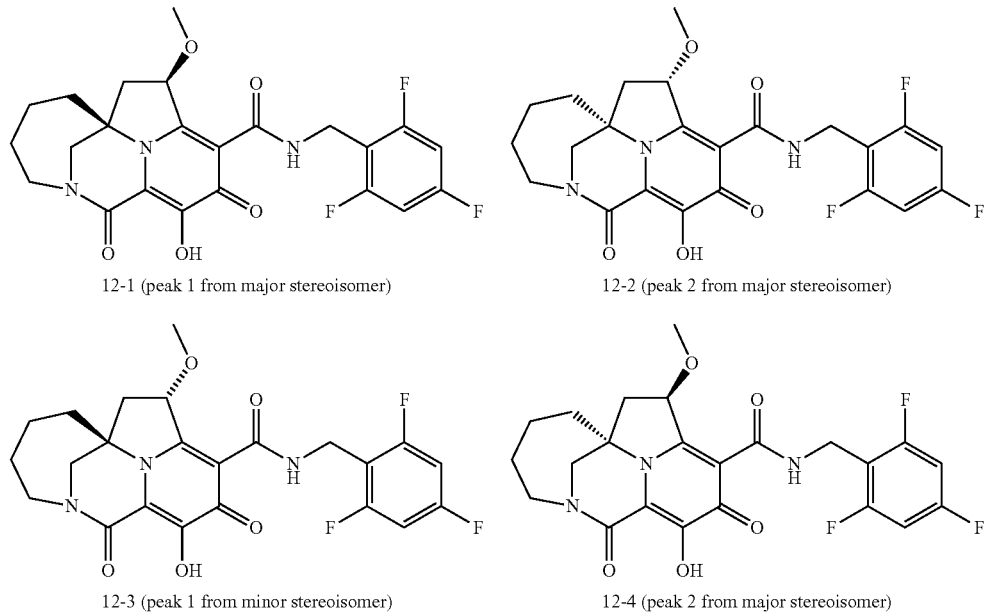

12-1 (peak 1 from major stereoisomer)   12-2 (peak 2 from major stereoisomer)

12-3 (peak 1 from minor stereoisomer)   12-4 (peak 2 from major stereoisomer)

Step 1. Synthesis of 11-(benzyloxy)-9-iodo-8-methoxy-3,4,5,6,7,8-hexahydro-2,6a-methano[1,4]diazonino[9,1,2-cd]indolizine-1,10-dione (12a)

To a solution of 11-(benzyloxy)-8-hydroxy-9-iodo-3,4,5,6,7,8-hexahydro-2,6a-methano[1,4]diazonino[9,1,2-cd]indolizine-1,10-dione (0.035 g, 0.071 mmol), prepared according to the preparation of intermediate 9b in Example 9, in DMF (1 mL) at rt was added 60% sodium hydride (0.004 g, 0.107 mmol). After 5 min, iodomethane (0.009 mL, 0.142 mmol) was added. The reaction was stirred for 2 h, quenched with MeOH, concentrated, and purified by column chromatography (0-10% MeOH/CH$_2$Cl$_2$). The impure residue was purified again by column chromatography (20-100% EtOAc/hexanes) to provide 11-(benzyloxy)-9-iodo-8-methoxy-3,4,5,6,7,8-hexahydro-2,6a-methano[1,4]diazonino[9,1,2-cd]indolizine-1,10-dione. MS (m/z) 507.10 [M+H]$^+$.

Step 2. Synthesis of 11-(benzyloxy)-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12b)

To a solution of 11-(benzyloxy)-9-iodo-8-methoxy-3,4,5,6,7,8-hexahydro-2,6a-methano[1,4]diazonino[9,1,2-cd]indolizine-1,10-dione (0.016 g, 0.032 mmol) in DMSO (1 mL) was added 2,4,6-trifluorobenzylamine (0.026 g, 0.160 mmol), i-Pr$_2$NEt (0.028 mL, 0.160 mmol), and Pd(PPh$_3$)$_4$ (0.002 g, 0.002 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (1×), saturated aqueous NaHCO$_3$ (1×), and brine (1×). The organic phase was dried over Na$_2$SO$_4$, filtered, and concentrated. The residue was purified by column chromatography (0-10% MeOH/CH$_2$Cl$_2$) to provide 11-(benzyloxy)-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide as two separable stereoisomers.

Peak 1 (major): MS (m/z) 568.15 [M+H]$^+$.
Peak 2 (minor): MS (m/z) 568.18 [M+H]$^+$.

Step 3. Synthesis of (6aS,8R)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-1), (6aR,8S)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-2), (6aS,8S)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-3), and (6aR,8R)-11-hydroxy-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (12-4)

The major diastereomer of 11-(benzyloxy)-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (Peak 1 from 12b) was separated into its individual stereoisomers by preparative SFC on an AD-H column using 40% MeOH co-solvent to provide two separate peaks. The separated stereoisomers were each dissolved in 1:1 toluene/TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are assigned not confirmed.

Peak 1: MS (m/z) 478.19 [M+H]$^+$. $^1$H NMR (400 MHz, DMSO-$d_6$) δ 10.83 (t, J=5.6 Hz, 1H), 7.32-7.13 (m, 2H), 5.68 (d, J=5.6 Hz, 1H), 4.63 (dd, J=14.4, 6.1 Hz, 1H), 4.47 (dd, J=14.4, 5.1 Hz, 1H), 4.18 (dt, J=13.6, 7.1 Hz, 1H), 3.81 (d, J=14.2 Hz, 1H), 3.63 (d, J=14.3 Hz, 1H), 3.39 (s, 3H), 3.02 (dt, J=12.7, 5.7 Hz, 1H), 2.27 (d, J=13.5 Hz, 1H), 2.13-2.02 (m, 3H), 1.87-1.76 (m, 2H), 1.72-1.61 (m, 1H), 1.31-1.24 (m, 1H). $^{19}$F NMR (376 MHz, DMSO-$d_6$) δ −109.34 (tt, J=9.7, 6.4 Hz), −112.45 (t, J=7.3 Hz).

Peak 2: MS (m/z) 478.18 [M+H]$^+$. $^1$H NMR (400 MHz, DMSO-$d_6$) δ 10.83 (t, J=5.6 Hz, 1H), 7.26-7.16 (m, 2H), 5.68 (d, J=5.6 Hz, 1H), 4.63 (dd, J=14.5, 6.0 Hz, 1H), 4.47 (dd, J=14.5, 5.2 Hz, 1H), 4.18 (dt, J=13.8, 7.1 Hz, 1H), 3.81 (d, J=14.2 Hz, 1H), 3.63 (d, J=14.3 Hz, 1H), 3.39 (s, 3H), 3.02 (dt, J=12.5, 5.7 Hz, 1H), 2.27 (d, J=13.5 Hz, 1H), 2.13-2.03 (m, 3H), 1.86-1.76 (m, 2H), 1.71-1.62 (m, 1H), 1.31-1.24 (m, 1H). $^{19}$F NMR (376 MHz, DMSO-$d_6$) δ −109.34 (ddd, J=9.0, 6.4, 2.9 Hz), −112.45 (t, J=7.2 Hz).

The minor diastereomer of 11-(benzyloxy)-8-methoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (Peak 2 from 12b) was separated into its individual stereoisomers by preparative SFC on an OJ-H column using 20% EtOH co-solvent to provide two separate peaks. The separated stereoisomers were each dissolved in 1:1 toluene/TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are assigned not confirmed.

Peak 1: MS (m/z) 478.12 [M+H]$^+$. $^1$H NMR (400 MHz, DMSO-$d_6$) δ 9.66 (t, J=5.6 Hz, 1H), 7.22-7.14 (m, 2H), 5.37 (t, J=7.6 Hz, 1H), 4.55 (dd, J=14.3, 6.2 Hz, 1H), 4.41 (dd, J=14.5, 5.1 Hz, 1H), 4.16 (dt, J=14.2, 7.6 Hz, 1H), 3.85-3.74 (m, 2H), 3.27 (s, 3H), 3.09-3.00 (m, 1H), 2.76 (dd, J=12.4, 7.2 Hz, 1H), 1.89-1.72 (m, 5H), 1.67-1.56 (m, 1H), 1.16-1.05 (m, 1H). $^{19}$F NMR (376 MHz, DMSO-$d_6$) δ −109.64 (ddd, J=9.4, 6.4, 3.0 Hz), −112.09 (t, J=7.1 Hz).

Peak 2: MS (m/z) 478.13 [M+H]$^+$. $^1$H NMR (400 MHz, DMSO-$d_6$) δ 9.67 (t, J=5.6 Hz, 1H), 7.25-7.17 (m, 2H), 5.37 (t, J=7.6 Hz, 1H), 4.56 (dd, J=14.2, 6.1 Hz, 1H), 4.42 (dd, J=14.4, 5.0 Hz, 1H), 4.17 (dt, J=14.0, 7.6 Hz, 1H), 3.87-3.74 (m, 2H), 3.28 (s, 3H), 3.09-3.01 (m, 1H), 2.77 (dd, J=12.3, 7.2 Hz, 1H), 1.94-1.75 (m, 5H), 1.69-1.52 (m, 1H), 1.21-1.00 (m, 1H). $^{19}$F NMR (376 MHz, DMSO-$d_6$) δ −109.64 (tt, J=9.0, 6.1 Hz), −112.09 (t, J=7.2 Hz).

Example 13: Preparation of (6aR,7S,8S)-11-hydroxy-7,8-dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (13-1), (6aS,7R,8R)-11-hydroxy-7,8-dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (13-2), (6aR,7R,8R)-11-hydroxy-7,8-dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (13-3), and (6aS,7S,8S)-11-hydroxy-7,8-dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (13-4)

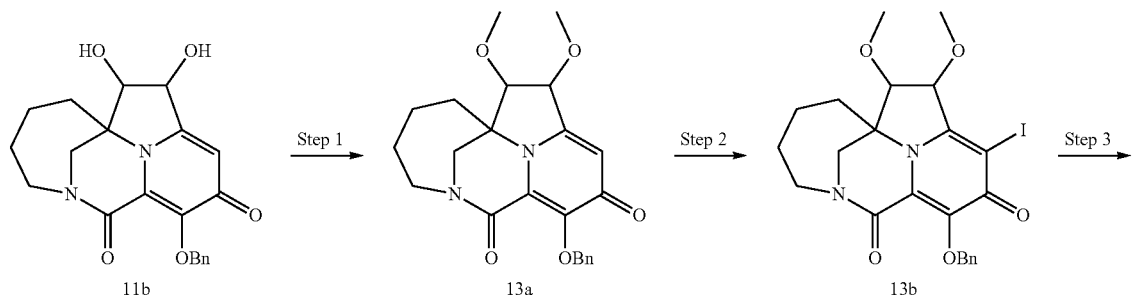

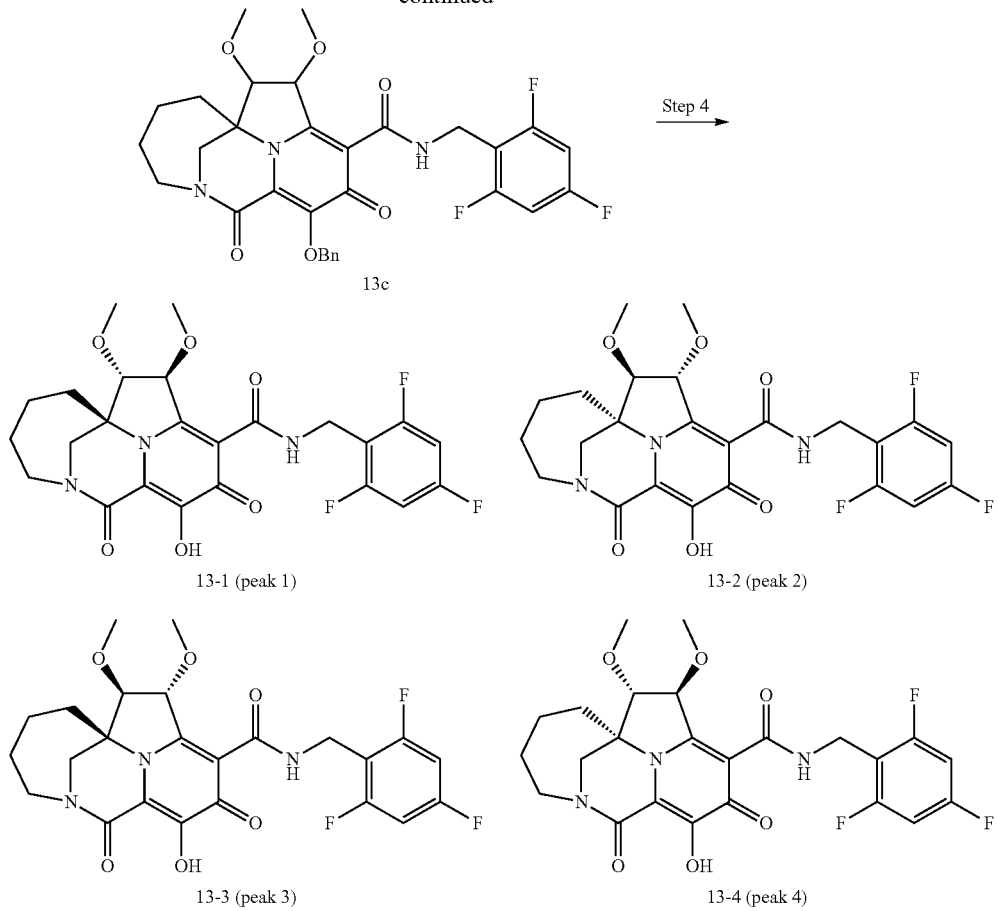

Step 1. Synthesis of 11-(benzyloxy)-7,8-dimethoxy-3,4,5,6,7,8-hexahydro-2,6a-methano[1,4]diazonino[9,1,2-cd]indolizine-1,10-dione (13a)

To a solution of 11-(benzyloxy)-7,8-dihydroxy-3,4,5,6,7,8-hexahydro-2,6a-methano[1,4]diazonino[9,1,2-cd]indolizine-1,10-dione (0.250 g, 0.654 mmol), prepared according to the preparation of intermediate 11b in Example 11, in DMF (20 mL) at rt was added 60% sodium hydride (0.063 g, 1.63 mmol). After 5 min, iodomethane (0.163 mL, 2.61 mmol) was added. The reaction was stirred for 2 h, quenched with MeOH, concentrated, and purified by column chromatography (0-100% EtOAc/heptane then 0-10% MeOH/CH$_2$Cl$_2$) to provide 11-(benzyloxy)-7,8-dimethoxy-3,4,5,6,7,8-hexahydro-2,6a-methano[1,4]diazonino[9,1,2-cd]indolizine-1,10-dione. MS (m/z) 411.28 [M+H]$^+$.

Step 2. Synthesis of 11-(benzyloxy)-9-iodo-7.8 dimethoxy-3,4,5,6,7,8-hexahydro-2,6a-methano[1,4]diazonino[9,1,2-cd]indolizine-1,10-dione (13b)

To a solution 11-(benzyloxy)-7,8-dimethoxy-3,4,5,6,7,8-hexahydro-2,6a-methano[1,4]diazonino[9,1,2-cd]indolizine-1,10-dione (0.036 g, 0.088 mmol) in anhydrous methanol (1 mL) was added 77% m-CPBA (0.079 g, 0.351 mmol) and N-iodosuccinimide (0.079 g, 0.351 mmol). The reaction mixture was heated at 80° C. for 1 h and cooled to room temperature. The solution was diluted with CH$_2$Cl$_2$ and washed with 10% aqueous Na$_2$SO$_3$ solution. The aqueous phase was extracted with CH$_2$Cl$_2$ and the combined organic phase was washed with brine, dried over Na$_2$SO$_4$, filtered, and concentrated. The residue was purified by column chromatography (0-10% MeOH/CH$_2$Cl$_2$) to provide 11-(benzyloxy)-9-iodo-7,8-dimethoxy-3,4,5,6,7,8-hexahydro-2,6a-methano[1,4]diazonino[9,1,2-cd]indolizine-1,10-dione. MS (m/z) 537.08 [M+H]$^+$.

Step 3. Synthesis of 11-(benzyloxy-7.8 dimethoxy-1,10-dioxo-N-(2,4,6-trifluorobenzyl-1,3,4,5,6,7,8,10-octahydro-2,6a-methano[1,4]diazonino[9,1,2-cd]indolizine-9-carboxamide (13c)

To a solution of 11-(benzyloxy)-9-iodo-7,8-dimethoxy-3,4,5,6,7,8-hexahydro-2,6a-methano[1,4]diazonino[9,1,2-cd]indolizine-1,10-dione (0.034 g, 0.064 mmol) in DMSO (1.4 mL) was added 2,4,6-trifluorobenzylamine (0.052 g, 0.322 mmol), i-Pr$_2$NEt (0.056 mL, 0.322 mmol), and Pd(PPh$_3$)$_4$ (0.004 g, 0.003 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (1×), saturated aqueous NaHCO$_3$ (1×), and brine (1×). The organic phase was dried over Na$_2$SO$_4$, filtered, and concentrated. The residue was purified by column chromatography (0-100% EtOAc/heptane) to provide 11-(benzyloxy)-7,8-dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide. MS (m/z) 598.15 [M+H]$^+$.

Step 4. Synthesis of (6aR,7S,8S)-11-hydroxy-7.8 dimethoxy-1,10-dioxo-N-(2,4,6-trifluorobenzyl-1,3, 4,5,6,7,8,10-octahydro-2,6a-methano[1,4]diazonino [9,1,2-cd]indolizine-9-carboxamide (13-1), (6aS,7R, 8R)-11-hydroxy-7.8 dimethoxy-1,10-dioxo-N-(2,4, 6-trifluorobenzyl)-1,3,4,5,6,7,8,10-octahydro-2,6a-methano[1,4]diazonino[9,1,2-cd]indolizine-9-carboxamide (13-2), (6aR,7R,8R)-11-hydroxy-7.8 dimethoxy-1,10-dioxo-N-(2,4,6-trifluorobenzyl)-1,3, 4,5,6,7,8,10-octahydro-2,6a-methano[1,4]diazonino [9,1,2-cd]indolizine-9-carboxamide (13-3), and (6aS,7S,8S)-11-hydroxy-7.8 dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (13-4)

11-(benzyloxy)-7,8-dimethoxy-1,10-dioxo-N-(2,4,6-trifluorobenzyl)-1,3,4,5,6,7,8,10-octahydro-2,6a-methano[1,4]diazonino[9,1,2-cd]indolizine-9-carboxamide was separated into its individual stereoisomers by preparative SFC on an IA column using 50% i-PrOH (containing 0.1% NH₃) co-solvent to provide four separate peaks, sequentially numbered as peak 1 through 4 according to order of eluting. The separated stereoisomers were each dissolved in 1:1 toluene/ TFA (2 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford the title compounds. Absolute configurations are assigned not confirmed.

Peak 1: MS (m/z) 508.22 [M+H]$^+$. $^1$H NMR (400 MHz, DMSO-d$_6$) δ 10.80 (t, J=5.6 Hz, 1H), 7.32-7.13 (m, 2H), 5.76 (s, 1H), 5.52 (s, 1H), 4.61 (dd, J=14.5, 5.9 Hz, 1H), 4.51 (dd, J=14.5, 5.4 Hz, 1H), 4.20 (dt, J=13.0, 6.3 Hz, 1H), 4.05 (s, 1H), 3.79 (s, 2H), 3.53 (s, 3H), 3.40 (s, 3H), 3.04 (dt, J=12.8, 5.8 Hz, 1H), 2.21-2.07 (m, 1H), 1.94-1.73 (m, 4H), 1.42-1.22 (m, 1H). $^{19}$F NMR (376 MHz, DMSO-d$_6$) δ −109.24 (tt, J=9.4, 6.3 Hz), −112.28--112.58 (m).

Peak 2: MS (m/z) 508.24 [M+H]$^+$. $^1$H NMR (400 MHz, DMSO-d$_6$) δ 10.80 (t, J=5.6 Hz, 1H), 7.23 (t, J=8.6 Hz, 2H), 5.76 (s, 1H), 5.52 (s, 1H), 4.61 (dd, J=14.5, 5.9 Hz, 1H), 4.51 (dd, J=14.5, 5.4 Hz, 1H), 4.26-4.15 (m, 1H), 4.05 (s, 1H), 3.79 (s, 2H), 3.53 (s, 3H), 3.40 (s, 3H), 3.04 (dt, J=12.7, 5.9 Hz, 1H), 2.15 (dd, J=15.5, 10.0 Hz, 1H), 1.92-1.75 (m, 4H), 1.40-1.25 (m, 1H). $^{19}$F NMR (376 MHz, DMSO-d$_6$) δ −109.24 (tt, J=9.4, 6.3 Hz), −112.45 (t, J=7.3 Hz).

Peak 3: MS (m/z) 508.20 [M+H]$^+$. $^1$H NMR (400 MHz, DMSO-d$_6$) δ 9.35 (t, J=5.6 Hz, 1H), 7.26-7.09 (m, 2H), 4.89 (d, J=7.4 Hz, 1H), 4.46 (qd, J=14.4, 5.5 Hz, 2H), 4.14 (dt, J=14.3, 7.4 Hz, 1H), 4.02-3.81 (m, 3H), 3.48 (s, 3H), 3.39 (s, 3H), 3.09-3.00 (m, 1H), 2.15-1.99 (m, 1H), 1.89-1.76 (m, 2H), 1.75-1.61 (m, 1H), 1.54 (dd, J=15.3, 6.5 Hz, 1H), 1.26-1.09 (m, 1H). $^{19}$F NMR (376 MHz, DMSO-d$_6$) δ −109.66 (tt, J=9.5, 6.2 Hz), −112.01 (t, J=7.0 Hz).

Peak 4: MS (m/z) 508.21 [M+H]$^+$. $^1$H NMR (400 MHz, DMSO-d$_6$) δ 9.35 (t, J=5.6 Hz, 1H), 7.31-7.09 (m, 2H), 4.90 (d, J=7.3 Hz, 1H), 4.47 (qd, J=14.4, 5.7 Hz, 2H), 4.15 (dt, J=14.1, 7.4 Hz, 1H), 3.98-3.82 (m, 3H), 3.48 (s, 3H), 3.40 (s, 3H), 3.10-3.02 (m, 1H), 2.13-2.02 (m, 1H), 1.89-1.78 (m, 2H), 1.75-1.64 (m, 1H), 1.54 (dd, J=15.2, 6.6 Hz, 1H), 1.28-1.12 (m, 1H). $^{19}$F NMR (376 MHz, DMSO-d$_6$) δ −109.66 (tt, J=9.1, 6.3 Hz), −112.01 (t, J=7.1 Hz).

Example 14: Preparation of (6aR,8R)—N-(3-chloro-2,4-difluorobenzyl)-8,11-dihydroxy-1,10-dioxo-1,3,4,5,6,7,8,10-octahydro-2,6a-methano[1,4] diazonino[9,1,2-cd]indolizine-9-carboxamide (14-1) and (6aR,8S)—N-(3-chloro-2,4-difluorobenzyl)-8, 11-dihydroxy-1,10-dioxo-1,3,4,5,6,7,8,10-octahydro-2,6a-methano[1,4]diazonino[9,1,2-cd]indolizine-9-carboxamide (14-2)

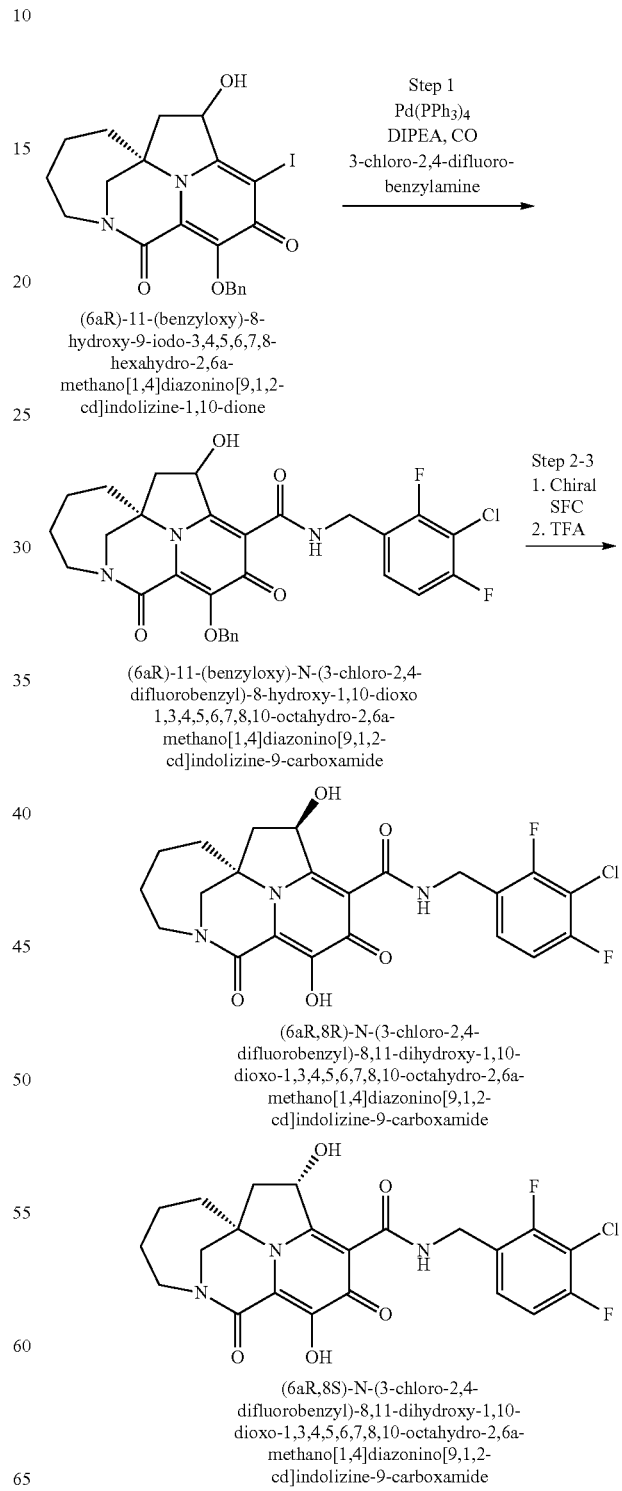

Synthesis of (6aR)-11-(benzyloxy)-N-(3-chloro-2.4 difluorobenzyl)-8-hydroxy-1,10-dioxo-1,3,4,5,6,7,8, 10-octahydro-2,6a-methano[1,4]diazonino[9,1,2-cd] indolizine-9-carboxamide To a solution of (6aR)-11-(benzyloxy)-8-hydroxy-9-iodo-3,4,5,6,7,8-hexahydro-2,6a-methano[1,4]diazonino[9,1,2-cd]indolizine-1,10-dione (0.261 g, 0.530 mmol) (intermediate 9b), in DMSO (10 mL) was added 3-chloro-2,4-difluorobenzylamine (0.471 g, 2.65 mmol), i-$Pr_2$NEt (0.462 mL, 2.65 mmol), and Pd($PPh_3$)$_4$ (0.031 g, 0.026 mmol). The reaction flask was evacuated and backfilled with CO (g) three times, then heated to 80° C. for 4 h under 1 atm of CO (g). After cooling to rt, the reaction was diluted with EtOAc and washed with 0.05 N HCl (1×), saturated aqueous $NaHCO_3$ (1×), and brine (1×). The organic phase was dried over $Na_2SO_4$, filtered, and concentrated. The residue was purified by column chromatography (0-100% EtOAc/heptane) to provide (6aR)-11-(benzyloxy)-N-(3-chloro-2,4-difluorobenzyl)-8-hydroxy-1,10-dioxo-1,3,4,5,6,7,8,10-octahydro-2,6a-methano[1,4]diazonino[9,1,2-cd]indolizine-9-carboxamide. MS (m/z) 570.15 $[M+H]^+$.

Synthesis of (6aR,8R)—N-(3-chloro-2.4 difluorobenzyl)-8,11-dihydroxy-1,10-dioxo-1,3,4,5,6,7,8, 10-octahydro-2,6a-methano[1,4]diazonino[9,1,2-cd] indolizine-9-carboxamide (14-1) and (6aR,8S)—N-(3-chloro-2.4 difluorobenzyl)-8,11-dihydroxy-1,10-dioxo-1,3,4,5,6,7,8,10-octahydro-2,6a-methano[1,4] diazonino[9,1,2-cd]indolizine-9-carboxamide (14-2)

(6aR)-11-(benzyloxy)-N-(3-chloro-2,4-difluorobenzyl)-8-hydroxy-1,10-dioxo-1,3,4,5,6,7,8,10-octahydro-2,6a-methano[1,4]diazonino[9,1,2-cd]indolizine-9-carboxamide was separated into its individual stereoisomers by preparative SFC on an IB column using 45% methanol co-solvent to provide two separate peaks. The separated stereoisomers were each dissolved in 1:1 toluene/TFA (10 mL for Peak 1; 6 mL for Peak 2). The reaction mixture was allowed to stir at rt for 2 h and concentrated. The residue was dissolved in MeCN and purified by preparative HPLC (column, Gemini 10μ C18 110A, AXI/; 250×21.2 mm) eluting 5-100/0 acetonitrile (0.1% TFA) in water (0.1% TFA) over 30 minutes. The combined fractions were lyophilized to afford the title compounds.

Peak 1 (14-1): MS (m/z) 480.31 $[M+H]^+$. $^1$H NMR (400 MHz, DMSO-$d_6$) δ 10.84 (t, J=5.9 Hz, 1H), 7.42 (td, J=8.5, 6.2 Hz, 1H), 7.31 (td, J=8.8, 1.7 Hz, 1H), 5.67 (dd, J=6.7, 3.5 Hz, 1H), 5.34 (d, J=3.4 Hz, 1H), 4.68-4.54 (m, 2H), 4.18 (dt, J=13.0, 7.5 Hz, 1H), 3.82 (d, J=14.2 Hz, 1H), 3.67 (d, J=13.9 Hz, 1H), 3.05 (ddd, J=13.2, 6.5, 4.6 Hz, 1H), 2.27 (dd, J=13.4, 6.8 Hz, 1H), 2.19 (dd, J=15.5, 6.4 Hz, 1H), 2.14-2.00 (m, 2H), 1.92-1.77 (m, 2H), 1.74-1.59 (m, 1H), 1.30-1.14 (m, 1H). $^{19}$F NMR (376 MHz, DMSO-$d_6$) δ −116.15 (td, J=7.4, 6.1, 2.2 Hz), −118.37 (d, J=8.2 Hz).

Peak 2 (14-2): MS (m/z) 480.21 $[M+H]^+$. $^1$H NMR (400 MHz, DMSO-$d_6$) δ 11.45 (t, J=5.9 Hz, 1H), 7.43 (td, J=8.4, 6.2 Hz, 1H), 7.31 (td, J=8.8, 1.7 Hz, 1H), 5.60 (dd, J=9.4, 7.0 Hz, 1H), 4.64 (qd, J=15.1, 5.9 Hz, 2H), 4.17 (dt, J=13.2, 7.4 Hz, 1H), 3.84 (s, 2H), 3.06 (dt, J=13.2, 5.7 Hz, 1H), 2.62 (dd, J=12.2, 7.1 Hz, 1H), 2.02-1.90 (m, 2H), 1.90-1.76 (m, 3H), 1.70-1.56 (m, 1H), 1.23-1.08 (m, 1H). $^{19}$F NMR (376 MHz, DMSO-$d_6$) δ −115.86 (ddd, J=8.7, 6.1, 2.4 Hz), −118.16 (d, J=8.0 Hz).

Example 15: Preparation of (6aS,8S)-8,11-dihydroxy-8-methyl-1,10-dioxo-N-(2,4,6-trifluorobenzyl)-1,3,4,5,6,7,8,10-octahydro-2,6a-methano[1,4] diazonino[9,1,2-cd]indolizine-9-carboxamide (15)

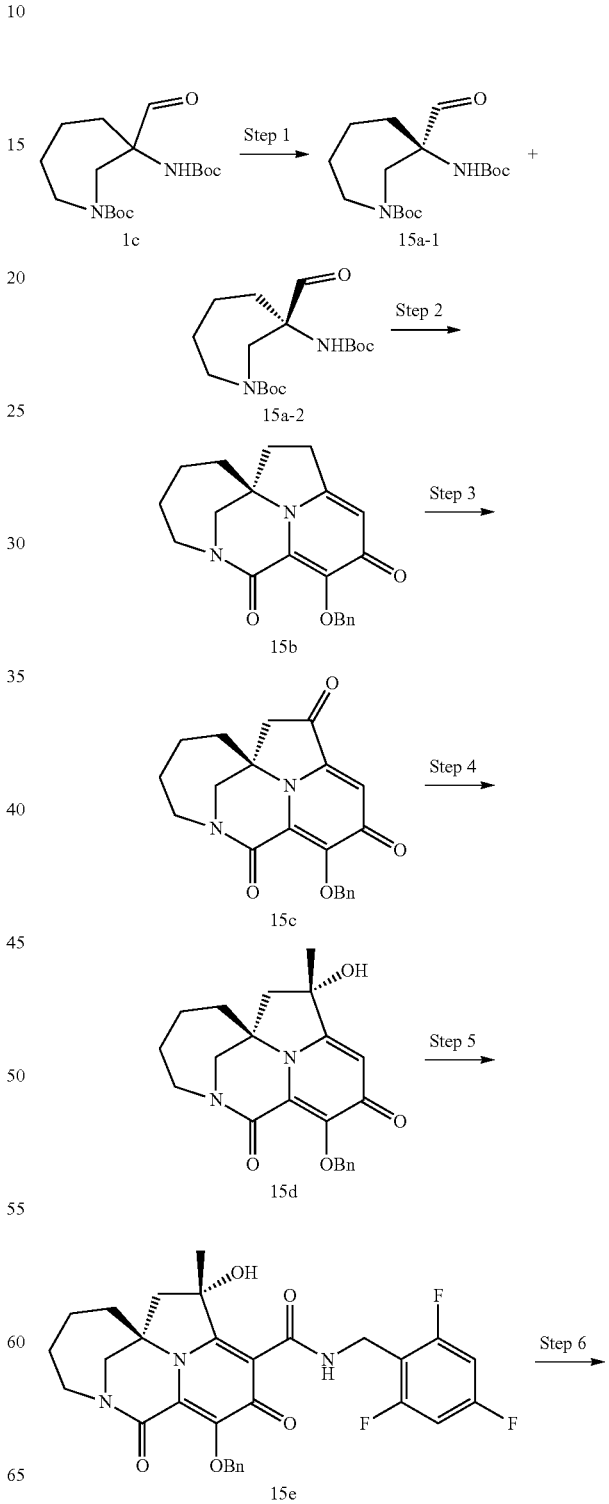

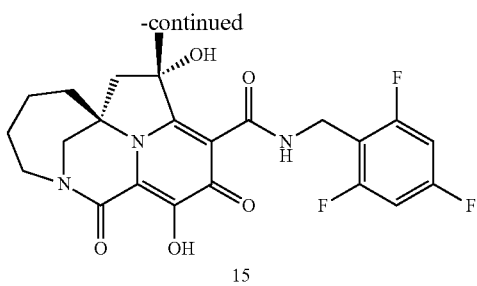

15

Step 1. Resolution of tert-butyl (R)-3-((tert-butoxycarbonyl)amino)-3-formylazepane-1-carboxylate (15a-1) and tert-butyl (S)-3-((tert-butoxycarbonyl)amino)-3-formylazepane-1-carboxylate (15a-2)

Racemic tert-butyl-3-((tert-butoxycarbonyl)amino)-3-formylazepane-1-carboxylate was resolved using chiral SFC (15% ACN) to give tert-butyl (R)-3-((tert-butoxycarbonyl)amino)-3-formylazepane-1-carboxylate (15a-1) and tert-butyl (S)-3-((tert-butoxycarbonyl)amino)-3-formylazepane-1-carboxylate (15a-2).

Step 2. Synthesis of (6aS)-11-(benzyloxy)-3,4,5,6,7,8-hexahydro-2,6a-methano[1,4]diazonino [9,1,2-cd]indolizine-1,10-dione (15b)

The title compound was synthesized in a similar manner to 11-(benzyloxy)-3,4,5,6,7,8-hexahydro-2,6a-methano[1,4]diazonino[9,1,2-cd]indolizine-1,10-dione (1f), using tert-butyl (R)-3-((tert-butoxycarbonyl)amino)-3-formylazepane-1-carboxylate (15a-1) in place of tert-butyl 3-((tert-butoxycarbonyl)amino)-3-formylazepane-1-carboxylate (1c).

Step 3. Synthesis of (6aS)-11-(benzyloxy-3,4,5,6-tetrahydro-2,6a-methano[1,4]diazonino[9,1,2-cd]indolizine-1,8,10(7H)-trione (15c)

To a solution of (6aS)-11-(benzyloxy)-3,4,5,6,7,8-hexahydro-2,6a-methano[1,4]diazonino [9,1,2-cd]indolizine-1,10-dione (15b, 2.0 g, 5.7 mmol) in THF (100 mL) was added LiHMDS (1.0M in THF, 17.1 mL) dropwise at −78° C., and the resulting dark solution was stirred for 30 min. Oz (g) was bubbled through the reaction, which was warmed to rt, while bubbling O₂ (g) through the reaction for 20 min. The reaction was quenched with MeOH, concentrated, and purified via combiflash (24 g, MeOH/DCM) to give the title product.

Step 4. Synthesis of (6aS,8S)-11-(benzyloxy)-8-hydroxy-8-methyl-3,4,5,6,7,8-hexahydro-2,6a-methano[1,4]diazonino[9,1,2-cd]indolizine-1,10-dione (15d)

MeLi (3.1M in diethoxymethane, 0.32 mL) followed by MeMgBr (3.0M in THF, 0.165 mL) was added to THF (6 mL) at −78° C., and the resulting solution was stirred for 1 hour. A solution of (6aS)-11-(benzyloxy)-3,4,5,6-tetrahydro-2,6a-methano[1,4]diazonino[9,1,2-cd]indolizine-1,8,10 (7H)-trione (15c, 120 mg, 0.33 mmol) in THF (6 mL) was added dropwise, and the solution was stirred at −78° C. for 1 hr. The reaction was quenched with water, filtered, and filter cake washed sequentially with DCM and MeOH. The filtrate was concentrated, dissolved in DMF/TFA, and purified by Gilson HPLC (0-100% ACN/H₂O) to give the title product as a single stereoisomer, assigned tentatively.

Step 5. Synthesis of (6aS,8S)-11-(benzyloxy)-8-hydroxy-8-methyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (15e)

The title compound was prepared in a similar manner to 11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1g) using (6aS,8S)-11-(benzyloxy)-8-hydroxy-8-methyl-3,4,5,6,7,8-hexahydro-2,6a-methano[1,4]diazonino[9,1,2-cd]indolizine-1,10-dione (15d) in place of 11-(benzyloxy)-3,4,5,6,7,8-hexahydro-2,6a-methano[1,4]diazonino[9,1,2-cd]indolizine-1,10-dione (1f). The reaction was purified using Gilson HPLC (5-100% ACN/H₂O+0.1% TFA) to give the title compound.

Step 6. Synthesis of (6aS,8S)-8,11-dihydroxy-8-methyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (15)

TFA (1 mL) was added to a solution of (6aS,8S)-11-(benzyloxy)-8-hydroxy-8-methyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (15e, 38 mg, 0.0067 mmol) in toluene (1 mL) and the resulting solution was stirred for 3 hr. The reaction was concentrated, dissolved in DMF, and purified by Gilson HPLC (0-100% ACN/H2O) to give the title product. 1H NMR (400 MHz, DMSO-d6) δ 11.68 (t, J=5.5 Hz, 1H), 7.73 (s, 1H), 7.35-7.16 (m, 2H), 4.81-4.38 (m, 2H), 4.24-4.12 (m, 1H), 3.86 (d, J=14.4 Hz, 1H), 3.74 (d, J=14.4 Hz, 1H), 3.00 (dt, J=13.3, 6.7 Hz, 1H), 2.41-2.36 (m, 1H), 2.26-2.13 (m, 2H), 1.89-1.71 (m, 5H), 1.69 (s, 3H); MS (m/z) 478.2 [M+H]⁺.

Example 16: Preparation of (6aS)-11-hydroxy-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide: (16)

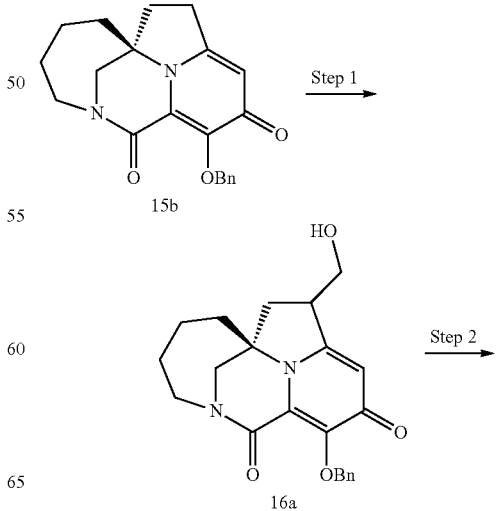

-continued

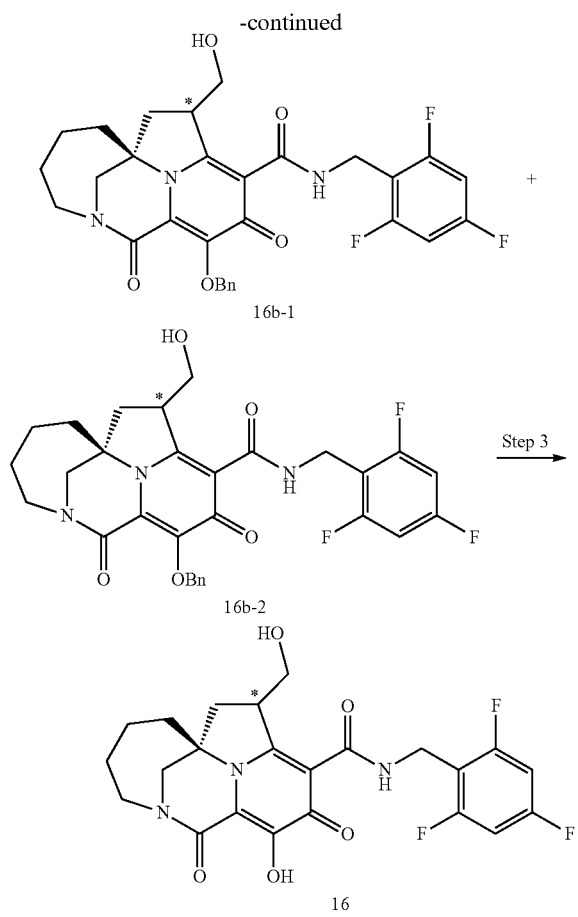

Step 1. Synthesis of (6aS)-11-(benzyloxy)-8-(hydroxymethyl)-3,4,5,6,7,8-hexahydro-2,6a-methano[1,4]diazonino[9,1,2-cd]indolizine-1,10-dione (16a)

To a solution of (6aS)-11-(benzyloxy)-3,4,5,6,7,8-hexahydro-2,6a-methano[1,4]diazonino [9,1,2-cd]indolizine-1,10-dione (15b, 100 mg, 0.43 mmol) in THF (4 mL) at −78° C., was added LDA (1.0M in THF/Hexanes, 0.86 mL), and the resulting solution was stirred for 10 min. A solution of 1H-benzotriazole-1-methanol in THF (2 mL) was added, and the solution was stirred at −78° C. for 1 hour. Reaction was quenched with MeOH, concentrated, and purified via combiflash (12 g, MeOH/DCM) to give desired product as a mixture of diastereomers.

Step 2. Synthesis of (6aS,8S)-11-(benzyloxy)-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (16b-1) and (6aS,8R)-11-(benzyloxy-(hydroxymethyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (16b-2)

The title compounds were prepared in a similar manner to 11-(benzyloxy)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (1g) using (6aS)-11-(benzyloxy)-8-(hydroxymethyl)-3,4,5,6,7,8-hexahydro-2,6a-methano[1,4]diazonino[9,1,2-cd]indolizine-1,10-dione (16a) in place of 11-(benzyloxy)-3,4,5,6,7,8-hexahydro-2,6a-methano[1,4]diazonino[9,1,2-cd]indolizine-1,10-dione (1f). The mixture was purified using Gilson HPLC (5-100% ACN/H$_2$O+0.1% TFA) to give the title compounds as separated diastereomers.

Step 3. Synthesis of (6aS)-11-hydroxy-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (16)

To a solution of (6aS)-11-(benzyloxy)-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (16b-2, peak 2) in toluene (0.5 mL) was added TFA (0.5 mL), and the resulting solution was stirred for 3 hours. The reaction was concentrated, redissolved in 1:1 THF/MeOH (1 mL) and LiOH (2M in H2O, 0.05 mL) was added. The solution was stirred for 1.5 hrs, and 0.15 mL IN HCl was added. The reaction was concentrated, redissolved in DMF, and purified by Gilson HPLC (5-100% ACN/H$_2$O) to give the title compound. 1H NMR (400 MHz, Chloroform-d) δ 11.09 (s, 1H), 6.78-6.57 (m, 2H), 4.75-4.56 (m, 3H), 4.47 (dt, J=13.7, 6.9 Hz, 1H), 4.09 (dd, J=10.8, 6.4 Hz, 1H), 3.90 (dd, J=10.7, 6.3 Hz, 1H), 3.73-3.52 (m, 2H), 3.02 (dt, J=12.9, 6.1 Hz, 1H), 2.47-1.94 (m, 5H), 1.86 (dt, J=14.7, 7.4 Hz, 1H), 1.83-1.70 (m, 1H), 1.58 (dd, J=15.8, 7.8 Hz, 1H); MS (m/z) 478.2 [M+H]$^+$.

Example 17: Preparation of (6aR,8R)-8,11-dihydroxy-8-methyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (17)

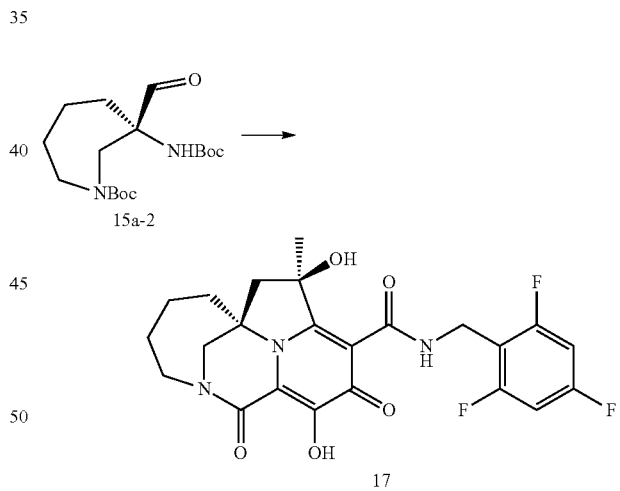

The title compound was prepared in a similar manner to (6aS,8S)-8,11-dihydroxy-8-methyl-1,10-dioxo-N-(2,4,6-trifluorobenzyl)-1,3,4,5,6,7,8,10-octahydro-2,6a-methano[1,4]diazonino [9,1,2-cd]indolizine-9-carboxamide (15), using tert-butyl (S)-3-((tert-butoxycarbonyl)amino)-3-formylazepane-1-carboxylate (15a-2) in place of (R)-3-((tert-butoxycarbonyl)amino)-3-formylazepane-1-carboxylate (15a-1), stereochemistry tentatively assigned. 1H NMR (400 MHz, DMSO-d6) δ 11.68 (t, J=5.5 Hz, 1H), 7.73 (s, 1H), 7.35-7.16 (m, 2H), 4.81-4.38 (m, 2H), 4.24-4.12 (m, 2H), 3.86 (d, J=14.4 Hz, 1H), 3.74 (d, J=14.4 Hz, 1H), 3.00 (dt, J=13.3, 6.7 Hz, 1H), 2.41-2.36 (m, 1H), 2.26-2.13 (m, 2H), 1.89-1.71 (m, 5H), 1.69 (s, 3H); MS (m/z) 478.1 [M+H]$^+$.

Example 18: Preparation of (6aR)-11-hydroxy-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (18)

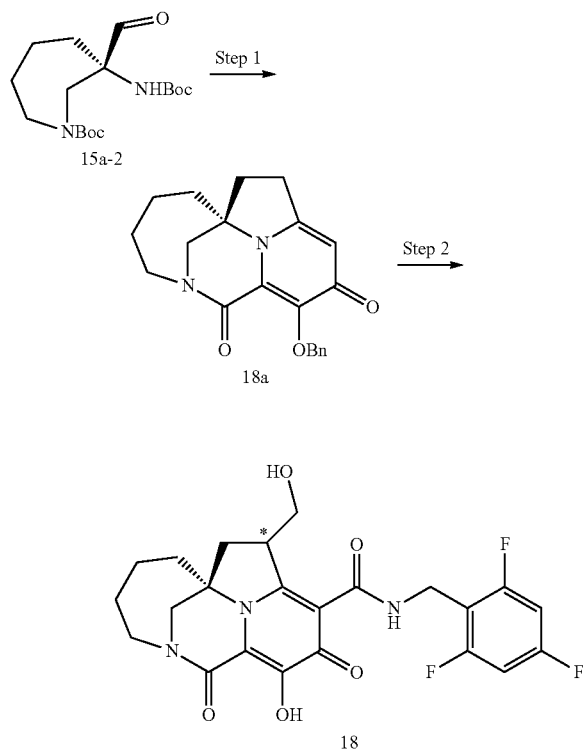

Step 1. Synthesis of (6aR)-11-(benzyloxy)-3,4,5,6,7,8-hexahydro-2,6a-methano[1,4]diazonino [9,1,2-cd]indolizine-1,10-dione (18a)

The title compound was synthesized in a similar manner to 11-(benzyloxy)-3,4,5,6,7,8-hexahydro-2,6a-methano[1,4]diazonino[9,1,2-cd]indolizine-1,10-dione (1f), using tert-butyl (S)-3-((tert-butoxycarbonyl)amino)-3-formylazepane-1-carboxylate (15a-2) in place of tert-butyl 3-((tert-butoxycarbonyl)amino)-3-formylazepane-1-carboxylate (1c).

Step 2. Synthesis of (6aR)-11-hydroxy-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (18)

The title compound was prepared in a similar to (6aS)-11-hydroxy-8-(hydroxymethyl)-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (16), using (6aR)-11-(benzyloxy)-3,4,5,6,7,8-hexahydro-2,6a-methano [1,4]diazonino [9,1,2-cd]indolizine-1,10-dione (18a) in place of (6aS)-11-(benzyloxy)-3,4,5,6,7,8-hexahydro-2,6a-methano[1,4]diazonino [9,1,2-cd]indolizine-1,10-dione (15b). 1H NMR (400 MHz, Methanol-d4) δ 6.96-6.86 (m, 2H), 4.72-4.56 (m, 2H), 4.37 (dt, J=14.6, 7.8 Hz, 1H), 4.26 (tt, J=8.3, 3.8 Hz, 1H), 4.00-3.90 (m, 1H), 3.87 (d, J=18.4 Hz, 1H), 3.83-3.72 (m, 1H), 3.25-3.11 (m, 1H), 2.37 (dd, J=13.0, 8.3 Hz, 1H), 2.26 (dd, J=13.0, 8.8 Hz, 1H), 2.07-1.87 (m, 4H), 1.78 (d, J=14.7 Hz, 1H), 1.32 (dq, J=15.7, 7.7 Hz, 1H); MS (m/z) 478.1 [M+H]$^+$.

Example 19: Preparation of (1R,11S,14S)—N-[(2,4-difluorophenyl)methyl]-3,7-dihydroxy-14-methoxy-11-methyl-6,9-dioxo-10,15-diazatetracyclo[6.6.1.11,10.04,15]hexadeca-4,7,12-triene-5-carboxamide (19-1, 19-2, and 19-3)

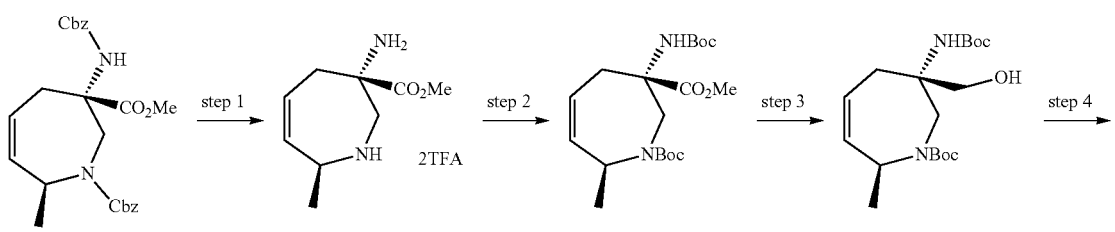

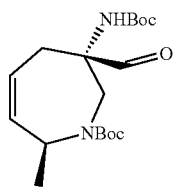

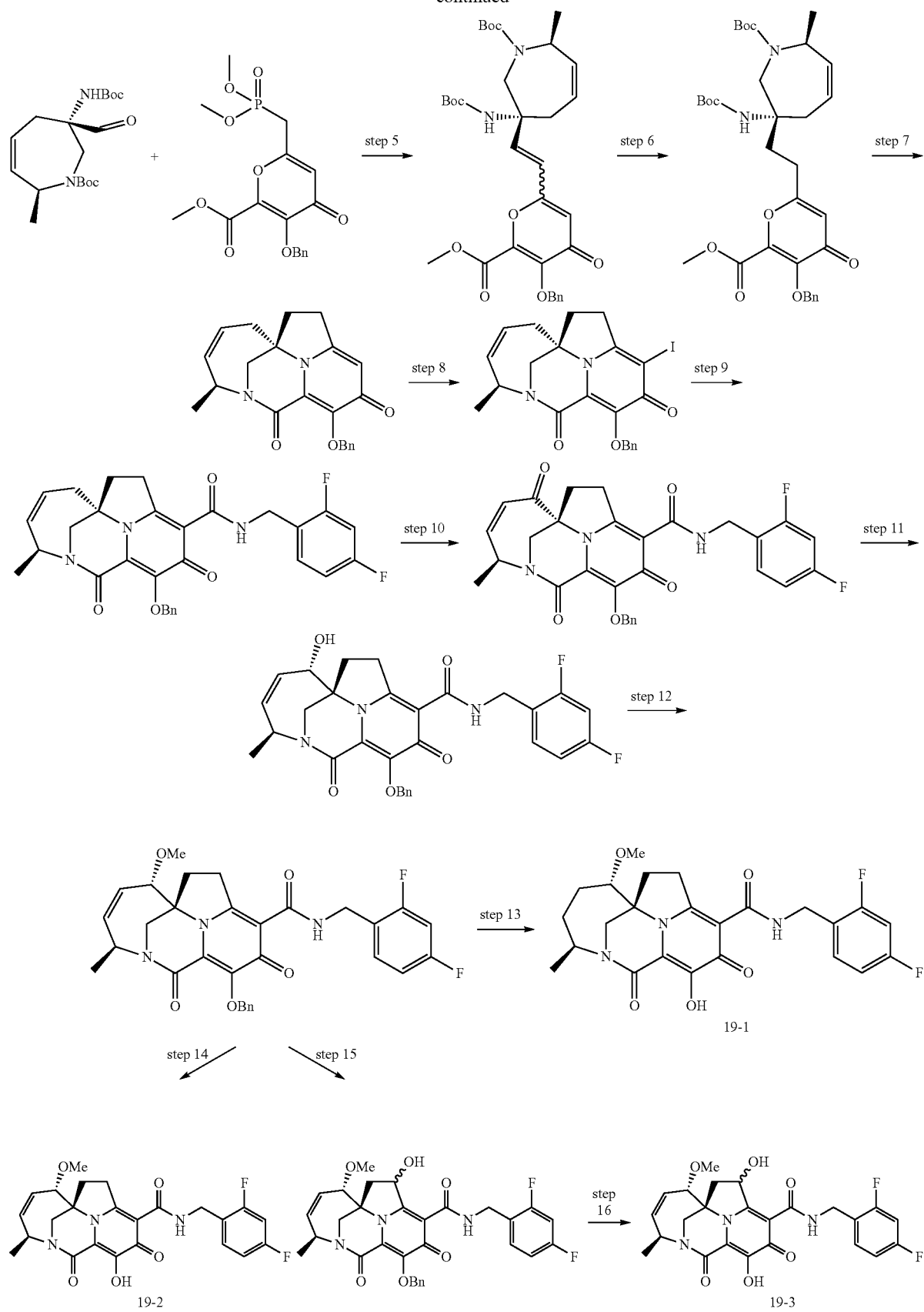

Step 1: synthesis of methyl (3S,7S)-3-amino-7-methyl-1,2,4,7-tetrahydroazepine-3-carboxylate bis TFA Salt O1-benzyl O3-methyl (3S,7S)-3-(benzyloxycarbonylamino)-7-methyl-4,7-dihydro-2H-azepine-1,3-dicarboxylate (5 g, 11.0 mmol) was heated in TFA (25 mL) at 100° C. for 4 hours.

The reaction was cooled to Mt concentrated, the resulting residue was coevaporated with EtOAc (8×20 mL) and used directly in next step. LCMS-ESI+ (m/z): calcd H+ for C9H16N2O2, Theoretical: 184.12, Found: 185.02.

Step 2: Synthesis of O1-tert-butyl O3-methyl (3S,7S)-3-(tert-butoxycarbonylamino)-7-methyl-4,7-dihydro-2H-azepine-1,3-dicarboxylate Methyl (3S,7S)-3-amino-7-methyl-1,2,4,7-tetrahydroazepine-3-carboxylate bis TFA salt (4.556 g, 11.1 mol) was dissolved in EtOAc (84.0 mL) at room temperature. Saturated aqueous sodium carbonate solution (13.2 mL) was added followed by Di-tert-butyl dicarbonate (7.235 g, 33.2 mmol). The resulting mixture was heated to 70° C. for overnight. The reaction was cooled to room temperature, diluted with EtOAc, washed with water, brine, dried over sodium sulfate, filtered and concentrated, purified by normal phase chromatography. LCMS-ESI+ (m/z): calcd H+ for C19H32N2O6, Theoretical: 384.23, Found: 384.746.

Step 3: Synthesis of tert-butyl (3S,7S)-3-(tert-butoxycarbonylamino)-3-(hydroxymethyl)-7-methyl-4.7 dihydro-2H-azepine-1-carboxylate O1-tert-butyl O3-methyl (3S,7S)-3-(tert-butoxycarbonylamino)-7-methyl-4,7-dihydro-2H-azepine-1,3-dicarboxylate (3.756 g, 9.77 mmol) was dissolved in THF (97.0 mL) and cooled to 0° C. The resulting mixture was flushed with nitrogen before 1.0 M LAH in THF (12.7 mL, 12.7 mmol) was added. The reaction was stirred at 0° C. for 10 minutes and then was removed from cooling bath and stirred at room temperature for 30 minutes. The reaction was cooled back to 0° C. and quenched with saturated Rochelle's salt dropwise. The mixture was then diluted with EtOAc, organic layer was washed with brine, dried over sodium sulfate, filtered and concentrated and used directly in next step. LCMS-ESI+ (m/z): calcd H+ for C18H32N2O5, Theoretical: 356.23, Found: 356.837.

Step 4: Synthesis of tert-butyl (3S,7S)-3-(tert-butoxycarbonylamino)-3-formyl-7-methyl-4.7 dihydro-2H-azepine-1-carboxylate tert-Butyl (3S,7S)-3-(tert-butoxycarbonylamino)-3-(hydroxymethyl)-7-methyl-4,7-dihydro-2H-azepine-1-carboxylate (3.48 g, 9.76 mmol) was dissolved in DCM (65 mL) and cooled to 0° C. Dess-Martin periodinane (6.21 g, 14.6 mmol) was added in portions. The reaction was warmed up to room temperature after addition and stirred for overnight. The reaction was cooled back to 0° C., 1 N sodium thiosulfate (80 mL) was added, saturated sodium bicarbonate (80 mL) was added. The mixture was stirred vigorously for 30 minutes. Layers were separated, aqueous layer was extracted with DCM (×2). Combined organic layers were washed with brine, dried over sodium sulfate, filtered and concentrated. The resulting product was purified by normal phase chromatography (80 g silica gel 0-40% EtOAc/Hexane). LCMS-ESI+ (m/z): calcd H+ for C18H30N2O5, Theoretical: 354.22, Found: 355.016.

Step 5: Synthesis of tert-butyl (3R,7S)-3-[(E)-2-(5-benzyloxy-6-methoxycarbonyl-4-oxo-pyran-2-yl)vinyl]-3-(tert-butoxycarbonylamino)-7-methyl-4,7-dihydro-2H-azepine-1-carboxylate Methyl 3-benzyloxy-6-(dimethoxyphosphorylmethyl)-4-oxo-pyran-2-carboxylate (1.96 g, 5.12 mmol) was dissolved in THF (25 mL) and cooled to −78° C. 1.0M LDA in THF/Hexane (5.12 mL, 5.12 mmol) was added dropwise. The resulting mixture was stirred at −78° C. for 45 minutes. After that, a solution of tert-butyl (3S,7S)-3-(tert-butoxycarbonylamino)-3-formyl-7-methyl-4,7-dihydro-2H-azepine-1-carboxylate (1.21 g, 3.4 mmol) in THF (9 mL) was added into the cold mixture. The newly formed mixture was stirred at −78° C. for 10 minutes and then warmed up to −10° C. in one hour and stirred at −10° C. for another 60 minutes. The reaction was quenched with saturated ammonium chloride slowly. The mixture was diluted with EtOAc, washed with saturated ammonium chloride, brine, dried over sodium sulfate, filtered and concentrated and purified by normal phase chromatography. LCMS-ESI+ (m/z): calcd H+ for C33H42N2O9, Theoretical: 610.29, Found: 610.897.

Step 6: Synthesis of tert-butyl (3S,7S)-3-[2-(5-benzyloxy-6-methoxycarbonyl-4-oxo-pyran-2-yl)ethyl]-3-(tert-butoxycarbonylamino)-7-methyl-4.7 dihydro-2H-azepine-1-carboxylate The solution of tert-butyl (3R,7S)-3-[(E)-2-(5-benzyloxy-6-methoxycarbonyl-4-oxo-pyran-2-yl)vinyl]-3-(tert-butoxycarbonylamino)-7-methyl-4,7-dihydro-2H-azepine-1-carboxylate (650 mg, 1.06 mmol) in Toluene (32.5 mL) was purged with nitrogen. Poly(methylhydrosiloxane) (0.64 g, 10.6 mmol) was added under nitrogen followed by chloro[1,3-bis(2,6-di-i-propylphenyl)imidazol-2-ylidene]copper (I) (78 mg, 0.16 mmol) and 2.0M sodium tert-butoxide in THF (0.16 mL, 0.319 mmol). The reaction was then stirred under nitrogen balloon for 1 hour. The reaction was quenched with water, stirred vigorously for 30 minutes, brine (20 mL) was added, stirred for another 10 minutes, extracted with EtOAc. The organic layer was washed with brine, dried over sodium sulfate, filtered and concentrated. Purified by normal phase chromatography. LCMS-ESI+ (m/z): calcd H+ for C33H44N2O9, Theoretical: 612.30, Found: 612.746.

Step 7: Synthesis of (1S,11S)-7-benzyloxy-11-methyl-10,15-diazatetracyclo[6.6.1.11,10.04,15]hexadeca-4,7,12-triene-6,9-dione tert-Butyl (3S,7S)-3-[2-(5-benzyloxy-6-methoxycarbonyl-4-oxo-pyran-2-yl)ethyl]-3-(tert-butoxycarbonylamino)-7-methyl-4,7-dihydro-2H-azepine-1-carboxylate (0.41 g, 0.669 mmol) was dissolved in DCM (16 mL) and cooled to 0° C., TFA was added slowly dropwise along the side of the flask. The newly formed mixture was stirred at 0° C. for 30 minutes and then at room temperature for 2 hours. The reaction was concentrated, coevaporated with DCM (3×5 mL), further dried over the vacuum line for 3 hours. Then the residue was dissolved in EtOH (40 mL) and heated to 90° C. for 2 hours. The reaction was cooled to room temperature, concentrated, purified by normal phase chromatography. LCMS-ESI+ (m/z): calcd H+ for C22H22N2O3, Theoretical: 362.16, Found: 363.30.

Step 8: Synthesis of (1S,11S-7-benzyloxy-5-iodo-11-methyl-10,15-diazatetracyclo[6.6.1.11,10.04,15] hexadeca-4,7,12-triene-6,9-dione To a solution of (1S,11S)-7-benzyloxy-11-methyl-10,15-diazatetracyclo[6.6.1.11,10.04,15]hexadeca-4,7,12-triene-6,9-dione (640 mg, 1.77 mmol) in MeOH (34 mL) at room temperature was added MCPBA (792 mg, 3.53 mmol) and NIS (795 mg, 3.53 mmol). The resulting mixture was heated to 80° C. for 20 minutes. The reaction was cooled to room temperature, diluted with DCM, washed with 1 N sodium thiosulfate, saturated NaHCO$_3$, dried over sodium sulfate, filtered and concentrated and purified by normal phase chromatography. LCMS-ESI+ (m/z): calcd H+ for C22H21N2O3, Theoretical: 488.06, Found: 489.139.

Step 9: Synthesis of (1S,11S)-7-benzyloxy-N-[(2.4 difluorophenyl)methyl]-11-methyl-6,9-dioxo-10,15-diazatetracyclo[6.6.1.11,10.04,15]hexadeca-4,7,12-triene-5-carboxamide To the solution of (1S,11S)-7-benzyloxy-5-iodo-11-methyl-10,15-diazatetracyclo[6.6.1.11,10.04,15]hexadeca-4,7,12-triene-6,9-dione (285 mg, 0.584 mmol) in DMSO (12 mL) at room temperature was added (2,4-difluorophenyl) methanamine (418 mg, 2.92 mmol) followed by DIPEA (377 mg, 2.92 mmol), Tetrakis(triphenylphosphine)palladium(0) (33.7 mg, 0.0292 mmol) and PdCl$_2$dppf (21.4 mg, 0.0292 mmol). The resulting mixture was degassed and flushed with CO three times and then under CO balloon, heated to 85° C. for 3 hours. The reaction was cooled to room temperature, diluted with EtOAc, washed with water, saturated NH$_4$Cl, brine, dried over sodium sulfate, filtered and concentrated and purified by normal phase chromatography. LCMS-ESI+ (m/z): calcd H+ for C30H27F2N3O4, Theoretical: 531.20, Found: 532.203.

Step 10: Synthesis of (1R,1S)-7-benzyloxy-N-[(2.4 difluorophenyl)methyl]-11-methyl-6,9,14-trioxo-10,15-diazatetracyclo[6.6.1.11,10.04,15]hexadeca-4,7,12-triene-5-carboxamide (1S,11S)-7-benzyloxy-N-[(2,4-difluorophenyl)methyl]-11-methyl-6,9-dioxo-10,15-diazatetracyclo[6.6.1.11,10.04,15]hexadeca-4,7,12-triene-5-carboxamide (210 mg, 0,395 mmol) was dissolved in 1,4-dioxane (4 mL). Selenium dioxide (263 mg, 2.37 mmol) was added. The resulting mixture was heated at 100° C. for 6 hours. The reaction was cooled to room temperature, filtered through Celite, concentrated and purified by normal phase chromatography. LCMS-ESI+ (m/z): calcd H+ for C30H25F2N3O5, Theoretical: 545.18, Found: 546.174.

Step 11: Synthesis of (1R,11S,14S)-7-benzyloxy-N-[(2.4 difluorophenyl)methyl]-14-hydroxy-11-methyl-6,9-dioxo-10,15-diazatetracyclo[6.6.1.11, 10.04,15]hexadeca-4,7,12-triene-5-carboxamide The solution of (1R,11S)-7-benzyloxy-N-[(2,4-difluorophenyl)methyl]-11-methyl-6,9,14-trioxo-10,15-diazatetracyclo[6.6.1.11,10.04,15]hexadeca-4,7,12-triene-5-carboxamide (189 mg, 0.346 mmol) in MeOH (5 mL) was cooled to 0° C., CeCl3·7H2O (129 mg, 0.346 mmol) was added followed by sodium borohydride (15.27 mg, 0.4 mmol). The reaction was stirred for 5 minutes before it was quenched with water. The reaction was extracted with DCM, the organic layer was washed with brine, dried over sodium sulfate, filtered and concentrated and purified by normal phase chromatography. LCMS-ESI+ (m/z): calcd H+ for C30H27F2N3O5, Theoretical: 547.19, Found: 548.124.

Step 12: Synthesis of (1R,11S,14S)-7-benzyloxy-N-[(2.4 difluorophenyl)methyl]-14-methoxy-11-methyl-6,9-dioxo-10,15-diazatetracyclo[6.6.1.11, 10.04,15]hexadeca-4,7,12-triene-5-carboxamide The solution of (1R,11S,14S)-7-benzyloxy-N-[(2,4-difluorophenyl)methyl]-14-hydroxy-11-methyl-6,9-dioxo-10,15-diazatetracyclo[6.6.1.11,10.04,15]hexadeca-4,7,12-triene-5-carboxamide (100 mg, 0.183 mmol) in DMF (3.6 mL) was cooled to 0° C., NaH (60% dispersion in mineral oil) (9.5 mg, 0.237 mmol) was added, the newly formed mixture was stirred for 10 minutes before a solution of Iodomethane (28.5 mg, 0.20 mmol) in DMF (1 mL) was added dropwise. After stirred for 10 minutes at 0° C., the reaction was quenched with saturated NH4Cl, extracted with EtOAc, the organic layer was washed with water, brine, dried over sodium sulfate, filtered and concentrated and purified by normal phase chromatography. Stereochemistry at C4 position is not confirmed. LCMS-ESI+ (m/z): calcd H+ for C31H29F2N3O5, Theoretical: 561.21, Found: 562.149.

Step 13: Synthesis of (1R,11S,14S)—N-[(2.4 difluorophenyl)methyl]-7-hydroxy-14-methoxy-11-methyl-6,9-dioxo-10,15-diazatetracyclo[6.6.1.11, 10.04,15]hexadeca-4.7 diene-5-carboxamide (19-1)

To the solution of (1R,11S,14S)-7-benzyloxy-N-[(2,4-difluorophenyl)methyl]-14-methoxy-11-methyl-6,9-dioxo-10,15-diazatetracyclo[6.6.1.11,10.04,15]hexadeca-4,7,12-triene-5-carboxamide (13.5 mg, 0.024 mmol) in EtOH (10 mL) was added 20% Pd(OH)2/C (50 wt % water) (3.0 mg), the resulting mixture was degassed and flushed with nitrogen three times, then it was degassed and flushed with hydrogen three times before it was hydrogenated under hydrogen balloon for 4 hours at room temperature. The reaction was degassed and flushed with nitrogen, filtered through 0.45 um syringe filter, concentrated, redissolved in DMF, filtered and purified by reverse phase prep HPLC. LCMS-ESI+ (m/z): calcd H+ for C24H25F2N3O5, Theoretical: 473.18, Found: 474.263. 1H NMR (400 MHz, Acetone-d6) δ 10.88 (s, 1H), 7.53-7.43 (m, 1H), 7.08-6.94 (m, 2H), 4.62 (pd, J=15.2, 6.1 Hz, 3H), 3.96-3.82 (m, 2H), 3.63-3.57 (m, 1H), 3.57-3.51 (m, 1H), 3.45 (s, 3H), 3.43-3.32 (m, 2H), 2.92-2.88 (m, 1H), 2.16 (dd, J=16.1, 3.4 Hz, 1H), 2.00-1.81 (m, 3H), 1.28 (d, J=6.7 Hz, 3H), 1.24-1.16 (m, 1H).

Step 14: Synthesis of (1R,11S,14S)—N-[(2.4 difluorophenyl)methyl]-7-hydroxy-14-methoxy-11-methyl-6,9-dioxo-10,15-diazatetracyclo[6.6.1.11, 10.04,15]hexadeca-4,7,12-triene-5-carboxamide (19-2)

(1R,11S,14S)-7-benzyloxy-N-[(2,4-difluorophenyl) methyl]-14-methoxy-11-methyl-6,9-dioxo-10,15-diazatetracyclo[6.6.1.11,10.04,15]hexadeca-4,7,12-triene-5-carboxamide (6 mg, 0.0107 mmol) was treated with a 1:1 mixture of Toluene/TFA (3.0 mL) at room temperature overnight. The reaction was concentrated, redissolved in DMF, filtered and purified by reverse phase prep HPLC. LCMS-ESI+ (m/z): calcd H+ for C24H23F2N3O5, Theoretical: 471.16, Found: 472.203. 1H NMR (400 MHz, Chloroform-d) δ

10.79 (s, 1H), 7.39 (td, J=8.7, 6.5 Hz, 1H), 6.92-6.76 (m, 2H), 5.66 (dt, J=11.6, 3.2 Hz, 1H), 5.52 (ddd, J=11.5, 2.6, 1.6 Hz, 1H), 5.36 (dq, J=7.2, 2.6 Hz, 2H), 4.65 (s, 2H), 4.28 (q, J=3.0 Hz, 1H), 4.07-3.92 (m, 2H), 3.63 (ddd, J=18.7, 10.1, 8.4 Hz, 1H), 3.38 (d, J=13.7 Hz, 1H), 3.28 (s, 3H), 2.72 (dd, J=12.8, 8.3 Hz, 1H), 1.78 (dt, J=12.7, 9.7 Hz, 1H), 1.38 (d, J=7.3 Hz, 3H).

Step 15: Synthesis of (1R,11S,14S)-7-benzyloxy-N-[(2.4 difluorophenyl)methyl]-3-hydroxy-14-methoxy-11-methyl-6,9-dioxo-10,15-diazatetracyclo[6.6.1.11,10.04,15]hexadeca-4,7,12-triene-5-carboxamide The solution of (1R,11S,14S)-7-benzyloxy-N-[(2,4-difluorophenyl)methyl]-14-methoxy-11-methyl-6,9-dioxo-10,15-diazatetracyclo[6.6.1.11,10.04,15]hexadeca-4,7,12-triene-5-carboxamide (41.8 mg, 0.0744 mmol) in THF (2 mL) was cooled to −78° C., 1.0 M LHMDS in THF (0.373 mL, 0.373 mmol) was added. The resulting mixture was stirred for 25 minutes and then a solution of 2-(benzenesulfonyl)-3-phenyl-oxaziridine (77.8 mg, 0.298 mmol) in THF (0.8 mL) was added to the cold mixture dropwise. After stirred at −78° C. for 30 minutes, the reaction was warmed up to −10° C. and stirred at that temperature for 90 minutes. The reaction was quenched with MeOH, concentrated, purified by normal phase chromatography. LCMS-ESI+(m/z): calcd H+ for C31H29F2N3O6, Theoretical: 577.20, Found: 578.211.

Step 16: Synthesis of (1R,11S,14S)—N-[(2.4 difluorophenyl)methyl]-3.7 dihydroxy-14-methoxy-11-methyl-6,9-dioxo-10,15-diazatetracyclo[6.6.1.11,10.04,15]hexadeca-4,7,12-triene-5-carboxamide (19-3)

The residue from previous step was dissolved in toluene (0.3 mL), cooled to 0° C., TFA (0.3 mL) was added. The reaction was slowly warmed up to room temperature as ice melted and stirred at room temperature for overnight. The reaction was concentrated, redissolved in DMF, filtered and purified by reverse phase prep HPLC. LCMS-ESI+ (m/z): calcd H+ for C24H23F2N3O6, Theoretical: 487.16, Found: 488.255. 1H NMR (400 MHz, Chloroform-d) δ 11.14 (s, 1H), 7.46-7.33 (m, 1H), 6.93-6.79 (m, 2H), 5.73 (t, J=7.7 Hz, 1H), 5.67 (dt, J=11.5, 3.2 Hz, 1H), 5.53 (ddd, J=11.5, 2.6, 1.6 Hz, 1H), 5.42-5.32 (m, 1H), 4.68 (d, J=5.5 Hz, 2H), 4.13 (q, J=3.0 Hz, 1H), 4.05 (d, J=13.8 Hz, 1H), 3.55 (d, J=13.8 Hz, 1H), 3.25 (s, 4H), 3.18-3.08 (m, 2H), 1.90 (dd, J=12.8, 7.9 Hz, 1H), 1.40 (d, J=7.2 Hz, 3H).

Intermediate 20a

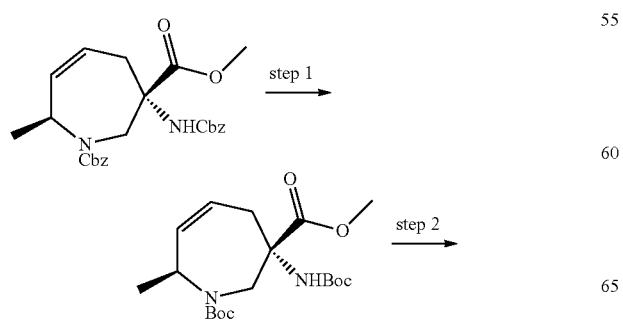

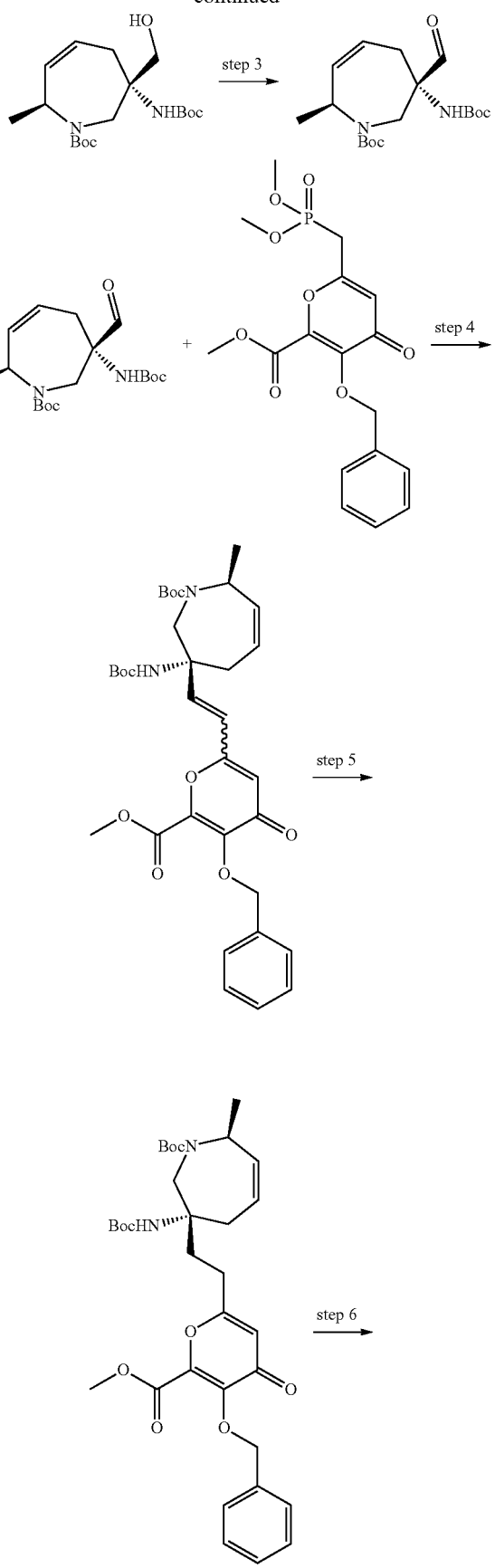

133

-continued

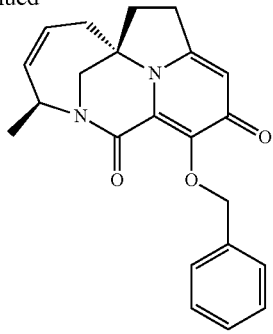

20a

Step 1: synthesis of methyl (3S,7S)-3-amino-7-methyl-1,2,4,7-tetrahydroazepine-3-carboxylate bis TFA Salt O1-benzyl O3-methyl (3S,7S)-3-(benzyloxycarbonylamino)-7-methyl-4,7-dihydro-2H-azepine-1,3-dicarboxylate (5 g, 11.0 mmol) was heated in TFA (25 mL) at 100° C. for 4 hours. The reaction was cooled to rt, concentrated, the resulting residue was coevaporated with EtOAc (8×20 mL) and used directly in next step. LCMS-ESI+ (m/z): calcd H+ for C9H16N2O2, Theoretical: 184.12, Found: 185.02. Methyl (3S,7S)-3-amino-7-methyl-1,2,4,7-tetrahydroazepine-3-carboxylate bis TFA salt (4.556 g, 11.1 mol) was dissolved in EtOAc (84.0 mL) at room temperature. Saturated aqueous sodium carbonate solution (13.2 mL) was added followed by Di-tert-butyl dicarbonate (7.235 g, 33.2 mmol). The resulting mixture was heated to 70° C. for overnight. The reaction was cooled to room temperature, diluted with EtOAc, washed with water, brine, dried over sodium sulfate, filtered and concentrated, purified by normal phase chromatography. LCMS-ESI+ (m/z): calcd H+ for C19H32N2O6, Theoretical: 384.23, Found: 384.746.

Step 2: Synthesis of tert-butyl (3S,7S)-3-(tert-butoxycarbonylamino)-3-(hydroxymethyl)-7-methyl-4.7 dihydro-2H-azepine-1-carboxylate O1-tert-butyl O3-methyl (3S,7S)-3-(tert-butoxycarbonylamino)-7-methyl-4,7-dihydro-2H-azepine-1,3-dicarboxylate (3.756 g, 9.77 mmol) was dissolved in THF (97.0 mL) and cooled to 0° C. The resulting mixture was flushed with nitrogen before 1.0M LAH in THF (12.7 mL, 12.7 mmol) was added. The reaction was stirred at 0° C. for 10 minutes and then was removed from cooling bath and stirred at room temperature for 30 minutes. The reaction was cooled back to 0° C. and quenched with saturated Rochelle's salt dropwise. The mixture was then diluted with EtOAc, organic layer was washed with brine, dried over sodium sulfate, filtered and concentrated and used directly in next step. LCMS-ESI+ (m/z): calcd H+ for C18H32N2O5, Theoretical: 356.23, Found: 356.837.

Step 3: Synthesis of tert-butyl (3S,7S)-3-(tert-butoxycarbonylamino)-3-formyl-7-methyl-4.7 dihydro-2H-azepine-1-carboxylate tert-butyl (3S,7S)-3-(tert-butoxycarbonylamino)-3-(hydroxymethyl)-7-methyl-4,7-dihydro-2H-azepine-1-carboxylate (3.48 g, 9.76 mmol) was dissolved in DCM (65 mL) and cooled to 0° C. Dess-Martin periodinane (6.21 g,

134

14.6 mmol) was added in portions. The reaction was warmed up to room temperature after addition and stirred for overnight. The reaction was cooled back to 0° C., IN sodium thiosulfate (80 mL) was added, saturated sodium bicarbonate (80 mL) was added. The mixture was stirred vigorously for 30 minutes. Layers were separated, aqueous layer was extracted with DCM (×2). Combined organic layers were washed with brine, dried over sodium sulfate, filtered and concentrated. The resulting product was purified by normal phase chromatography (80 g silica gel 0-40% EtOAc/Hexane). LCMS-ESI+ (m/z): calcd H+ for C18H30N2O5, Theoretical: 354.22, Found: 355.016.

Step 4: Synthesis of tert-butyl (3R,7S)-3-[(E)-2-(5-benzyloxy-6-methoxycarbonyl-4-oxo-pyran-2-yl)vinyl]-3-(tert-butoxycarbonylamino)-7-methyl-4,7-dihydro-2H-azepine-1-carboxylate Methyl 3-benzyloxy-6-(dimethoxyphosphorylmethyl)-4-oxo-pyran-2-carboxylate (1.96 g, 5.12 mmol) was dissolved in THF (25 mL) and cooled to −78° C. 1.0M LDA in THF/Hexane (5.12 mL, 5.12 mmol) was added dropwise. The resulting mixture was stirred at −78° C. for 45 minutes. After that, a solution of tert-butyl (3S,7S)-3-(tert-butoxycarbonylamino)-3-formyl-7-methyl-4,7-dihydro-2H-azepine-1-carboxylate (1.21 g, 3.4 mmol) in THF (9 mL) was added into the cold mixture. The newly formed mixture was stirred at −78° C. for 10 minutes and then warmed up to −10° C. in one hour and stirred at −10° C. for another 60 minutes. The reaction was quenched with saturated ammonium chloride slowly. The mixture was diluted with EtOAc, washed with saturated ammonium chloride, brine, dried over sodium sulfate, filtered and concentrated and purified by normal phase chromatography. LCMS-ESI+ (m/z): calcd H+ for C33H42N2O9, Theoretical: 610.29, Found: 610.897.

Step 5: Synthesis of tert-butyl (3S,7S)-3-[2-(5-benzyloxy-6-methoxycarbonyl-4-oxo-pyran-2-yl)ethyl]-3-(tert-butoxycarbonylamino)-7-methyl-4.7 dihydro-2H-azepine-1-carboxylate The solution of tert-butyl (3R,7S)-3-[(E)-2-(5-benzyloxy-6-methoxycarbonyl-4-oxo-pyran-2-yl)vinyl]-3-(tert-butoxycarbonylamino)-7-methyl-4,7-dihydro-2H-azepine-1-carboxylate (650 mg, 1.06 mmol) in Toluene (32.5 mL) was purged with nitrogen. poly(methylhydrosiloxane) (0.64 g, 10.6 mmol) was added under nitrogen followed by Chloro[1,3-bis(2,6-di-i-propylphenyl)imidazol-2-ylidene]copper (I) (78 mg, 0.16 mmol) and 2.0M Sodium tert-butoxide in THF (0.16 mL, 0.319 mmol). The reaction was then stirred under nitrogen balloon for 1 hour. The reaction was quenched with water, stirred vigorously for 30 minutes, brine (20 mL) was added, stirred for another 10 minutes, extracted with EtOAc. The organic layer was washed with brine, dried over sodium sulfate, filtered and concentrated. Purified by normal phase chromatography. LCMS-ESI+ (m/z): calcd H+ for C33H44N2O9, Theoretical: 612.30, Found: 612.746.

Step 6: Synthesis of (1S,11S)-7-benzyloxy-11-methyl-10,15-diazatetracyclo[6.6.1.11,10.04,15]hexadeca-4,7,12-triene-6,9-dione tert-butyl (3S,7S)-3-[2-(5-benzyloxy-6-methoxycarbonyl-4-oxo-pyran-2-yl)ethyl]-3-(tert-butoxycarbonylamino)-7-methyl-4,7-dihydro-2H-azepine-1-carboxylate (0.41 g, 0.669 mmol) was dissolved in DCM (16 mL) and cooled to 0° C., TFA was added slowly dropwise along the side of the flask. The newly formed mixture was stirred at 0° C. for 30 minutes and then at room temperature for 2 hours. The reaction was concentrated, coevaporated with DCM (3×5 mL), further dried over the vacuum line for 3 hours. Then the residue was dissolved in EtOH (40 mL) and heated to 90° C. for 2 hours. The reaction was cooled to room temperature, concentrated, purified by normal phase chromatography. LCMS-ESI+ (m/z): calcd H+ for C22H22N2O3, Theoretical: 362.16, Found: 363.30.

Intermediate 20b

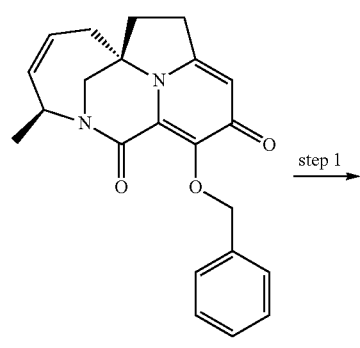

20a

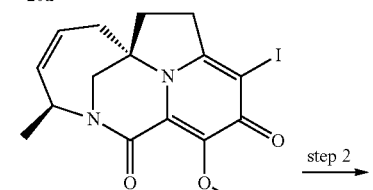

20b

Step 1: Synthesis of (1S,11S)-7-benzyloxy-5-iodo-11-methyl-10,15-diazatetracyclo[6.6.1.11,10.04,15]hexadeca-4,7,12-triene-6,9-dione To a solution of (1S,11S)-7-benzyloxy-11-methyl-10,15-diazatetracyclo[6.6.1.11,10.04,15]hexadeca-4,7,12-triene-6,9-dione (640 mg, 1.77 mmol) in MeOH (34 mL) at room temperature was added MCPBA (792 mg, 3.53 mmol) and NIS (795 mg, 3.53 mmol). The resulting mixture was heated to 80° C. for 20 minutes. The reaction was cooled to room temperature, diluted with DCM, washed with 1N sodium thiosulfate, saturated NaHCO3, dried over sodium sulfate, filtered and concentrated and purified by normal phase chromatography. 1H NMR (400 MHz, Chloroform-d) δ 7.68-7.57 (m, 2H), 7.39-7.26 (m, 3H), 5.64-5.51 (m, 2H), 5.51-5.39 (m, 2H), 5.15 (d, J=10.1 Hz, 1H), 3.74 (d, J=13.6 Hz, 1H), 3.30-3.19 (m, 3H), 2.59-2.49 (m, 2H), 2.25-2.09 (m, 2H), 1.23 (d, J=5.8 Hz, 3H). LCMS-ESI+ (m/z): [M+H]+ calcd for C22H21IN2O3: 489.07, found: 489.1.

Step 2: Synthesis of (1S,11S)-7-benzyloxy-N-[(2.4 difluorophenyl)methyl]-11-methyl-6,9-dioxo-10,15-diazatetracyclo[6.6.1.11,10.04,15]hexadeca-4,7,12-triene-5-carboxamide To the solution of (1S,11S)-7-benzyloxy-5-iodo-11-methyl-10,15-diazatetracyclo[6.6.1.11,10.04,15]hexadeca-4,7,12-triene-6,9-dione (285 mg, 0.584 mmol) in DMSO (12 mL) at room temperature was added (2,4-difluorophenyl)methanamine (418 mg, 2.92 mmol) followed by DIPEA (377 mg, 2.92 mmol), Tetrakis(triphenylphosphine)palladium(0) (33.7 mg, 0.0292 mmol) and PdCl2dppf (21.4 mg, 0.0292 mmol). The resulting mixture was degassed and flushed with CO three times and then under CO balloon, heated to 85° C. for 3 hours. The reaction was cooled to room temperature, diluted with EtOAc, washed with water, saturated NH4Cl, brine, dried over sodium sulfate, filtered and concentrated and purified by normal phase chromatography to give Intermediate 20b. LCMS-ESI+ (m/z): [M+H]+ calcd for C30H27F2N3O4, Theoretical: 531.20, Found: 532.203.

Intermediate 20c

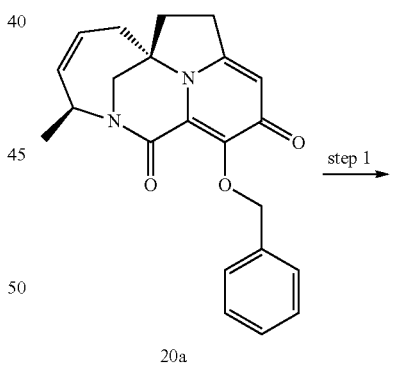

20a

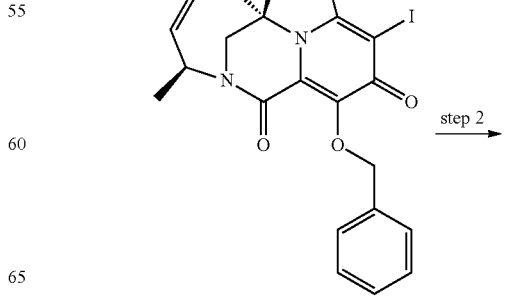

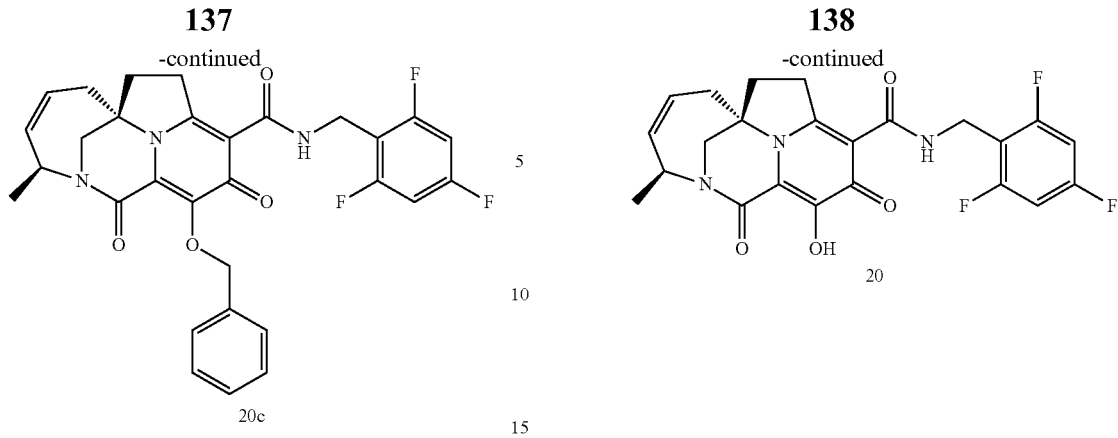

Intermediate 20c was prepared in a manner similar to that of Intermediate 20b. 1H NMR (400 MHz, Chloroform-d) δ 10.83 (t, J=5.7 Hz, 1H), 7.61-7.49 (m, 2H), 7.39-7.27 (m, 3H), 6.72-6.59 (m, 2H), 5.59 (ddd, J=13.0, 7.3, 3.8 Hz, 1H), 5.50-5.40 (m, 3H), 5.19 (d, J=10.3 Hz, 1H), 4.64 (d, J=5.6 Hz, 2H), 4.10 (dd, J=18.5, 8.4 Hz, 1H), 3.81 (d, J=13.6 Hz, 1H), 3.49 (ddd, J=19.0, 11.7, 7.9 Hz, 1H), 3.07 (d, J=13.6 Hz, 1H), 2.52 (d, J=7.5 Hz, 2H), 2.22 (dd, J=12.8, 7.8 Hz, 1H), 1.93 (td, J=12.2, 8.8 Hz, 1H), 1.28 (d, J=7.2 Hz, 3H). LCMS-ESI+(m/z): [M+H]+ calcd for C30H26F3N3O4: 550.19, found: 550.2.

Example 20: Preparation of (3S,6aS)-11-hydroxy-3-methyl-1,10-dioxo-N-(2,4,6-trifluorobenzyl)-1,3,6,7,8,10-hexahydro-2,6a-methano[1,4]diazonino[9,1,2-cd]indolizine-9-carboxamide (20)

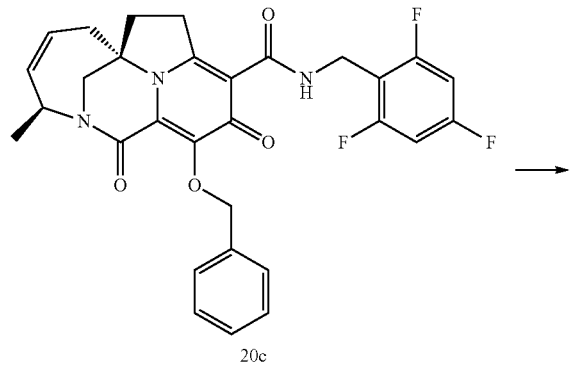

To Intermediate 20c (20 mg) was added toluene (0.75 mL) then TFA (0.75 mL). The reaction was stirred under ambient atmosphere at 20° C., with monitoring by LCMS, until all starting material was consumed. The reaction was diluted with acetonitrile and concentrated in vacuo. Purification by silica gel flash column chromatography (0 to 20% methanol in dichloromethane) yielded compound 20. 1H NMR (400 MHz, Chloroform-d) δ 10.59 (t, J=5.8 Hz, 1H), 6.68 (dd, J=8.7, 7.5 Hz, 2H), 5.62 (ddt, J=8.1, 4.4, 2.0 Hz, 1H), 5.58-5.48 (m, 1H), 5.48-5.36 (m, 1H), 4.66 (d, J=5.6 Hz, 2H), 4.17 (dd, J=19.1, 9.2 Hz, 1H), 3.97 (d, J=13.6 Hz, 1H), 3.51 (ddd, J=18.9, 11.2, 7.9 Hz, 1H), 3.34 (d, J=13.6 Hz, 1H), 2.57 (dd, J=16.5, 8.3 Hz, 1H), 2.56-2.45 (m, 1H), 2.30 (dd, J=12.8, 7.8 Hz, 1H), 2.10-1.97 (m, 1H), 1.37 (d, J=7.3 Hz, 3H). LCMS-ESI+ (m/z): [M+H]+ calcd for C23H20F3N3O4: 460.1, found: 460.2.

Example 21: Preparation of (3S,6aR,8R)-8,11-dihydroxy-3-methyl-1,10-dioxo-N-(2,4,6-trifluorobenzyl)-1,3,6,7,8,10-hexahydro-2,6a-methano[1,4]diazonino[9,1,2-cd]indolizine-9-carboxamide and (3S,6aR,8S)-8,11-dihydroxy-3-methyl-1,10-dioxo-N-(2,4,6-trifluorobenzyl)-1,3,6,7,8,10-hexahydro-2,6a-methano[1,4]diazonino[9,1,2-cd]indolizine-9-carboxamide (21-1 and 21-2)

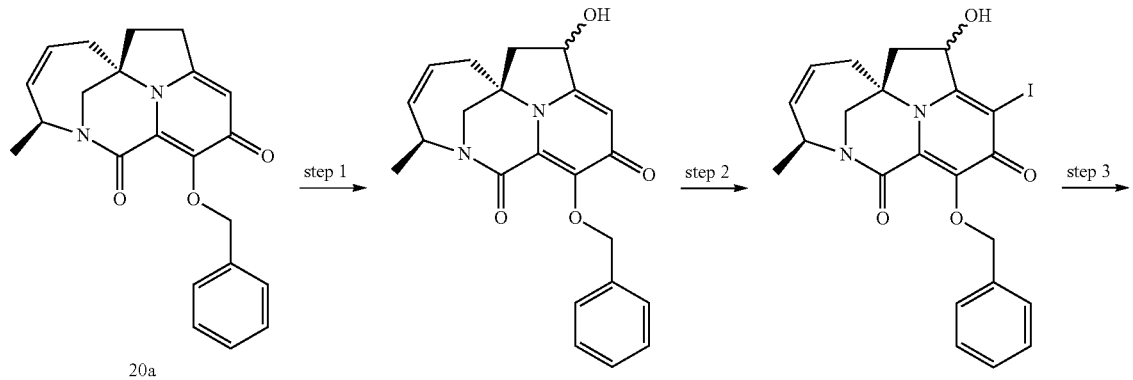

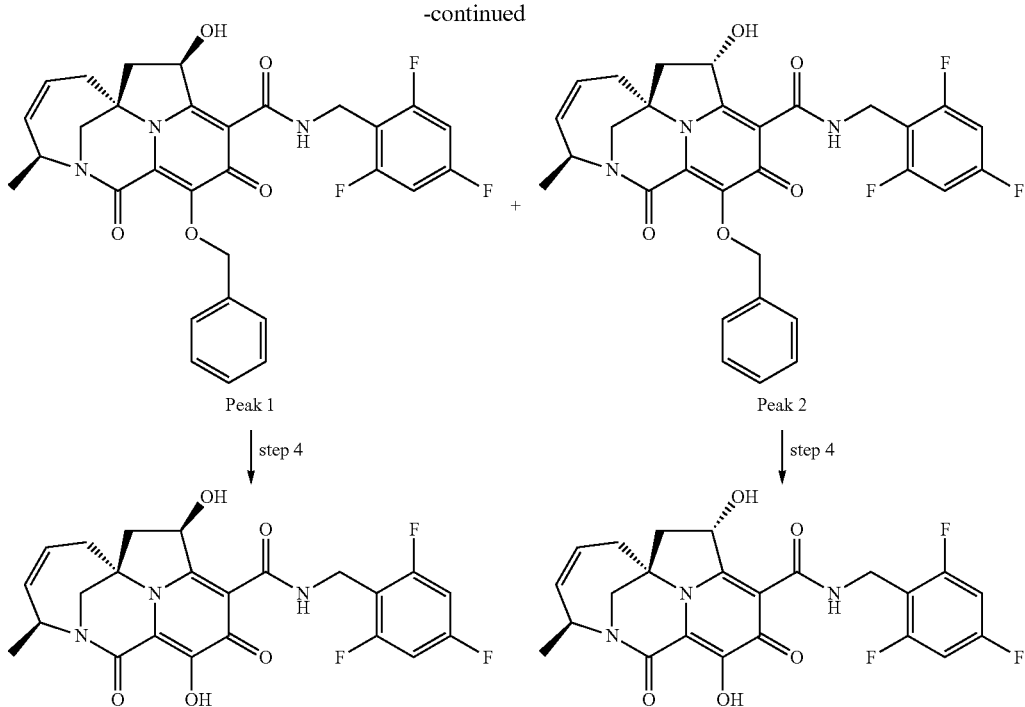

Step 1. To 20a (25 mg) was added THF (0.7 mL). The reaction flask was cooled to −80° C., then LiHMDS (1 M in THF, 50 uL) was added dropwise. After 5 min at −80° C., (rac)-3-phenyl-2-(phenylsulfonyl)-1,2-oxaziridine (36 mg, 2 equiv) was added as solution in THF (1 mL). The reaction was stirred at −80° C. After 30 min, more LiHMDS (1 M in THF, 30 uL), then more Davis oxaziridine (36 mg) in THF (1 mL) were added. The reaction was allowed to slowly warm over 60 min to −10° C., then it was quenched by addition of methanol. The mixture was removed from cooling bath and concentrated in vacuo. Purification by silica gel flash column chromatography (0 to 20% MeOH in DCM) yielded the desired product as a mixture of diastereomers. LCMS-ESI+ (m/z): [M+H]+ calcd for C22H22N2O4: 379.17, found: 379.3.

Step 2. To the product from Step 1 (28 mg) was added mCPBA (66 mg, 4 equiv), then NIS (66 mg, 4 equiv), then MeOH (3 mL). Vial was sealed under ambient atmosphere and stirred in metal heating block at 80° C. After 1 hr, the reaction was allowed to cool to 20° C. The reaction was diluted with DCM, then washed with 1 N aq sodium thiosulfate, then once with satd aq NaHCO3. The combined aqueous phases were extracted with DCM. The combined organic phases were dried over MgSO4, filtered, and concentrated in vacuo. Purification by silica gel flash column chromatography (0 to 20% MeOH in DCM) yielded the desired product. LCMS-ESI+ (m/z): [M+H]+ calcd for C22H21IN2O4: 505.06, found: 505.1.

Step 3. To the product from Step 2 (35 mg) under argon in DMSO (1.5 mL) was added 2,4,6-trifluorobenzylamine (56 mg, 5 equiv) then DIPEA (60 μL, 5 equiv). The flask was cycled five times between high vacuum and CO atmosphere. Then Pd(PPh3)4 (4 mg, 0.05 equiv) was added. The flask was again cycled five times between high vacuum and CO atmosphere, then the reaction was warmed to 85° C. in metal heating block for 2 hr, at which point all starting material was consumed by LCMS. The reaction was allowed to cool to 20° C. Diluted with ethyl acetate. The organic phase was washed with 0.2 N HCl (2×), then water (2×), then brine (1×). The organic phase was dried over MgSO4, filtered, and concentrated in vacuo. Purification by silica gel flash column chromatography (25 to 100% ethyl acetate in hexane) yielded the desired product as a mixture of diastereomers. Further purification by chiral SFC (Daicel Chiralpak AD-H column, 50% iPrOH in CO2 with NH3 modifier) yielded two diastereomers. Peak 1 (earlier-eluting product, structure tentatively assigned): H NMR (400 MHz, Chloroform-d) δ 10.78 (t, J=5.6 Hz, 1H), 7.59-7.53 (m, 2H), 7.37-7.29 (m, 3H), 6.68 (dd, J=8.7, 7.5 Hz, 2H), 5.69 (d, J=7.2 Hz, 1H), 5.66-5.57 (m, 1H), 5.49 (d, J=10.3 Hz, 1H), 5.48-5.42 (m, 2H), 5.18 (d, J=10.3 Hz, 1H), 4.70 (dd, J=14.5, 5.9 Hz, 1H), 4.62 (dd, J=14.5, 5.5 Hz, 1H), 3.82 (d, J=13.6 Hz, 1H), 3.05 (d, J=13.6 Hz, 1H), 2.90 (dd, J=16.6, 8.9 Hz, 1H), 2.69 (dq, J=16.7, 3.5 Hz, 1H), 2.37 (d, J=14.0 Hz, 1H), 2.10 (dd, J=14.0, 7.4 Hz, 1H), 1.27 (d, J=7.3 Hz, 3H). LCMS-ESI+ (m/z): [M+H]+ calcd for C30H26F3N3O5: 566.19, found: 566.2. Peak 2 (later-eluting product, structure tentatively assigned): 1H NMR (400 MHz, Chloroform-d) δ 11.42 (t, J=5.6 Hz, 1H), 7.56-7.45 (m, 2H), 7.39-7.27 (m, 3H), 7.08 (s, 1H), 6.68 (t, J=8.1 Hz, 2H), 5.70 (dd, J=9.3, 7.4 Hz, 1H), 5.64-5.54 (m, 1H), 5.52-5.38 (m, 3H), 5.23 (d, J=10.5 Hz, 1H), 4.68 (d, J=5.6 Hz, 2H), 3.82 (d, J=13.8 Hz, 1H), 3.14 (d, J=13.7 Hz, 1H), 2.71 (dd, J=12.9, 7.3 Hz, 1H), 2.55-2.39 (m, 2H), 2.01 (dd, J=12.9, 9.3 Hz, 1H), 1.29 (d, J=7.2 Hz, 3H). LCMS-ESI+ (m/z): [M+H]+ calcd for C30H26F3N3O5: 566.19, found: 566.2.

Step 4. To Peak 1 from Step 3 was added toluene, then TFA. The reaction was stirred at 20° C., with monitoring by LCMS until starting material was consumed. The reaction was diluted with acetonitrile and concentrated in vacuo. Purification by reverse-phase preparative HPLC (acetonitrile/water, 0.1% TFA modifier) yielded 21-1. 1H NMR (400 MHz, Acetonitrile-d3) δ 10.68 (s, 1H), 6.86 (t, J=8.5 Hz, 2H), 5.62 (d, J=5.3 Hz, 2H), 5.49 (d, J=11.4 Hz, 1H), 5.28

(s, 1H), 4.63 (d, J=5.2 Hz, 2H), 3.95 (d, J=13.8 Hz, 1H), 3.35 (d, J=13.7 Hz, 1H), 2.81 (dd, J=17.0, 8.7 Hz, 1H), 2.65 (d, J=17.0 Hz, 1H), 2.28 (d, J=1.6 Hz, 2H), 1.29 (d, J=6.9 Hz, 3H). LCMS-ESI+ (m/z): [M+H]+ calcd for C23H20F3N3O5: 476.14, found: 476.3.

Step 4. To Peak 2 from Step 3 was added toluene, then TFA. The reaction was stirred at 20° C., with monitoring by LCMS until starting material was consumed. The reaction was diluted with acetonitrile and concentrated in vacuo. Purification by reverse-phase preparative HPLC (acetonitrile/water, 0.1% TFA modifier) yielded 21-2. 1H NMR (400 MHz, Acetonitrile-d3) δ 11.34 (s, 1H), 6.97 (s, 1H), 6.86 (t, J=8.6 Hz, 2H), 5.58 (dt, J=8.1, 6.0 Hz, 2H), 5.48 (dt, J=11.7, 2.3 Hz, 1H), 5.27 (s, 1H), 4.73-4.53 (m, 2H), 3.96 (d, J=13.9 Hz, 1H), 3.48 (d, J=13.8 Hz, 1H), 2.76 (dd, J=12.7, 7.2 Hz, 1H), 2.56 (dd, J=16.8, 8.6 Hz, 1H), 2.46-2.34 (m, 1H), 2.02-1.96 (m, 1H), 1.30 (d, J=7.2 Hz, 3H). LCMS-ESI+ (m/z): [M+H]+ calcd for C23H20F3N3O5: 476.14, found: 476.2.

Intermediate 22a

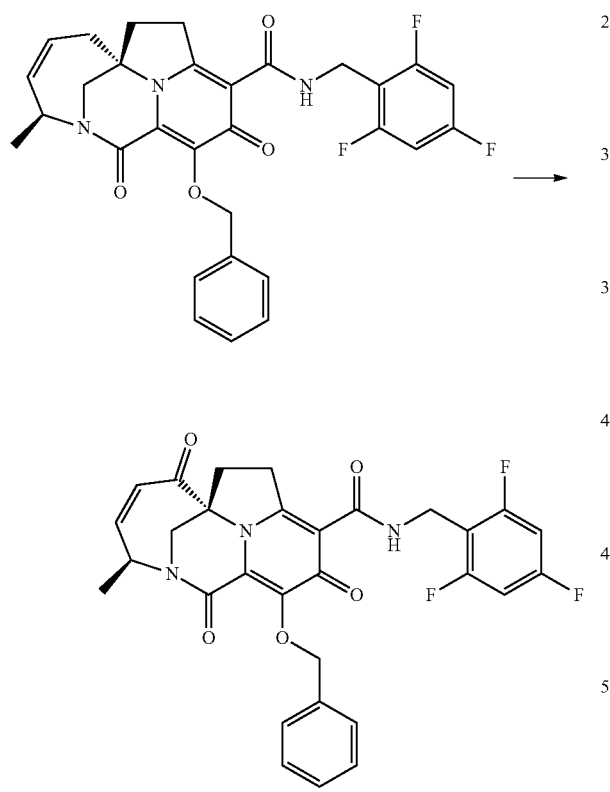

To screw-top vial under argon was added 20c (130 mg), then dioxane (4.8 mL), then selenium dioxide (210 mg, 8 equiv). The vial was sealed under argon and stirred at 100° C. for 6 hr. The mixture was filtered through Celite to remove insolubles, washing with ethyl acetate, and concentrated in vacuo. Purification by silica gel flash column chromatography (25 to 100% ethyl acetate in hexane) yielded 22a. 1H NMR (400 MHz, Chloroform-d) δ 10.74 (t, J=5.7 Hz, 1H), 7.60-7.49 (m, 2H), 7.41-7.26 (m, 3H), 6.67 (dd, J=8.8, 7.5 Hz, 2H), 6.28 (dd, J=11.9, 2.5 Hz, 1H), 5.99 (dd, J=11.9, 1.7 Hz, 1H), 5.60 (qt, J=7.5, 2.2 Hz, 1H), 5.46 (d, J=10.1 Hz, 1H), 5.08 (d, J=10.2 Hz, 1H), 4.65 (d, J=5.5 Hz, 2H), 4.11 (dd, J=18.8, 8.8 Hz, 1H), 3.97 (d, J=14.3 Hz, 1H), 3.81 (ddd, J=18.8, 10.9, 8.5 Hz, 1H), 3.45 (d, J=14.3 Hz, 1H), 2.31 (dd, J=13.3, 8.4 Hz, 1H), 2.03-1.93 (m, 1H), 1.39 (d, J=7.4 Hz, 3H). LCMS-ESI+ (m/z): [M+H]+ calcd for C30H26F3N3O5: 564.2, found: 564.1.

Intermediate 22b

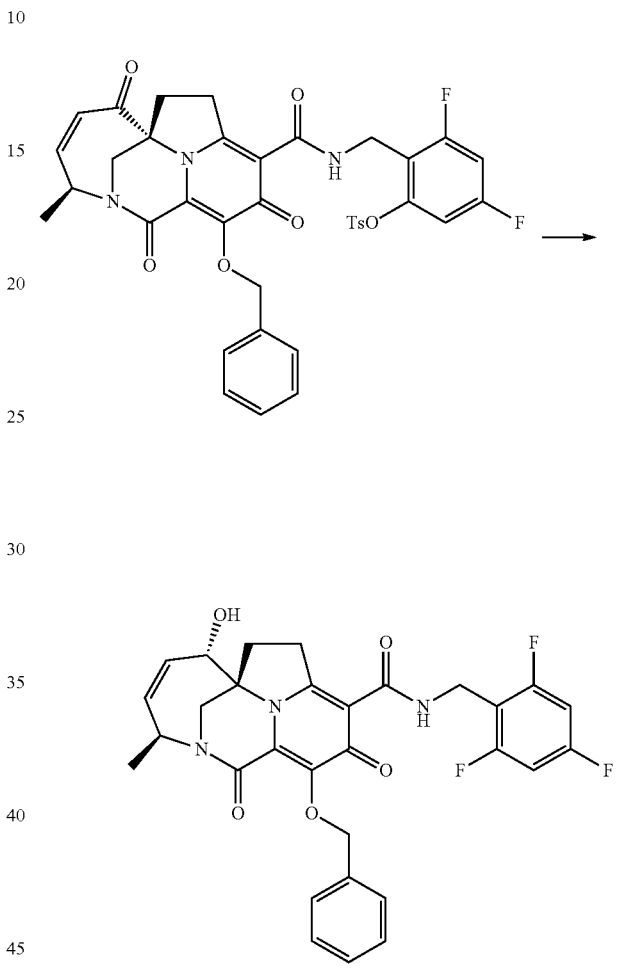

To a glass screw-top vial charged with Intermediate 22a (80 mg) was added methanol (4 mL), then cerium chloride heptahydrate (69 mg, 1.3 equiv), then sodium borohydride (5.5 mg, 1 equiv). The reaction was stirred at 20° C. for 30 min, quenched with saturated aqueous sodium bicarbonate, then extracted with 95:5 dichloromethane:methanol. The combined organic phases were dried over magnesium sulfate, filtered and concentrated to yield Intermediate 22b, which was used in subsequent steps without any further purification. 1H NMR (400 MHz, Chloroform-d) δ 10.89-10.77 (m, 1H), 7.60-7.50 (m, 2H), 7.39-7.29 (m, 3H), 6.67 (dd, J=8.7, 7.5 Hz, 2H), 5.56 (dt, J=11.4, 3.2 Hz, 1H), 5.47-5.40 (m, 1H), 5.38 (dt, J=7.2, 2.3 Hz, 1H), 5.32-5.26 (m, 1H), 5.19 (d, J=10.4 Hz, 1H), 4.96 (s, 1H), 4.74 (dd, J=14.5, 6.6 Hz, 1H), 4.47 (dd, J=14.4, 4.6 Hz, 1H), 3.94-3.78 (m, 2H), 3.68-3.54 (m, 1H), 3.05 (d, J=13.8 Hz, 1H), 2.72 (dd, J=12.7, 8.4 Hz, 1H), 1.72-1.64 (m, 1H), 1.26 (d, J=7.3 Hz, 3H). LCMS-ESI+(m/z): [M+H]+ calcd for C30H26F3N3O5: 566.2, found: 566.2.

Example 22: Preparation of (3S,6S,6aR)-11-hydroxy-6-methoxy-3-methyl-1,10-dioxo-N-(2,4,6-trifluorobenzyl)-1,3,6,7,8,10-hexahydro-2,6a-methano[1,4]diazonino[9,1,2-cd]indolizine-9-carboxamide (22)

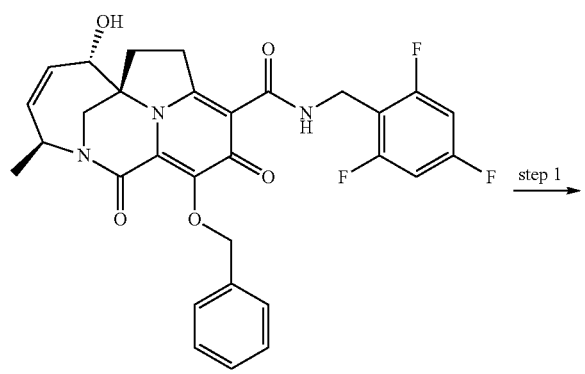

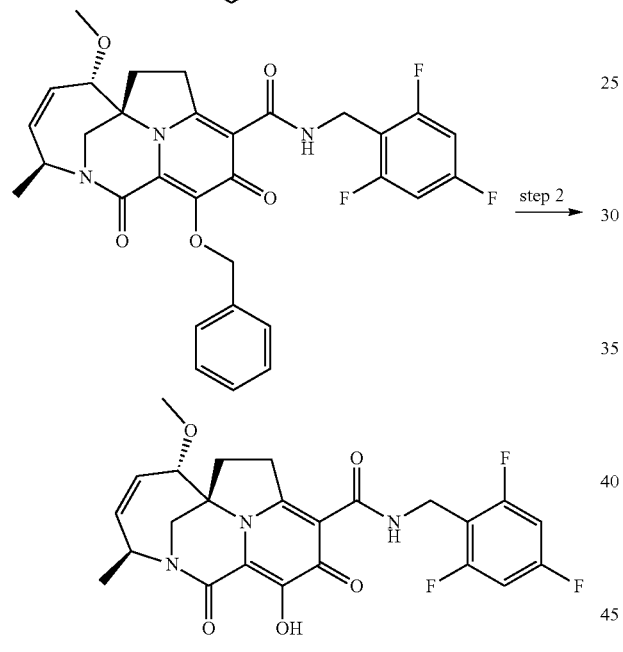

Step 1. To glass vial charged with Intermediate 22b (80 mg) under argon was added DMF (2.8 mL). The vial was cooled to 0° C., then NaH (60% in mineral oil, 7.4 mg, 1.3 equiv) was added. The reaction was stirred at 0° C. for 5 min, then MeI (10 µL, 1.1 equiv). The reaction was stirred at 0° C. for 1 hr. Then the reaction was quenched with saturated aqueous NH4Cl, and extracted into ethyl acetate. The organic phase was washed with water, then brine. The combined aqueous phases were back-extracted with more ethyl acetate. The combined organic phases were dried over MgSO$_4$, filtered, and concentrated in vacuo. Silica gel flash column chromatography (25 to 100% ethyl acetate in hexane) yielded the desired product. 1H NMR (400 MHz, Chloroform-d) δ 10.87 (s, 1H), 7.62-7.53 (m, 2H), 7.35 (dd, J=8.0, 6.1 Hz, 3H), 6.76-6.63 (m, 2H), 5.62 (dt, J=11.4, 3.1 Hz, 1H), 5.53 (d, J=10.5 Hz, 1H), 5.50-5.45 (m, 1H), 5.42 (dq, J=7.5, 2.3 Hz, 1H), 5.24 (d, J=10.4 Hz, 1H), 4.67 (d, J=4.2 Hz, 2H), 4.26 (d, J=3.2 Hz, 1H), 3.95 (dd, J=18.5, 8.9 Hz, 1H), 3.85 (d, J=13.8 Hz, 1H), 3.62 (ddd, J=18.8, 10.7, 8.5 Hz, 1H), 3.28 (s, 3H), 3.05 (d, J=13.7 Hz, 1H), 2.63 (dd, J=12.7, 8.3 Hz, 1H), 1.66 (ddd, J=12.9, 10.8, 9.1 Hz, 1H), 1.29 (d, J=7.3 Hz, 3H). LCMS-ESI+ (m/z): [M+H]+ calcd for C31H28F3N3O5: 580.2, found: 580.2.

Step 2. To the product from Step 1 (5 mg) was added toluene (0.18 mL) then TFA (0.18 mL). The reaction was sealed under ambient atmosphere and stirred at 60° C., with monitoring by LCMS, until all starting material was consumed. The reaction was diluted with acetonitrile and concentrated in vacuo. Purification by silica gel flash column chromatography (0 to 20% methanol in dichloromethane) yielded compound 22. 1H NMR (400 MHz, Acetonitrile-d3) δ 10.61 (s, 1H), 6.85 (t, J=8.5 Hz, 2H), 5.63 (dt, J=11.5, 3.2 Hz, 1H), 5.49 (ddd, J=11.6, 2.7, 1.6 Hz, 1H), 5.22 (d, J=7.9 Hz, 1H), 4.65-4.50 (m, 2H), 4.26 (q, J=3.0 Hz, 1H), 3.97 (d, J=13.9 Hz, 1H), 3.77 (dd, J=18.5, 9.1 Hz, 1H), 3.43 (d, J=9.0 Hz, 1H), 3.40-3.32 (m, 1H), 3.21 (s, 3H), 2.53 (dd, J=12.8, 8.2 Hz, 1H), 1.85-1.72 (m, 1H), 1.28 (d, J=7.3 Hz, 3H). LCMS-ESI+ (m/z): [M+H]+ calcd for C24H22F3N3O5: 490.2, found: 490.2.

Example 23: Preparation of (3S,6S,6aR)-6,11-dihydroxy-3-methyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide and (3S,6S,6aR)-11-hydroxy-6-methoxy-3-methyl-1,10-dioxo-N-(2,4,6-trifluorobenzyl)-1,3,4,5,6,7,8,10-octahydro-2,6a-methano[1,4]diazonino[9,1,2-cd]indolizine-9-carboxamide (23-1 and 23-2)

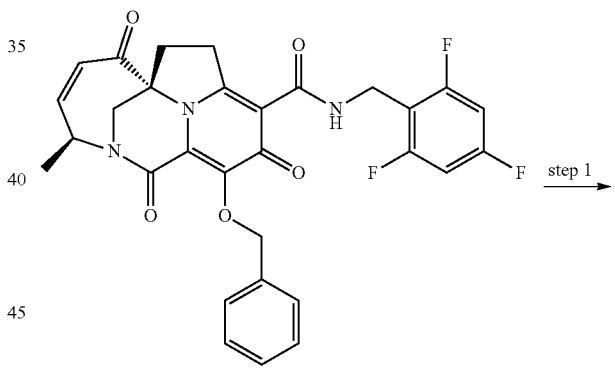

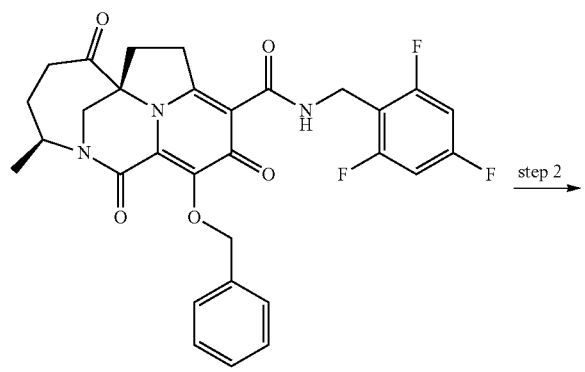

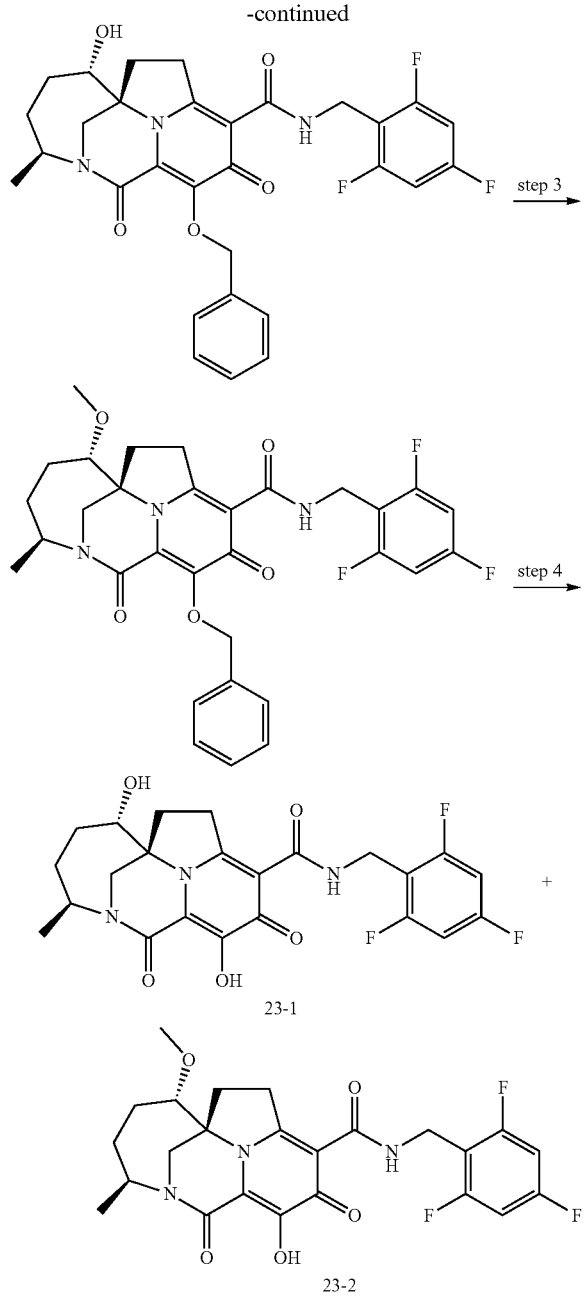

Step 1. To a glass screw-top vial charged with Intermediate 22a (50 mg) was added THF (2.5 mL). The vial was cooled under argon to −80° C., then lithium tri-sec-butylborohydride (1 M in THF, 90 μL, 1 equiv) was added. After 15 min at −80° C., the reaction was quenched with saturated aqueous ammonium chloride, then extracted with ethyl acetate. The combined organic phases were washed once with sat aq sodium bicarbonate, then once with brine, then dried over magnesium sulfate, filtered and concentrated in vacuo. Purification by silica gel flash column chromatography (25 to 100% ethyl acetate in hexane) yielded the desired product. 1H NMR (400 MHz, Chloroform-d) δ 10.76 (t, J=5.6 Hz, 1H), 7.64-7.49 (m, 3H), 7.39-7.28 (m, 4H), 6.67 (dd, J=8.7, 7.5 Hz, 2H), 5.46 (d, J=10.2 Hz, 1H), 5.10 (d, J=10.2 Hz, 1H), 4.98 (td, J=6.9, 2.8 Hz, 1H), 4.70-4.61 (m, 2H), 4.11-4.05 (m, 1H), 3.99 (d, J=14.9 Hz, 1H), 3.58 (ddd, J=18.9, 11.2, 8.4 Hz, 1H), 3.39 (d, J=15.0 Hz, 1H), 3.02 (td, J=12.7, 2.6 Hz, 1H), 2.46 (ddd, J=13.0, 7.0, 2.7 Hz, 1H), 2.37-2.27 (m, 1H), 2.22 (tdd, J=12.3, 6.5, 2.7 Hz, 1H), 2.03-1.94 (m, 1H), 1.83-1.72 (m, 1H), 1.30 (d, J=7.1 Hz, 3H). LCMS-ESI+ (m/z): [M+H]+ calcd for C30H26F3N3O5: 566.2, found: 566.2.

Step 2. To a glass screw-top vial charged with the product from Step 1 (27 mg) was added methanol (1.4 mL), then sodium borohydride (1.8 mg, 1.0 equiv). Vigorous gas evolution was observed during sodium borohydride addition. After 10 min at 20° C., the reaction was quenched with saturated aqueous sodium bicarbonate, then extracted with dichloromethane. The combined organic phases were dried over magnesium sulfate, filtered and concentrated in vacuo to give the desired product, which was carried forward to subsequent steps without further purification. 1H NMR (400 MHz, Chloroform-d) δ 10.97 (t, J=5.6 Hz, 1H), 7.67-7.57 (m, 2H), 7.42-7.30 (m, 3H), 6.67 (dd, J=8.7, 7.5 Hz, 2H), 5.38 (d, J=10.0 Hz, 1H), 5.24 (d, J=10.1 Hz, 1H), 4.86 (dt, J=10.5, 6.7 Hz, 1H), 4.68 (dd, J=14.5, 5.5 Hz, 1H), 4.58 (dd, J=14.5, 4.8 Hz, 1H), 3.86-3.71 (m, 2H), 3.63 (dd, J=18.3, 9.3 Hz, 1H), 3.41 (d, J=14.7 Hz, 1H), 3.20 (d, J=14.7 Hz, 1H), 2.35 (dd, J=12.6, 8.0 Hz, 1H), 2.06-1.92 (m, 2H), 1.69 (ddd, J=14.5, 7.3, 3.8 Hz, 1H), 1.49-1.35 (m, 1H), 1.33-1.22 (m, 1H), 1.18 (d, J=6.7 Hz, 3H). LCMS-ESI+ (m/z): [M+H]+ calcd for C30H28F3N3O5: 568.2, found: 568.2.

Step 3. To a glass vial charged with the product from Step 2 (13 mg) under argon was added DMF (0.5 mL). The vial was cooled to 0° C. Sodium hydride (60% in mineral oil, 1.2 mg, 1.3 equiv) was added. The reaction was stirred at 0° C. for 5 min, then MeI (2.6 mg, 0.8 equiv) was added. The reaction was stirred at 0° C. for 45 min, then quenched with saturated aq NH4Cl, and extracted into ethyl acetate. The organic phase was washed with water, then brine. The combined aqueous phases were extracted with more ethyl acetate. The combined organic phases were dried over MgSO4, filtered, concentrated in vacuo. Silica gel flash column chromatography (25 to 100% ethyl acetate in hexane) yielded the desired product as a mixture with unreacted starting material. LCMS-ESI+ (m/z): [M+H]+ calcd for C31H30F3N3O5: 582.2, found: 582.3.

Step 4. To the product mixture from Step 3 (7 mg) was added toluene (0.25 mL) then TFA (0.25 mL). The reaction was sealed under ambient atmosphere, and stirred in at 60° C. for 15 min. The reaction was diluted with acetonitrile and concentrated in vacuo. The crude was redissolved in 1:1 DMF:water, and purified by reverse-phase preparative HPLC (20 to 100% acetonitrile in water, 0.1% TFA) to yield 23-1 and 23-2.

23-2: 1H NMR (400 MHz, Acetonitrile-d3) δ 10.79 (s, 1H), 6.84 (t, J=8.5 Hz, 2H), 4.64-4.56 (m, 1H), 4.56 (s, 2H), 3.68 (d, J=3.4 Hz, 1H), 3.65 (s, 1H), 3.63 (s, 1H), 3.52 (dd, J=10.4, 8.2 Hz, 1H), 3.42 (d, J=4.6 Hz, 1H), 3.39 (d, J=2.7 Hz, 1H), 3.31 (s, 3H), 2.26 (dd, J=12.8, 7.9 Hz, 1H), 2.21-1.99 (m, 2H), 1.51-1.36 (m, 1H), 1.19 (d, J=6.6 Hz, 3H), 1.00-0.85 (m, 1H). LCMS-ESI+ (m/z): [M+H]+ calcd for C24H24F3N3O5: 492.2, found: 492.2.

23-1: 1H NMR (400 MHz, Acetonitrile-d3) δ 10.84 (s, 1H), 6.84 (t, J=8.5 Hz, 2H), 4.65-4.57 (m, 1H), 4.56 (d, J=5.6 Hz, 2H), 3.76 (dd, J=11.6, 4.1 Hz, 1H), 3.66 (d, J=14.7 Hz, 1H), 3.63-3.47 (m, 2H), 3.44 (s, 1H), 2.28 (dd, J=12.7, 7.8 Hz, 1H), 2.16-2.07 (m, 1H), 2.01 (dd, J=14.5, 7.3 Hz, 1H), 1.71 (ddd, J=15.0, 7.6, 4.1 Hz, 1H), 1.55-1.42 (m, 1H), 1.25-1.09 (m, 4H). LCMS-ESI+ (m/z): [M+H]+ calcd for C23H22F3N3O5: 478.2, found: 478.2.

Example 24: HIV MT-4 Antiviral and Cytotoxicity Assay

Antiviral Assay in MT-4 Cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (No Drug Control) and 5 μM AZT positive controls. MT-4 cells were pre-infected with 10 μL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates and chemiluminescence read using an Envision plate-reader. $EC_{50}$ values were defined as the compound concentration that causes a 50% decrease in luminescence signal, and were calculated using a sigmoidal dose-response model to generate curve fits.

Cytotoxicity Assay in MT-4 Cells

Assays were performed as above except uninfected MT-4 cells were added to each well containing test compound. In addition, 10 μM puromycin was added to the last column of each assay plate to assess a base level of cytotoxicity.

Example 25: HIV MT-4 Serum Shift Antiviral Reporter Assay

To quantify the amount of protein binding to human serum, compounds were serially diluted (1:3) in DMSO and acoustically transferred onto 384-well assay plates via a Labcyte ECHO robot. Each plate contained up to 8 test compounds, including negative and positive controls, (DMSO, 5 μM AZT respectively). Assay plates were prepared in duplicate, and tested in either CCM (cell culture media) or HS/CCM (human serum/cell culture media). MT-4 cells were first pre-infected with pLai RLuc reporter virus for 2 h at 37° C., then further diluted in either CCM (RPMI media, 10% FBS, 1% P/S) or HS/CCM (RPMI media, 10% FBS, 50% HS, 1% P/S), and subsequently added to each plate using a Biotek Micro Flow dispenser. After a 72-h incubation in a humidified and temperature controlled incubator (37° C.), Renilla Glo (Promega) was added to all assay plates and chemiluminescence read using an Envision plate-reader. $EC_{50}$ values were defined as the compound concentration that causes a 50% decrease in luminescence signal, and were calculated using a sigmoidal dose-response model to generate curve fits. To determine the amount of protein binding, $EC_{50}$ fold shifts (or $EC_{50}$ shifts) were calculated by dividing $EC_{50}$ (HS/CCM)/$EC_{50}$ (CCM).

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

TABLE 1

| Compound No. | $EC_{50}$ (nM) | $CC_{50}$ (nM) | Antiviral Serum Shift RLuc | | |
|---|---|---|---|---|---|
| | | | CCM | 50% HS | $EC_{50}$ shift |
| 1 | 1.35 | 4299 | 0.299 | 8.707 | 29 |
| 2 | 2.26 | 6159 | 0.351 | 20.79 | 59 |
| 3 | 1.78 | 4935 | 0.175 | 3.107 | 18 |
| 4 | 3.09 | 5140 | 0.72 | 32.31 | 45 |
| 5 | 2.24 | 4041 | 0.278 | 6.04 | 22 |
| 6 | 2.60 | 3681 | | | |
| 7 | 3.80 | 3800 | 0.997 | 60.83 | 61 |
| 8-1 | 0.86 | 7382 | 0.429 | 25.42 | 59 |
| 8-2 | 2.286 | | | | |
| 9-1 | 3.063 | 8084 | 0.685 | 200.38 | 292 |
| 9-2 | 1.234 | 5174 | 0.347 | 34.06 | 98 |
| 9-3 | 1.06 | 6311 | 0.384 | 28.5 | 74 |
| 9-4 | 0.703 | 6395 | 0.388 | 5.186 | 13 |
| 10-1 | 4.98 | 9565 | 0.715 | 120.63 | 168.7 |
| 10-2 | 1.05 | 4123 | 0.417 | 21.07 | 50.5 |
| 10-3 | 3.31 | 9473 | 0.632 | 25.584 | 40.48 |
| 10-4 | 2.47 | 4608 | 0.405 | 3.297 | 8.14 |
| 11-1 | 3.996 | 50000 | 1.16 | 3.91 | 3.36 |
| 11-2 | | | 1.52 | 48.4 | 31.78 |
| 11-3 | 5.277 | 50000 | 4.08 | 7.565 | 1.85 |
| 11-4 | 4.016 | 50000 | 1.02 | 20.51 | 20.13 |
| 12-1 | 1.54 | 9692 | 0.77 | 16.89 | 22 |
| 12-2 | 3.26 | 11082 | 1.136 | 98.434 | 86 |
| 12-3 | 4.47 | 14789 | | | |
| 12-4 | 7.33 | | | | |
| 13-1 | 1.7 | 27821 | | | |
| 13-2 | 1.1 | 24660 | | | |
| 13-3 | 9.5 | 10132 | | | |
| 13-4 | 10.7 | 30737 | | | |
| 14-1 | 1.1 | 2310 | 0.22 | 26 | 121 |
| 14-2 | 0.73 | 2112 | 0.41 | 11 | 26 |
| 15 | 1.2 | 3729 | 0.29 | 51 | 174 |
| 16 | 2.8 | 7446 | | | |
| 17 | 1.2 | 3169 | 0.13 | 1.1 | 8 |
| 18 | 10.7 | 25218 | 0.87 | 0.97 | 1 |
| 19-1 | 2.1 | 4597 | | | |
| 19-2 | 0.86 | 1872 | | | |
| 19-3 | 1.2 | 6953 | | | |
| 20 | 0.83 | 3342 | 0.31 | 16 | 53 |
| 21-1 | 1.04 | 4838 | 0.26 | 27 | 104 |
| 21-2 | 0.8 | 5371 | 0.27 | 12 | 45 |
| 22 | 1.8 | 1939 | | | |
| 23-1 | 5.7 | 26584 | | | |
| 23-2 | 2.5 | 14115 | 0.46 | 21 | 46 |

The data in Table 1 represents an average over time of each assay for each compound. For certain compounds, multiple assays have been conducted.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments have been described herein for purposes of illustration, various modifications may be made without deviating from the spirit and scope of the disclosure. Accordingly, the disclosure is not limited except as by the appended claims.

We claim:
1. A compound selected from the group consisting of:
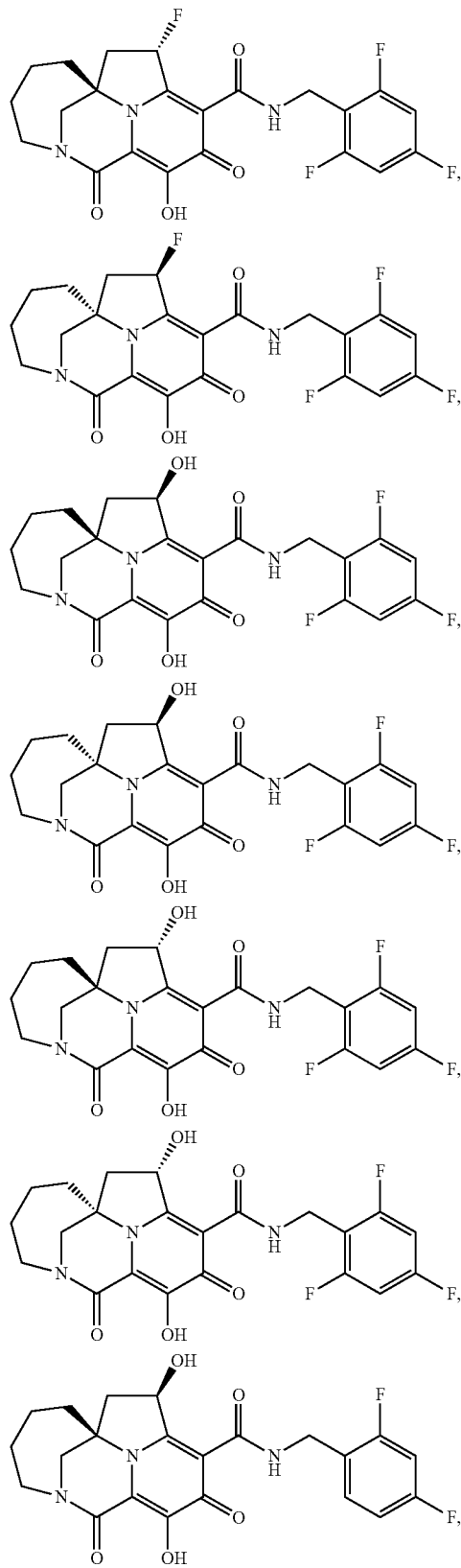
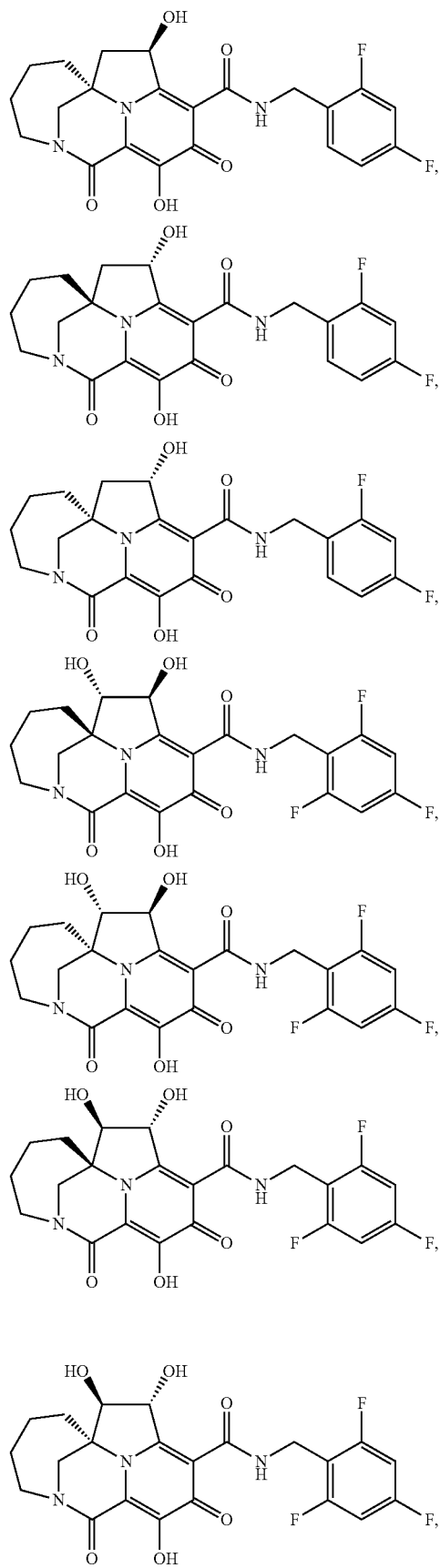

151
-continued
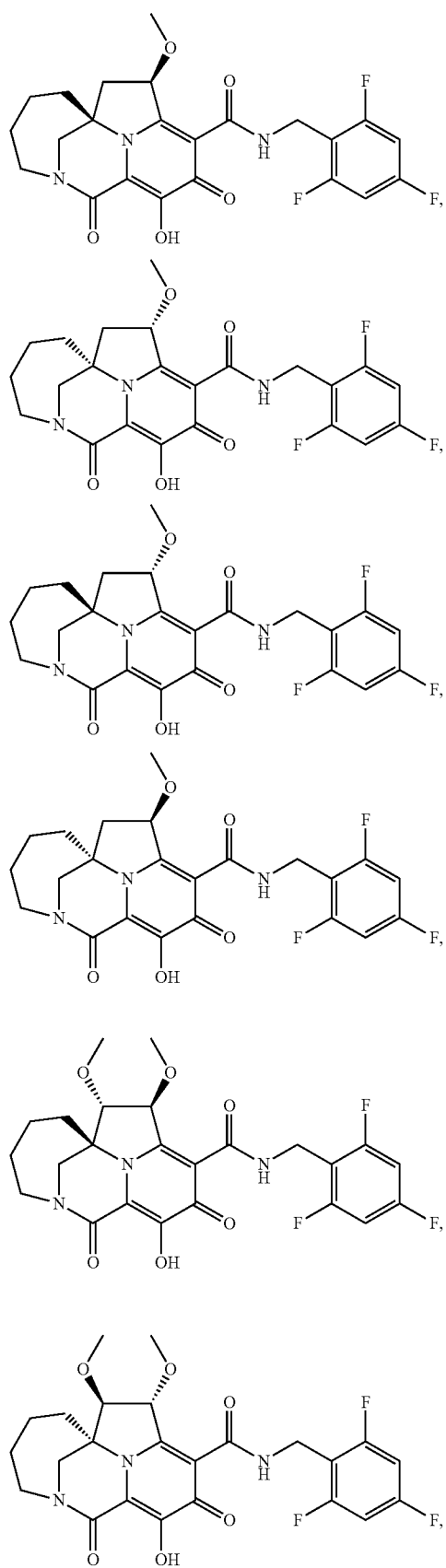
152
-continued
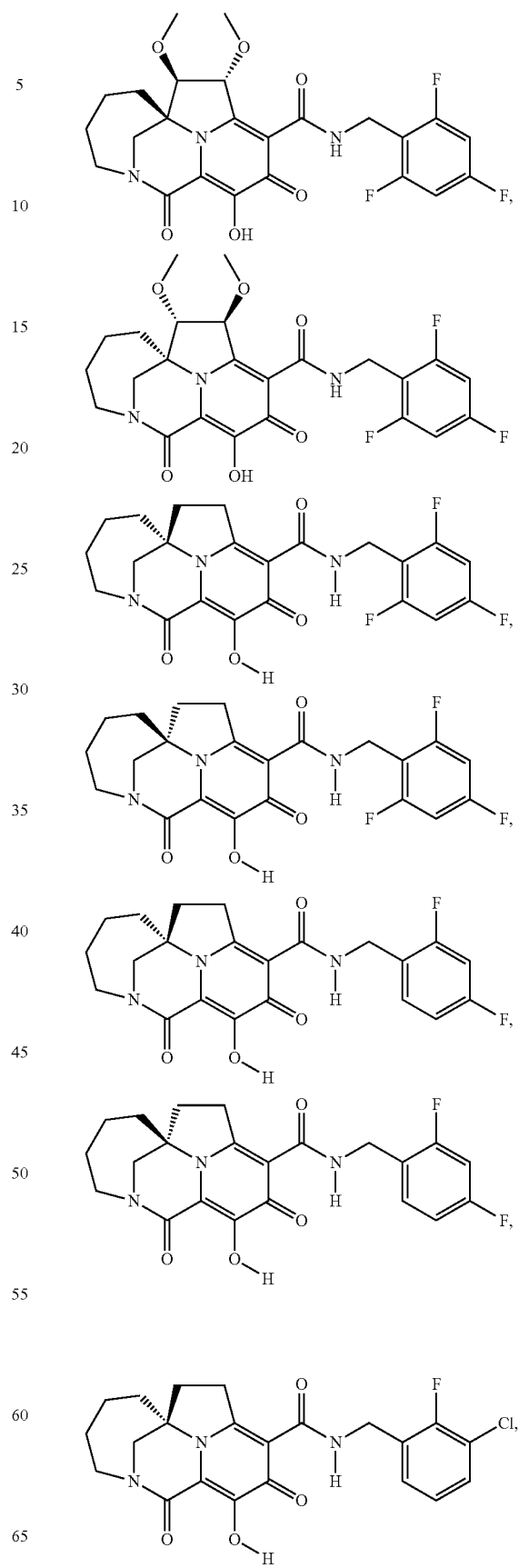

153
-continued
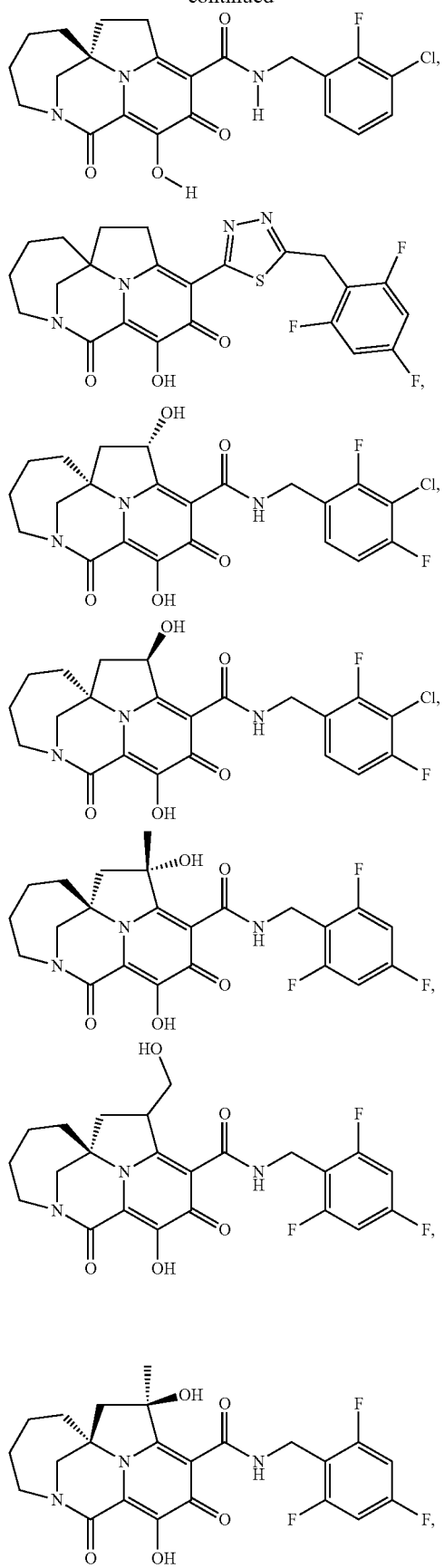
154
-continued
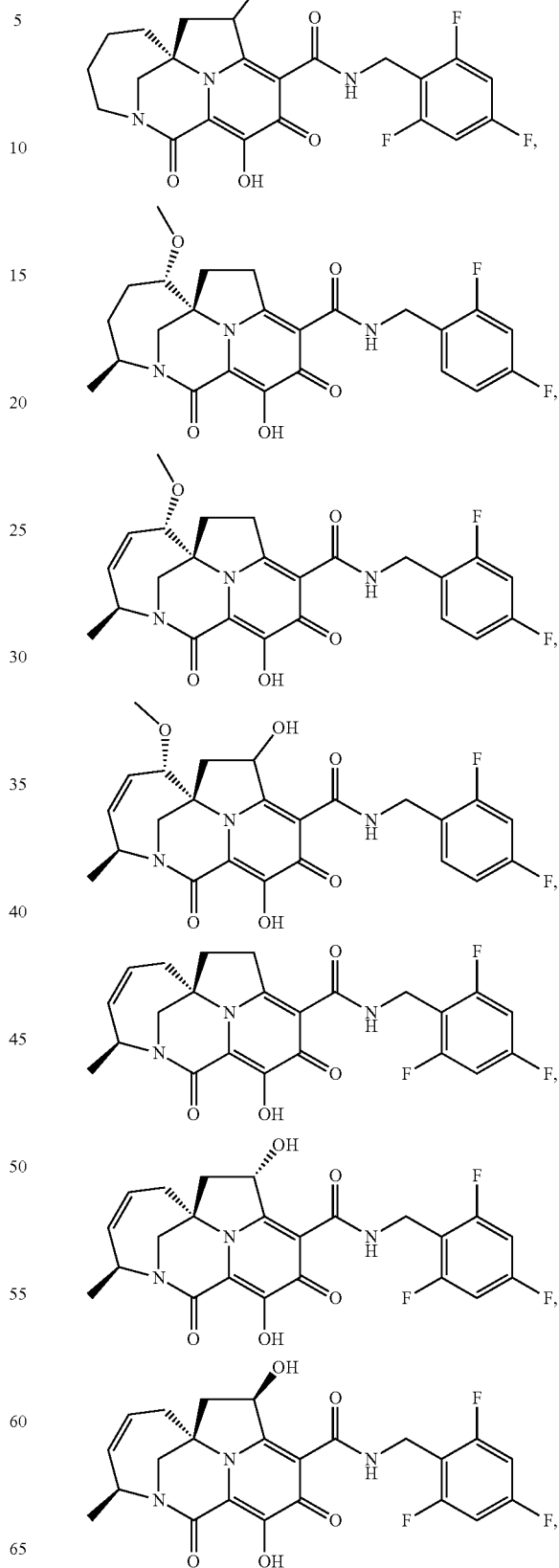

155
-continued
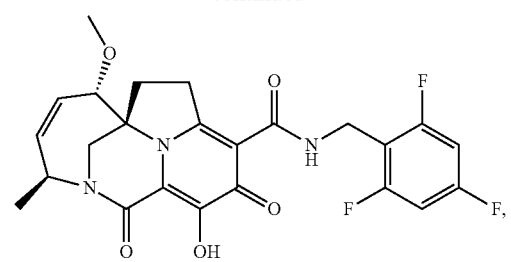
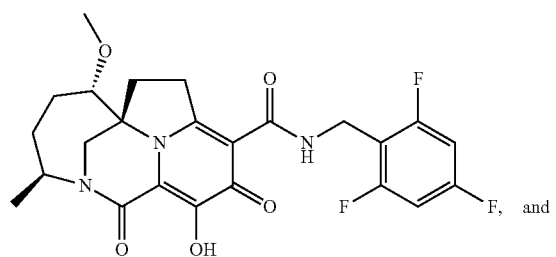
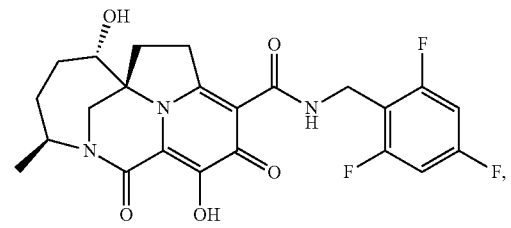
or a pharmaceutically acceptable salt thereof.
2. The compound of claim 1, wherein the compound is selected from the group consisting of:
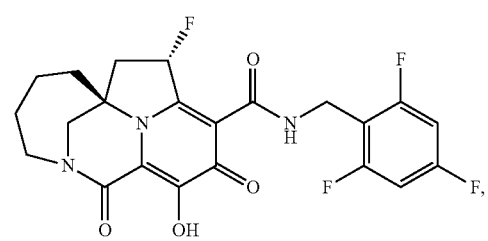
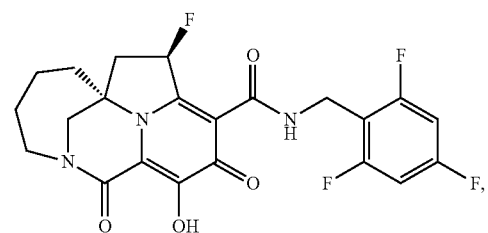
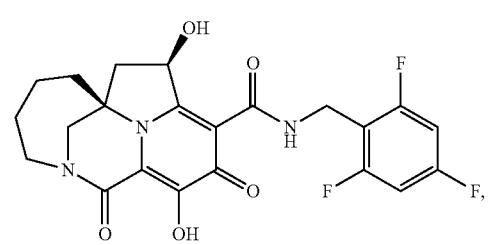
156
-continued
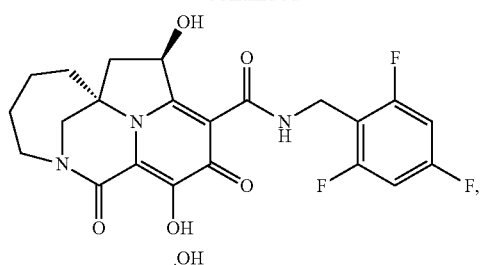
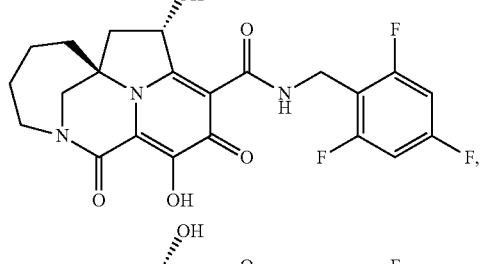
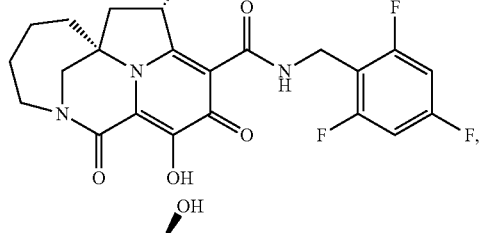
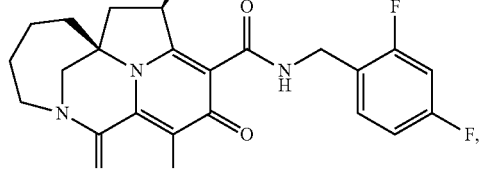
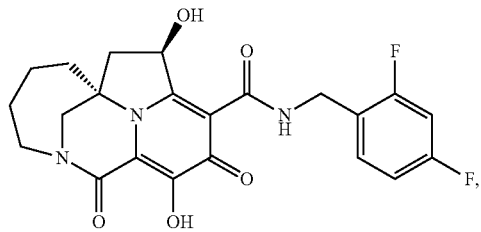
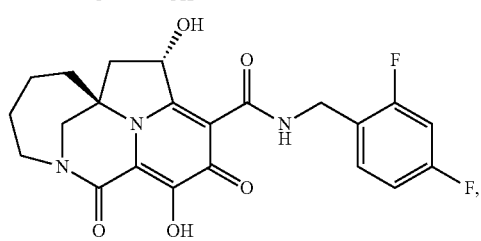
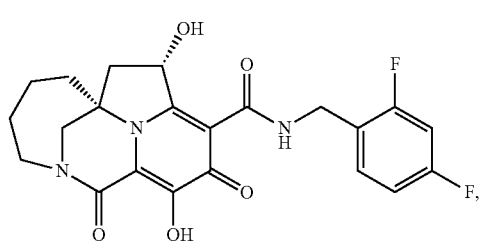

157
-continued
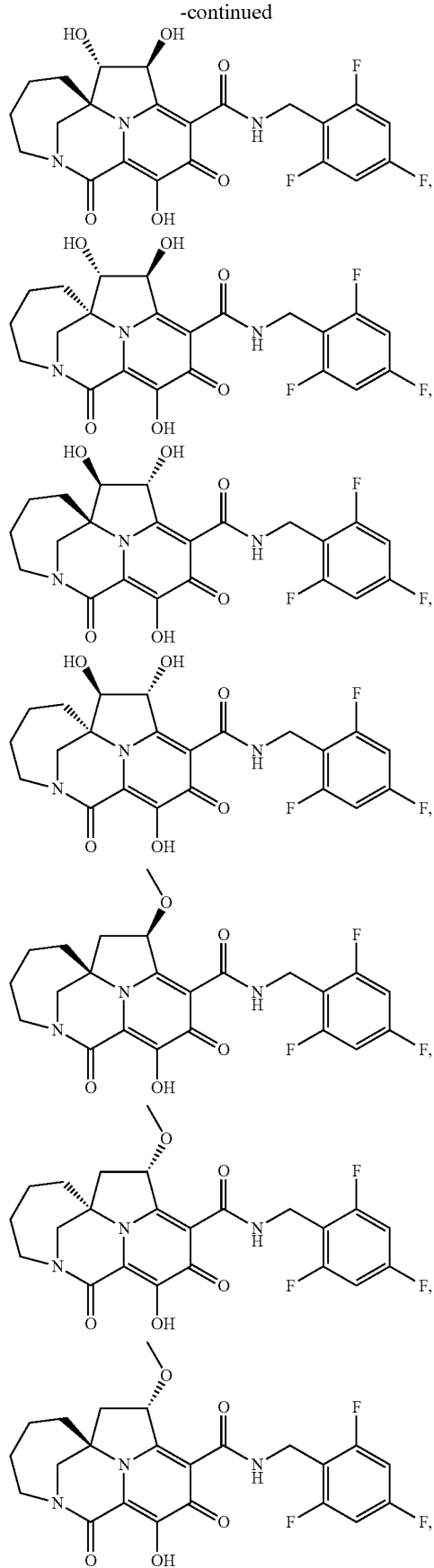
158
-continued
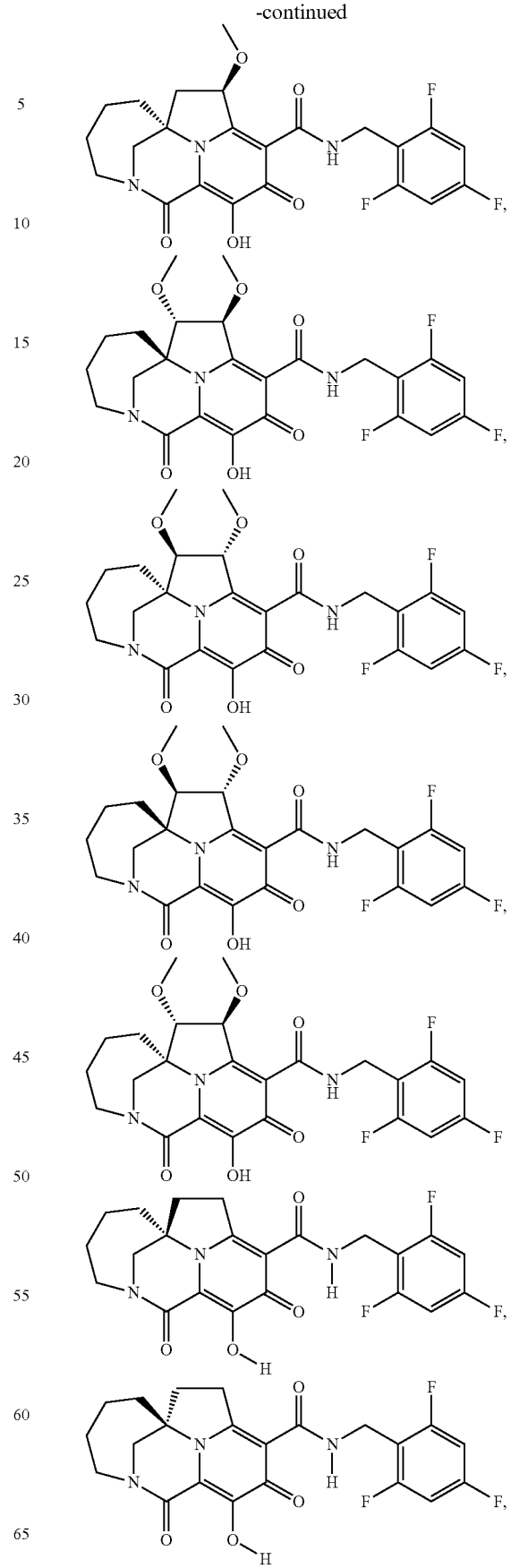

159
-continued
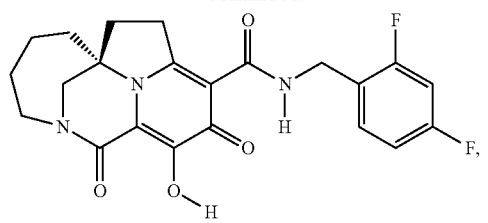
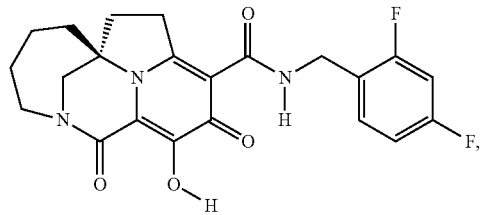
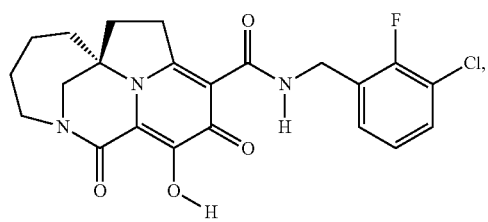
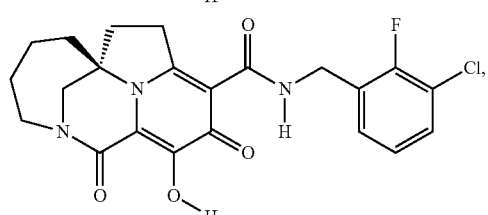
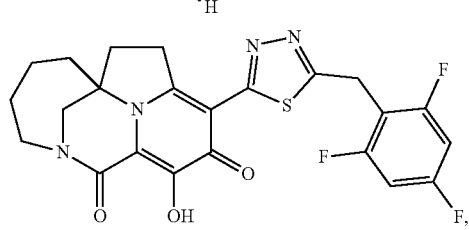
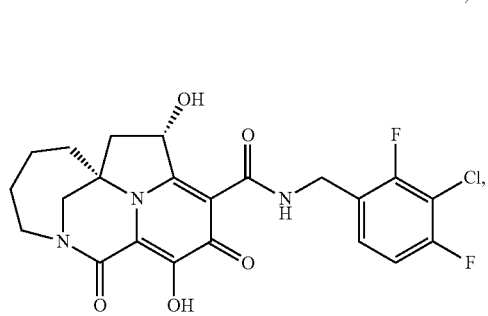
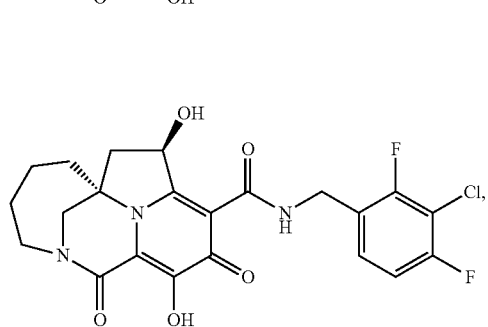
160
-continued
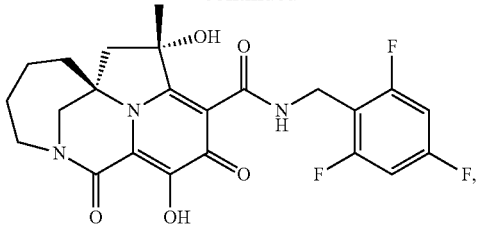
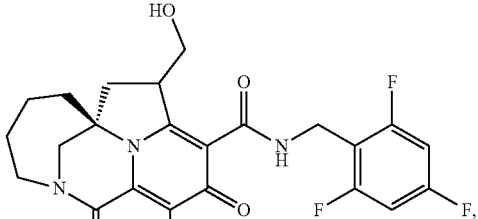
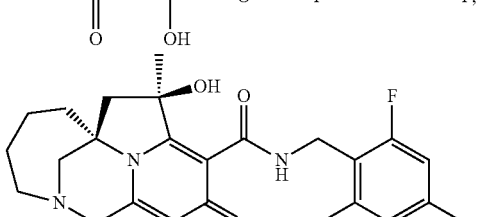
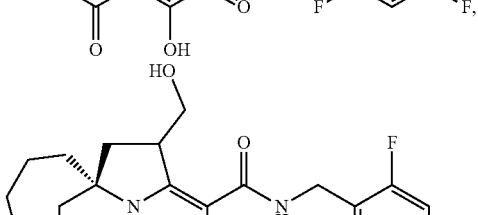
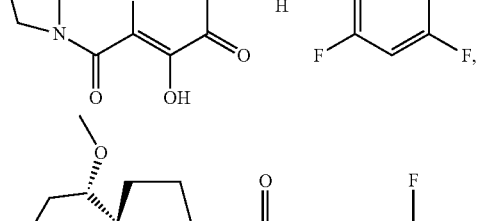
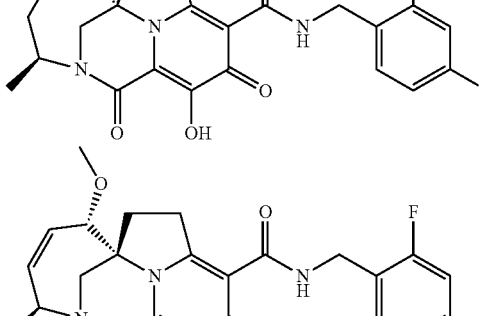
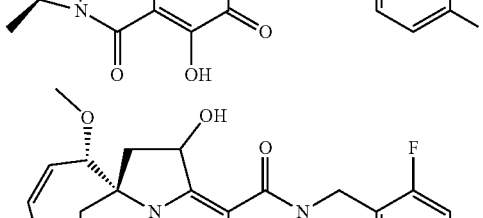
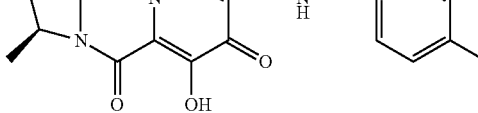

-continued
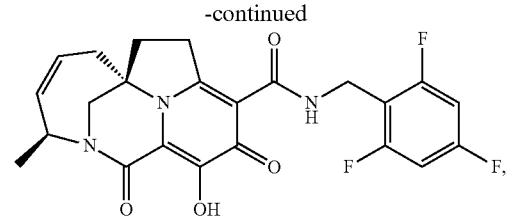
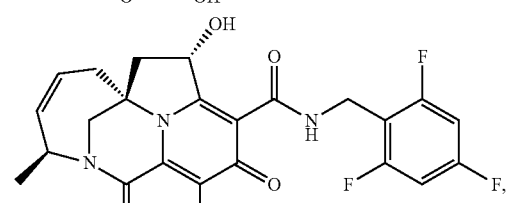
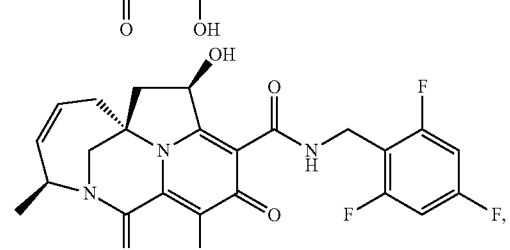
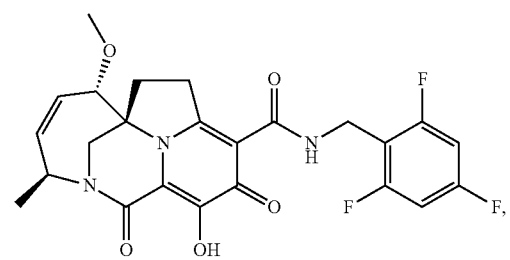
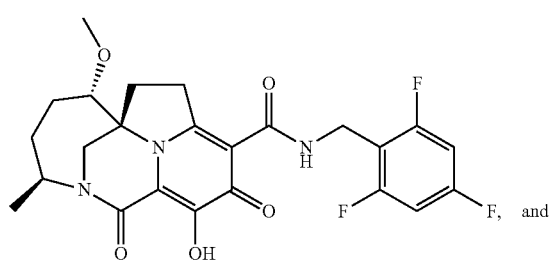
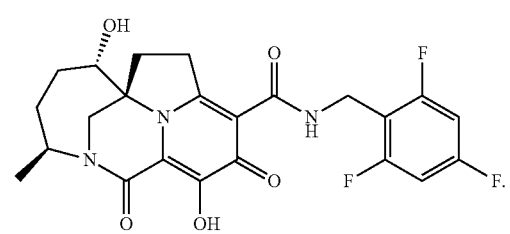
3. The compound of claim 1, or the pharmaceutically acceptable salt thereof, wherein the compound is selected from the group consisting of:
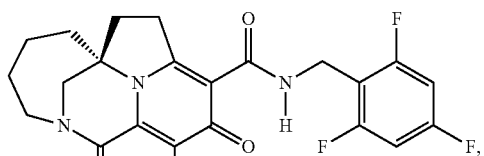
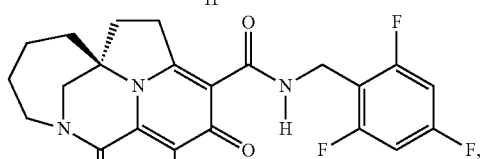
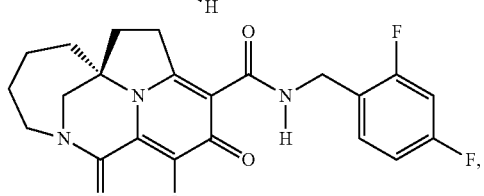
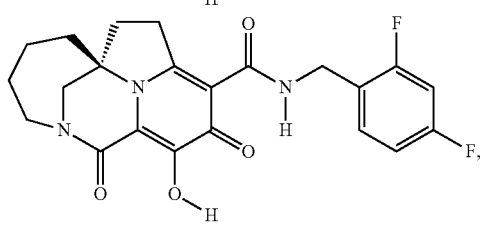
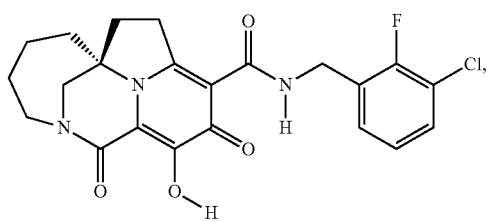
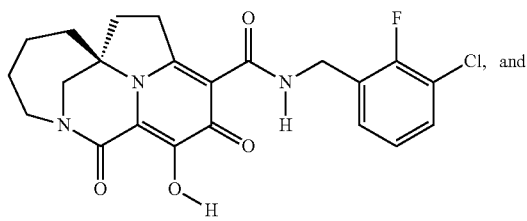
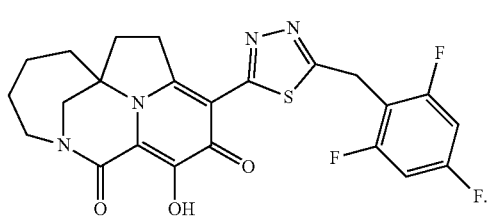

4. The compound of claim 1, or the pharmaceutically acceptable salt thereof, wherein the compound is selected from the group consisting of:
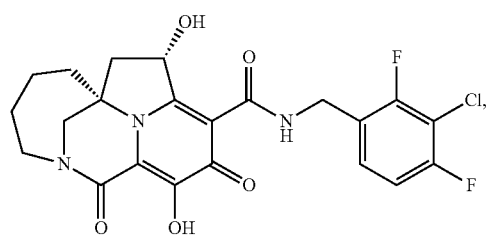
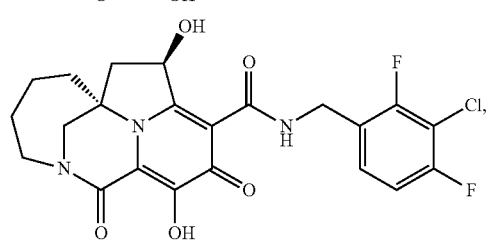
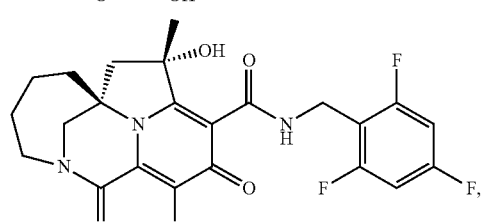
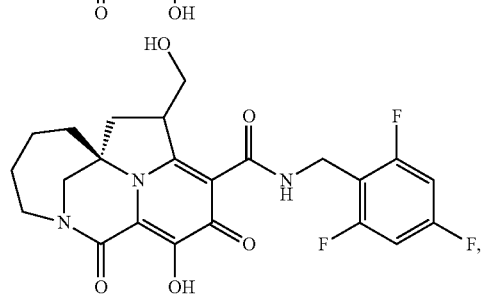
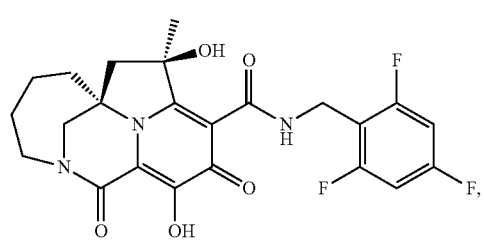
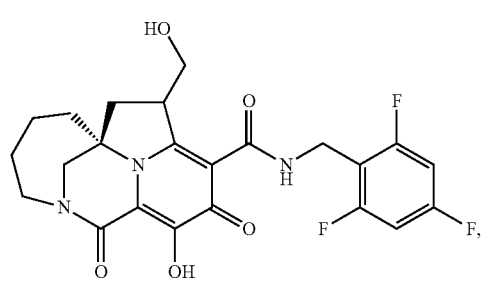
-continued
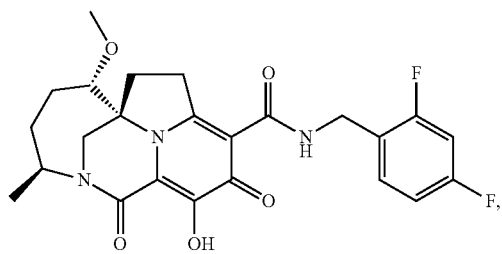
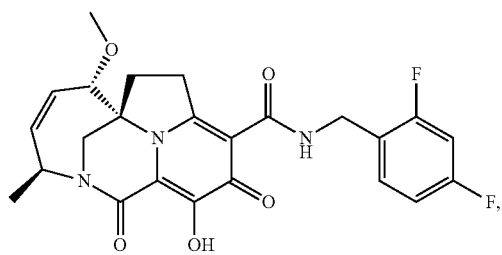
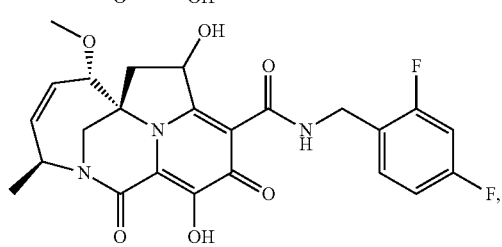
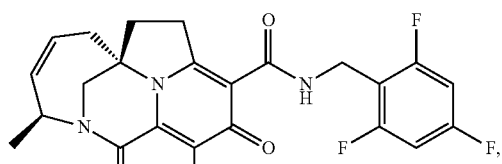
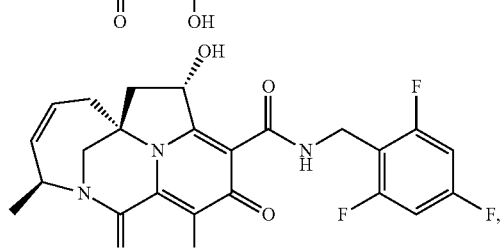
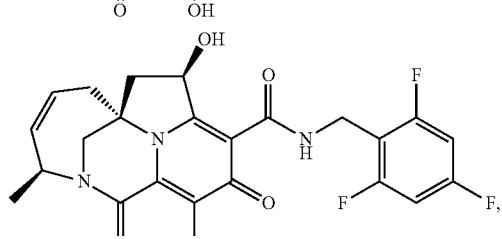
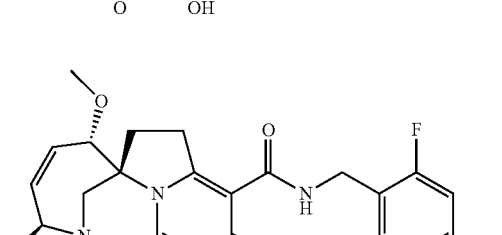

-continued

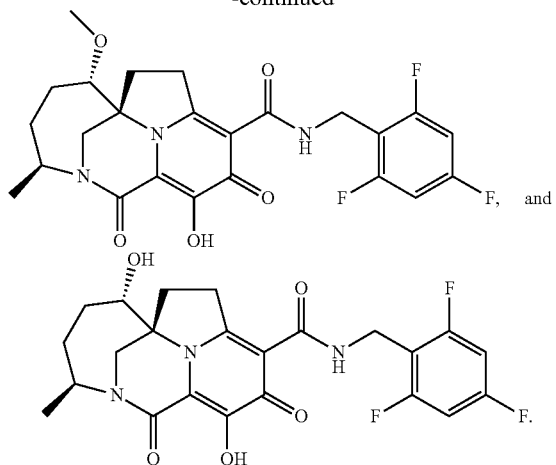

5. A pharmaceutical composition comprising a therapeutically effective amount of a compound of claim 1, or the pharmaceutically acceptable salt thereof, and a pharmaceutically acceptable excipient.

6. The pharmaceutical composition of claim 5, further comprising one, two, three, or four additional therapeutic agents.

7. The pharmaceutical composition of claim 6, wherein the additional therapeutic agent or agents are anti-HIV agents.

8. The pharmaceutical composition of claim 6, wherein the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof.

9. The pharmaceutical composition of claim 6, wherein the additional therapeutic agent or agents comprise a HIV capsid inhibitor.

10. The pharmaceutical composition of claim 6, wherein the pharmaceutical composition is for oral or parenteral administration.

11. A kit comprising a compound of claim 1, or a pharmaceutically acceptable salt thereof, and instructions for use.

12. The kit of claim 5, further comprising one, two, three, or four additional therapeutic agent or agents.

13. The kit of claim 12, wherein the additional therapeutic agent or agents are anti-HIV agents.

14. The kit of claim 12, wherein the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof.

15. The kit of claim 12, wherein the additional therapeutic agent or agents comprise a HIV capsid inhibitor.

16. A method of treating an HIV infection in a human having or at risk of having the infection, comprising administering to the human a therapeutically effective amount of a compound of claim 1, or a pharmaceutically acceptable salt thereof.

17. The method of claim 16, further comprising administering to the human a therapeutically effective amount of one, two, three, or four additional therapeutic agents.

18. The method of claim 17, wherein the additional therapeutic agent or agents are anti-HIV agents.

19. The method of claim 17, wherein the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof.

20. The method of claim 17, wherein the additional therapeutic agent or agents comprise a HIV capsid inhibitor.

* * * * *

UNITED STATES PATENT AND TRADEMARK OFFICE
CERTIFICATE OF CORRECTION

PATENT NO. : 12,122,776 B2
APPLICATION NO. : 18/316579
DATED : October 22, 2024
INVENTOR(S) : Lan Jiang et al.

It is certified that error appears in the above-identified patent and that said Letters Patent is hereby corrected as shown below:

On the Title Page

Column 2, Item [56], delete "2020)" and insert -- (2020) --.

In the Claims

Column 152, Lines 12-22, Claim 1, delete " 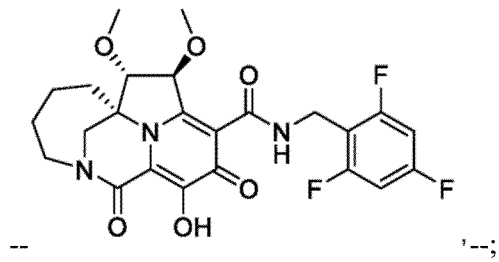 " and insert -- 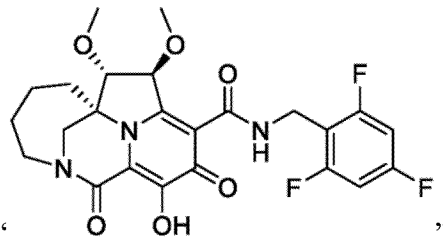 --;

Column 158, Lines 42-50, Claim 2, delete " 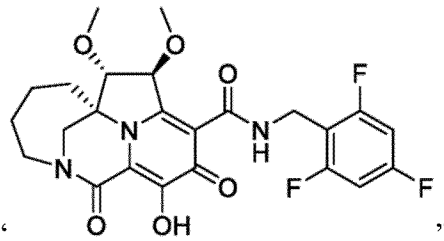 " and insert

Signed and Sealed this
Fifteenth Day of April, 2025

Coke Morgan Stewart
*Acting Director of the United States Patent and Trademark Office*

-- 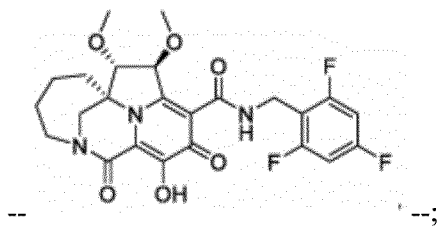 --;
Column 166, Line 7, Claim 12, delete "claim 5," and insert -- claim 11, --.